US008399462B2

(12) United States Patent
Dunn et al.

(10) Patent No.: US 8,399,462 B2
(45) Date of Patent: Mar. 19, 2013

(54) JNK MODULATORS

(75) Inventors: James Patrick Dunn, Los Altos, CA (US); Leyi Gong, San Mateo, CA (US); David Michael Goldstein, San Jose, CA (US); Xiaochun Han, Sunnyvale, CA (US); Joan Heather Hogg, Sunnyvale, CA (US); Wylie Solang Palmer, Mountain View, CA (US); Lubica Raptova, Sunnyvale, CA (US); Tania Silva, Sunnyvale, CA (US); Parcharee Tivitmahaisoon, Redwood City, CA (US); Teresa Alejandra Trejo-Martin, Union City, CA (US); Christophe Michoud, New York, NY (US); Achyutharao Sidduri, Livingston, NJ (US)

(73) Assignee: Roche Palo Alto LLC, Palo Alto, CA (US)

( * ) Notice: Subject to any disclaimer, the term of this patent is extended or adjusted under 35 U.S.C. 154(b) by 1037 days.

(21) Appl. No.: 12/001,021

(22) Filed: Dec. 7, 2007

(65) Prior Publication Data
US 2008/0146565 A1 Jun. 19, 2008

Related U.S. Application Data

(60) Provisional application No. 60/873,625, filed on Dec. 8, 2006.

(51) Int. Cl.
*C07D 403/04* (2006.01)
*A61K 31/506* (2006.01)
(52) U.S. Cl. ............ 514/235.8; 514/248; 514/275; 544/122; 544/236; 544/324
(58) Field of Classification Search .......... 544/122, 544/236, 324; 514/235.8, 248, 275
See application file for complete search history.

(56) References Cited

U.S. PATENT DOCUMENTS

| 4,788,195 | A * | 11/1988 | Torley et al. | 514/252.18 |
|---|---|---|---|---|
| 6,855,719 | B1 * | 2/2005 | Thomas et al. | 514/269 |
| 8,227,478 | B2 * | 7/2012 | Gong et al. | 514/275 |
| 2004/0097506 | A1 * | 5/2004 | Thomas | 514/243 |
| 2004/0106574 | A1 * | 6/2004 | Berg et al. | 514/54 |
| 2004/0171630 | A1 * | 9/2004 | Kim et al. | 514/275 |
| 2005/0090507 | A1 * | 4/2005 | Badiang et al. | 514/259.3 |
| 2006/0183900 | A1 * | 8/2006 | Huang et al. | 544/331 |

FOREIGN PATENT DOCUMENTS

| WO | WO 01/00213 A1 | 1/2001 |
|---|---|---|
| WO | 01/14375 | 3/2001 |
| WO | WO 01/60816 A1 | 8/2001 |
| WO | 02/066480 | 8/2002 |
| WO | 02/066481 | 8/2002 |
| WO | 03/051886 | 6/2003 |
| WO | 03/068754 | 8/2003 |
| WO | WO 2004/005283 A1 | 1/2004 |
| WO | 2005/075461 | 8/2005 |
| WO | 2006/050076 | 5/2006 |
| WO | 2006/124863 | 11/2006 |
| WO | 2007/107221 | 9/2007 |
| WO | 2008/028860 | 3/2008 |
| WO | 2008/042639 | 4/2008 |
| WO | 2008/045484 | 4/2008 |

OTHER PUBLICATIONS

Paul et al., Preparation of substituted N-phenyl-4-aryl-2-pyrimidinamines as mediator release inhibitors, Journal of Medicinal Chemistry (1993), 36(19), pp. 2716-2725.*
Katritzky et al., QSAR modeling of the inhibition of GSK-3, Bioorganic & Medicinal Chemistry (2006), 14(14), pp. 4987-5002.*
Sabat et al., The development of 2-benzimidazole substituted pyrimidine based inhibitors of lymphocyte specific kinase (lck), Bioorganic & Medicinal Chemistry Letters (2006), 16(23), pp. 5973-5977.*
Huang et al., Synthesis of 2-amino-4-(7-azaindol-3-yl)pyrimidines as CDK1 inhibitors, Bioorganic & Medicinal Chemistry Letters (2006), 16(18), pp. 4818-4821.*
Office Action in Corresponding Chilean Appl. 3502-2007, (2007).
Alam, M. et. al., "Synthesis and SAR of Aminopyrimidines as Novel c-Jun N-terminal Kinase (JNK) Inhibitors," *Bioorganic & Medicinal Chem. Lett.*, 2007, pp. 1-5.
Bradley, B. L., et. al. "Eosinophils, T-lymphocytes, mast cells, neutrophils, and macrophages in bronchial biopsy specimens from atopic subjects with asthma: Comparison with biopsy specimens from atopic subjects without asthma and normal control subjects and relationship to bronchial hyperresponsiveness," *Journal of Allergy Clin. Immunology* 1991, vol. 88, pp. 661-674.
Derijard, B., et. al. "JNK1: A Protein Kinase Stimulated by UV Light and Ha-Ras That Binds and Phosphorylates the c-Jun Activation Domain," *Cell*, 1994, vol. 76, pp. 1025-1037.
Han, Z., et. al., "Joint Damage and Inflammation in c-Jun N-Terminal Kinase 2 Knockout Mice With Passive Murine Collagen-Induced Arthritis," *Arthritis & Rheumatism*, 2002, vol. 46 (3), pp. 818-823.
Han, Z., et. al., "c-Jun N-terminal kinase is required for metalloproteinase expression and joint destruction in inflammatory arthritis," *J. Clinical Investigation*, 2001 vol. 108 (1), pp. 73-81.
Ip, Y. T., et. al., "Signal transduction by the c-Jun N-terminal kinase (JNK)—from inflammation to development," *Current Opinion Cell Biology*, 1998, vol. 10, pp. 205-219.

(Continued)

*Primary Examiner* — Deepak Rao
(74) *Attorney, Agent, or Firm* — George W. Johnston; Dennis P. Tramaloni; Jennifer L. Kisko

(57) ABSTRACT

Compounds of formula I modulate JNK:

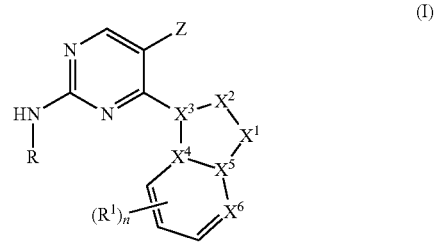

(I)

wherein the variables are as defined herein.

19 Claims, No Drawings

OTHER PUBLICATIONS

Jaeschke, A, et. al. "Disruption of the Jnk2 (Mapk9) gene reduces destructive insulitis and diabetes in a mouse model of type 1 diabetes," *PNAS*, 2005, vol. 102 (19), pp. 6931-6935.

Lee, Y. H., et. al. "c-Jun N-terminal Kinase (JNK) Mediates Feedback Inhibition of the Insulin Signaling Cascade" *Journal of Biological Chemistry*, 2003, vol. 278 (5), pp. 2896-2902.

Manning, A. M., et. al., "Targeting JNK for Therapeutic Benefit: From Junk to Gold?" *Nature* 2003, vol. 2, pp. 554-565.

Nakatani, Y., et. al. "Modulation of the JNK Pathway in Liver Affects Insulin Resistance Status" *Journal of Biological Chemistry*, 2004, vol. 279 (44), pp. 45803-45809.

Schett, G., et. al., "Activation, Differential Localization, and Regulation of the Stress-Activated Protein kinases, Extracellular Signal-Regulated Kinase, c-Jun N-Terminal Kinase, and p38 Mitogen-Activated Protein Kinase, in Synovial Tissue and Cells in Rheumatoid Arthritis," *Arthritis & Rheumatism*, 2000, vol. 43 (11), pp. 2501-2512.

Yang, D. D., et. al., Absence of excitotoxicity-induced apoptosis in the hippocampus of mice lacking the Jnk3 gene, *Nature*, 1997, vol. 389, pp. 865-870.

Yasuda, J., et. al., "The JIP Group of Mitogen-Activated Protein Kinase Scaffold Proteins," *Molecular and Cellular Biology*, 1999, vol. 19 (10), pp. 7245-7254.

Antonyak, M. A., et al. "Elevated JNK activation contributes to the pathogenesis of human brain tumors," *Oncogene* 2002, vol. 21, pp. 5038-5046.

Bennett, B. L., et. al. "JNK: a new therapeutic target for diabetes," *Current Opinion in Pharma.*, 2003, vol. 3, pp. 420-425.

Blease, K., et. al. "Emerging Treatment for Asthma," *Expert. Opin. Emerging Drugs*, 2003, vol. 8 (1), pp. 73-81.

Bousquet, J., et. al. "Asthma from Bronchoconstriction to Airways Inflammation and Remodeling," *American J. Respiratory and Critical Care Med.* 2000, vol. 161, pp. 1720-1745.

Bozyczko-Coyne, D., et. al. "Targeting the JNK Pathway for Therapeutic Benefit in CNS Disease," *Current Drug Target*, 2002, vol. 1, pp. 31-49.

Cripe, L.D., et. al. "Role for c-jun N-terminal kinase in treatment-refractory acute myeloid leukemia (AML): signaling to multidrug-efflux and hyperproliferation," *Leukemia*, 2002, vol. 16, pp. 799-812.

Eynott, P. R., et. al. "Allergen-induced inflammation and airway epithelial and smooth muscle cell proliferation: role of Jun N-terminal kinase," *British J. Pharmacology*, 2003, vol. 140, pp. 1373-1380.

Hess, P., et. al. "Survival signaling mediated by c-Jun NH2-terminal kinase in transformed B lymphoblasts," *Nature Genetics* 2002, vol. 32, pp. 201-205.

Hirosumi, J., et. al. "A Central Role for JNK in Obesity and Insulin Resistance," *Nature*, 2002, vol. 420, pp. 333-336.

Kaneto, H., et. al. "Possible novel therapy for diabetes with cell-permeable JNK-inhibitory peptide," *Nature Medicine* 2004, vol. 10 (10), pp. 1128-1132.

Kaneto, H., et al "The JNK pathway as a therapeutic target for diabetes," *Expert Opin. Ther. Targets*, 2005, vol. 9 (3), pp. 581-592.

Nath, P., et. al. "Potential role of c-Jun NH2-terminal kinase in allergic airway inflammation and remodeling: effects of SP600125," *European J. Pharmacology*, 2005, vol. 506, pp. 273-283.

Pei, J., et. al. "Localization of active forms of C-jun kinase (JNK) and p38 kinase in Alzheimer's disease brains at different stages of neurofibrillary degeneration," *J. Alzheimer's Disease*, 2001, vol. 3, pp. 41-48.

Saporito, M. S., et. al. "MPTP Activates c-Jun NH2-Terminal Kiinase (JNK) and Its Upstream Regulatory Kinase MKK4 in Nigrostriatal Neurons In Vivo," *J. Neurochemistry*, 2000, vol. 75 (3), pp. 1200-1208.

Xia, X. G., et. al. "Gene transfer of the JNK interacting protein-1 protects dopaminergic neurons in the MPTP model of Parkinson's disease," *PNAS*, 2001, vol. 98 (18), pp. 10433-10438.

Stebbins, J. L., et. al., "Identification of a new JNK inhibitor targeting the JNK-JIP interaction site," *PNAS*, 2008, vol. 105 (43), pp. 16809-16813.

(Translated Japanese Off Act in Corres Appl 2009539701 Mar. 13, 2012).

\* cited by examiner

JNK MODULATORS

This application claims benefit of U.S. Provisional Application No. 60/873,625 filed Dec. 8, 2006.

FIELD OF THE INVENTION

The present invention relates to a method for modulating c-Jun N-terminal kinases (JNK), and a method for treating a subject afflicted with a disease or condition that can be alleviated by modulating JNKs with heterocyclic compounds. The invention further relates to novel hetero-cyclic compounds and pharmaceutical compositions comprising said compound.

BACKGROUND OF THE INVENTION

The c-Jun N-terminal kinases (JNKs) are members of mitogen-activated protein kinase family along with p38 and extracellular signal-regulated kinases (ERKs). Three distinct genes (jnk1, jnk2 and jnk3) encoding 10 splice variants have been identified (Y. T. Ip and R. J. Davis, *Curr. Opin. Cell Biol.* (1998) 10:205-19). JNK1 and JNK2 are expressed in a wide variety of tissues, whereas JNK3 is mainly expressed in neurons, and to a lesser extent in heart and testes (D. D. Yang et al., *Nature* (1997) 389:865-70). Members of JNK family are activated by pro-inflammatory cytokines such as tumor necrosis factor cc (TNF-α) and interleukin-1β (IL-1β), as well as environmental stresses. The activation of JNKs is mediated by its upstream kinases, MKK4 and MKK7, via dual phosphorylation of Thr-183 and Tyr-185 (B. Derijard et al., *Cell* (1994) 76:1025-37). It has been shown that MKK4 and MMK7 can be activated by the diverse upstream kinases, including MEKK1 and MEKK4, depending upon the external stimuli and cellular context (D. Boyle et al., *Arthritis Rheum* (2003) 48:2450-24). The specificity of JNK signaling is achieved by forming a JNK-specific signaling complex containing multiple components of the kinase cascade using scaffold proteins called JNK-interacting proteins (J. Yasuda et al., *Mol. Cell. Biol.* (1999) 19:7245-54). JNKs have been shown to play important roles in inflammation, T cell functions, apoptosis and cellular survival by phosphorylating specific substrates, including transcription factors such as c-Jun, the component of activator protein-1 (AP1) family, and ATF2, as well as non-transcription factors such as IRS-1 and Bcl-2 (A. M. Manning and R. J. Davis, *Nat. Rev. Drug Discov.* (2003) 2:554-65). Over-activation of JNK is believed to be an important mechanism in autoimmune, inflammatory, metabolic, neurological diseases as well as cancer and pain.

Rheumatoid arthritis (RA) is a systemic autoimmune disease characterized by chronic inflammation of the joints. In addition to the joint swelling and pain caused by the inflammatory process, most RA patients ultimately develop debilitating joint damage and deformation. Several lines of compelling pharmacological and genetic evidence in cellular and animal models strongly suggest the relevance and importance of the activated JNK in the pathogenesis of RA. First, abnormal activation of JNK was detected in both human arthritic joints from RA patients (G. Schett et al., *Arthritis Rheum* (2000) 43:2501-12) and rodent arthritic joints from animal models of arthritis (Z. Han et al., *J. Clin. Invest.* (2001) 108:73-81). In addition, inhibition of JNK activation by selective JNK inhibitors blocked proinflammatory cytokines and MMP production in human synoviocytes, macrophages and lymphocytes (Z. Han et al., (2001) supra). Importantly, administration of the selective JNK inhibitors in rats with adjuvant arthritis (Z. Han et al., (2001) supra) or in mice with collagen-induced arthritis (P. Gaillard et al., *J Med. Chem.* (2005) 14:4596-607) effectively protected joints from destruction and significantly reduced paw swelling by inhibiting cytokine and collagenase expression. Furthermore, JNK2 deficient mice were partially protected from joint destruction, but showed little effect on paw swelling and inflammation in the passive collagen-induced arthritis model. These studies indicate that JNK2 is functionally redundant with JNK1 in regard to their roles in matrix degradation, inflammation and paw swelling. Therefore, combined inhibition of both JNK1 and JNK2 activities is required for effective therapy for RA (Z. Han et al., *Arthritis Rheum.* (2002) 46:818-23).

Asthma is a chronic inflammatory disease of airways, characterized by the presence of a cellular inflammatory process and by bronchial hyper-responsiveness associated with structural changes of the airways (B. Bradley et al., *J. Allergy Clin. Immunol.* (1991) 88:661-74). This disorder has been shown to be driven by many cell types in the airways, including T lymphocytes, eosinophils, mast cells, neutrophils and epithelial cells (J. Bousquet et al., *Am. J. Respir. Crit. Care Med.* (2000) 161:1720-45). JNKs have emerged as promising therapeutic targets for asthma based upon the recent proof-of-concept studies in the cellular and animal models of asthma using selective JNK inhibitors (K. Blease et al., *Expert Opin. Emerg. Drugs* (2003) 8:71-81). It was shown that JNK inhibitors significantly blocked RANTES production in activated human airway smooth cells (K. Kujime et al., *J. Immunol.* (2000) 164:3222-28). More importantly, the JNK inhibitors showed good efficacy in chronic rat and mouse models for their abilities to reduce cellular infiltration, inflammation, hyper-responsiveness, smooth muscle proliferation, and IgE production (P. Nath et al., *Eur. J. Pharmacol.* (2005) 506:273-83; P. Eynott et al., *Br. J. Pharmacol.* (2003) 140:1373-80). These observations suggest important roles of JNKs in the allergic inflammation, airway remodeling process associated with hyper-responsiveness. Therefore, blockade of JNK activity is expected to be beneficial for the treatment of asthma.

Type 2 diabetes is the most serious and prevalent metabolic disease characterized by insulin resistance and insulin secretion impairment as a result of chronic low-level inflammation and abnormal lipid metabolism associated with oxidative stress. It has been reported that JNK activity is abnormally elevated in various diabetic target tissues under obese and diabetic conditions (J. Hirosumi et al., *Nature* (2002) 420: 333-36; H. Kaneto, *Expert. Opin. Ther. Targets* (2005) 9:581-92). Activation of the JNK pathway by pro-inflammatory cytokines and oxidative stresses negatively regulates insulin signaling via phosphorylation of insulin receptor substrate-1 (IRS-1) at $Ser^{307}$, therefore contributes to insulin resistance and glucose tolerance (J. Hirosumi et al., *Nature* (2002) supra; Y. Lee et al., *J. Biol. Chem.* (2003) 278:2896-902; Y. Nakatani et al., *J. Biol. Chem.* (2004) 279:45803-09). Compelling genetic evidence came from elegant animal model studies using $jnk^{-/-}$ mice crossed with either genetic (ob/ob) obese mice or dietary obese mice. Loss of JNK1($JNK1^{-/-}$), but not JNK2 functions ($jnk2^{-/-}$), protected obese mice from body gains, increased steady-state levels of blood glucose, and decreased plasma insulin levels (J. Hirosumi et al., *Nature* (2002) supra). Furthermore, the beneficial effects were observed in a genetic diabetic model (db/db mice) by administration of either a small molecule JNK inhibitor, CC105 (B. Bennett et al., *Curr. Opin. Pharmacol.* (2003) 3:420-25) or a JNK inhibitory peptide I(JIP) derived from the JNK binding domain of the JNK-interacting protein-1(JIP-1) (H. Kaneto et al., *Nat. Med.* (2004) 10:1128-32), including significant lower blood glucose and higher plasma insulin levels. More interestingly, another recent report (A. Jaeschke et al., *Proc. Natl. Acad. Sci. USA*. (2005) 102:6931-35) revealed that JNK2 plays an important role in type 1 diabetes caused by autoimmune destruction of insulin-producing a cells. Non-obese diabetic mice deficient in JNK2 expression showed reduced destructive insulitis and less disease progression to diabetes, probably due to biased polarization toward the Th2 phenotype. Taken together, these studies demonstrated the utility of JNK inhibitors in the treatment of obesity/type 2 diabetes.

Neurodegenerative diseases, such as Alzheimer's (AD), Parkinson's (PD) and stroke are characterized by synaptic loss, neuronal atrophy and death. The JNK pathway leading to c-Jun activation has been shown to play a causal role in apoptosis of isolated primary embryonic neurons and multiple neuronal cell lines upon induction of a variety of stimuli (D. Bozyczko-Coyne et al., *Curr. Drug Targets CNS Neurol. Disord.* (2002) 1:31-49). Over-activation of JNK was observed in human brains from AD patients (J. Pei et al., *J. Alzheimers Dis*. (2001) 3:41-48) or rodent brain sections derived from animal models of neurodegenerative diseases (M. Saporito et al., *J. Neurochem*. (2000) 75:1200-08). For example, increased phospho-JNKs were detected in the postmortem brains from the AD patients. Administration of JNK inhibitory peptide (JIP-1 peptide) in the rodent model of AD induced by β-amyloid peptide administration prevented the impairment of synaptic plasticity. In the animal models of PD (MPTP model), elevated phospho-MKK4 and phospho-JNKs were observed concomitantly with the neuronal cell death. Adenoviral gene transfer of JNK inhibitory peptide (JIP-1 peptide) into striatum of mice attenuated behavioral impairment by inhibiting MPTP-mediated JNK, c-Jun and caspase activation, therefore blocking neuronal cell death in the substantia nigra (X. Xia et al., *Proc. Natl. Acad. Sci. USA*. (2001) 98:10433-38). In addition, in the animal model of ischemic stroke induced by glutamate excitotoxicity, mice deficient in JNK3, but not JNK1 or JNK2, were resistant to kainic acid (glutamate receptor agonist)-mediated seizure or neuronal death (D. D. Yang et al., *Nature* (1997) 389:865-70). These data suggest JNK3 was mainly responsible for glutamate excitotoxicity, an important component in ischemic conditions. Taken together, the data suggests that JNKs are an attractive target for multiple CNS diseases associated with neuronal cell death.

Uncontrolled cellular growth, proliferation and migration along with de-regulated angiogenesis lead to the formation of malignant tumors. The JNK signal transduction pathway may not act exclusively in apoptosis, sustained JNK activation leading to AP1 activation has recently been implicated to contribute to the cellular survival of specific cancer types such as glial tumors and BCL-ABL transformed B lymphoblasts (M. Antonyak et al., *Oncogene* (2002) 21:5038-46; P. Hess et al., *Nat. Genet*. (2002) 32:201-05). In the case of glial tumors, enhanced JNK/AP1 activity was seen in most of the primary brain tumor samples. For the transformed B lymphoblasts, BCL-ABL was shown to activate the JNK pathway which in turn up-regulated expression of anti-apoptotic bcl-2 gene. Interestingly, the multi-drug resistance and hyper-proliferation seen in treatment-refractory AML patients has been causally linked to the sustained JNK activity present in these AML samples (L. Cripe et al., *Leukemia* (2002) 16:799-812). Activation of JNK in leukemic cells resulted in induced expression of efflux pumps such as mdr1 and MRP1 responsible for multidrug resistance. Also, genes with a survival benefit in response to oxidative stress including glutathione-S-transferase π and γ-glutamyl cysteine synthase were also upregulated by the activated JNK pathway.

Accordingly, JNK modulators are useful in treating a variety of diseases and/or conditions.

SUMMARY OF THE INVENTION

One aspect of the invention provides a compound of formula I:

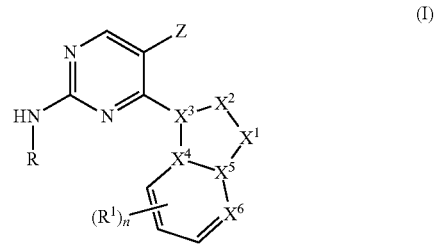

wherein
  $X^1$ is N, N—$R^3$, C—$R^3$, or O;
  $X^2$ is N, NH, N—$CH_3$, CH, or C—$CH_3$;
  $X^3$ is N or C,
  where only one or two of $X^1$, $X^2$, and $X^3$ are N;
  $X^4$, $X^5$ are each independently C or N;
  $X^6$ is N or C—$R^1$;
  where not more than two of $X^4$, $X^5$, and $X^6$ are N;
  and where the bonds between $X^1$ and $X^2$, $X^2$ and $X^3$, $X^3$ and $X^4$, $X^4$ and $X^5$, $X^1$ and $X^1$, and $X^5$ and $X^6$ may each independently be either single, double, or form an aromatic ring, with the proviso that a chemically stable structure results;
  R is

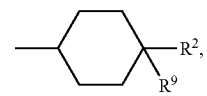

or -(phenyl)-$R^8$, where (phenyl) is optionally substituted with methyl, fluoro, chloro, or hydroxy, and where $R^9$ is H, halo, or lower alkyl, or $R^2$ and $R^9$ together form ═O or a ketal thereof;
  n is 0, 1, or 2;
  Each $R^1$ is independently halo, nitro, —CN, —$CH_2$CN, —OH, —$NH_2$, —COOH, —$OCH_2$C≡N, H, cyano-lower alkyl, —$Y^1R^4$, (lower alkyl)-$Y^1R^4$, (lower alkoxy)-$Y^1R^4$, -(lower alkylamino)-$Y^1R^4$-lower alkyl(lower alkyl)amino)-$Y^1R^4$-lower alkylsulfanyl)-$Y^1R^4$, -(lower alkoxy-alkyl)-$Y^1R^4$, -(lower alkylamino-alkyl)-$Y^1R^4$, where lower alkyl may be substituted with one or two hydroxy, or $R^1$ is

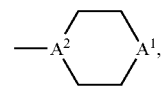

where $A^1$ is CHR$^c$, O, S, S(O), S(O)$_2$, or NR$^c$, where R$^c$, is H, OH, lower alkyl, lower acyl, $SO_2CH_3$, or benzyloxy-carbonyl, and $A^2$ is N or C—R$^d$, where R$^d$ is H, —$CH_3$, or —OH;
  $Y^1$ is —O—, —NH—, —N(lower alkyl)-, —S—, —SO—, —$SO_2$—, —$NHSO_2$—, —N(lower alkyl)$SO_2$—, —NHC(O)—, —C(O)NH—, —C(O)O—, —OC(O)NH—, or a bond;

$R^4$ is —CN, —CF$_3$, —NH$_2$, —NH(lower alkyl), —N(lower alkyl)$_2$, lower alkyl, cycloalkyl, cycloalkyl-lower alkyl, acyl, phenyl, benzyl, heterocyclyl (having one or two N, O, or S), heterocyclyl-lower alkyl, heteroaryl (having one or two N, O, or S), or heteroaryl-lower alkyl, each of which is substituted with 0-1 methylsulfanyl, 0-3 hydroxy and 0-3 halo;

$R^3$ is H, lower alkyl, lower alkoxy, —SO$_2$NH$_2$, —SO$_2$-lower alkyl, —SO$_2$-phenyl, —C(O)-lower alkyl, —C(O)-lower alkoxy, —C(O)NH$_2$, —C(O)NH-lower alkyl, cyano, or hydroxy-lower alkyl;

$R^2$ is H, halo, —OH, —SO$_2$NH$_2$, —CN, or —Y$^2$—Y$^3$—Y—R$^5$, where
  Y$^2$ is —C(O)—, —C(O)NR$^a$—, —SO$_2$—, —O—, —NH—, —N(lower alkyl)-, —N(hydroxy-lower alkyl)-, —NHC(O)—, —NHSO$_2$—, or a bond;
  Y$^3$ is lower alkylene or a bond;
  Y$^4$ is —O—, —NR$^a$—, —S—, —SO$_2$—, —C(O)—, —C(O)NR$^a$—, —NR$^a$C(O)—, —NR$^a$C(O)O—, —NR$^a$C(O)NR$^a$—, —NHSO$_2$—, —SO$_2$NH—, —SO$_2$N(R$^a$)—, or a bond;
  R$^5$ is H, lower alkyl, cycloalkyl, phenyl, heterocyclyl, or heteroaryl, wherein R$^5$ is optionally substituted with —OH, halo, lower alkyl, hydroxy-lower alkyl, alkoxy-lower alkyl, oxo, cyano, or —NR$^a$R$^b$ wherein each R$^a$ and R$^b$ is independently H or lower alkyl;

$R^8$ is H, lower alkyl, —OR$^e$, —SO$_2$NH$_2$, —NHSO$_2$R$^e$, —COOR$^e$, —SO$_2$R$^e$, —NH$_2$, —CONR$^a$R$^e$, —NHC(O)R$^e$, —CF$_3$, —NO$_2$, halo, or —CN, where R$^e$ is H, lower alkyl, benzyl, or phenyl;

Z is hydrogen, halo, alkyl, or NH$_2$;

or a pharmaceutically acceptable salt thereof.

The invention also provides pharmaceutical compositions, methods of using, and methods of preparing the aforementioned compounds.

Compounds and compositions of the invention are useful in the treatment and/or prevention of a c-Jun N-terminal kinase mediated disorder, such as autoimmune disorders, inflammatory disorders, metabolic disorders, neurological diseases, pain, and cancer. In some embodiments, compounds and compositions of the invention are useful in treating and/or preventing rheumatoid arthritis, asthma, type II diabetes, Alzheimer's disease, Parkinson's disease and/or stroke.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Alkyl" means the monovalent linear or branched saturated hydrocarbon moiety, consisting solely of carbon and hydrogen atoms, having from one to twelve carbon atoms.

"Lower alkyl" refers to an alkyl group of one to six carbon atoms, i.e. $C_1$-$C_6$ alkyl. Examples of alkyl groups include, but are not limited to, methyl, ethyl, propyl, isopropyl, isobutyl, sec-butyl, tert-butyl, pentyl, n-hexyl, octyl, dodecyl, and the like. "Branched alkyl" refers to an alkyl moiety having at least one branch, for example, isopropyl, isobutyl, tert-butyl, and the like. Similarly, "lower alkoxy" refers to a moiety of the form —OR, and "acyl" refers to a moiety of the form —C(O)R, where R is lower alkyl.

"Alkylene" means a linear saturated divalent hydrocarbon moiety of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkylene dioxy" means a divalent moiety of the formula —O—R—O—, where R is alkylene as defined herein.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxy-phenyl, and the like, including partially hydrogenated derivatives thereof.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof.

"Cycloalkylalkyl" mean a moiety of the formula —R$^a$—R$^b$, where R$^a$ is alkylene and R$^b$ is cycloalkyl as defined above.

"Heteroalkyl" means an alkyl moiety as defined herein, including a branched $C_4$-$C_7$ alkyl, wherein one, two or three hydrogen atoms have been replaced with a substituent independently selected from the group consisting of —OR$^a$, —NR$^b$R$^c$, and —S(O)$_n$R$^d$ (where n is an integer from 0 to 2), with the understanding that the point of attachment of the heteroalkyl radical is through a carbon atom, wherein R$^a$ is hydrogen, acyl, alkyl, cycloalkyl, or cycloalkylalkyl; R$^b$ and R$^c$ are independently of each other hydrogen, acyl, alkyl, cycloalkyl, or cycloalkylalkyl; and when n is 0, R$^d$ is hydrogen, alkyl, cycloalkyl, or cycloalkylalkyl; when n is 1, R$^d$ is alkyl, cycloalkyl, or cycloalkylalkyl; and when n is 2, R$^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Heteroaryl" means a monocyclic or bicyclic moiety of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, thiophenyl, furanyl, pyranyl, pyridinyl, pyrrolyl, pyrazolyl, pyrimidyl, pyridazinyl, quinolinyl, isoquinolinyl, benzofuryl, benzofuranyl, benzothiophenyl, benzothiopyranyl, benzimidazolyl, benzoxazolyl, benzooxadiazolyl, benzothiazolyl, benzothiadiazolyl, benzopyranyl, indolyl, isoindolyl, indazolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

The terms "halo," "halogen," and "halide" are used interchangeably herein and refer to a substituent fluoro, chloro, bromo, or iodo. The term "oxo" refers to a double-bonded oxygen, i.e., =O. The term "ketal" as used herein refers to a ketone derivative, wherein two alkoxy groups are bound to the same carbon atom, or both ends of a group of the formula —O-(lower alkyl)-O— are bound to a single carbon atom.

"Haloalkyl" means alkyl as defined herein in which one or more hydrogen has been replaced with same or different halogen. Exemplary haloalkyls include —$CH_2Cl$, —$CH_2CF_3$, —$CH_2CCl_3$, perfluoroalkyl (e.g., —$CF_3$), and the like.

"Heterocyclyl" means a monovalent saturated moiety, consisting of one to three rings, incorporating one, two, or three or four heteroatoms chosen from nitrogen, oxygen or sulfur. The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, dioxolanyl, thiamorpholinyl, thiamorpholinylsulfoxide, thiamorpholinylsulfone, dihydroquinolinyl, dihydroisoquinolinyl, tetrahydroquinolinyl, tetrahydrisoquinolinyl, and the like.

"Optionally substituted" means that the referenced radical can be substituted independently with one or more substituents, preferably one to four, and more preferably, one to three substituents as set forth. For example, "cycloalkyl optionally substituted with OH" would include all cycloalkyl radicals within the definition thereof, unsubstituted or substituted with one or more hydroxy groups. Exemplary groups meeting that description include, without limitation, cyclobutyl, cyclohexyl, cyclopentyl, cyclopropyl, 2-hydroxycyclobutyl, hydroxycyclopropyl, 3,4-dihydroxycyclohexyl, 3-hydroxycyclopentyl, and the like.

"Leaving group" means a group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucamine, triethanolamine, tromethamine, and the like. Acceptable inorganic bases include aluminum hydroxide, calcium hydroxide, potassium hydroxide, sodium carbonate, sodium hydroxide, and the like.

The preferred pharmaceutically acceptable salts are the salts formed from acetic acid, hydrochloric acid, sulfuric acid, methanesulfonic acid, maleic acid, phosphoric acid, tartaric acid, citric acid, sodium, potassium, calcium, zinc, and magnesium.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. Skilled persons will know how to choose a group for the ease of removal and for the ability to withstand the following reactions.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like.

Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:

(i) preventing the disease state, i.e. causing the clinical symptoms of the disease state not to develop in a subject that may be exposed to or predisposed to the disease state, but does not yet experience or display symptoms of the disease state.

(ii) inhibiting the disease state, i.e., arresting the development of the disease state or its clinical symptoms, or (iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Compounds of Formula I are useful for, without limitation, the treatment of inflammation and/or pain in a subject. Compounds of the invention can be used to treat pain and inflammation caused by arthritis, including without limitation, rheumatoid arthritis, spondyloarthropathies, gouty arthritis, osteoarthritis, systemic lupus erythematosus and juvenile arthritis, osteoarthritis, gouty arthritis and other arthritic conditions. Such compounds are also useful for the treatment of pulmonary disorders or lung inflammation, including adult respiratory distress syndrome, pulmonary sarcoidosis, asthma, silicosis, and chronic pulmonary inflammatory disease. The compounds are also useful for the treatment of inflammation caused by viral and bacterial infections, including sepsis, septic shock, gram negative sepsis, malaria, meningitis, cachexia secondary to infection or malignancy, pneumonia, and herpes virus.

"Pain" means the more or less localized sensation of discomfort, distress, or agony, resulting from the stimulation of specialized nerve endings. There are many types of pain, including, without limitation, lightning pains, phantom pains, shooting pains, acute pain, inflammatory pain, neuropathic pain, complex regional pain, neuralgia, neuropathy, and the like (*Dorland's Illustrated Medical Dictionary*, 28th Edition, W. B. Saunders Company, Philadelphia, Pa.). The goal of treatment of pain is to reduce the degree of severity of pain perceived by a treatment subject. "Neuropathic pain" means the pain resulting from functional disturbances and/or pathological changes as well as noninflammatory lesions in the peripheral nervous system. Examples of neuropathic pain include, but are not limited to, thermal or mechanical hyperalgesia, thermal or mechanical allodynia, diabetic pain, entrapment pain, and the like.

Nomenclature and Structures

In general, the nomenclature used in this Application is based on AUTONOM™ v.4.0, a Beilstein Institute computerized system for the generation of IUPAC systematic nomenclature. Chemical structures shown herein were prepared using ISIS® version 2.2. Any open valency appearing on a carbon, oxygen or nitrogen atom in the structures herein indicates the presence of a hydrogen atom.

Whenever a chiral carbon is present in a chemical structure, it is intended that all stereoisomers associated with that chiral carbon are encompassed by the structure.

All patents and publications identified herein are incorporated herein by reference in their entirety.

General Method

One aspect of the invention provides A compound of formula I:

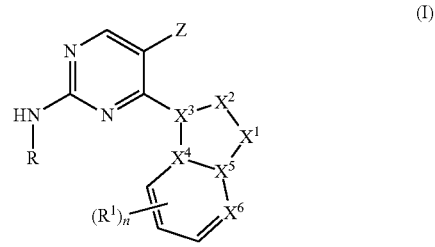

(I)

wherein $X^1$ is N, N—$R^3$, C—$R^3$, or O;

$X^2$ is N, NH, N—$CH_3$, CH, or C—$CH_3$;

$X^3$ is N or C, where only one or two of $X^1$, $X^2$, and $X^3$ are N;

$X^4$, $X^5$ are each independently C or N;

$X^6$ is N or C—$R^1$;

where not more than two of $X^4$, $X^5$, and $X^6$ are N;

and where the bonds between $X^1$ and $X^2$, $X^2$ and $X^3$, $X^3$ and $X^4$, $X^4$ and $X^5$, $X^5$ and $X^1$, and $X^5$ and $X^6$ may each independently be either single, double, or form an aromatic ring, with the proviso that a chemically stable structure results;

R is

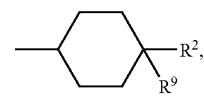

or -(phenyl)-$R^8$, where (phenyl) is optionally substituted with methyl, fluoro, chloro, or hydroxy, and where $R^9$ is H, halo, or lower alkyl, or $R^2$ and $R^9$ together form =O or a ketal thereof;

n is 0, 1, or 2;

Each $R^1$ is independently halo, nitro, —CN, —$CH_2CN$, —OH, —$NH_2$, —COOH, —$OCH_2C\equiv N$, H, cyano-lower alkyl, —$Y^1R^4$, -(lower alkyl)-$Y^1R^4$, lower alkoxy)-$Y^1R^4$, lower alkylamino)-$Y^1R^4$, -(lower alkyl(lower alkyl)amino)-$Y^1R^4$, -(lower alkylsulfanyl)-$Y^1R^4$, -(lower alkoxy-alkyl)-$Y^1R^4$, -(lower alkylamino-alkyl)-$Y^1R^4$, where lower alkyl may be substituted with one or two hydroxy, or $R^1$ is

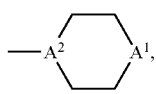

where $A^1$ is $CHR^c$, O, S, S(O), S(O)$_2$, or $NR^c$, where $R^c$ is H, OH, lower alkyl, lower acyl, SO$_2$CH$_3$, or benzyloxy-carbonyl, and $A^2$ is N or C—$R^d$, where $R^d$ is H, —CH$_3$, or —OH;

$Y^1$ is —O—, —NH—, —N(lower alkyl)-, —S—, —SO—, —SO$_2$—, —NHSO$_2$—, —N(lower alkyl)SO$_2$—, —NHC(O)—, —C(O)NH—, —C(O)O—, —OC(O)NH—, or a bond;

$R^4$ is —CN, —CF$_3$, —NH$_2$, —NH(lower alkyl), —N(lower alkyl)$_2$, lower alkyl, cycloalkyl, cycloalkyl-lower alkyl, acyl, phenyl, benzyl, heterocyclyl (having one or two N, O, or S), heterocyclyl-lower alkyl, heteroaryl (having one or two N, O, or S), or heteroaryl-lower alkyl, each of which is substituted with 0-1 methylsulfanyl, 0-3 hydroxy and 0-3 halo;

$R^3$ is H, lower alkyl, lower alkoxy, —SO$_2$NH$_2$, —SO$_2$-lower alkyl, —SO$_2$-phenyl, —C(O)-lower alkyl, —C(O)-lower alkoxy, —C(O)NH$_2$, —C(O)NH-lower alkyl, cyano, or hydroxy-lower alkyl;

$R^2$ is H, halo, —OH, —SO$_2$NH$_2$, —CN, or —Y$^2$—Y$^3$—Y$^4$—R$^5$, where $Y^2$ is —C(O)—, —C(O)NR$^a$—, —SO$_2$—, —O—, —NH—, —N(lower alkyl)-, —N(hydroxy-lower alkyl)-, —NHC(O)—, —NHSO$_2$—, or a bond;

$Y^3$ is lower alkylene or a bond;

$Y^4$ is —O—, —NR$^a$—, —S—, —SO$_2$—, —C(O)—, —C(O)NR)$^a$—, —NR$^a$C(O)—, —NR$^a$C(O)O—, —NR$^a$C(O)NR$^a$—, —NHSO$_2$—, —SO$_2$NH—, —SO$_2$N(R$^a$), or a bond;

$R^5$ is H, lower alkyl, cycloalkyl, phenyl, heterocyclyl, or heteroaryl, wherein $R^5$ is optionally substituted with —OH, halo, lower alkyl, hydroxy-lower alkyl, alkoxy-lower alkyl, oxo, cyano, or —NR$^a$R$^b$ wherein each R$^a$ and R$^b$ is independently H or lower alkyl;

$R^8$ is H, lower alkyl, —OR$^e$, —SO$_2$NH$_2$, —NHSO$_2$R$^e$, —COOR$^e$, —SO$_2$R$^e$, —NH$_2$, —CONR$^a$R$^e$, —NHC(O)R$^e$, —CF$_3$, —NO$_2$, halo, or —CN, where R$^e$ is H, lower alkyl, benzyl, or phenyl;

Z is hydrogen, halo, alkyl, or NH$_2$;

or a pharmaceutically acceptable salt thereof.

In some embodiments, $X^4$, $X^5$, and $X^6$ are each C. In other embodiments, R is -(cyclo-hexyl)-R$^2$. In further embodiments, $X^3$ is N and $X^1$ is C. In additional embodiments, $R^2$ is OH. In some embodiments, $R^1$ is benzyloxy and n is 1. In still other embodiments, $R^1$ is —CN.

In some embodiments, $X^2$ is N. In other embodiments, $R^2$ is —Y$^2$—Y$^3$—Y$^4$—R$^5$, where Y$^2$ is —C(O)NR$^a$—, R$^a$ is H, and Y$^3$ is lower alkylene. In other embodiments, Y$^4$ is —SO$_2$—. In further embodiments, R$^5$ is lower alkyl.

In some embodiments, Y$^4$ is —S—. In some embodiments, R$^5$ is lower alkyl.

In other embodiments, Y$^4$ is a bond, and R$^5$ is lower alkyl.

Another aspect of the invention is a method for treating inflammation, comprising administering an effective amount of a compound of the invention to a subject in need thereof.

Another aspect of the invention is a pharmaceutical composition, comprising a compound of the invention and a pharmaceutically acceptable excipient.

It should be appreciated that combinations of the different groups described herein may form other embodiments. In this manner, a variety of different compounds are embodied within the present invention.

Representative compounds of the invention are shown in Table 1 below.

TABLE 1

Representative compounds of Formula I.

| Structure | Name | Compound No. |
|---|---|---|
| 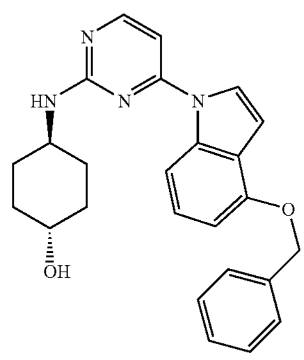 [SMILES: O[C@H]1CC[C@H](Nc2nccc(-n3ccc4c(OCc5ccccc5)cccc43)n2)CC1] | 4-[4-(4-benzyloxy-indol-1-yl)-pyrimidin-2-yl-amino]-cyclohexanol | 1 |
| 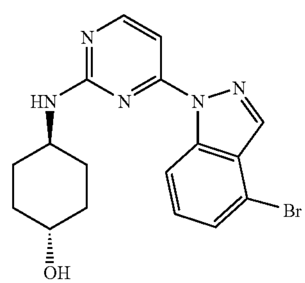 [SMILES: O[C@H]1CC[C@H](Nc2nccc(-n3ncc4c(Br)cccc43)n2)CC1] | 4-[4-(4-bromoindol-1-yl)-pyrimidin-2-yl-amino]-cyclohexanol | 2 |

TABLE 1-continued

Representative compounds of Formula I.

| Structure | Name | Compound No. |
|---|---|---|
| 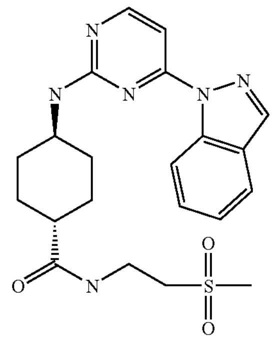 [SMILES: CS(=O)(=O)CCNC(=O)[C@H]1CC[C@H](Nc2nccc(-n3ncc4ccccc43)n2)CC1] | 4-(4-indol-1-yl)-pyrimidin-2-ylamino]-cyclohexane carboxylic acid (2-methane-sulfonylethyl)amide | 3 |
| 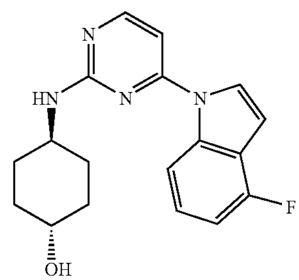 [SMILES: O[C@H]1CC[C@H](Nc2nccc(-n3ccc4c(F)cccc43)n2)CC1] | 4-[4-(4-fluoroindol-1-yl)-pyrimidin-2-yl-amino]-cyclohexanol | 4 |
| 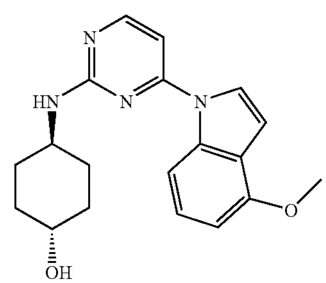 [SMILES: COc1cccc2c1ccn2-c1ccnc(N[C@H]2CC[C@H](O)CC2)n1] | 4-[4-(4-methoxy-indol-1-yl)-pyrimidin-2-yl-amino]-cyclohexanol | 5 |
| 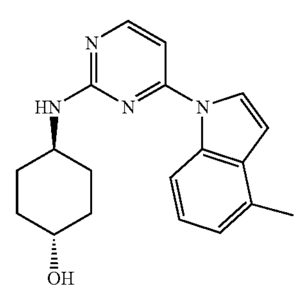 [SMILES: Cc1cccc2c1ccn2-c1ccnc(N[C@H]2CC[C@H](O)CC2)n1] | 4-[4-(4-methyl-indol-1-yl)-pyrimidin-2-yl-amino]-cyclohexanol | 6 |
| 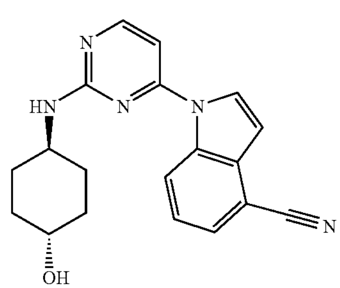 [SMILES: N#Cc1cccc2c1ccn2-c1ccnc(N[C@H]2CC[C@H](O)CC2)n1] | 4-[4-(4-cyano-indol-1-yl)-pyrimidin-2-yl-amino]-cyclohexanol | 7 |

TABLE 1-continued

Representative compounds of Formula I.

| Structure | Name | Compound No. |
|---|---|---|
| 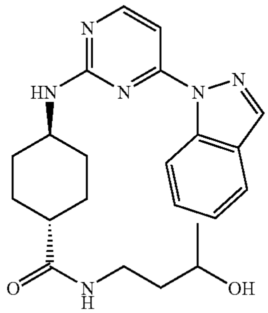 [SMILES: CC(O)CCNC(=O)[C@H]1CC[C@H](Nc2nccc(-n3ncc4ccccc43)n2)CC1] | 4-(4-indazol-1-yl)-pyrimidin-2-ylamino]-cyclohexane carboxylic acid (3-hydroxybutyl)-amide | 8 |
| 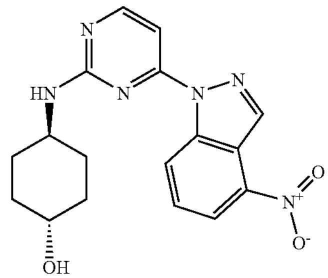 [SMILES: O=[N+]([O-])c1cccc2c1cnn2-c1ccnc(N[C@H]2CC[C@H](O)CC2)n1] | 4-[4-(4-nitro-indazol-1-yl)-pyrimidin-2-yl-amino]-cyclohexanol | 9 |
| 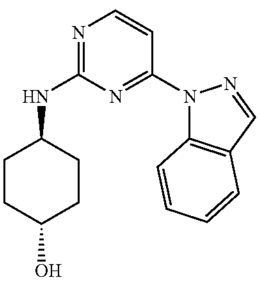 [SMILES: O[C@H]1CC[C@H](Nc2nccc(-n3ncc4ccccc43)n2)CC1] | 4-(4-indazol-1-yl)-pyrimidin-2-ylamino-cyclohexanol mp = 232.6-233.7° C. MS = 310 [M + H]$^+$ | 10 |
| 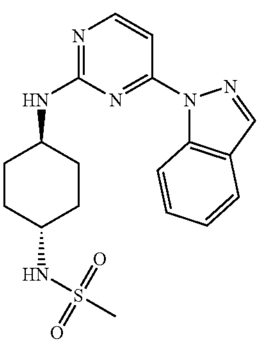 [SMILES: CS(=O)(=O)N[C@H]1CC[C@H](Nc2nccc(-n3ncc4ccccc43)n2)CC1] | N-[4-(4-indazol-1-yl)-pyrimidin-2-ylamino-cyclohexyl]methane-sulfonamide | 11 |
| 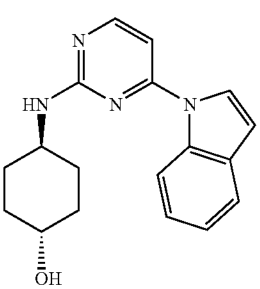 [SMILES: O[C@H]1CC[C@H](Nc2nccc(-n3ccc4ccccc43)n2)CC1] | 4-(4-indol-1-yl)-pyrimidin-2-ylamino-cyclohexanol | 12 |

TABLE 1-continued

Representative compounds of Formula I.

| Structure | Name | Compound No. |
|---|---|---|
| 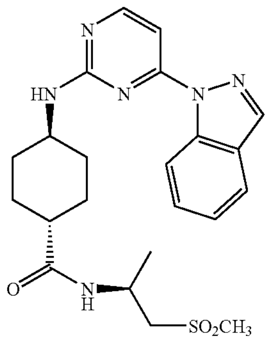 [SMILES: C[C@@H](CS(C)(=O)=O)NC(=O)[C@H]1CC[C@H](Nc2nccc(-n3ncc4ccccc43)n2)CC1] | 4-(4-indazol-1-yl)-pyrimidin-2-ylamino]-cyclohexane carboxylic acid (1-methylsulfonyl-prop-2-yl)-amide | 13 |
| 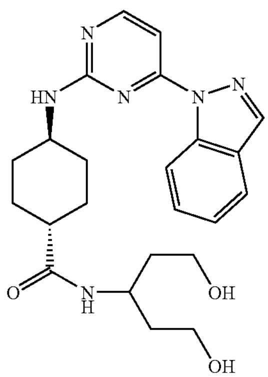 [SMILES: O=C(NC(CCO)CCO)[C@H]1CC[C@H](Nc2nccc(-n3ncc4ccccc43)n2)CC1] | 4-(4-indazol-1-yl)-pyrimidin-2-ylamino]-cyclohexane carboxylic acid (1,5-dihydroxy-pent-3-yl)-amide | 14 |
| 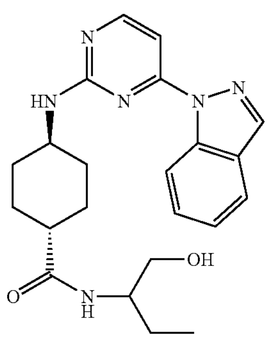 [SMILES: CCC(CO)NC(=O)[C@H]1CC[C@H](Nc2nccc(-n3ncc4ccccc43)n2)CC1] | 4-(4-indazol-1-yl)-pyrimidin-2-ylamino]-cyclohexane carboxylic acid (1-hydroxy-but-2-yl)-amide | 15 |
| 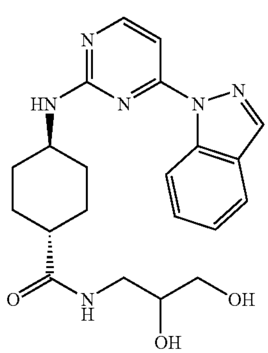 [SMILES: O=C(NCC(O)CO)[C@H]1CC[C@H](Nc2nccc(-n3ncc4ccccc43)n2)CC1] | 4-(4-indazol-1-yl)-pyrimidin-2-ylamino]-cyclohexane carboxylic acid (2,3-dihydroxy-prop-1-yl)-amide | 16 |

TABLE 1-continued

Representative compounds of Formula I.

| Structure | Name | Compound No. |
|---|---|---|
| 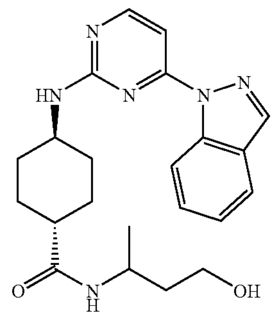 [SMILES: CC(CCO)NC(=O)[C@H]1CC[C@H](Nc2nccc(-n3ncc4ccccc43)n2)CC1] | 4-(4-indazol-1-yl)-pyrimidin-2-ylamino]-cyclohexane carboxylic acid (1-hydroxybut-3-yl)-amide | 17 |
| 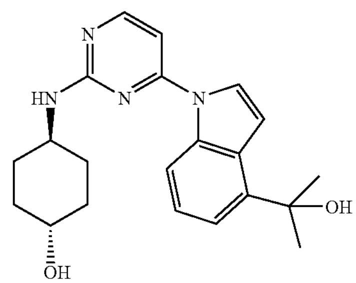 [SMILES: CC(C)(O)c1cccc2c1ccn2-c1ccnc(N[C@H]2CC[C@H](O)CC2)n1] | 4-[4-(4-(2-hydroxyprop-2-yl)-indol-1-yl)-pyrimidin-2-ylamino]-cyclohexanol | 18 |
| 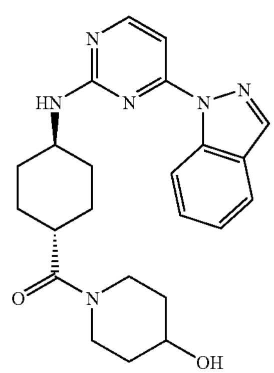 [SMILES: O=C([C@H]1CC[C@H](Nc2nccc(-n3ncc4ccccc43)n2)CC1)N1CCC(O)CC1] | (4-hydroxypiperidin-1-yl)-[4-(4-indazol-1-yl-pyrimidin-2-ylamino)-cyclohexyl]-methanone | 19 |
| 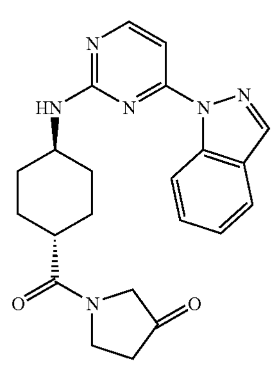 [SMILES: O=C1CCN(C(=O)[C@H]2CC[C@H](Nc3nccc(-n4ncc5ccccc54)n3)CC2)C1] | (3-pyrrolidon-1-yl)-[4-(4-indazol-1-yl-pyrimidin-2-ylamino)-cyclohexyl]-methanone | 20 |

TABLE 1-continued

Representative compounds of Formula I.

| Structure | Name | Compound No. |
|---|---|---|
| 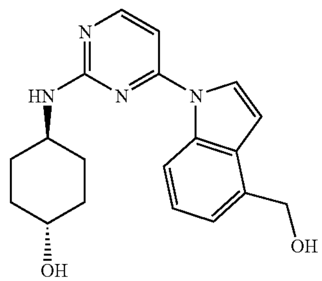 [SMILES: OCc1cccc2c1ccn2-c1ccnc(N[C@H]2CC[C@H](O)CC2)n1] | 4-[4-(4-hydroxymethyl-indol-1-yl)-pyrimidin-2-ylamino]-cyclohexanol | 21 |
| 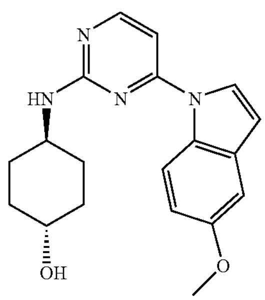 [SMILES: COc1ccc2c(ccn2-c2ccnc(N[C@H]3CC[C@H](O)CC3)n2)c1] | 4-[4-(5-methoxy-indol-1-yl)-pyrimidin-2-yl-amino]-cyclohexanol | 22 |
| 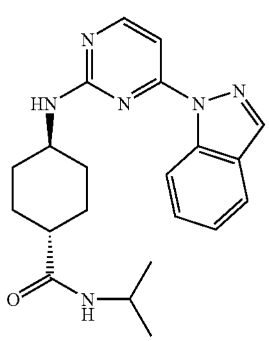 [SMILES: CC(C)NC(=O)[C@H]1CC[C@H](Nc2nccc(-n3ncc4ccccc43)n2)CC1] | 4-(4-indazol-1-yl-pyrimidin-2-ylamino)-cyclohexane carboxylic acid isopropylamide | 23 |
| 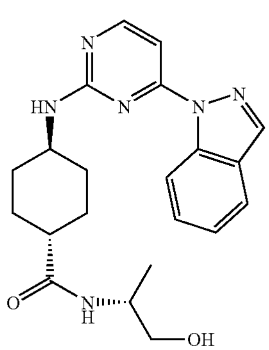 [SMILES: C[C@H](CO)NC(=O)[C@H]1CC[C@H](Nc2nccc(-n3ncc4ccccc43)n2)CC1] | 4-(4-indazol-1-yl-pyrimidin-2-ylamino)-cyclohexane carboxylic acid 1-hydroxyprop-2-ylamide | 24 |

TABLE 1-continued

Representative compounds of Formula I.

| Structure | Name | Compound No. |
|---|---|---|
| 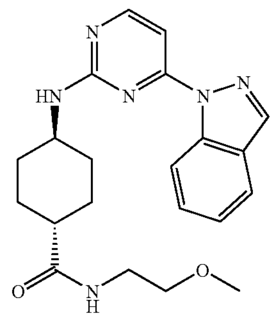 [SMILES: COCCNC(=O)[C@H]1CC[C@H](Nc2nccc(-n3ncc4ccccc43)n2)CC1] | 4-(4-indazol-1-yl-pyrimidin-2-ylamino)-cyclohexane carboxylic acid 2-methoxyethy-amide | 25 |
| 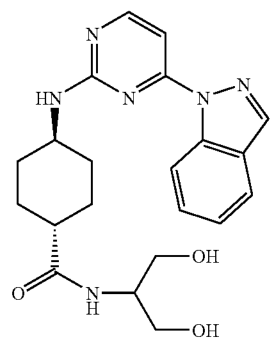 [SMILES: O=C(NC(CO)CO)[C@H]1CC[C@H](Nc2nccc(-n3ncc4ccccc43)n2)CC1] | 4-(4-indazol-1-yl-pyrimidin-2-ylamino)-cyclohexane carboxylic acid 1,3-dihydroxyprop-2-ylamide | 26 |
| | 4-[4-(6-nitroindazol-1-ylpyrimidin-2-ylamino)-cyclohexanol<br>mp = 221.8-223.0° C.<br>MS = 355 [M + H]$^+$ | 27 |
| 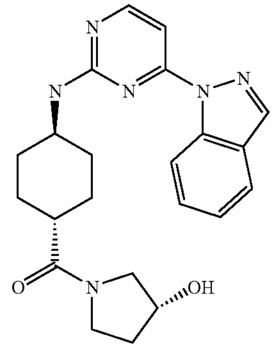 [SMILES: O=C([C@H]1CC[C@H](Nc2nccc(-n3ncc4ccccc43)n2)CC1)N1CC[C@@H](O)C1] | (3-hydroxypyrrolidin-1-yl)-[4-(4-indazol-1-yl-pyrimidin-2-ylamino)--cyclohexyl]-methanone | 28 |

TABLE 1-continued

Representative compounds of Formula I.

| Structure | Name | Compound No. |
|---|---|---|
|  | (3-hydroxypyrrolidin-1-yl)-[4-(4-indazol-1-yl-pyrimidin-2-ylamino)-cyclohexyl]-methanone | 29 |
| 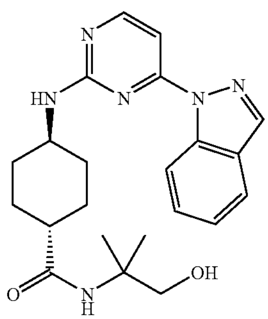 [SMILES: CC(C)(CO)NC(=O)[C@H]1CC[C@H](Nc2nccc(-n3ncc4ccccc43)n2)CC1] | 4-(4-indazol-1-yl-pyrimidin-2-ylamino)-cyclohexane carboxylic acid 3-hydroxy-2-methylprop-2-yl-amide | 30 |
| 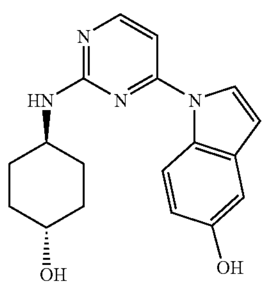 [SMILES: Oc1ccc2c(ccn2-c2ccnc(N[C@H]3CC[C@H](O)CC3)n2)c1] | 1-[2-(4-hydroxycyclo-hexylamino)-pyrimidin-4-yl]-1H-indol-5-ol | 31 |
| 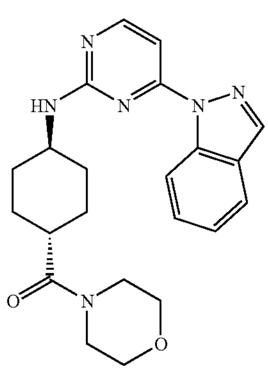 [SMILES: O=C([C@H]1CC[C@H](Nc2nccc(-n3ncc4ccccc43)n2)CC1)N1CCOCC1] | [4-(4-indazol-1-yl-pyrimidin-2-ylamino)-cyclohexyl]-morpholin-4-yl-methanone | 32 |

TABLE 1-continued

Representative compounds of Formula I.

| Structure | Name | Compound No. |
|---|---|---|
| 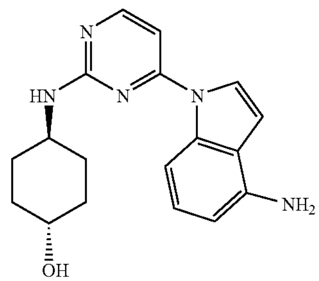 [SMILES: Nc1cccc2c1ccn2-c1ccnc(N[C@H]2CC[C@H](O)CC2)n1] | 4-[4-(4-aminoindol-1-yl)-pyrimidin-2-yl-amino]-cyclohexanol | 33 |
| 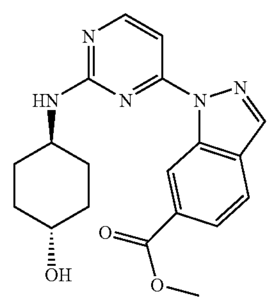 [SMILES: COC(=O)c1ccc2cnn(-c3ccnc(N[C@H]4CC[C@H](O)CC4)n3)c2c1] | 1-[2-(4-hydroxycyclo-hexylamino)-pyrimidin-4-yl]-1H-indazole-6-carboxylic acid methyl ester | 34 |
| 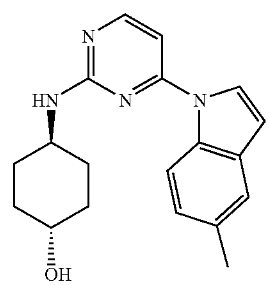 [SMILES: Cc1ccc2c(ccn2-c2ccnc(N[C@H]3CC[C@H](O)CC3)n2)c1] | 4-[4-(5-methylindol-1-yl)-pyrimidin-2-yl-amino]-cyclohexanol | 35 |
| 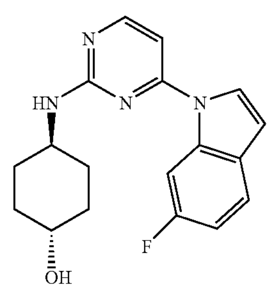 [SMILES: O[C@H]1CC[C@H](Nc2nccc(-n3ccc4ccc(F)cc43)n2)CC1] | 4-[4-(6-fluoroindol-1-yl)-pyrimidin-2-yl-amino]-cyclohexanol | 36 |
| 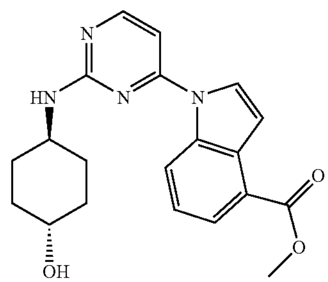 [SMILES: COC(=O)c1cccc2c1ccn2-c1ccnc(N[C@H]2CC[C@H](O)CC2)n1] | 1-[2-(4-hydroxycyclo-hexylamino)-pyrimidin-4-yl]-1H-indole-4-carboxylic acid methyl ester<br>mp = 206.7-208.3° C.<br>MS = 367 [M + H]+ | 37 |

TABLE 1-continued

Representative compounds of Formula I.

| Structure | Name | Compound No. |
|---|---|---|
| 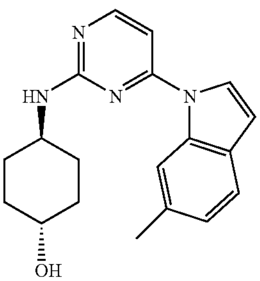 | 4-[4-(6-methylindol-1-yl)-pyrimidin-2-yl-amino]-cyclohexanol | 38 |
| 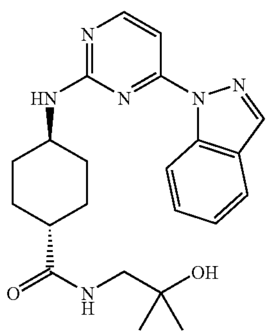 [SMILES: CC(C)(O)CNC(=O)[C@H]1CC[C@H](Nc2nccc(-n3ncc4ccccc43)n2)CC1] | 4-(4-indazol-1-yl-pyrimidin-2-ylamino)-cyclohexane carboxylic acid (2-hydroxy-2-methylpropyl)amide | 39 |
| 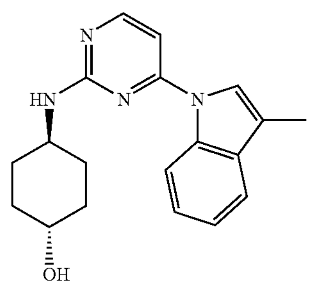 [SMILES: Cc1cn(-c2ccnc(N[C@H]3CC[C@H](O)CC3)n2)c2ccccc12] | 4-[4-(3-methylindol-1-yl)-pyrimidin-2-yl-amino]-cyclohexanol | 40 |
| 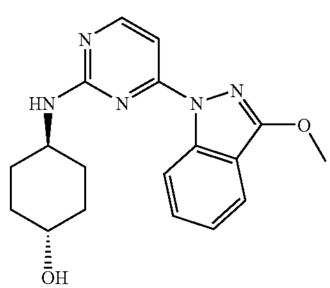 [SMILES: COc1nn(-c2ccnc(N[C@H]3CC[C@H](O)CC3)n2)c2ccccc12] | 4-[4-(3-methoxyindazol-1-yl)pyrimidin-2-yl-amino]-cyclohexanol | 41 |
| 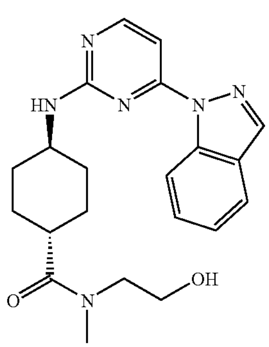 [SMILES: CN(CCO)C(=O)[C@H]1CC[C@H](Nc2nccc(-n3ncc4ccccc43)n2)CC1] | 4-(4-indazol-1-yl-pyrimidin-2-ylamino)-cyclohexane carboxylic acid (2-hydroxyethyl)-methyl-amide | 42 |

TABLE 1-continued

Representative compounds of Formula I.

| Structure | Name | Compound No. |
|---|---|---|
| 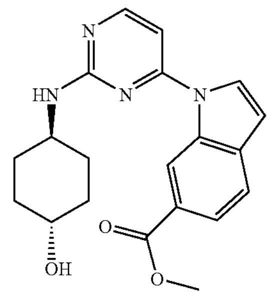 [SMILES: COC(=O)c1ccc2ccn(-c3ccnc(N[C@H]4CC[C@H](O)CC4)n3)c2c1] | 1-[2-(4-hydroxycyclo-hexylamino)-pyrimidin-2-yl]-1H-indole-6-carboxylic acid methyl ester | 43 |
| 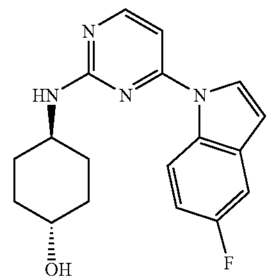 | 4-[4-(5-fluoroindol-1-yl)-pyrimidin-2-yl-amino]-cyclohexanol | 44 |
| 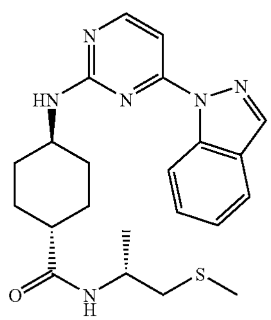 [SMILES: CSC[C@@H](C)NC(=O)[C@H]1CC[C@H](Nc2nccc(-n3ncc4ccccc43)n2)CC1] | 4-(4-indazol-1-yl-pyrimidin-2-ylamino)-cyclohexane carboxylic acid (1-methyl-2-methylsulfanyl)ethyl-amide | 45 |
| 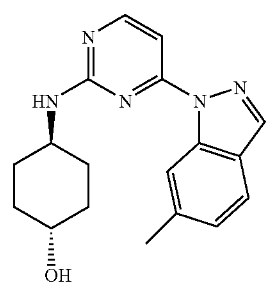 [SMILES: Cc1ccc2cnn(-c3ccnc(N[C@H]4CC[C@H](O)CC4)n3)c2c1] | 4-[4-(6-methylindazol-1-yl)-pyrimidin-2-yl-amino]-cyclohexanol | 46 |
| 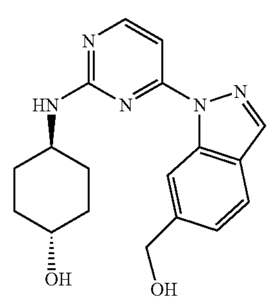 [SMILES: OCc1ccc2cnn(-c3ccnc(N[C@H]4CC[C@H](O)CC4)n3)c2c1] | 4-[4-(6-hydroxymethyl-indazol-1-yl)-pyrimidin-2-ylamino]-cyclo-hexanol | 47 |

TABLE 1-continued

Representative compounds of Formula I.

| Structure | Name | Compound No. |
|---|---|---|
| 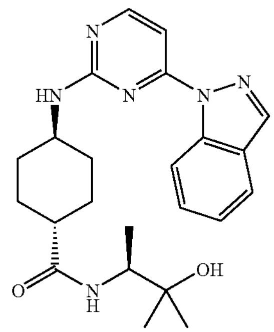 [SMILES: C[C@H](NC(=O)[C@H]1CC[C@H](Nc2nccc(-n3ncc4ccccc43)n2)CC1)C(C)(C)O] | 4-(4-indazol-1-yl-pyrimidin-2-ylamino)-cyclohexane carboxylic acid (2-hydroxy-2-methylbut-3-yl)amide | 48 |
| 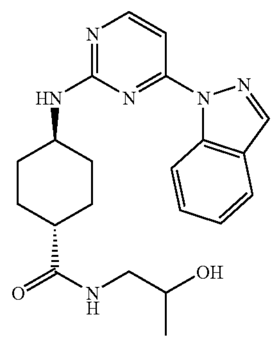 [SMILES: CC(O)CNC(=O)[C@H]1CC[C@H](Nc2nccc(-n3ncc4ccccc43)n2)CC1] | 4-(4-indazol-1-yl-pyrimidin-2-ylamino)-cyclohexane carboxylic acid (2-hydroxypropyl)-amide | 49 |
| 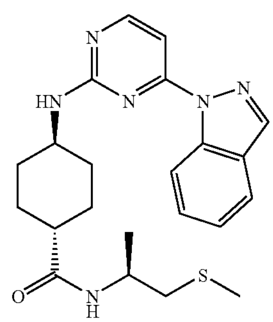 [SMILES: CSC[C@H](C)NC(=O)[C@H]1CC[C@H](Nc2nccc(-n3ncc4ccccc43)n2)CC1] | 4-(4-indazol-1-yl-pyrimidin-2-ylamino)-cyclohexane carboxylic acid (1-methylsulfanyl-prop-2-yl)amide | 50 |
| 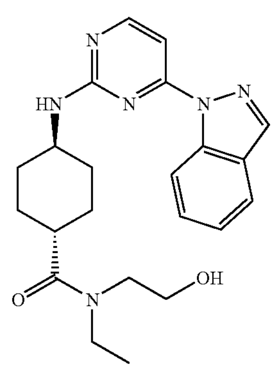 [SMILES: CCN(CCO)C(=O)[C@H]1CC[C@H](Nc2nccc(-n3ncc4ccccc43)n2)CC1] | 4-(4-indazol-1-yl-pyrimidin-2-ylamino)-cyclohexane carboxylic acid N-(2-hydroxy-ethyl)-N-ethyl-amide | 51 |

TABLE 1-continued

Representative compounds of Formula I.

| Structure | Name | Compound No. |
|---|---|---|
| | N-(4-indol-1-yl-pyrimidin-2-yl)-cyclo-hexane-1,4-diamine<br>mp = 270.1-273.3° C.<br>MS = 308 [M + H]+ | 52 |
| 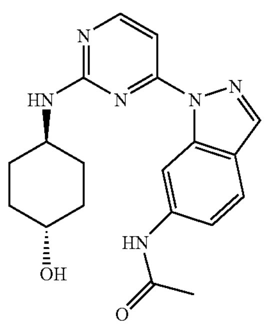 [SMILES: CC(=O)Nc1ccc2cnn(-c3ccnc(N[C@H]4CC[C@H](O)CC4)n3)c2c1] | N-(1-[2-(4-hydroxy-cyclohexylamino)-pyrimidin-4-yl]-1H-indazol-6-yl)-acetamide | 53 |
| 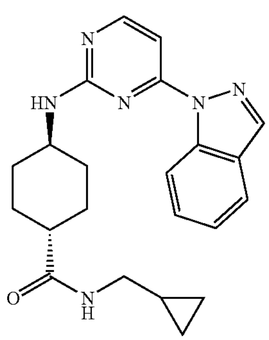 [SMILES: O=C(NCC1CC1)[C@H]1CC[C@H](Nc2nccc(-n3ncc4ccccc43)n2)CC1] | 4-(4-indazol-1-yl-pyrimidin-2-ylamino)-cyclohexane carboxylic acid cyclopropylmethyl amide | 54 |
| 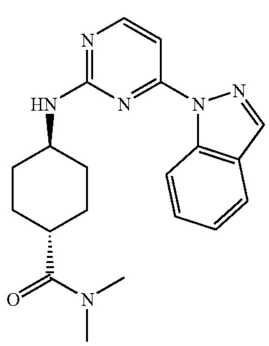 [SMILES: CN(C)C(=O)[C@H]1CC[C@H](Nc2nccc(-n3ncc4ccccc43)n2)CC1] | 4-(4-indazol-1-yl-pyrimidin-2-ylamino)-cyclohexane carboxylic acid dimethylamide | 55 |

TABLE 1-continued

Representative compounds of Formula I.

| Structure | Name | Compound No. |
|---|---|---|
| 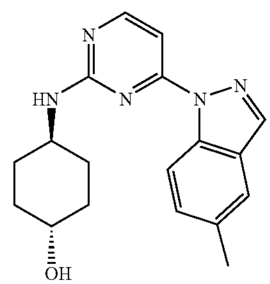 [SMILES: Cc1ccc2c(cnn2-c2ccnc(N[C@H]3CC[C@H](O)CC3)n2)c1] | 4-[4-(5-methylindazol-1-yl)-pyrimidin-2-yl-amino]-cyclohexanol | 56 |
| 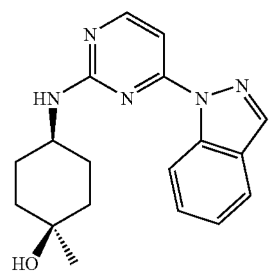 [SMILES: C[C@]1(O)CC[C@@H](Nc2nccc(-n3ncc4ccccc43)n2)CC1] | 4-(4-indazol-1-yl-pyrimidin-2-ylamino)-1-methylcyclohexanol | 57 |
| 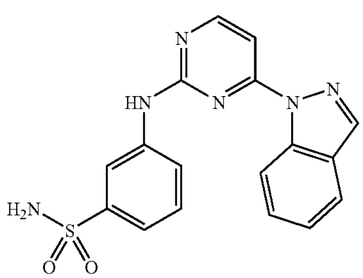 [SMILES: NS(=O)(=O)c1cccc(Nc2nccc(-n3ncc4ccccc43)n2)c1] | 3-(4-indazol-1-yl-pyrimidin-2-ylamino)-benzenesulfonamide | 58 |
| 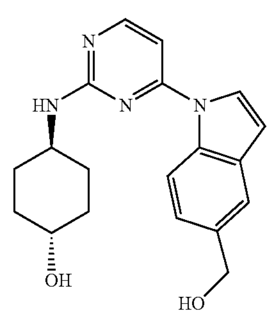 [SMILES: OCc1ccc2c(ccn2-c2ccnc(N[C@H]3CC[C@H](O)CC3)n2)c1] | 4-[4-(5-hydroxymethyl-indol-1-yl)pyrimidin-2-ylamino]-cyclohexanol | 59 |
| 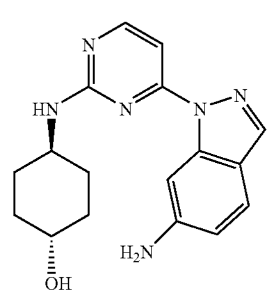 [SMILES: Nc1ccc2cnn(-c3ccnc(N[C@H]4CC[C@H](O)CC4)n3)c2c1] | 4-[4-(6-aminoindazol-1-yl)-pyrimidin-2-yl-amino]-cyclohexanol | 60 |

TABLE 1-continued

Representative compounds of Formula I.

| Structure | Name | Compound No. |
|---|---|---|
| 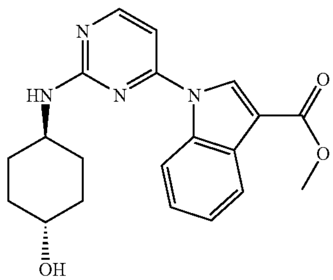 [SMILES: COC(=O)c1cn(-c2ccnc(N[C@H]3CC[C@H](O)CC3)n2)c2ccccc12] | 1-[2-(4-hydroxycyclo-hexylamino)-pyrimidin-4-yl]-1H-indole-3-carboxylic acid methyl ester | 61 |
| 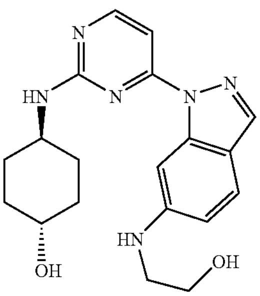 [SMILES: OCCNc1ccc2cnn(-c3ccnc(N[C@H]4CC[C@H](O)CC4)n3)c2c1] | 4-(4-[6-(2-hydroxyethyl-amino)-indazol-1-yl]-pyrimidin-2-ylamino)-cyclohexanol | 62 |
| 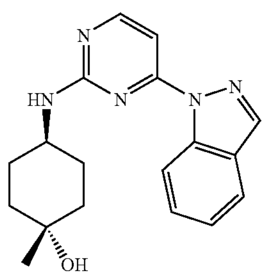 [SMILES: C[C@]1(O)CC[C@H](Nc2nccc(-n3ncc4ccccc43)n2)CC1] | 4-(4-indazol-1-yl-pyrimidin-2-ylamino)-1-methyl-cyclohexanol | 63 |
| 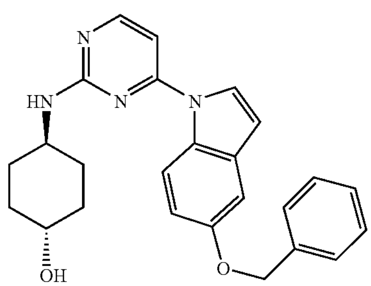 [SMILES: O[C@H]1CC[C@H](Nc2nccc(-n3ccc4cc(OCc5ccccc5)ccc43)n2)CC1] | 4-[4-(5-benzyloxyindol-1-yl)-pyrimidin-2-yl-amino]-cyclohexanol | 64 |
| 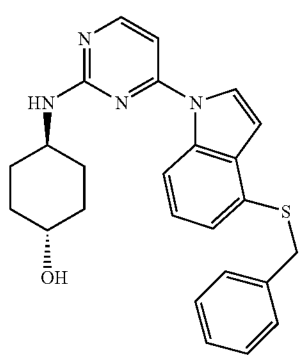 [SMILES: O[C@H]1CC[C@H](Nc2nccc(-n3ccc4c(SCc5ccccc5)cccc43)n2)CC1] | 4-[4-(4-benzylsulfanyl-indol-1-yl)-pyrimidin-2-ylamino]-cyclohexanol | 65 |

TABLE 1-continued

Representative compounds of Formula I.

| Structure | Name | Compound No. |
|---|---|---|
| | Cyclohexyl-(4-indol-1-ylpyrimidin-2-yl)amine<br>mp = 192.5-193.0° C.<br>MS = 293 [M + H]+ | 66 |
| 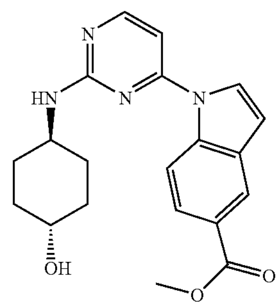 [SMILES: COC(=O)c1ccc2c(ccn2-c2ccnc(N[C@H]3CC[C@H](O)CC3)n2)c1] | 1-[2-(4-hydroxycyclo-hexylamino)-pyrimidin-4-yl]-1H-indole-5-carboxylic acid methyl ester | 67 |
| 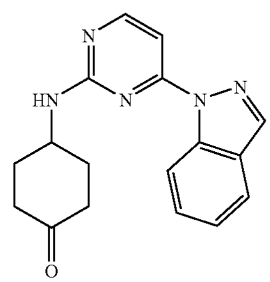 [SMILES: O=C1CCC(Nc2nccc(-n3ncc4ccccc43)n2)CC1] | 4-(4-indazol-1-yl-pyrimidin-2-ylamino)-cyclohexanone | 68 |
| 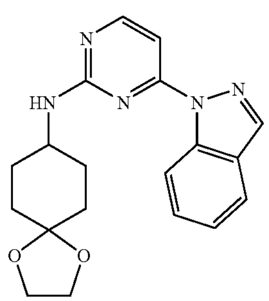 [SMILES: c1ccc2c(c1)cnn2-c1ccnc(NC2CCC3(CC2)OCCO3)n1] | (1,4-dioxaspiro[4.5]dec-8-yl)-(4-indazol-1-yl-pyrimidin-2-yl)amine | 69 |
| 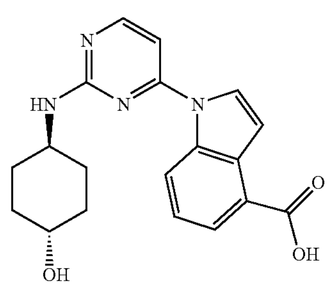 [SMILES: O=C(O)c1cccc2c1ccn2-c1ccnc(N[C@H]2CC[C@H](O)CC2)n1] | 1-[2-(4-hydroxycyclo-hexylamino)-pyrimidin-4-yl]-1H-indole-4-carboxylic acid | 70 |

TABLE 1-continued

Representative compounds of Formula I.

| Structure | Name | Compound No. |
|---|---|---|
| 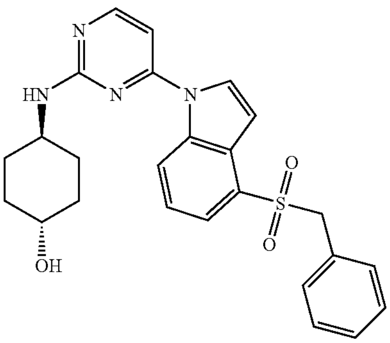 [SMILES: O=S(=O)(Cc1ccccc1)c1cccc2c1ccn2-c1ccnc(N[C@H]2CC[C@H](O)CC2)n1] | 4-[4-(4-benzylsulfonyl-indol-1-yl)pyrimidin-2-ylamino]cyclohexanol | 71 |
| 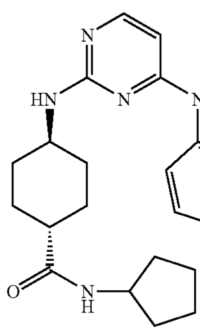 | 4-(4-indazol-1-yl-pyrimidin-2-ylamino)-cyclohexanecarboxylic acid cyclopentylamide | 7 |
| 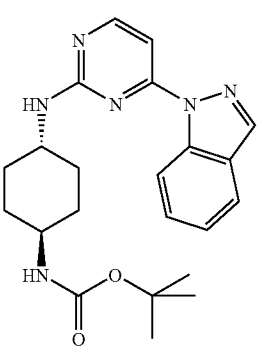 [SMILES: CC(C)(C)OC(=O)N[C@H]1CC[C@H](Nc2nccc(-n3ncc4ccccc43)n2)CC1] | [4-(4-indazol-1-yl-pyrimidin-2-ylamino)-cyclohexyl]-carbamic acid t-butyl ester | 73 |
| 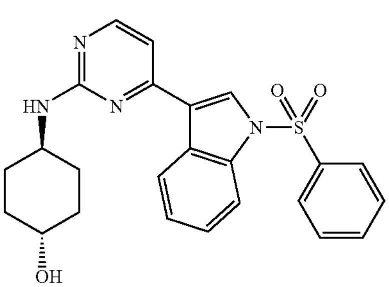 [SMILES: O=S(=O)(c1ccccc1)n1cc(-c2ccnc(N[C@H]3CC[C@H](O)CC3)n2)c2ccccc21] | 4-[4-(1-phenylsulfonyl-1H-indol-3-yl)-pyrimidin-2-ylamino]-cyclohexanol | 74 |

TABLE 1-continued

Representative compounds of Formula I.

| Structure | Name | Compound No. |
|---|---|---|
| 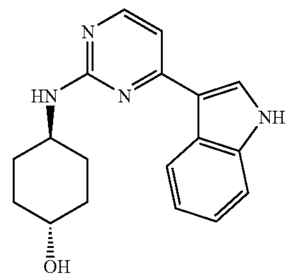 [SMILES: O[C@H]1CC[C@H](Nc2nccc(-c3c[nH]c4ccccc34)n2)CC1] | 4-[4-(1H-indol-3-yl)-pyrimidin-2-ylamino]-cyclohexanol | 75 |
| 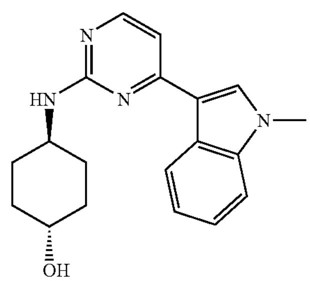 [SMILES: Cn1cc(-c2ccnc(N[C@H]3CC[C@H](O)CC3)n2)c2ccccc21] | 4-[4-(1-methyl-1H-indol-3-yl)pyrimidin-2-ylamino]-cyclohexanol | 76 |
| | 4-[4-(1-methyl-1H-indazol-3-yl)pyridimidin-2-ylamino]-cyclohexanol<br>Mp = 180-183.3° C.<br>MS = 324 [M + H]⁺ | 77 |
| 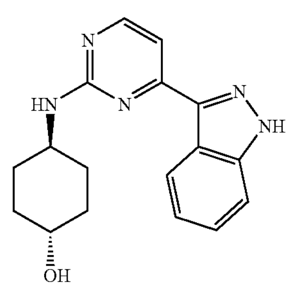 [SMILES: O[C@H]1CC[C@H](Nc2nccc(-c3n[nH]c4ccccc34)n2)CC1] | 4-[4-(1H-indazol-3-yl)-pyrimidin-2-ylamino]-cyclohexanol | 78 |
| 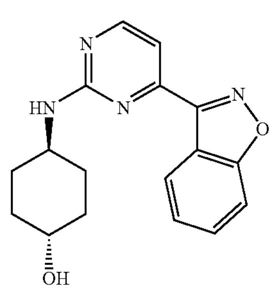 [SMILES: O[C@H]1CC[C@H](Nc2nccc(-c3noc4ccccc34)n2)CC1] | 4-(4-benzo[d]isoxazol-3-ylpyrimidin-2-ylamino)-cyclohexanol | 79 |

TABLE 1-continued

Representative compounds of Formula I.

| Structure | Name | Compound No. |
|---|---|---|
| | 4-[4-(7-methoxy-1H-indazol-3-yl)-pyrimidin-2-ylamino]-cyclohexanol<br>mp = 243.3-244.9° C.<br>MS = 341 [M + H]+ | 80 |
| | 4-[4-(7-methoxybenzo[d]isoxazol-3-yl)-pyrimidin-2-ylamino]-cyclohexanol | 81 |
| | 4-[4-(7-methyl-1H-indazol-3-yl)-pyrimidin-2-ylamino]-cyclohexanol | 82 |
| | 4-[4-(5-fluorobenzo[d]isoxazol-3-yl)-pyrimidin-2-ylamino]-cyclohexanol<br>mp = 172-173.9° C.<br>MS = 329 [M + H]+ | 83 |
| | 4-(4-pyrazolo[1,5-b]pyridazin-3-ylpyrimidin-2-ylamino)-cyclohexanol<br>mp = 214.9-215.6° C.<br>MS = 311 [M + H]+ | 84 |

TABLE 1-continued

Representative compounds of Formula I.

| Structure | Name | Compound No. |
|---|---|---|
| | 4-(4-[1,2,4]triazole[4,3-a]pyridine-3-yl-pyrimidin-2-ylamino)-cyclohexanol<br>mp = 253.4-255.7° C.<br>MS = 311 [M + H]+ | 85 |
| | 4-[4-(4-methoxyindazol-1-yl)-pyrimidin-2-yl-amino]-cyclohexanol | 86 |
| | (1-[2-(4-hydroxycyclo-hexylamino)-pyrimidin-4-yl]-1H-indazol-4-yl-oxy)acetonitrile | 87 |
| | N-(1-[2-(4-hydroxy-cyclohexylamino)-pyrimidin-4-yl]-1H-indol-4-yl)-isobutyr-amide<br>Mp 211.8-212.6° C.<br>MS(M + 1) = 394 | 88 |
| | 4-{4-[6-(2-hydroxy-ethoxy)-indazol-1-yl]-pyrimidin-2-ylamino}-cyclohexanol<br>m.p. 216.5-218.5° C.<br>MS(M + 1) = 370 | 89 |

TABLE 1-continued

Representative compounds of Formula I.

| Structure | Name | Compound No. |
|---|---|---|
| 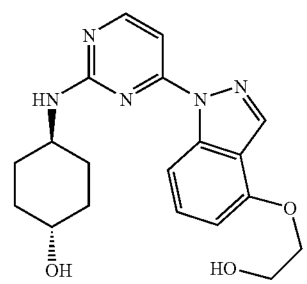 [SMILES: OCCOc1cccc2c1cnn2-c1ccnc(N[C@H]2CC[C@H](O)CC2)n1] | 4-{4-[4-(2-hydroxy-ethoxy)-indazol-1-yl]-pyrimidin-2-ylamino}-cyclohexanol<br>mp 208.2-210.2° C.<br>MS(M + 1) = 370 | 90 |
| 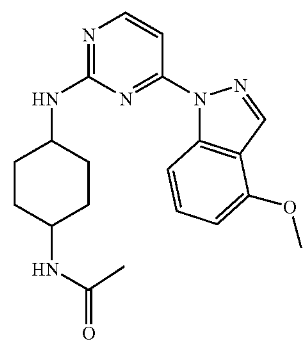 [SMILES: COc1cccc2c1cnn2-c1ccnc(NC2CCC(NC(C)=O)CC2)n1] | N-{4-[4-(4-methoxy-indazol-1-yl]-pyrimidin-2-ylamino}-cyclohexane}-acetamide<br>Mp 256.9-259.9° C.<br>MS(M + 1) = 381 | 91 |
| 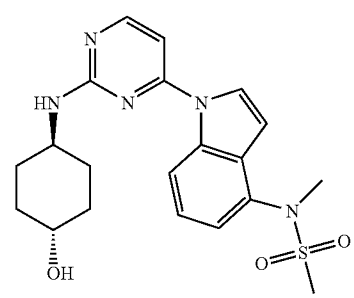 [SMILES: CN(c1cccc2c1ccn2-c1ccnc(N[C@H]2CC[C@H](O)CC2)n1)S(C)(=O)=O] | N-{1-[2-(4-hydroxy-cyclohexylamino)-pyrimidin-4-yl]-1H-indol-4-yl}-N-methyl-methanesulfonamide<br>Mp 235.8-236.2° C.<br>MS(M + 1) = 416 | 92 |
| 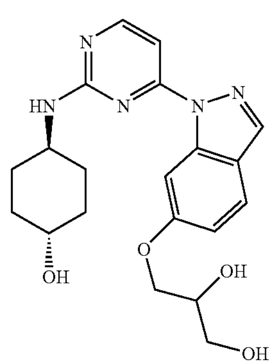 [SMILES: OCC(O)COc1ccc2cnn(-c3ccnc(N[C@H]4CC[C@H](O)CC4)n3)c2c1] | 3-{1-[2-(4-hydroxy-cyclohexylamino)-pyrimidin-4-yl]-1H-indazol-6-yloxy}-propane-1,2-diol<br>Mp 223.8-224.7° C.<br>MS(M + 1) = 400 | 93 |

TABLE 1-continued

Representative compounds of Formula I.

| Structure | Name | Compound No. |
|---|---|---|
| 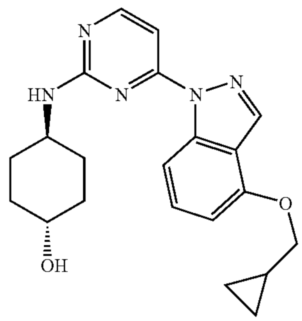 [SMILES: O[C@H]1CC[C@H](Nc2nccc(-n3ncc4c(OCC5CC5)cccc43)n2)CC1] | 4-[4-(4-cyclopropyl-methoxy-indazol-1-yl)-pyrimidin-2-ylamino]-cyclohexanol<br>Mp >300° C.<br>MS(M + 1) = 380 | 94 |
| 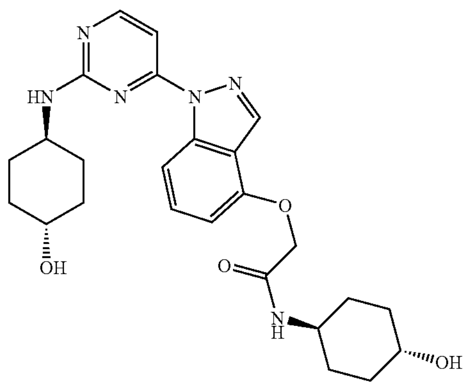 [SMILES: O=C(COc1cccc2c1cnn2-c1ccnc(N[C@H]2CC[C@H](O)CC2)n1)N[C@H]1CC[C@H](O)CC1] | N-(4-hydroxy-cyclo-hexyl)-2-{1-[2-(4-hydroxy-cyclohexyl-amino)-pyrimidin-4-yl]-1H-indazol-4-yloxy}-acetamide<br>Mp 220.0-222.3° C.<br>MS(M + 1) = 481 | 95 |
| 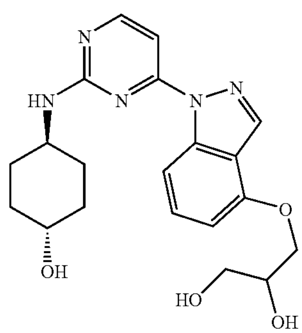 [SMILES: OCC(O)COc1cccc2c1cnn2-c1ccnc(N[C@H]2CC[C@H](O)CC2)n1] | 3-{1-[2-(4-hydroxy-cyclohexylamino)-pyrimidin-4-yl]-1H-indazol-4-yloxy}-propane-1,2-diol<br>Mp 206.1-207.5° C.<br>MS(M + 1) = 400 | 96 |
| 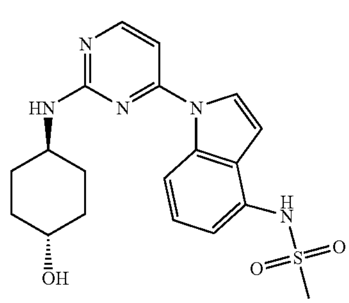 [SMILES: CS(=O)(=O)Nc1cccc2c1ccn2-c1ccnc(N[C@H]2CC[C@H](O)CC2)n1] | N-{1-[2-(4-hydroxy-cyclohexylamino)-pyrimidin-4-yl]-1H-indol-4-yl}-N-methane-sulfonamide<br>Mp 240.2-240.8° C.<br>MS(M + 1) = 402 | 97 |

TABLE 1-continued

Representative compounds of Formula I.

| Structure | Name | Compound No. |
|---|---|---|
| | 4-{4-[4-(2,2-dimethyl-[1,3]dioxolan-4-ylmethoxy)-indazol-1-yl]-pyrimidin-2-ylamino}-cyclohexanol<br>Mp 189.2-190.0° C.<br>MS(M + 1) = 440 | 98 |
| | 4-[4-(4-ethylindazol-1-yl)-pyrimidin-2-yl-amino]-cyclohexanol<br>Mp. 170.2-174.4° C.<br>MS(M + 1) = 338 | 99 |
| | Methyl-carbamic acid 1-[2-(4-hydroxy-cyclohexylamino)-pyrimidin-4-yl]-1H-indol-4-ylmethyl ester<br>Mp 132.0-133.0° C.<br>MS(M + 1) = 396 | 100 |
| | {1-[2-(4-hydroxy-cyclohexylamino)-pyrimidin-4-yl]-1H-indol-4-yl}-acetonitrile<br>mp 207-209° C.<br>MS(M + 1) = 348 | 101 |

TABLE 1-continued

Representative compounds of Formula I.

| Structure | Name | Compound No. |
|---|---|---|
| | 4-[4-(4-methoxymethyl-indol-1-yl)-pyrimidin-2-ylamino]-cyclohexanol<br>Mp 134.8-137.3° C.<br>MS(M + 1) = 353 | 102 |
| | 4-{4-[4-(pyridine-2-yl-methoxy)-indazol-1-yl]-pyrimidin-2-ylamino}-cyclohexanol<br>Mp 202.5-203.6° C.<br>MS(M + 1) = 417 | 103 |
| | 4-{4-[4-(3-methane-sulfonyl-propoxy)-indazol-1-yl]-pyrimidin-2ylamino}-cyclohexanol<br>Mp 223.0-223.9° C.<br>MS(M + 1) = 446 | 104 |
| | 4-[4-(4-methoxyindazol-1-yl)-pyrimidin-2-ylamino]-cyclo-hexanecarboxylic acid dimethylamide<br>Mp 278.8-280.0° C.<br>MS(M + 1) = 395 | 105 |

TABLE 1-continued

Representative compounds of Formula I.

| Structure | Name | Compound No. |
|---|---|---|
| 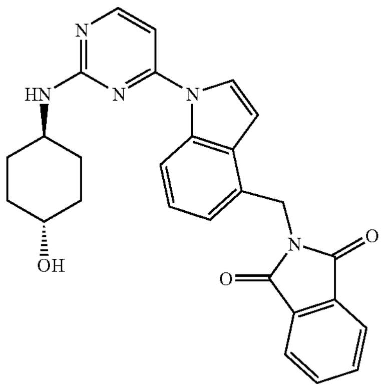 [SMILES: O=C1c2ccccc2C(=O)N1Cc1cccc2c1ccn2-c1ccnc(N[C@H]2CC[C@H](O)CC2)n1] | 2-{1-[2-(4-hydroxy-cyclohexylamino)-pyrimidin-4-yl]-1H-indol-4-ylmethyl}-isoindole-1,3-dione<br>Mp 251.7-253.0° C.<br>MS (M + H) = 468 | 106 |
| 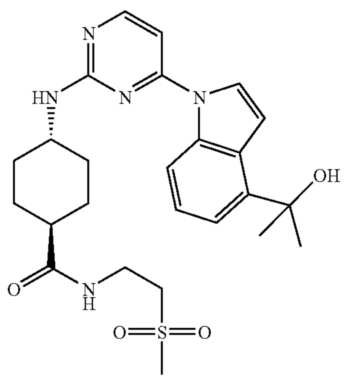 | 4-{4-[4-(1-hydroxy-1-methylethyl)-indol-1-yl]-pyrimidin-2-yl-amino}-cyclohexane-carboxylic acid (2-methanesulfonyl-ethyl)-amide<br>Mp 208.0-210.0° C.<br>MS (M + H) = 500 | 107 |
| 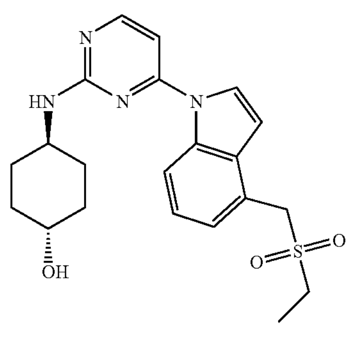 [SMILES: CCS(=O)(=O)Cc1cccc2c1ccn2-c1ccnc(N[C@H]2CC[C@H](O)CC2)n1] | 4-[4-(4-ethanesulfonyl-methyl-indol-1-yl)-pyrimidin-2-ylamino]-cyclohexanol<br>Mp 193.3-194.6° C.<br>MS (M + H) = 415 | 108 |
| 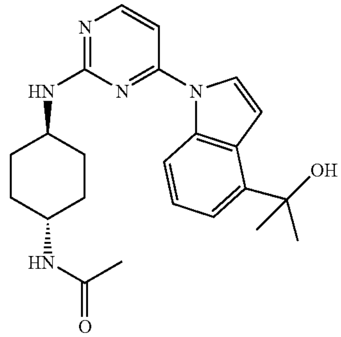 [SMILES: CC(=O)N[C@H]1CC[C@H](Nc2nccc(-n3ccc4c(C(C)(C)O)cccc43)n2)CC1] | N-(4-{4-[4-(1-hydroxy-1-methylethyl)-indol-1-yl]-pyrimidin-2-yl-amino}-cyclohexyl)-acetamide<br>Mp 172.0-173.6° C.<br>MS (M + H) = 408 | 109 |

TABLE 1-continued

Representative compounds of Formula I.

| Structure | Name | Compound No. |
|---|---|---|
| 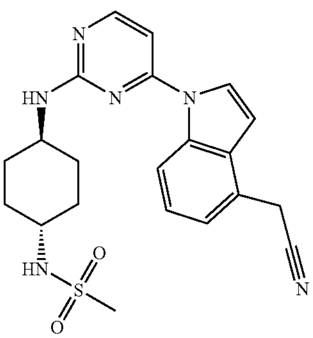 [SMILES: CS(=O)(=O)N[C@H]1CC[C@H](Nc2nccc(-n3ccc4c(CC#N)cccc43)n2)CC1] | N-{4-[4-(4-cyano-methyl-indol-1-yl)-pyrimidin-2ylamino]-cyclohexyl}-methane-sulfonamide<br>Mp 235.0-235.5° C.<br>MS (M + H) = 425 | 110 |
| 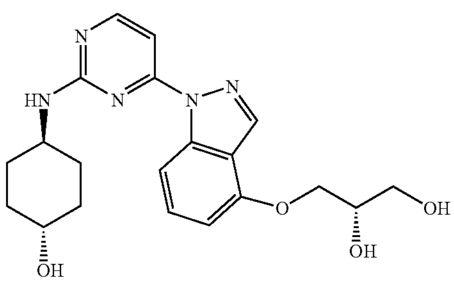 [SMILES: OC[C@H](O)COc1cccc2c1cnn2-c1ccnc(N[C@H]2CC[C@H](O)CC2)n1] | 3-{1-[2-(4-hydroxy-cyclohexylamino)-pyrimidin-4-yl]-1H-indazol-4-yloxy}-propane-1,2-diol<br>Mp 223.1-223.9° C.<br>MS (M + H) = 400 | 111 |
| 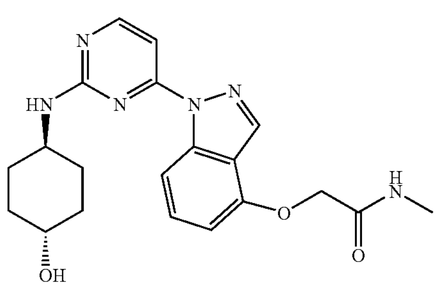 [SMILES: CNC(=O)COc1cccc2c1cnn2-c1ccnc(N[C@H]2CC[C@H](O)CC2)n1] | 2-{1-[2-(4-hydroxy-cyclohexylamino)-pyrimidin-4-yl]-1H-indazol-4-yloxy}-N-methyl-acetamide<br>Mp 226.0-227.0° C.<br>MS (M + H) = 397 | 112 |
| 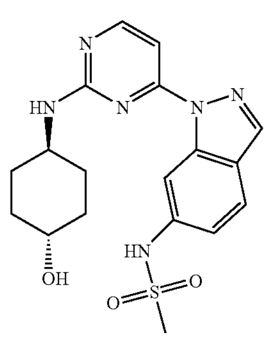 [SMILES: CS(=O)(=O)Nc1ccc2cnn(-c3ccnc(N[C@H]4CC[C@H](O)CC4)n3)c2c1] | N-{1-[2-(4-hydroxy-cyclohexyalamino)-pyrimidin-4-yl]-1H-indazol-6-yl}methane-sulfonamide<br>MS (M + H) = 403 | 113 |

TABLE 1-continued

Representative compounds of Formula I.

| Structure | Name | Compound No. |
|---|---|---|
| 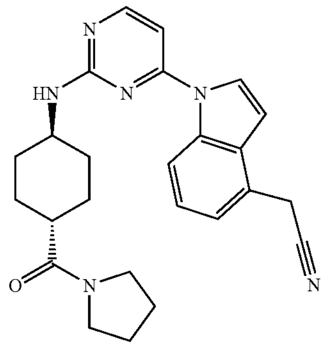 [SMILES: N#CCc1cccc2c1ccn2-c1ccnc(N[C@H]2CC[C@H](C(=O)N3CCCC3)CC2)n1] | (1-{2-[4-(pyrrolidino-1-carbonyl)-cyclohexyl-amino]-pyrimidin-4-yl}-1H-indol-4-yl)-acetonitrile<br>Mp 136.0-137.5° C.<br>MS (M + H) = 429 | 114 |
| 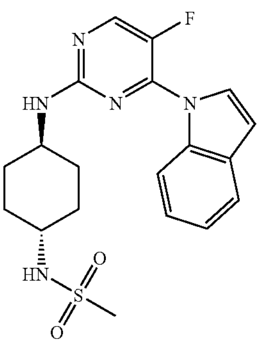 [SMILES: CS(=O)(=O)N[C@H]1CC[C@H](Nc2ncc(F)c(-n3ccc4ccccc43)n2)CC1] | N-[4-(5-fluoro-4-indol-1-yl-pyrimidin-2-yl-amino)-cyclohexyl]-methanesulfonamide<br>Mp 270.0-270.5° C.<br>MS (M + H) = 404 | 115 |
| 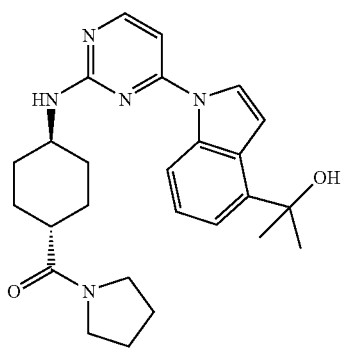 [SMILES: CC(C)(O)c1cccc2c1ccn2-c1ccnc(N[C@H]2CC[C@H](C(=O)N3CCCC3)CC2)n1] | (4-{4-[4-(1-hydroxy-1-methylethyl)-indol-1-yl]-pyrimidin-2-yl-amino}-cyclohexyl)-pyrrolidin-1-yl-methanone<br>Mp 207.8-209.8° C.<br>MS (M + H) = 448 | 116 |
| 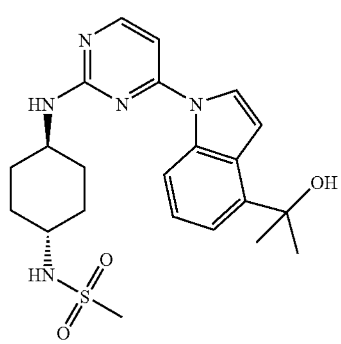 [SMILES: CC(C)(O)c1cccc2c1ccn2-c1ccnc(N[C@H]2CC[C@H](NS(C)(=O)=O)CC2)n1] | N-(4-{4-[4-(1-hydroxy-1-methylethyl)-indol-1-yl]-pyrimidin-2-yl-amino}-cyclohexyl)-methanesulfonamide<br>Mp 247.0-249.6° C.<br>MS (M + H) = 444 | 117 |

TABLE 1-continued

Representative compounds of Formula I.

| Structure | Name | Compound No. |
|---|---|---|
| 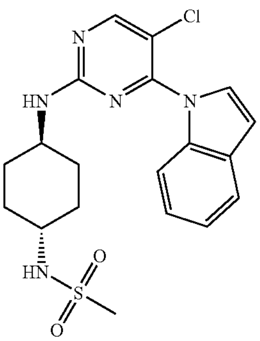 [SMILES: CS(=O)(=O)N[C@H]1CC[C@H](Nc2ncc(Cl)c(-n3ccc4ccccc43)n2)CC1] | N-[4-(5-chloro-4-indol-1-ylpyrimidin-2-yl-amino)-cyclohexyl]-methanesulfonamide<br>Mp 203.8-204.9° C.<br>MS (M + H) = 420 | 118 |
| 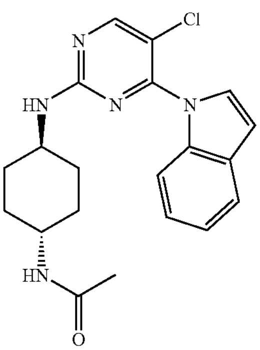 [SMILES: CC(=O)N[C@H]1CC[C@H](Nc2ncc(Cl)c(-n3ccc4ccccc43)n2)CC1] | N-[4-(5-chloro-4-indol-1-ylpyrimidin-2-yl-amino)-cyclohexyl]-acetamide<br>Mp 263.2-263.8° C.<br>MS (M + H) = 384 | 119 |
| 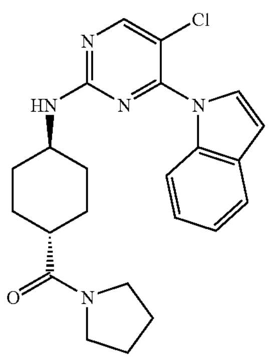 [SMILES: O=C([C@H]1CC[C@H](Nc2ncc(Cl)c(-n3ccc4ccccc43)n2)CC1)N1CCCC1] | [4-(5-chloro-4-indol-1-ylpyrimidin-2-ylamino)-cyclohexyl]-pyrrolidin-1-ylmethanone<br>Mp 182.0-182.5° C.<br>MS (M + H) = 424 | 120 |
| 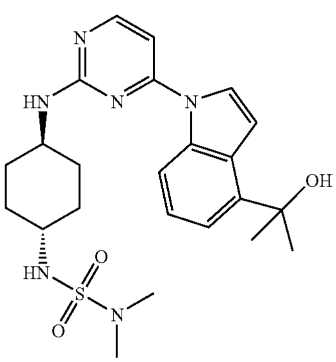 [SMILES: CN(C)S(=O)(=O)N[C@H]1CC[C@H](Nc2nccc(-n3ccc4c(C(C)(C)O)cccc43)n2)CC1] | Dimethyl sulfonamido (4-{4-[4-(1-hydroxy1-methylethyl)-indol-1-yl]-pyrimidin-2-ylamino}-cyclohexyl)-amine | 121 |

TABLE 1-continued

Representative compounds of Formula I.

| Structure | Name | Compound No. |
|---|---|---|
| 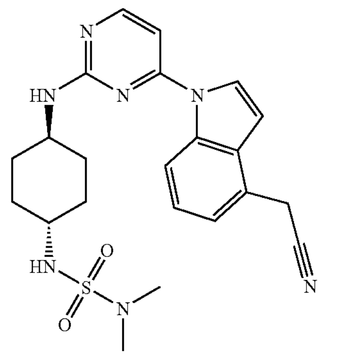 [SMILES: CN(C)S(=O)(=O)N[C@H]1CC[C@H](Nc2nccc(-n3ccc4c(CC#N)cccc43)n2)CC1] | Dimethyl sulfonamido {4-[4-(4-cyanomethyl-indol-1-yl)-pyrimidin-2-ylamino]-cyclohexyl}-amine<br>Mp 208.7-209.5° C.<br>MS (M + H) = 454 | 122 |
| 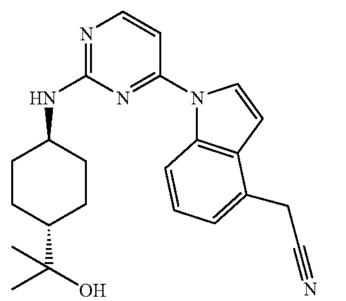 [SMILES: CC(C)(O)[C@H]1CC[C@H](Nc2nccc(-n3ccc4c(CC#N)cccc43)n2)CC1] | (1-{2-[4-(1-hydroxy-1-methylethyl)-cyclo-hexylamino]-pyrimidin-4-yl}-1H-indol-4-yl)-acetonitrile<br>Mp 188.0-191.7° C.<br>MS (M + H) = 390 | 123 |
| 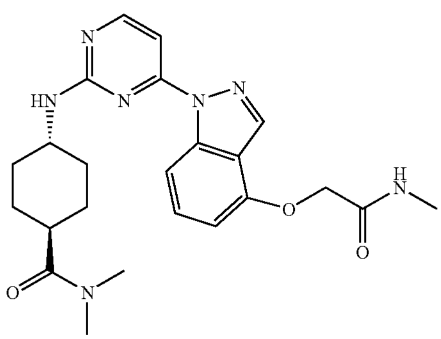 [SMILES: CNC(=O)COc1cccc2c1cnn2-c1ccnc(N[C@H]2CC[C@H](C(=O)N(C)C)CC2)n1] | 4-[4-(4-methylcarba-moylmethoxy-indazol-1-yl)-pyrimidin-2-yl-amino]-cyclohexane-carboxylic acid dimethylamide<br>Mp 183.0-185.0° C.<br>MS (M + H) = 452 | 124 |
| 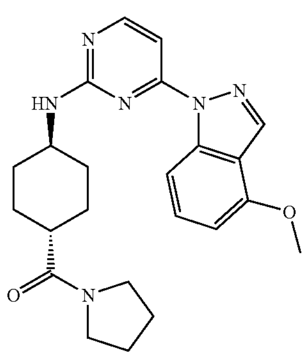 [SMILES: COc1cccc2c1cnn2-c1ccnc(N[C@H]2CC[C@H](C(=O)N3CCCC3)CC2)n1] | {4-[4-(4-methoxy-indazol-1-yl)-pyrimidin-2-ylamino]-cyclohexyl}-pyrrolidin-1-ylmethanone<br>Mp 246.5-247.0° C.<br>MS (M + H) = 421 | 125 |

TABLE 1-continued

Representative compounds of Formula I.

| Structure | Name | Compound No. |
|---|---|---|
|  | N-{4-[4-(4-methoxy-indazol-1-yl)-pyrimidin-2-ylamino]-cyclohexyl}-methanesulfonamide<br>Mp 291.5-292.5° C.<br>MS (M + H) = 417 | 126 |
|  | (4-{4-[4-(2,2-dimethyl-[1,3]dioxolan-4-yl-methoxy)-indazol-1-yl]-pyrimidin-2-ylamino}-cyclohexyl)-pyrrolidin-1-ylmethanone<br>Mp 196.0-198.0° C.<br>MS (M + H) = 521 | 127 |
|  | N-(4-{4-[4-(2,2-dimethyl[1,3]dioxolan-4-ylmethoxy)-indazol-1-yl]-pyrimidin-2-yl-amino}-cyclohexyl)-methanesulfonamide<br>Mp 247.0-247.8° C.<br>MS (M + H) = 517 | 128 |
|  | N-{4-[4-(4-bromo-indol-1-yl)-pyrimidin-2-ylamino]-cyclohexyl}-methanesulfonamide<br>Mp 198.5-199.3° C.<br>MS (M + H) = 387 | 129 |

TABLE 1-continued

Representative compounds of Formula I.

| Structure | Name | Compound No. |
|---|---|---|
| 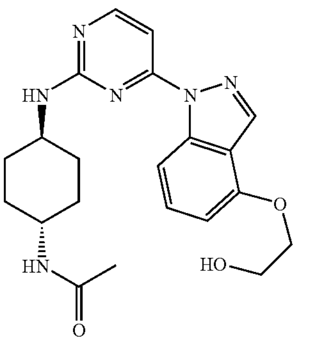 [SMILES: CC(=O)N[C@H]1CC[C@H](Nc2nccc(-n3ncc4c(OCCO)cccc43)n2)CC1] | N-(4-{4-[4-(2-hydroxy-ethoxy)-indazol-1-yl]-pyrimidin-2-ylamino}-cyclohexyl)-acetamide<br>Mp 242.7-245.5° C.<br>MS (M + H) = 411 | 130 |
| 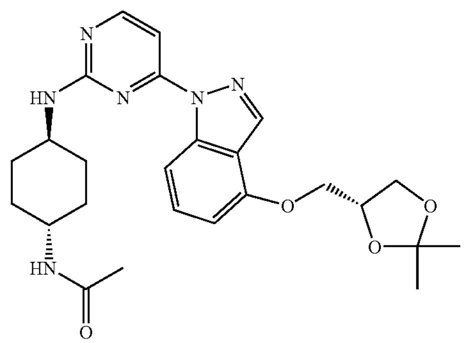 [SMILES: CC(=O)N[C@H]1CC[C@H](Nc2nccc(-n3ncc4c(OC[C@@H]5COC(C)(C)O5)cccc43)n2)CC1] | N-(4-{4-[4-(2,2-di-methyl[1,3]dioxolan-4-ylmethoxy)-indazol-1-yl]-pyrimidin-2-yl-amino}-cyclohexyl)-acetamide<br>Mp 214.5-215.5° C.<br>MS (M + H) = 481 | 131 |
| 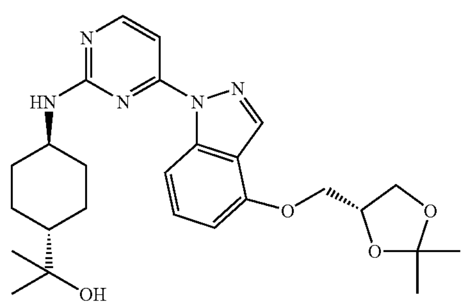 [SMILES: CC1(C)OC[C@@H](COc2cccc3c2cnn3-c2ccnc(N[C@H]3CC[C@H](C(C)(C)O)CC3)n2)O1] | 2-(4-{4-[4-(2,2-di-methyl[1,3]dioxolan-4-ylmethoxy)-indazol-1-yl]-pyrimidin-2-yl-amino}-cyclohexyl)-propan-2-ol<br>Mp 178.5-180.0° C.<br>MS (M + H) = 482 | 132 |
| 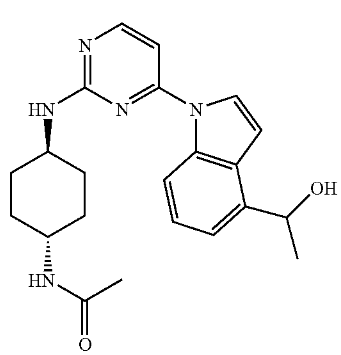 [SMILES: CC(=O)N[C@H]1CC[C@H](Nc2nccc(-n3ccc4c(C(C)O)cccc43)n2)CC1] | N-(4-{4-[4-(1-hydroxy-ethyl)-indol-1-yl]-pyrimidin-2-ylamino}-cyclohexyl)-acetamide<br>MS (M + H) = 394 | 133 |

TABLE 1-continued

Representative compounds of Formula I.

| Structure | Name | Compound No. |
|---|---|---|
| | N-{4-[4-(4-fluoro-indol-1-yl)-pyrimidin-2-ylamino]-cyclohexyl}-methane sulfonamide<br>Mp 248.7-249.4° C.<br>MS (M + H) = 404 | 134 |
| | N-(4-{4-[4-(1-hydroxy-ethyl)-indol-1-yl]-pyrimidin-2-ylamino}-cyclohexyl)-methane-sulfonamide<br>Mp 244.5-245.3° C.<br>MS (M + H) = 430 | 135 |
| | Dimethyl sulfonamide [4-(4-indazol-1-yl)-pyrimidin-2-ylamino]-cyclohexyl amine<br>Mp 238.5-239.7° C.<br>MS (M + H) = 416 | 136 |
| | N-(N',N'-dimethyl sulfonamido) N-{4-[4-(1-hydroxyethyl)-indol-1-yl-pyrimidin-2-yl-amino]-cyclohexyl} amine<br>Mp >300° C.<br>MS (M + H) = 459 | 137 |

TABLE 1-continued

Representative compounds of Formula I.

| Structure | Name | Compound No. |
|---|---|---|
| 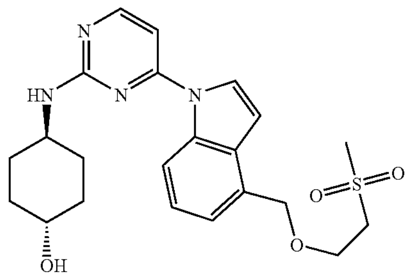 [SMILES: CS(=O)(=O)CCOCc1cccc2c1ccn2-c1ccnc(N[C@H]2CC[C@H](O)CC2)n1] | 4-{4-[4-(2-methane-sulfonyl-ethoxymethyl)-indol-1-yl]-pyrimidin-2-ylamino}-cyclohexanol<br>Mp 119.5-121.0° C.<br>MS (M + H) = 445 | 138 |
| 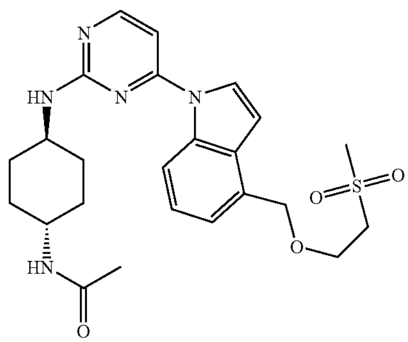 [SMILES: CC(=O)N[C@H]1CC[C@H](Nc2nccc(-n3ccc4c(COCCS(C)(=O)=O)cccc43)n2)CC1] | N-(4-{4-[4-(2-methane-sulfonyl-ethoxymethyl)-indol-1-yl]-pyrimidin-2-ylamino}-cyclohexyl)-acetamide<br>Mp 208.5-209.7° C.<br>MS (M + H) = 486 | 139 |
| 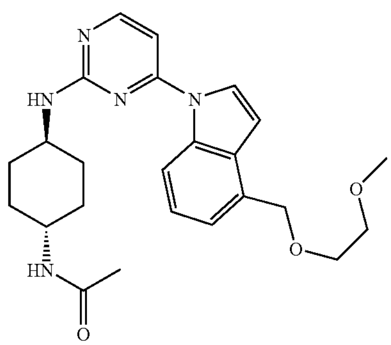 [SMILES: COCCOCc1cccc2c1ccn2-c1ccnc(N[C@H]2CC[C@H](NC(C)=O)CC2)n1] | N-(4-{4-[4-(2-methoxy-ethoxymethyl)-indol-1-yl]-pyrimidin-2-ylamino}-cyclohexyl)-acetamide<br>Mp 177.0-177.8° C.<br>MS (M + H) = 438 | 140 |
| 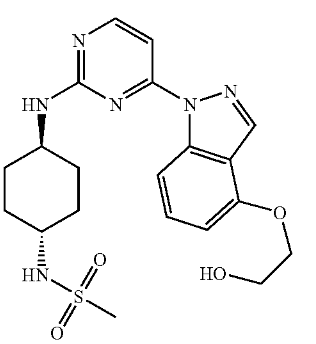 [SMILES: CS(=O)(=O)N[C@H]1CC[C@H](Nc2nccc(-n3ncc4c(OCCO)cccc43)n2)CC1] | N-(4-{4-[4-(2-hydroxy-ethoxy)-indazol-1-yl]-pyrimidin-2-ylamino}-cyclohexyl)-methane-sulfonamide<br>Mp 268.1-269.1° C.<br>MS (M + H) = 447 | 141 |

TABLE 1-continued

Representative compounds of Formula I.

| Structure | Name | Compound No. |
|---|---|---|
| 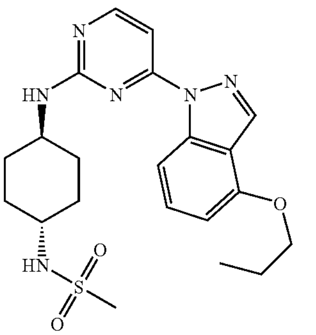 [SMILES: CCCOc1cccc2c1cnn2-c1ccnc(N[C@H]2CC[C@H](NS(C)(=O)=O)CC2)n1] | N-{4-[4-(4-propoxy-indazol-1-yl)-pyrimidin-2-ylamino]-cyclohexyl}-methanesulfonamide<br>Mp 253.0-254.0° C.<br>MS (M + H) = 445 | 142 |
| 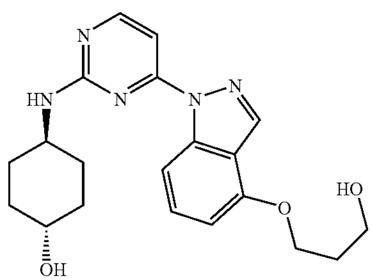 [SMILES: OCCCOc1cccc2c1cnn2-c1ccnc(N[C@H]2CC[C@H](O)CC2)n1] | 4-{4-[4-(3-hydroxy-propoxy)-indazol-1-yl]-pyrimidin-2-ylamino}-cyclohexanol<br>Mp 206.2-208.0° C.<br>MS (M + H) = 384 | 143 |
| 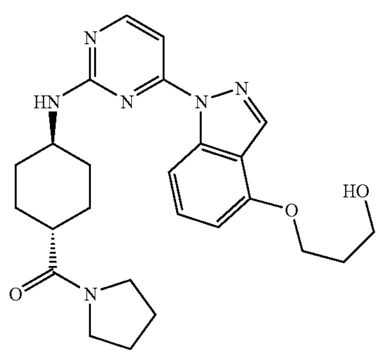 [SMILES: O=C([C@H]1CC[C@H](Nc2nccc(-n3ncc4c(OCCCO)cccc43)n2)CC1)N1CCCC1] | (4-{4-[4-(3-hydroxy-propoxy)-indazol-1-yl]-pyrimidin-2-ylamino}-cyclohexyl)-pyrrolidin-1-ylmethanone<br>Mp 187.5-188.5° C.<br>MS (M + H) = 465 | 144 |
| 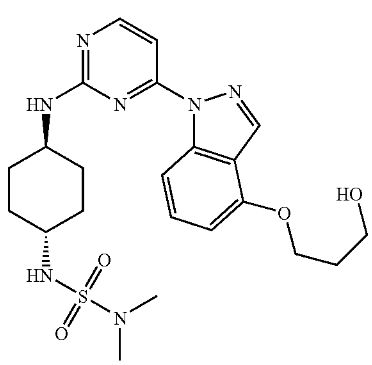 [SMILES: CN(C)S(=O)(=O)N[C@H]1CC[C@H](Nc2nccc(-n3ncc4c(OCCCO)cccc43)n2)CC1] | N-(N',N'-dimethyl sulfonamido) N-(4-{4-[4-(3-hydroxy-propoxy)-indazol-1-yl]-pyrimidin-2-ylamino}-cyclohexyl) amine<br>Mp 248.0-250.0° C.<br>MS (M + H) = 490 | 145 |

TABLE 1-continued

Representative compounds of Formula I.

| Structure | Name | Compound No. |
|---|---|---|
| | 2-(4-{4-[4-(2-hydroxy-ethoxymethyl)-indazol-1-yl]-pyrimidin-2-yl-amino}-cyclohexyl)-propan-2-ol<br>Mp 224.0-225.0° C.<br>MS (M + H) = 412 | 146 |
| | 4-[4-(4-propoxy-indazol-1-yl)-pyrimidin-2-ylamino]-cyclohexanol<br>Mp 208.5-209.5° C.<br>MS (M + H) = 368 | 147 |
| | N-(4-{4-[4-(3-hydroxy-propoxymethyl)-indazol-1-yl]-pyrimidin-2-yl-amino}cyclohexyl)-methanesulfonamide<br>Mp 257.5-258.5° C.<br>MS (M + H) = 461 | 148 |
| | N-[4-(4-fluoro-indol-1-yl)-pyrimidin-2-yl]-cyclohexane-1,4-diamine hydrochloride<br>Mp >300° C.<br>MS (M + H) = 326 | 149 |
| | 4-{4-[4-(pyridine-2-yl-methoxy)-indazol-1-yl]-pyrimidin-2-ylamino}-cyclohexanecarboxylic acid dimethylamide<br>Mp 217.3-219.0° C.<br>MS (M + H) = 472 | 150 |

TABLE 1-continued

Representative compounds of Formula I.

| Structure | Name | Compound No. |
|---|---|---|
| 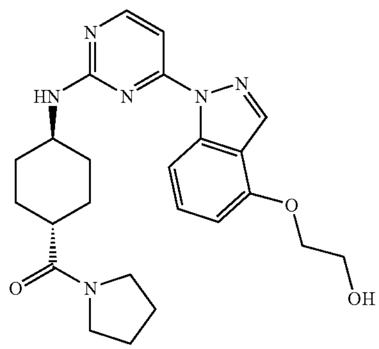 [SMILES: O=C([C@H]1CC[C@H](Nc2nccc(-n3ncc4c(OCCO)cccc43)n2)CC1)N1CCCC1] | (4-{4-[4-(2-hydroxy-ethoxy)-indazol-1-yl]-pyrimidin-2-ylamino}-cyclohexyl)-pyrrolidin-1-ylmethanone<br>Mp 164.0-166.0° C.<br>MS (M + H) = 451 | 151 |
| 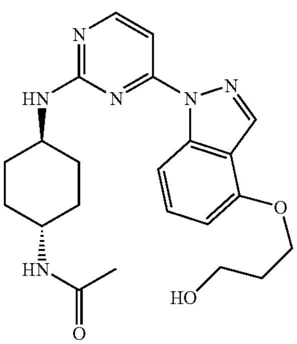 [SMILES: CC(=O)N[C@H]1CC[C@H](Nc2nccc(-n3ncc4c(OCCCO)cccc43)n2)CC1] | N-(4-{4-[4-(3-hydroxy-propoxy)-indazol-1-yl]-pyrimidin-2ylamino}-cyclohexyl)-acetamide<br>Mp 226.0-228.0° C.<br>MS (M + H) = 425 | 152 |
| 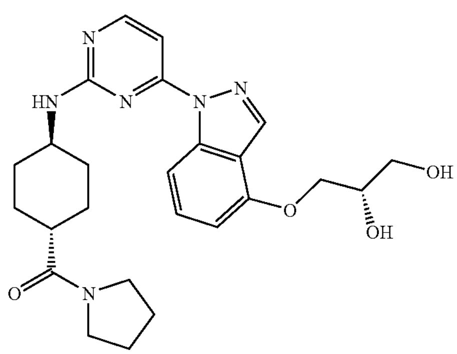 [SMILES: O=C([C@H]1CC[C@H](Nc2nccc(-n3ncc4c(OC[C@@H](O)CO)cccc43)n2)CC1)N1CCCC1] | (4-{4-[4-(2,3-dihydroxy-propoxy)-indazol-1-yl]-pyrimidin-2ylamino}-cyclohexyl)-pyrrolidin-1-ylmethanone<br>Mp 166.0-167.0° C.<br>MS (M + H) = 481 | 153 |
| 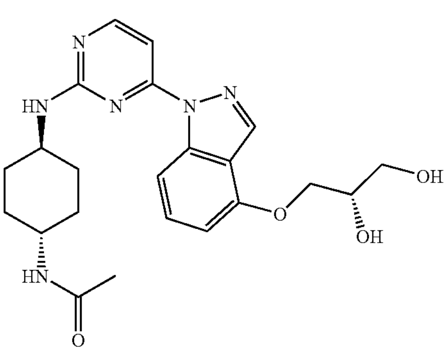 [SMILES: CC(=O)N[C@H]1CC[C@H](Nc2nccc(-n3ncc4c(OC[C@@H](O)CO)cccc43)n2)CC1] | N-(4-{4-[4-(2,3-di-hydroxy-propoxy)-indazol-1-yl]-pyrimidin-2-ylamino}-cyclohexyl)-acetamide<br>Mp 202.0-205.0° C.<br>MS (M + H) = 441 | 154 |

TABLE 1-continued

Representative compounds of Formula I.

| Structure | Name | Compound No. |
|---|---|---|
| 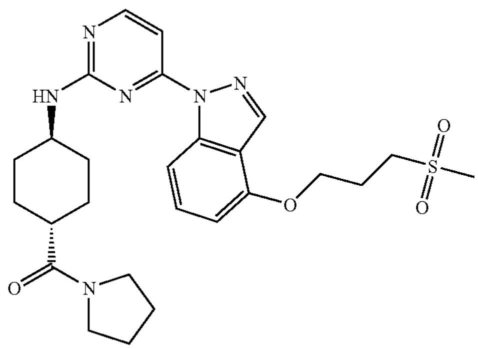 [SMILES: CS(=O)(=O)CCCOc1cccc2c1cnn2-c1ccnc(N[C@H]2CC[C@H](C(=O)N3CCCC3)CC2)n1] | (4-{4-[4-(3-methane-sulfonyl-propoxy)-indazol-1-yl]-pyrimidin-2-ylamino}-cyclohexyl)-pyrrolidin-1-ylmethanone<br>Mp 183.4-184.5° C.<br>MS (M + H) = 527 | 155 |
| 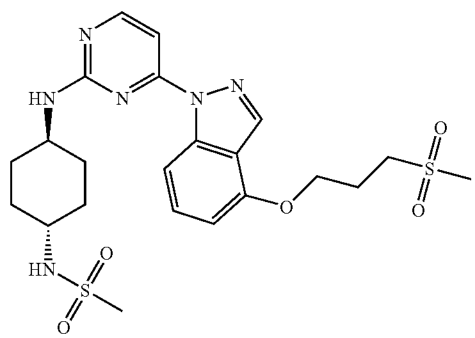 [SMILES: CS(=O)(=O)CCCOc1cccc2c1cnn2-c1ccnc(N[C@H]2CC[C@H](NS(C)(=O)=O)CC2)n1] | N-(4-{4-[4-(3-methane-sulfonyl-propoxy)-indazol-1-yl]-pyrimidin-2-ylamino}-cyclohexyl)-methanesulfonamide<br>Mp 247.0-248.0° C.<br>MS (M + H) = 523 | 156 |
| 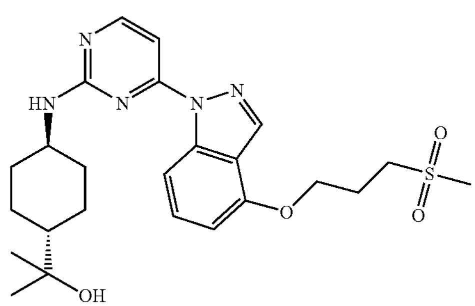 | 2-(4-{4-[4-(3-methane-sulfonyl-propoxy)-indazol-1-yl]-pyrimidin-2-ylamino}-cyclohexyl)-propan-2-ol<br>Mp 199.2-200.5° C.<br>MS (M + H) = 488 | 157 |
| 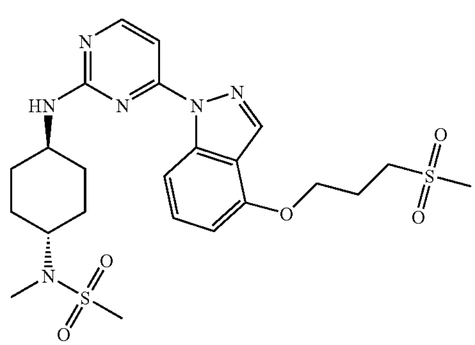 [SMILES: CN([C@H]1CC[C@H](Nc2nccc(-n3ncc4c(OCCCS(C)(=O)=O)cccc43)n2)CC1)S(C)(=O)=O] | N-(4-{4-[4-(3-methane-sulfonyl-propoxy)-indazol-1-yl]-pyrimidin-2-ylamino}-cyclohexyl)-N-methyl-methane-sulfonamide<br>Mp 208.8-209.6° C.<br>MS (M + H) = 537 | 158 |

TABLE 1-continued

Representative compounds of Formula I.

| Structure | Name | Compound No. |
|---|---|---|
| | N-(4-{4-[4-(3-methane-sulfonyl-propoxy)-indazol-1-yl]-pyrimidin-2-ylamino}-cyclohexyl)-2-morpholin-4-yl-acetamide<br>Mp 219.2-221.1° C.<br>MS (M + H) = 572 | 159 |
| | N-(4-{4-[4-(2-methoxy-ethoxymethyl)-indol-1-yl]-pyrimidin-2-ylamino}-cyclohexyl)-N-methyl-methane-sulfonamide<br>Mp 154.0-156.5° C.<br>MS (M + H) = 488 | 160 |
| | N-(4-{4-[4-(1-hydroxy-1-methyl-ethyl)-indol-1-yl]-pyrimidin-2-yl-amino}-cyclohexyl)-N-methyl-methane-sulfonamide<br>Mp 149.0-150.0° C.<br>MS (M + H) = 458 | 161 |
| | N-(4-{4-[4-(2-methane-sulfonyl-ethoxymethyl)-indol-1-yl]-pyrimidin-2-ylamino}-cyclohexyl)-N-methyl-methanesulfonamide<br>MS (M + H) = 536 | 162 |

TABLE 1-continued

Representative compounds of Formula I.

| Structure | Name | Compound No. |
|---|---|---|
| | N-{4-[4-(4-cyano-methyl-indol-1-yl)-pyrimidin-2-ylamino]-cyclohexyl}-N-methyl-methanesulfonamide<br>Mp 187.8-189.0° C.<br>MS (M + H) = 439 | 163 |
| | N-(1-{2-[4-(1-hydroxy-1-methyl-ethyl)-cyclo-hexylamino]-pyrimidin-4-yl}-1H-indol-4-yl)-N-methyl-methanesulfonamide<br>Mp 216.5-217.5° C.<br>MS (M + H) = 458 | 164 |
| | N-(4-{4-[4-(3-methane-sulfonyl-propoxy)-indol-1-yl]-pyrimidin-2-ylamino}-cyclohexyl)-methanesulfonamide<br>Mp 232.2-233.5° C.<br>MS (M + H) = 522 | 165 |
| | 2-(4-{4-[4-(3-methane-sulfonyl-propoxy)-indol-1-yl]-pyrimidin-2-ylamino}-cyclohexyl)-propan-2-ol<br>Mp 190.0-191.0° C.<br>MS (M + H) = 487 | 166 |

TABLE 1-continued

Representative compounds of Formula I.

| Structure | Name | Compound No. |
|---|---|---|
| 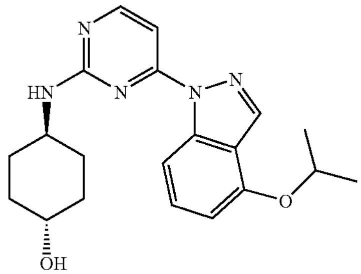 [SMILES: CC(C)Oc1cccc2c1cnn2-c1ccnc(N[C@H]2CC[C@H](O)CC2)n1] | 4-[4-(4-isopropoxy-indazol-1-yl)-pyrimidin-2-ylamino]-cyclohexanol<br>Mp 188.2-189.2° C.<br>MS (M + H) = 368 | 167 |
| 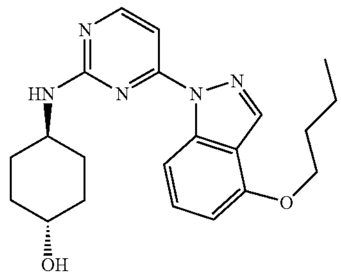 [SMILES: CCCCOc1cccc2c1cnn2-c1ccnc(N[C@H]2CC[C@H](O)CC2)n1] | 4-[4-(4-butoxy-indazol-1-yl)-pyrimidin-2-yl-amino]-cyclohexanol<br>Mp 195.0-196.0° C.<br>MS (M + H) = 382 | 168 |
| 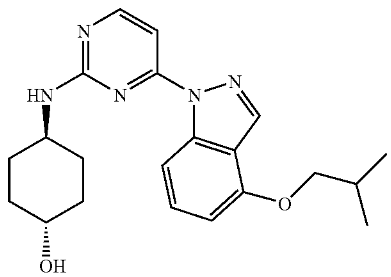 [SMILES: CC(C)COc1cccc2c1cnn2-c1ccnc(N[C@H]2CC[C@H](O)CC2)n1] | 4-[4-(4-isobutoxy-indazol-1-yl)-pyrimidin-2-ylamino]-cyclohexanol<br>Mp 189.3-190.3° C.<br>MS (M + H) = 382 | 169 |
| 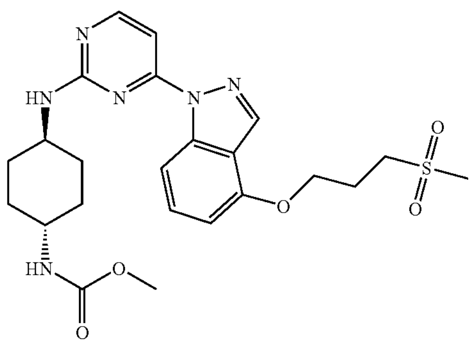 [SMILES: COC(=O)N[C@H]1CC[C@H](Nc2nccc(-n3ncc4c(OCCCS(C)(=O)=O)cccc43)n2)CC1] | (4-{4-[4-(3-methane-sulfonyl-propoxy)-indazol-1-yl]-pyrimidin-2-ylamino}-cyclohexyl)-carbamic acid methyl ester<br>Mp 226.8-227.3° C.<br>MS (M + H) = 503 | 170 |
| 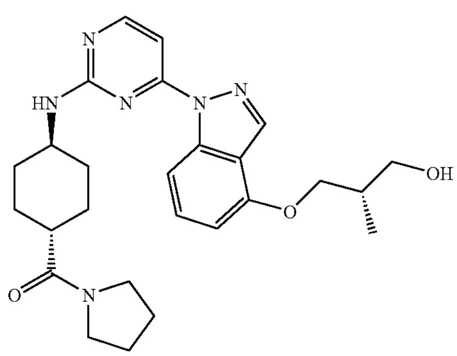 [SMILES: C[C@@H](CO)COc1cccc2c1cnn2-c1ccnc(N[C@H]2CC[C@H](C(=O)N3CCCC3)CC2)n1] | (4-{4-[4-(3-hydroxy-2-methylpropoxy)-indazol-1-yl]-pyrimidin-2-ylamino}-cyclohexyl)-pyrrolidin-1-ylmethanone<br>Mp 199.4-200.4° C.<br>MS (M + H) = 479 | 171 |

TABLE 1-continued

Representative compounds of Formula I.

| Structure | Name | Compound No. |
|---|---|---|
| 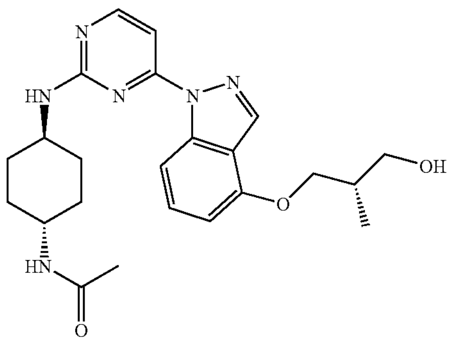 [SMILES: CC(=O)N[C@H]1CC[C@H](Nc2nccc(-n3ncc4c(OC[C@@H](C)CO)cccc43)n2)CC1] | N-(4-{4-[4-(3-hydroxy-2-methylpropoxy)-indazol-1-yl]-pyrimidin-2-ylamino}-cyclohexyl)-acetamide<br>Mp 215.0-216.0° C.<br>MS (M + H) = 439 | 172 |
| 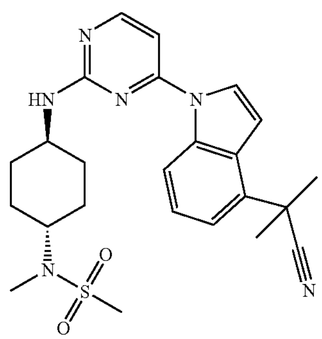 [SMILES: CN([C@H]1CC[C@H](Nc2nccc(-n3ccc4c(C(C)(C)C#N)cccc43)n2)CC1)S(C)(=O)=O] | N-(4-{4-[4-(2-cyano-prop-2-yl)-indol-1-yl]-pyrimidin-2-ylamino}-cyclohexyl)-N-methyl-methanesulfonamide<br>Mp 189.0-190.0° C.<br>MS (M + H) = 469 | 173 |
| 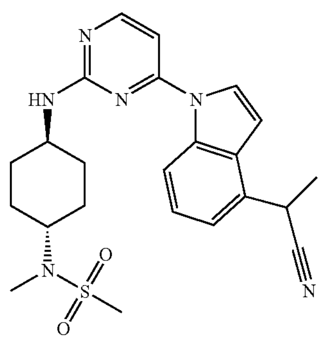 [SMILES: CC(C#N)c1cccc2c1ccn2-c1ccnc(N[C@H]2CC[C@H](N(C)S(C)(=O)=O)CC2)n1] | N-(4-{4-[4-(1-cyano-ethyl)-indol-1-yl]-pyrimidin-2-ylamino}-cyclohexyl)-N-methyl-methanesulfonamide<br>Mp 196.0-197.0° C.<br>MS (M + H) = 453 | 174 |
| 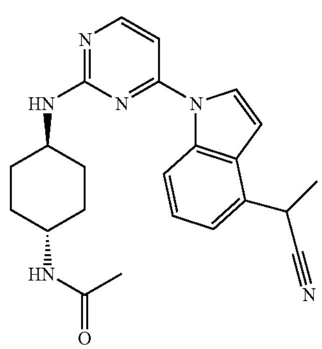 [SMILES: CC(=O)N[C@H]1CC[C@H](Nc2nccc(-n3ccc4c(C(C)C#N)cccc43)n2)CC1] | N-(4-{4-[4-(1-cyano-ethyl)-indol-1-yl]-pyrimidin-2-ylamino}-cyclohexyl)-acetamide<br>Mp 244.0-245.0° C.<br>MS (M + H) = 403 | 175 |

TABLE 1-continued

Representative compounds of Formula I.

| Structure | Name | Compound No. |
|---|---|---|
| 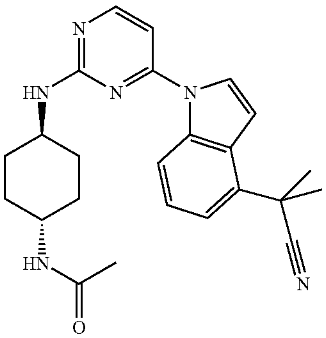 [SMILES: CC(=O)N[C@H]1CC[C@H](Nc2nccc(-n3ccc4c(C(C)(C)C#N)cccc43)n2)CC1] | N-(4-{4-[4-(2-cyano-prop-2-yl)-indol-1-yl]-pyrimidin-2-ylamino}-cyclohexyl)-acetamide<br>Mp 238.0-239.0° C.<br>MS (M + H) = 417 | 176 |
| 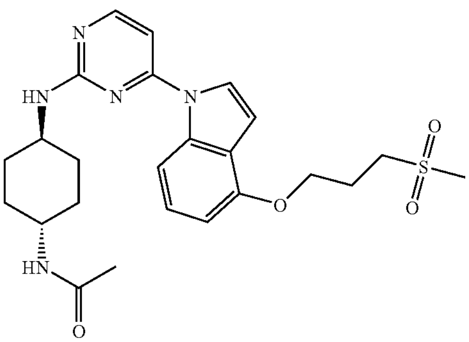 [SMILES: CC(=O)N[C@H]1CC[C@H](Nc2nccc(-n3ccc4c(OCCCS(C)(=O)=O)cccc43)n2)CC1] | N-(4-{4-[4-(3-methane-sulfonyl-propoxy)-indazol-1-yl]-pyrimidin-2-ylamino}-cyclohexyl)-acetamide<br>Mp 284.5-285.5° C.<br>MS (M + H) = 487 | 177 |
| | N-(4-{4-[4-(3-hydroxy-propoxy)indazole-1-yl]-pyrimidin-2-ylamino}-cyclohexyl)-N-methyl-methanesulfonamide<br>Mp 208.4-209.0° C.<br>MS (M + H) = 475 | 178 |
| 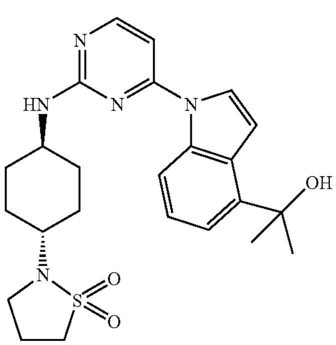 [SMILES: CC(C)(O)c1cccc2c1ccn2-c1ccnc(N[C@H]2CC[C@H](N3CCCS3(=O)=O)CC2)n1] | 2-(1-{2-[4-(1,1-dioxo-isothiazolidin-2yl)-cyclohexylamino}-pyrimidin-4-yl}-1H-indol-4-yl)-propan-2-ol<br>Mp 206.9-207.6° C.<br>MS (M + H) = 470 | 179 |

TABLE 1-continued

Representative compounds of Formula I.

| Structure | Name | Compound No. |
|---|---|---|
| 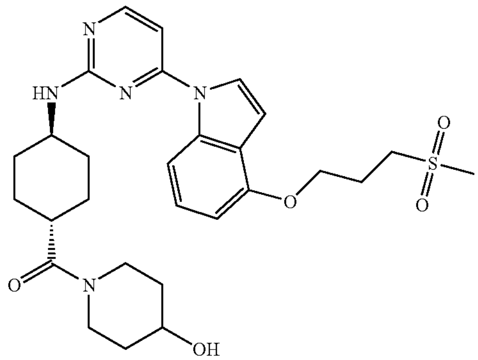 [SMILES: CS(=O)(=O)CCCOc1cccc2c1ccn2-c1ccnc(N[C@H]2CC[C@H](C(=O)N3CCC(O)CC3)CC2)n1] | (4-hydroxy-piperidin-1-yl)-(4-{4-[4-(3-methane-sulfonyl-propoxy)-indol-1-yl]-pyrimidin-2-ylamino}-cyclohexyl)-methanone<br>Mp 136.0-137.0° C.<br>MS (M + H) = 556 | 180 |
| 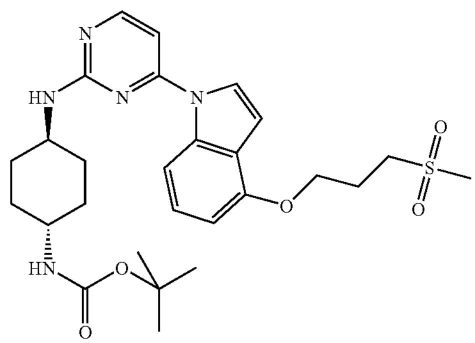 [SMILES: CC(C)(C)OC(=O)N[C@H]1CC[C@H](Nc2nccc(-n3ccc4c(OCCCS(C)(=O)=O)cccc43)n2)CC1] | (4-{4-[4-(3-methane-sulfonyl-propoxy)-indol-1-yl]-pyrimidin-2-ylamino}-cyclohexyl)-carbamic acid t-butyl ester<br>Mp 227.5-228.5° C.<br>MS (M + H) = 544 | 181 |
| 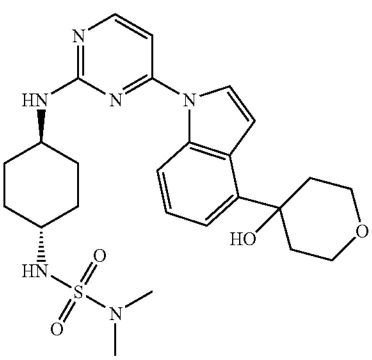 [SMILES: CN(C)S(=O)(=O)N[C@H]1CC[C@H](Nc2nccc(-n3ccc4c(C5(O)CCOCC5)cccc43)n2)CC1] | N-(4-{4-[4-(4-hydroxy-tetrahydropyran-4-yl)-indol-1-yl]-pyrimidin-2-ylamino}-cyclohexyl)-(N',N'-dimethylamino)-sulfonamide<br>Mp >300° C.<br>MS (M + H) = 515 | 182 |
| 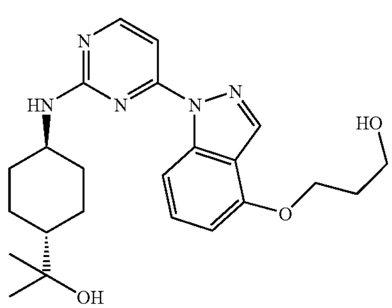 [SMILES: CC(C)(O)[C@H]1CC[C@H](Nc2nccc(-n3ncc4c(OCCCO)cccc43)n2)CC1] | 3-(1-{2-[4-(2-hydroxy-prop-2-yl)-cyclohexyl-amino]-pyrimidin-4-yl}-1H-indazol-4-yloxy)-propan-1-ol<br>Mp 229.5-231.0° C.<br>MS (M + H) = 426 | 183 |

TABLE 1-continued

Representative compounds of Formula I.

| Structure | Name | Compound No. |
|---|---|---|
| 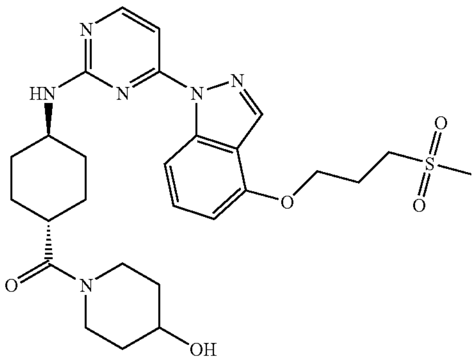 | (4-hydroxy-piperidin-1-yl)-(4-{4-[4-(3-methane-sulfonyl-propoxy)-indazol-1-yl]-pyrimidin-2-ylamino}-cyclohexyl)-methanone<br>Mp 143.0-145.0° C.<br>MS (M + H) = 557 | 184 |
| 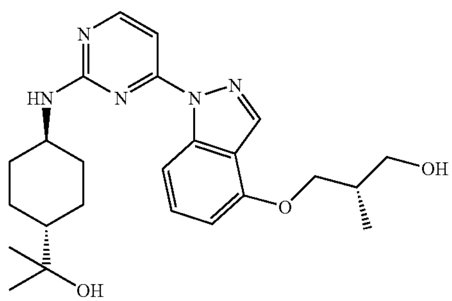 [SMILES: C[C@@H](CO)COc1cccc2c1cnn2-c1ccnc(N[C@H]2CC[C@H](C(C)(C)O)CC2)n1] | 3-(1-{2-[4-(2-hydroxy-prop-2-yl)-cyclohexyl-amino]-pyrimidin-4-yl}-1H-indazol-4-yloxy)-2-methylpropan-1-ol<br>Mp 211.0-212.5° C.<br>MS (M + H) = 440 | 185 |
| 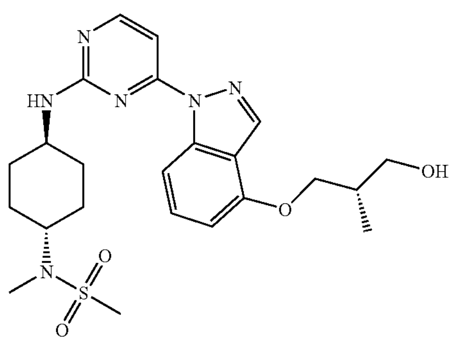 [SMILES: C[C@@H](CO)COc1cccc2c1cnn2-c1ccnc(N[C@H]2CC[C@H](N(C)S(C)(=O)=O)CC2)n1] | N-(4-{4-[4-(3-hydroxy-2-methylpropoxy)-indazol-1-yl]-pyrimidin-2-ylamino}-cyclohexyl)-N-methyl-methanesulfonamide<br>Mp 222.0-224.0° C.<br>MS (M + H) = 489 | 186 |
| 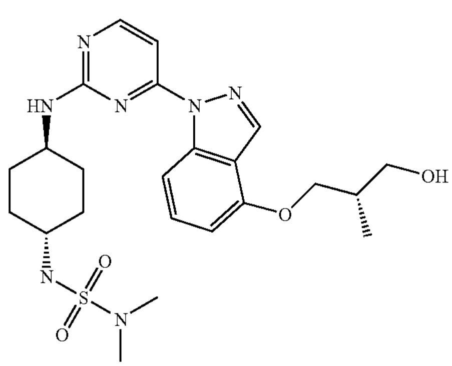 [SMILES: C[C@@H](CO)COc1cccc2c1cnn2-c1ccnc(N[C@H]2CC[C@H](NS(=O)(=O)N(C)C)CC2)n1] | N-(4-{4-[4-(3-hydroxy-2-methylpropoxy)-indazol-1-yl]-pyrimidin-2-ylamino}-cyclohexyl)-N-(N',N'-dimethylamino)-sulfonamide<br>Mp 217.5-219.0° C.<br>MS (M + H) = 504 | 187 |

TABLE 1-continued

Representative compounds of Formula I.

| Structure | Name | Compound No. |
|---|---|---|
| 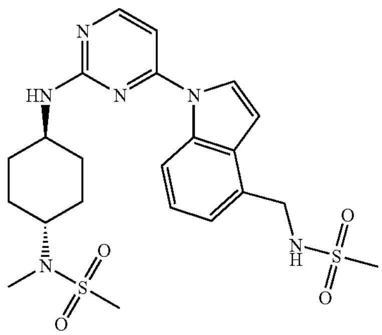 [SMILES: CN([C@H]1CC[C@H](Nc2nccc(-n3ccc4c(CNS(C)(=O)=O)cccc43)n2)CC1)S(C)(=O)=O] | N-(4-{4-[4-(methane-sulfonylamino-methyl)-indol-1-yl]-pyrimidin-2-ylamino}-cyclohexyl)-N-methyl-methane-sulfonamide<br>Mp 226.5-228.0° C.<br>MS (M + H) = 507 | 188 |
| 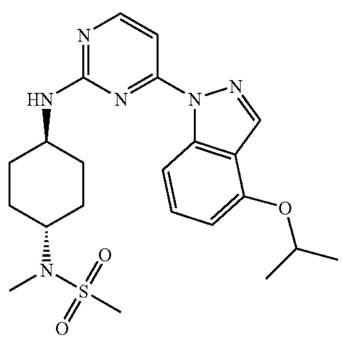 [SMILES: CC(C)Oc1cccc2c1cnn2-c1ccnc(N[C@H]2CC[C@H](N(C)S(C)(=O)=O)CC2)n1] | N-{4-[4-(4-isopropoxy-indazol-1-yl)-pyrimidin-2-ylamino]-cyclohexyl}-N-methyl-methanesulfonamide<br>Mp 222.0-223.0° C.<br>MS (M + H) = 459 | 189 |
| 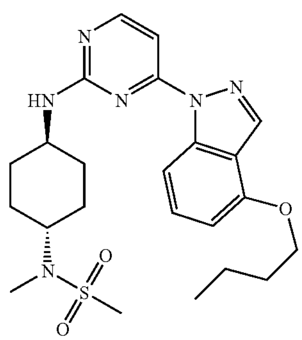 [SMILES: CCCCOc1cccc2c1cnn2-c1ccnc(N[C@H]2CC[C@H](N(C)S(C)(=O)=O)CC2)n1] | N-{4-[4-(4-butoxy-indazol-1-yl)-pyrimidin-2-ylamino]-cyclohexyl}-N-methyl-methanesulfonamide<br>Mp 191.0-192.0° C.<br>MS (M + H) = 473 | 190 |
| 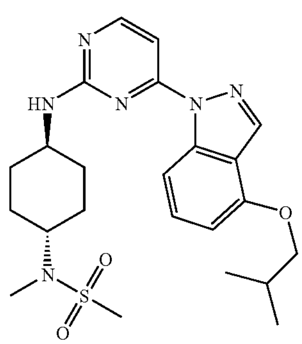 [SMILES: CC(C)COc1cccc2c1cnn2-c1ccnc(N[C@H]2CC[C@H](N(C)S(C)(=O)=O)CC2)n1] | N-{4-[4-(4-isobutoxy-indazol-1-yl)-pyrimidin-2-ylamino]-cyclohexyl}-N-methyl-methanesulfonamide<br>Mp 227.0-228.0° C.<br>MS (M + H) = 473 | 191 |

TABLE 1-continued

Representative compounds of Formula I.

| Structure | Name | Compound No. |
|---|---|---|
| | N-{4-[4-(3-methane-sulfonyl-propoxy)-indol-1-yl]-pyrimidin-2-yl}-cyclohexane-1,4-diamine hydrochloride<br>Mp 291.0-292.0° C.<br>MS (M + H) = 444 | 192 |
| | 3-amino-N-(4-{4-[4-(3-methanesulfonyl-propoxy)-indol-1-yl]-pyrimidin-2-ylamino}-cyclohexyl)-propion-amide hydrochloride<br>Mp 263.0-264.0° C.<br>MS (M + H) = 515 | 193 |
| | N-(4-{4-[4-(4-hydroxy-tetrahydropyran-4-yl)-indol-1-yl]-pyrimidin-2-ylamino}-cyclohexyl)-methanesulfonamide<br>Mp 248.3-249.0° C.<br>MS (M + H) = 486 | 194 |
| | 4-{1-[2-(4-methane-sulfonylamino-cyclo-hexylamino)-pyrimidin-4-yl]-1H-indol-4-yloxymethyl}-piperidine-1-carboxylic acid benzyl ester<br>Mp 179.0-180.0° C.<br>MS (M + H) = 633 | 195 |

TABLE 1-continued

Representative compounds of Formula I.

| Structure | Name | Compound No. |
|---|---|---|
| 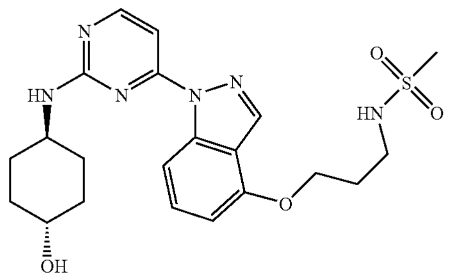 [SMILES: CS(=O)(=O)NCCCOc1cccc2c1cnn2-c1ccnc(N[C@H]2CC[C@H](O)CC2)n1] | N-(3-{1-[2-(4-hydroxy-cyclohexylamino)-pyrimidin-4-yl]-1H-indazol-4-yloxy}-propyl)-methane-sulfonamide<br>Mp 231.0-232.5° C.<br>MS (M + H) = 461 | 196 |
| 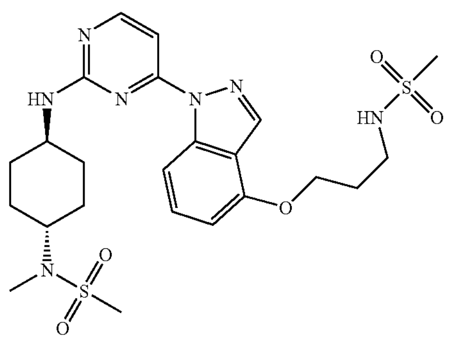 [SMILES: CN([C@H]1CC[C@H](Nc2nccc(-n3ncc4c(OCCCNS(C)(=O)=O)cccc43)n2)CC1)S(C)(=O)=O] | N-[3-(1-{2-[4-(methane-sulfonyl-methylamino)-cyclohexylamino]-pyrimidin-4-yl}-1H-indazol-4-yloxy)-propyl]-methane-sulfonamide<br>Mp 259.0-259.5° C.<br>MS (M + H) = 552 | 197 |
| 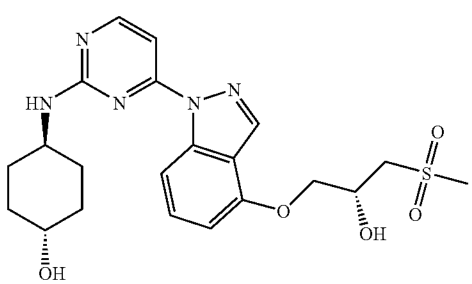 [SMILES: CS(=O)(=O)C[C@H](O)COc1cccc2c1cnn2-c1ccnc(N[C@H]2CC[C@H](O)CC2)n1] | 4-{4-[4-(2-hydroxy-3-methanesulfonyl-propoxy)-indazol-1-yl]-pyrimidin-2-ylamino}-cyclohexanol<br>Mp 211.0-212.0° C.<br>MS (M + H) = 462 | 198 |
| 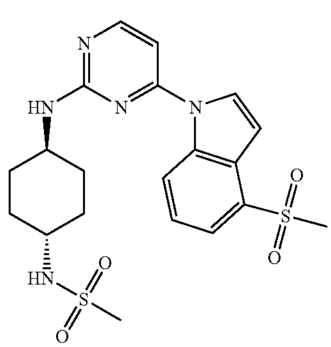 [SMILES: CS(=O)(=O)N[C@H]1CC[C@H](Nc2nccc(-n3ccc4c(S(C)(=O)=O)cccc43)n2)CC1] | N-{4-[4-(4-methane-sulfonyl-indol-1-yl)-pyrimidin-2-ylamino]-cyclohexyl}-methane-sulfonamide<br>MS (M + H) = 464 | 199 |

TABLE 1-continued

Representative compounds of Formula I.

| Structure | Name | Compound No. |
|---|---|---|
| 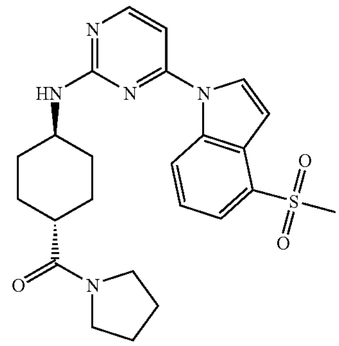 [SMILES: CS(=O)(=O)c1cccc2c1ccn2-c1ccnc(N[C@H]2CC[C@H](C(=O)N3CCCC3)CC2)n1] | {4-[4-(4-methane-sulfonyl-indol-1-yl)-pyrimidin-2-ylamino]-cyclohexyl}-pyrrolidin-1-yl-methanone<br>MS (M + H) = 468 | 200 |
| 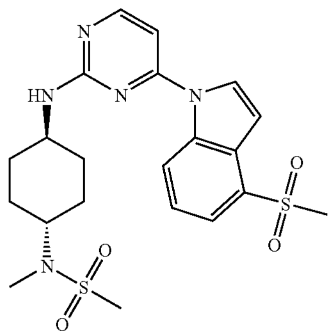 [SMILES: CN([C@H]1CC[C@H](Nc2nccc(-n3ccc4c(S(C)(=O)=O)cccc43)n2)CC1)S(C)(=O)=O] | N-{4-[4-(4-methane-sulfonyl-indol-1-yl)-pyrimidin-2-ylamino]-cyclohexyl}-N-methyl-methanesulfonamide<br>MS (M + H) = 478 | 201 |
| 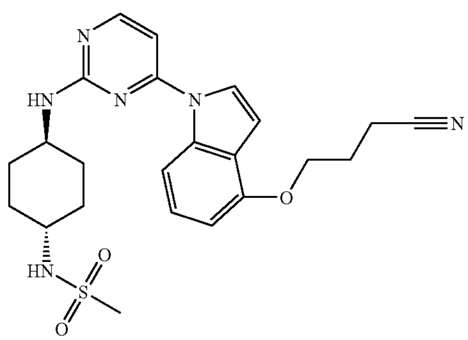 [SMILES: CS(=O)(=O)N[C@H]1CC[C@H](Nc2nccc(-n3ccc4c(OCCCC#N)cccc43)n2)CC1] | N-(4-{4-[4-(3-cyano-propoxy)-indol-1-yl]-pyrimidin-2-ylamino}-cyclohexyl)-methane-sulfonamide<br>Mp 247.0-248.0° C.<br>MS (M + H) = 469 | 202 |
| 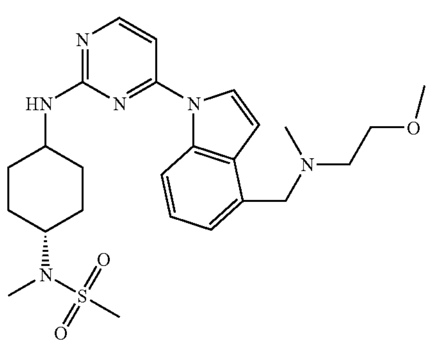 | N-{4-[4-(4-{[(2-methoxy-ethyl)-methyl-amino]-methyl}-indol-1-yl)-pyrimidin-2-yl-amino]-cyclohexyl}-N-methyl-methane-sulfonamide<br>MS (M + H) = 501 | 203 |

TABLE 1-continued

Representative compounds of Formula I.

| Structure | Name | Compound No. |
|---|---|---|
| 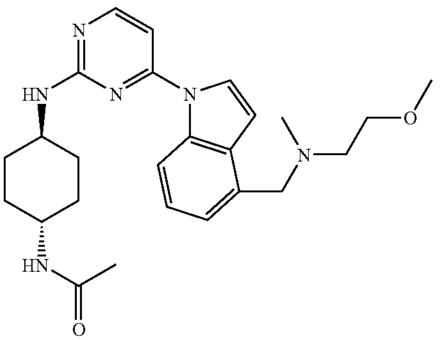 [SMILES: COCCN(C)Cc1cccc2c1ccn2-c1ccnc(N[C@H]2CC[C@H](NC(C)=O)CC2)n1] | N-{4-[4-(4-{[(2-methoxy-ethyl)-methyl-amino]-methyl}-indol-1-yl)-pyrimidin-2-yl-amino]-cyclohexyl}-acetamide<br>MS (M + H) = 451 | 204 |
| 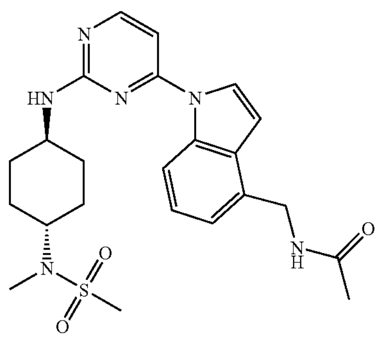 [SMILES: CC(=O)NCc1cccc2c1ccn2-c1ccnc(N[C@H]2CC[C@H](N(C)S(C)(=O)=O)CC2)n1] | N-(1-{2-[4-(methane-sulfonyl-methylamino)-cyclohexylamino]-pyrimidin-4-yl}-1H-indol-4-ylmethyl)-acetamide<br>Mp 210.5-212.0° C.<br>MS (M + H) = 471 | 205 |
| 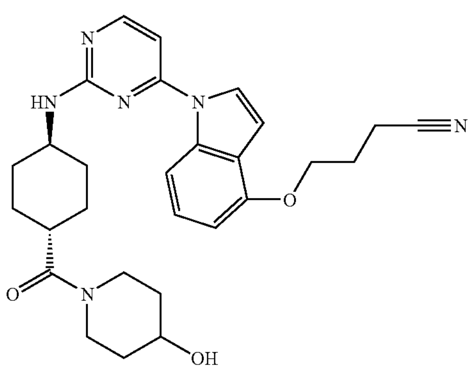 [SMILES: N#CCCCOc1cccc2c1ccn2-c1ccnc(N[C@H]2CC[C@H](C(=O)N3CCC(O)CC3)CC2)n1] | 4-(1-{2-[4-(4-hydroxy-piperidin-1-carbonyl)-cyclohexylamino]-pyrimidin-4-yl}-1H-indol-4-yloxy)-butyro-nitrile<br>Mp 134.0-136.0° C.<br>MS (M + H) = 503 | 206 |
| 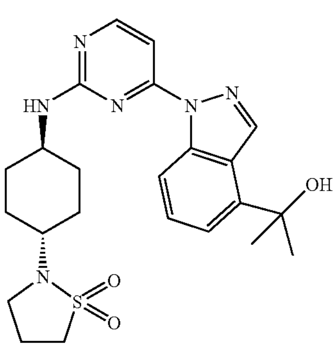 | 2-(1-{2-[4-(1,1-dioxo-isothiazolidin-2yl)-cyclohexylamino]-pyrimidin-4-yl}-1H-indazol-4-yl)-propan-2-ol<br>Mp 204.0-205.0° C.<br>MS (M + H) = 471 | 207 |

TABLE 1-continued

Representative compounds of Formula I.

| Structure | Name | Compound No. |
|---|---|---|
|  | (4-hydroxypiperidin-1-yl)-{4-[4-(4-methane-sulfonyl-indol-1-yl)-pyrimidin-2-ylamino]-cyclohexyl}-methanone<br>MS (M + H) = 498 | 208 |
|  | 2-{4-[4-(4-methane-sulfonyl-indol-1-yl)-pyrimidin-2-ylamino]-cyclohexyl}-propan-2-ol<br>Mp 217.8-218.5° C.<br>MS (M + H) = 429 | 209 |
|  | N-[3-(1-{2-[4-(2-hydroxyprop-2-yl)-cyclohexylamino]-pyrimidin-4-yl}-1H-indazol-4-yloxy)-propyl]-methane-sulfonamide<br>Mp 171.0-172.0° C.<br>MS (M + H) = 503 | 210 |
|  | 2-(4-{4-[4-(3-methane-sulfinyl-propoxy)-indol-1-yl]-pyrimidin-2-ylamino}-cyclohexyl)-propan-2-ol<br>Mp 190.5-191.0° C.<br>MS (M + H) = 471 | 211 |

TABLE 1-continued

Representative compounds of Formula I.

| Structure | Name | Compound No. |
|---|---|---|
|  | N-(4-{4-[4-(2-hydroxy-prop-2-yl)-indazol-1-yl]-pyrimidin-2-ylamino}-cyclohexyl)-methanesulfonamide Mp 250.0-251.0° C. MS (M + H) = 445 | 212 |
|  | N-[3-(1-{2-[4-(methane-sulfonyl-methylamino)-cyclohexylamino]-pyrimidin-4-yl}-1H-indazol-4-yloxy)-propyl]-acetamide Mp 226.0-227.0° C. MS (M + H) = 516 | 213 |
|  | (4-{4-[4-(3-methane-sulfonyl-propoxy)-indol-1-yl]-pyrimidin-2-ylamino}-cyclohexyl)-methanol Mp 207.0-208.0° C. MS (M + H) = 459 | 214 |
|  | [4-(1,1-dioxo-isothiazolidin-2-yl)-cyclohexyl]-{4-[4-(3-methane-sulfonyl-propoxy)-indazol-1-yl]-pyrimidin-2-yl}-amine Mp 206.0-207.0° C. MS (M + H) = 549 | 215 |

TABLE 1-continued

Representative compounds of Formula I.

| Structure | Name | Compound No. |
|---|---|---|
| 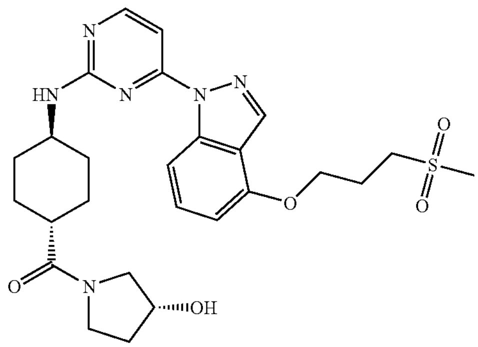 [SMILES: CS(=O)(=O)CCCOc1cccc2c1cnn2-c1ccnc(N[C@H]2CC[C@H](C(=O)N3CC[C@@H](O)C3)CC2)n1] | (3-hydroxy-pyrrolidin-1-yl)-(4-{4-[4-(3-methane-sulfonyl-propoxy)-indazol-1-yl]-pyrimidin-2-ylamino}-cyclohexyl)-methanone<br>Mp 174.0-175.0° C.<br>MS (M + H) = 543 | 216 |
| 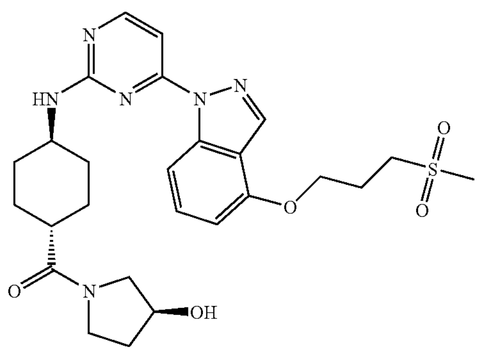 [SMILES: CS(=O)(=O)CCCOc1cccc2c1cnn2-c1ccnc(N[C@H]2CC[C@H](C(=O)N3CC[C@H](O)C3)CC2)n1] | (3-hydroxy-pyrrolidin-1-yl)-(4-{4-[4-(3-methane-sulfonyl-propoxy)-indazol-1-yl]-pyrimidin-2-ylamino}-cyclohexyl)-methanone<br>Mp 175.0-176.0° C.<br>MS (M + H) = 543 | 217 |
| 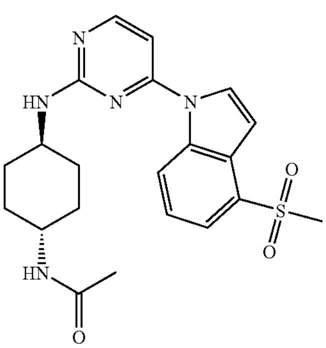 [SMILES: CC(=O)N[C@H]1CC[C@H](Nc2nccc(-n3ccc4c(S(C)(=O)=O)cccc43)n2)CC1] | N-{4-[4-(4-methane-sulfonyl-indol-1-yl)-pyrimidin-2-ylamino]-cyclohexyl}-acetamide<br>Mp 264.0-265.0° C.<br>MS (M + H) = 428 | 218 |
| 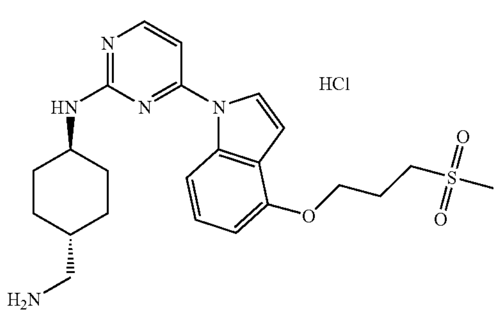 [SMILES: CS(=O)(=O)CCCOc1cccc2c1ccn2-c1ccnc(N[C@H]2CC[C@H](CN)CC2)n1 ; Cl] | (4-aminomethyl-cyclo-hexyl)-{4-[4-(3-methane-sulfonyl-propoxy)-indol-1-yl]-pyrimidin-2-yl}-amine hydrochloride<br>Mp 292.0-293.0° C.<br>MS (M + H) = 458 | 219 |

TABLE 1-continued

Representative compounds of Formula I.

| Structure | Name | Compound No. |
|---|---|---|
| 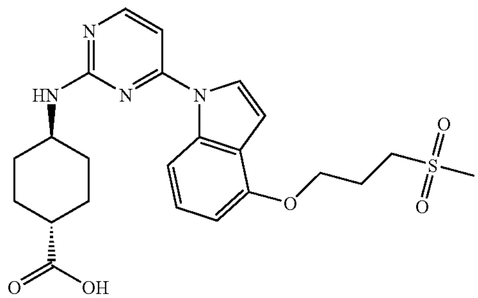 [SMILES: CS(=O)(=O)CCCOc1cccc2c1ccn2-c1ccnc(N[C@H]2CC[C@H](C(=O)O)CC2)n1] | 4-{4-[4-(3-methane-sulfonyl-propoxy)-indol-1-yl]-pyrimidin-2-ylamino}-cyclohexane-carboxylic acid<br>Mp 274.0-275.0° C.<br>MS (M + H) = 473 | 220 |
| 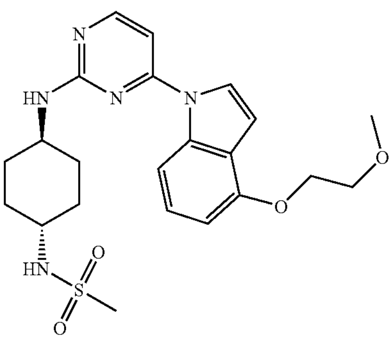 [SMILES: COCCOc1cccc2c1ccn2-c1ccnc(N[C@H]2CC[C@H](NS(C)(=O)=O)CC2)n1] | N-(4-{4-[4-(2-methoxy-ethoxy)-indol-1-yl]-pyrimidin-2-ylamino}-cyclohexyl)-methanesulfonamide<br>Mp 203.0-205.0° C.<br>MS (M + H) = 460 | 221 |
| 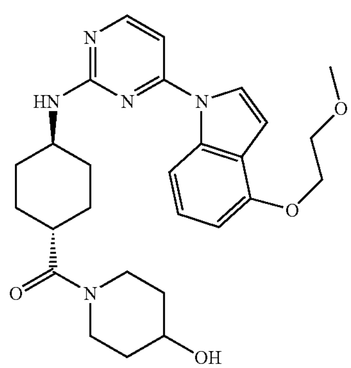 [SMILES: COCCOc1cccc2c1ccn2-c1ccnc(N[C@H]2CC[C@H](C(=O)N3CCC(O)CC3)CC2)n1] | (4-hydroxy-piperidin-1-yl)-(4-{4-[4-(2-methoxy-ethoxy)-indol-1-yl]-pyrimidin-2-ylamino}-cyclohexyl)-methanone<br>Mp 134.0-135.0° C.<br>MS (M + H) = 494 | 222 |
| 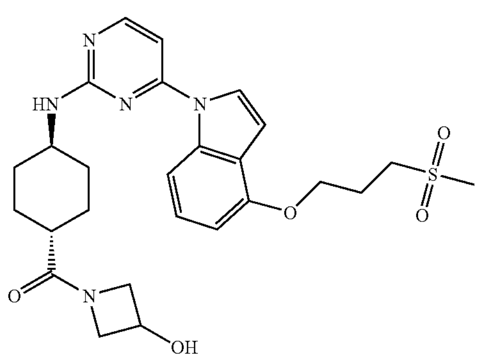 [SMILES: CS(=O)(=O)CCCOc1cccc2c1ccn2-c1ccnc(N[C@H]2CC[C@H](C(=O)N3CC(O)C3)CC2)n1] | (3-hydroxy-azetidin-1-yl)-(4-{4-[4-(3-methane-sulfonyl-propoxy)-indol-1-yl]-pyrimidin-2-ylamino}-cyclohexyl)-methanone<br>Mp 152.0-153.0° C.<br>MS (M + H) = 528 | 223 |

TABLE 1-continued

Representative compounds of Formula I.

| Structure | Name | Compound No. |
|---|---|---|
| 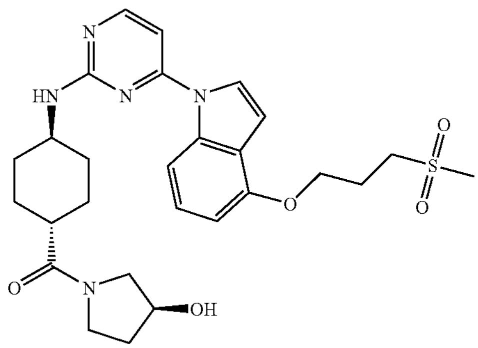 [SMILES: CS(=O)(=O)CCCOc1cccc2c1ccn2-c1ccnc(N[C@H]2CC[C@H](C(=O)N3CC[C@H](O)C3)CC2)n1] | (3-hydroxy-pyrrolidin-1-yl)-(4-{4-[4-(3-methane-sulfonyl-propoxy)-indol-1-yl]-pyrimidin-2-ylamino}-cyclohexyl)-methanone<br>Mp 100.4-101.7° C.<br>MS (M + H) = 542 | 224 |
| 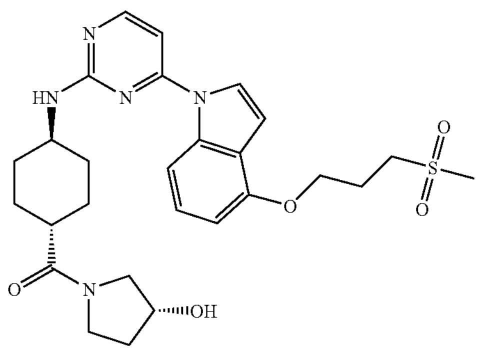 [SMILES: CS(=O)(=O)CCCOc1cccc2c1ccn2-c1ccnc(N[C@H]2CC[C@H](C(=O)N3CC[C@@H](O)C3)CC2)n1] | (3-hydroxy-pyrrolidin-1-yl)-(4-{4-[4-(3-methane-sulfonyl-propoxy)-indol-1-yl]-pyrimidin-2-ylamino}-cyclohexyl)-methanone<br>Mp 135.0-136.0° C.<br>MS (M + H) = 542 | 225 |
| 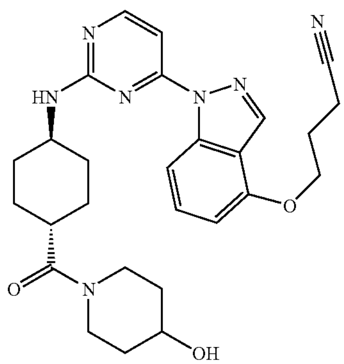 [SMILES: N#CCCCOc1cccc2c1cnn2-c1ccnc(N[C@H]2CC[C@H](C(=O)N3CCC(O)CC3)CC2)n1] | 4-(1-{2-[4-(4-hydroxy-piperidine-1-carbonyl)-cyclohexylamino]-pyrimidin-4-yl}-1H-indazol-4-yloxy)-butyro-nitrile<br>Mp 201.0-202.0° C.<br>MS (M + H) = 504 | 226 |
| 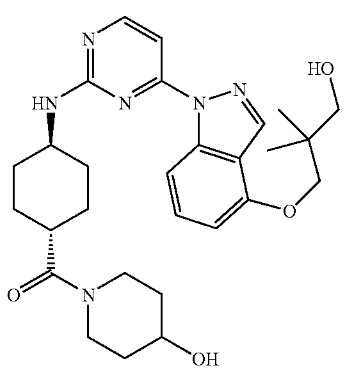 [SMILES: CC(C)(CO)COc1cccc2c1cnn2-c1ccnc(N[C@H]2CC[C@H](C(=O)N3CCC(O)CC3)CC2)n1] | (4-{4-[4-(3-hydroxy-2,2-dimethylpropoxy)-indazol-1-yl]-pyrimidin-2-ylamino}-cyclohexyl)-(4-hydroxy-piperidin-1-yl)-methanone<br>Mp 213.0-214.5° C.<br>MS (M + H) = 523 | 227 |

TABLE 1-continued

Representative compounds of Formula I.

| Structure | Name | Compound No. |
|---|---|---|
| 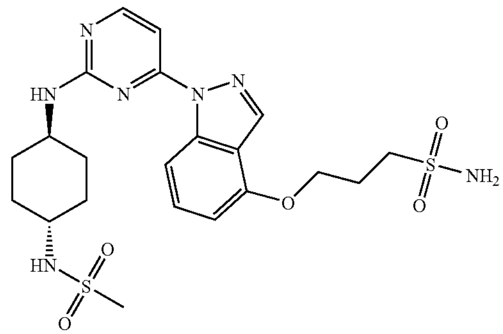 [SMILES: CS(=O)(=O)N[C@H]1CC[C@H](Nc2nccc(-n3ncc4c(OCCCS(N)(=O)=O)cccc43)n2)CC1] | 3-{1-[2-(4-methane-sulfonylamino-cyclo-hexylamino)-pyrimidin-4-yl]-1H-indazol-4-yloxy}-propane-1-sulfonic acid amide<br>Mp 250.0-251.0° C.<br>MS (M + H) = 524 | 228 |
| 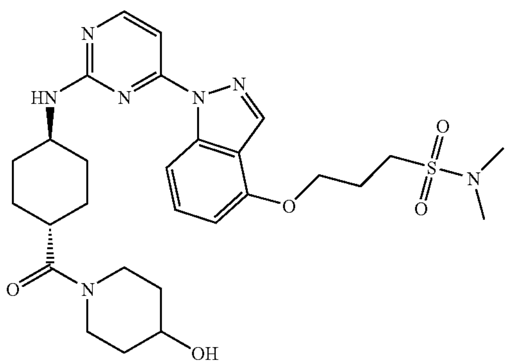 [SMILES: CN(C)S(=O)(=O)CCCOc1cccc2c1cnn2-c1ccnc(N[C@H]2CC[C@H](C(=O)N3CCC(O)CC3)CC2)n1] | 3-(1-{2-[4-(4-hydroxy-piperidin-1-carbonyl)-cyclohexylamino]-pyrimidin-4-yl}-1H-indazol-4-yloxy)-propane-1-sulfonic acid dimethylamide<br>Mp 190.0-191.0° C.<br>MS (M + H) = 586 | 229 |
| 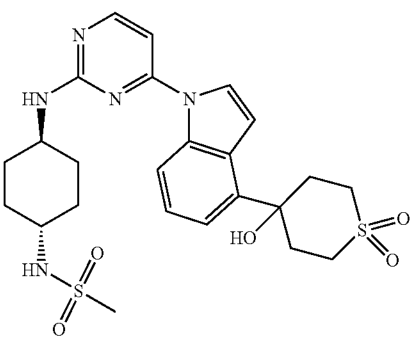 [SMILES: CS(=O)(=O)N[C@H]1CC[C@H](Nc2nccc(-n3ccc4c(C5(O)CCS(=O)(=O)CC5)cccc43)n2)CC1] | N-(4-{4-[4-(4-hydroxy-1,1-dioxohexahydro-thiopyran-4-yl)-indol-1-yl]-pyrimidin-2-yl-amino}-cyclohexyl)-methanesulfonamide<br>Mp >300° C.<br>MS (M + H) = 534 | 230 |
| 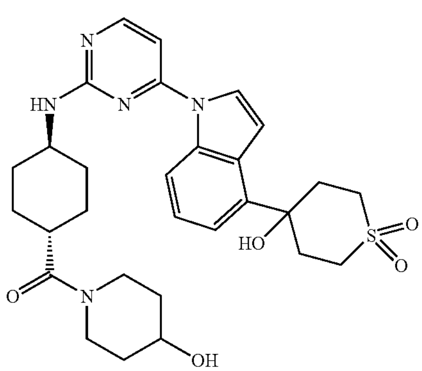 [SMILES: O=C([C@H]1CC[C@H](Nc2nccc(-n3ccc4c(C5(O)CCS(=O)(=O)CC5)cccc43)n2)CC1)N1CCC(O)CC1] | (4-{4-[4-(4-hydroxy-1,1-dioxo-hexahydro-thiopyran-4-yl)-indol-1-yl]-pyrimidin-2-yl-amino}-cyclohexyl)-(4-hydroxy-piperidin-1-yl)-methanone<br>Mp 271.0-272.0° C.<br>MS (M + H) = 568 | 231 |

TABLE 1-continued

Representative compounds of Formula I.

| Structure | Name | Compound No. |
|---|---|---|
| 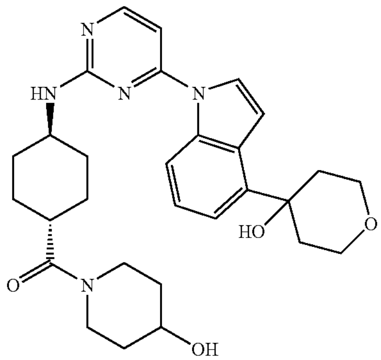 [SMILES: O=C([C@H]1CC[C@H](Nc2nccc(-n3ccc4c(C5(O)CCOCC5)cccc43)n2)CC1)N1CCC(O)CC1] | (4-hydroxy-piperidin-1-yl)-(4-{4-[4-(4-hydroxy-tetrahydro-pyran-4-yl)-indol-1-yl]-pyrimidin-2-ylamino}-cyclohexyl)-methanone<br>Mp 168.0-169.0° C.<br>MS (M + H) = 520 | 232 |
| 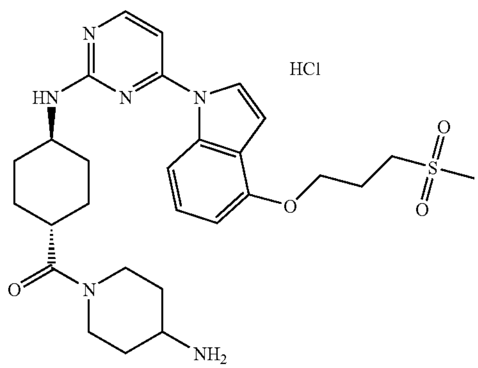 [SMILES: CS(=O)(=O)CCCOc1cccc2c1ccn2-c1ccnc(N[C@H]2CC[C@H](C(=O)N3CCC(N)CC3)CC2)n1 ; Cl] | (4-amino-piperidin-1-yl)-(4-{4-[4-(3-methane-sulfonyl-propoxy)-indol-1-yl]-pyrimidin-2-ylamino}-cyclohexyl)-methanone<br>Mp 247.0-248.0° C.<br>MS (M + H) = 555 | 233 |
| 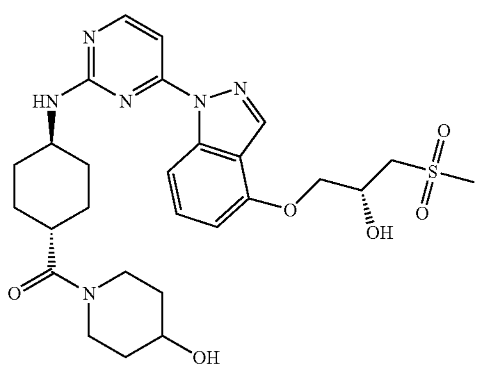 [SMILES: CS(=O)(=O)C[C@H](O)COc1cccc2c1cnn2-c1ccnc(N[C@H]2CC[C@H](C(=O)N3CCC(O)CC3)CC2)n1] | (4-{4-[4-(2-hydroxy-3-methanesulfonyl-propoxy)-indazol-1-yl]-pyrimidin-2-ylamino}-cyclohexyl)-(4-hydroxy-piperidin-1-yl)-methanone<br>Mp 232.0-233.0° C.<br>MS (M + H) = 573 | 234 |
| 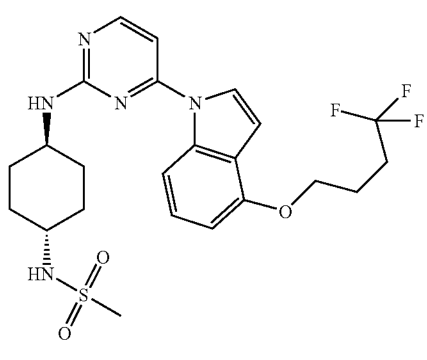 [SMILES: CS(=O)(=O)N[C@H]1CC[C@H](Nc2nccc(-n3ccc4c(OCCCC(F)(F)F)cccc43)n2)CC1] | N-(4-{4-[4-(4,4,4-tri-fluoro-butoxy)-indol-1-yl]-pyrimidin-2-yl-amino}-cyclohexyl)-methanesulfonamide<br>Mp 241.0-242.0° C.<br>MS (M + H) = 512 | 235 |

TABLE 1-continued

Representative compounds of Formula I.

| Structure | Name | Compound No. |
|---|---|---|
| | N-(4-{4-[4-(3-methoxy-propoxy)-indol-1-yl]-pyrimidin-2-ylamino}-cyclohexyl)-methanesulfonamide<br>Mp 207.0-208.0° C.<br>MS (M + H) = 474 | 236 |
| | (4,4-difluoro-piperidin-1-yl)-(4-{4-[4-(3-methane-sulfonyl-propoxy)-indol-1-yl]-pyrimidin-2ylamino}-cyclohexyl)-methanone<br>Mp 153.0-154.0° C.<br>MS (M + H) = 576 | 237 |
| | (3-fluoro-pyrrolidin-1-yl)-(4-{4-[4-(3-methane-sulfonyl-propoxy)-indol-1-yl]-pyrimidin-2-yl-amino}-cyclohexyl)-methanone<br>Mp 134.0-135.0° C.<br>MS (M + H) = 544 | 238 |
| | (4-fluoro-piperidin-1-yl)-(4-{4-[4-(3-methane-sulfonyl-propoxy)-indol-1-yl]-pyrimidin-2ylamino}-cyclohexyl)-methanone<br>Mp 115.0-116.0° C.<br>MS (M + H) = 558 | 239 |

TABLE 1-continued

Representative compounds of Formula I.

| Structure | Name | Compound No. |
|---|---|---|
| 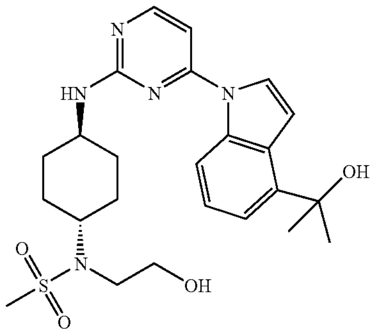 [SMILES: CC(C)(O)c1cccc2c1ccn2-c1ccnc(N[C@H]2CC[C@H](N(CCO)S(C)(=O)=O)CC2)n1] | N-(2-hydroxyethyl)-N-(4-{4-[4-(2-hydroxy-prop-2-yl)-indol-1-yl]-pyrimidin-2-ylamino}-cyclohexyl)-methane-sulfonamide<br>Mp 214.0-215.0° C.<br>MS (M + H) = 488 | 240 |
| | 4-{4-[4-(2-methane-sulfonyl-ethoxy)-indazol-1-yl]-pyrimidin-2-ylamino}-cyclohexanol<br>Mp 227.0-228.0° C.<br>MS (M + H) = 432 | 241 |
| 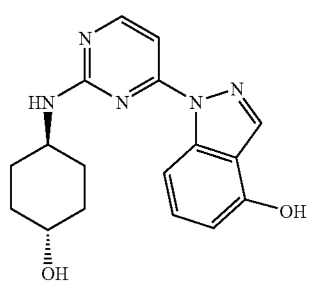 [SMILES: Oc1cccc2c1cnn2-c1ccnc(N[C@H]2CC[C@H](O)CC2)n1] | 1-[2-(4-hydroxy-cyclohexylamino)-pyrimidin-4-yl]-1H-indazol-4-ol<br>Mp >300° C.<br>MS (M + H) = 326 | 242 |
| 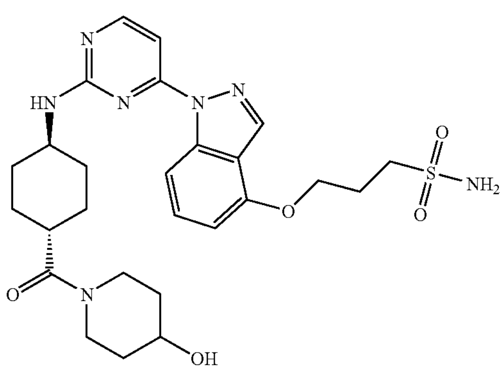 [SMILES: NS(=O)(=O)CCCOc1cccc2c1cnn2-c1ccnc(N[C@H]2CC[C@H](C(=O)N3CCC(O)CC3)CC2)n1] | 3-(1-{2-[4-(4-hydroxy-piperidine-1-carbonyl)-cyclohexylamino]-pyrimidin-4-yl}-1H-indazol-4yloxy)-propane-1-sulfonic acid amide<br>Mp 237.0-238.0° C.<br>MS (M + H) = 558 | 243 |

TABLE 1-continued

Representative compounds of Formula I.

| Structure | Name | Compound No. |
|---|---|---|
| 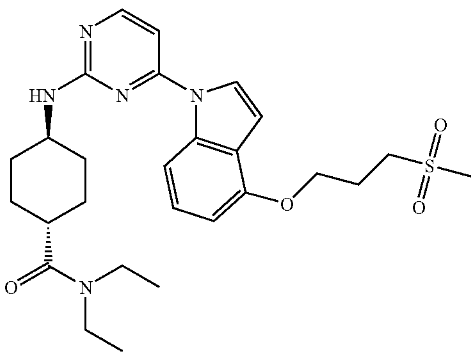 [SMILES: CCN(CC)C(=O)[C@H]1CC[C@H](Nc2nccc(-n3ccc4c(OCCCS(C)(=O)=O)cccc43)n2)CC1] | 4-{4-[4-(3-methane-sulfonyl-propoxy)-indol-1-yl]-pyrimidin-2-ylamino}-cyclohexane-carboxylic acid diethylamide<br>Mp 102.0-103.0° C.<br>MS (M + H) = 528 | 244 |
| 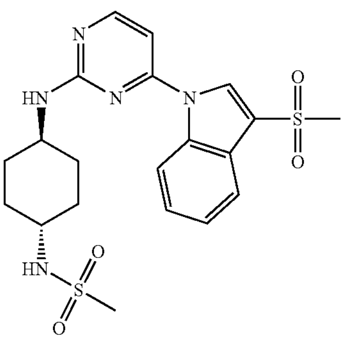 [SMILES: CS(=O)(=O)N[C@H]1CC[C@H](Nc2nccc(-n3cc(S(C)(=O)=O)c4ccccc43)n2)CC1] | N-{4-[4-(3-methane-sulfonyl-indol-1-yl)-pyrimidin-2-ylamino]-cyclohexyl}-methane-sulfonamide<br>MS (M + H) = 464 | 245 |
| 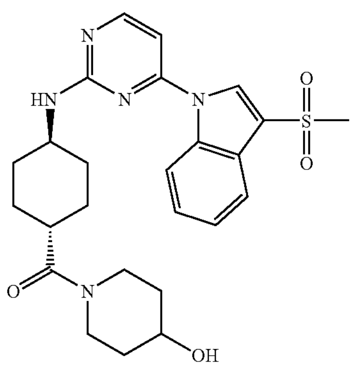 [SMILES: CS(=O)(=O)c1cn(-c2ccnc(N[C@H]3CC[C@H](C(=O)N4CCC(O)CC4)CC3)n2)c2ccccc12] | (4-hydroxy-piperidin-1-yl)-{4-[4-(3-methane-sulfonyl-indol-1-yl)-pyrimidin-2-ylamino]-cyclohexyl}-methanone<br>MS (M + H) = 498 | 246 |
| 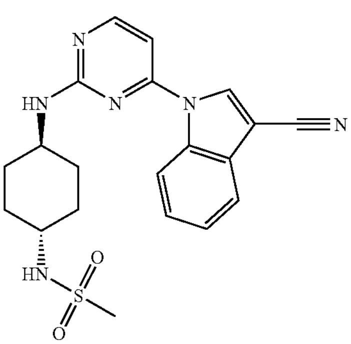 [SMILES: CS(=O)(=O)N[C@H]1CC[C@H](Nc2nccc(-n3cc(C#N)c4ccccc43)n2)CC1] | N-{4-[4-(3-cyano-indol-1-yl)-pyrimidin-2-ylamino]-cyclohexyl}-methanesulfonamide<br>Mp >300° C.<br>MS (M + H) = 411 | 247 |

TABLE 1-continued

Representative compounds of Formula I.

| Structure | Name | Compound No. |
|---|---|---|
| 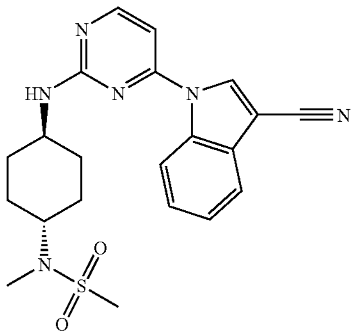 [SMILES: CN([C@H]1CC[C@H](Nc2nccc(-n3cc(C#N)c4ccccc43)n2)CC1)S(C)(=O)=O] | N-{4-[4-(3-cyano-indol-1-yl)-pyrimidin-2-ylamino]-cyclohexyl}-N-methyl-methane-sulfonamide<br>Mp 289.0-290.0° C.<br>MS (M + H) = 425 | 248 |
| 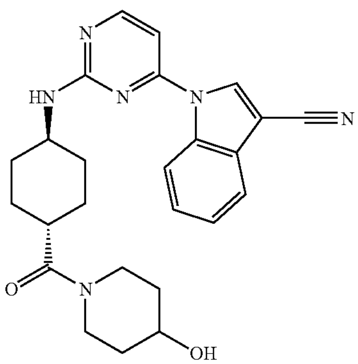 [SMILES: N#Cc1cn(-c2ccnc(N[C@H]3CC[C@H](C(=O)N4CCC(O)CC4)CC3)n2)c2ccccc12] | 1-{2-[4-(4-hydroxy-piperidine-1-carbonyl)-cyclohexylamino]-pyrimidin-4-yl}-1H-indol-3-carbonitrile<br>Mp 259.0-260.0° C.<br>MS (M + H) = 445 | 249 |
| 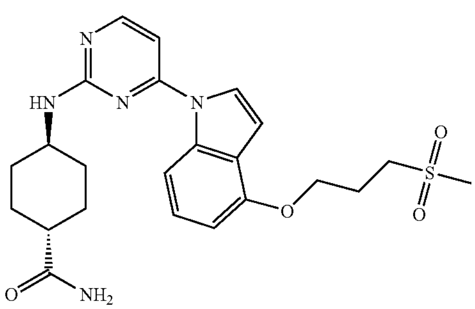 [SMILES: CS(=O)(=O)CCCOc1cccc2c1ccn2-c1ccnc(N[C@H]2CC[C@H](C(N)=O)CC2)n1] | 4-{4-[4-(3-methane-sulfonyl-propoxy)-indol-1-yl]-pyrimidin-2-ylamino}-cyclohexane-carboxylic acid amide<br>Mp 249.0-250.0° C.<br>MS (M + H) = 472 | 250 |
| 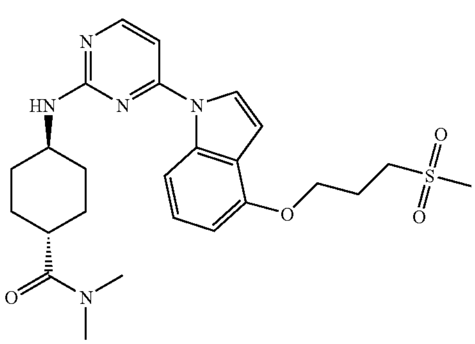 [SMILES: CN(C)C(=O)[C@H]1CC[C@H](Nc2nccc(-n3ccc4c(OCCCS(C)(=O)=O)cccc43)n2)CC1] | 4-{4-[4-(3-methane-sulfonyl-propoxy)-indol-1-yl]-pyrimidin-2-ylamino}-cyclohexane-carboxylic acid dimethylamide<br>Mp 169.0-170.0° C.<br>MS (M + H) = 500 | 251 |

TABLE 1-continued

Representative compounds of Formula I.

| Structure | Name | Compound No. |
|---|---|---|
| 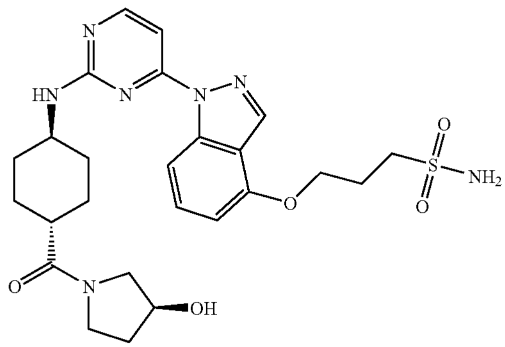 [SMILES: NS(=O)(=O)CCCOc1cccc2c1cnn2-c1ccnc(N[C@H]2CC[C@H](C(=O)N3CC[C@H](O)C3)CC2)n1] | 3-(1-{2-[4-(3-hydroxy-pyrrolidine-1-carbonyl)-cyclohexylamino]-pyrimidin-4-yl}-1H-indazol-4-yloxy)-propane-1-sulfonic acid amide<br>Mp 161.0-162.0° C.<br>MS (M + H) = 544 | 252 |
| 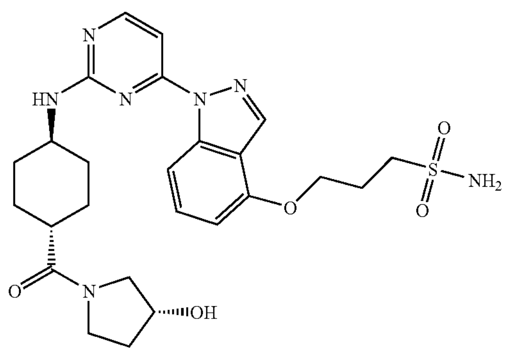 [SMILES: NS(=O)(=O)CCCOc1cccc2c1cnn2-c1ccnc(N[C@H]2CC[C@H](C(=O)N3CC[C@@H](O)C3)CC2)n1] | 3-(1-{2-[4-(3-hydroxy-pyrrolidine-1-carbonyl)-cyclohexylamino]-pyrimidin-4-yl}-1H-indazol-4-yloxy)-propane-1-sulfonic acid amide<br>Mp 178.0-179.0° C.<br>MS (M + H) = 544 | 253 |
| 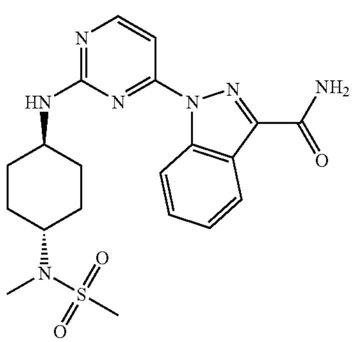 [SMILES: CN([C@H]1CC[C@H](Nc2nccc(-n3nc(C(N)=O)c4ccccc43)n2)CC1)S(C)(=O)=O] | 1-{2-[4-methane-sulfonyl-methyl-amino]-cyclohexylamino}-pyrimidin-4-yl}-1H-indol-3-carboxylic acid amide<br>Mp 234.0-235.0° C.<br>MS (M + H) = 443 | 254 |
| 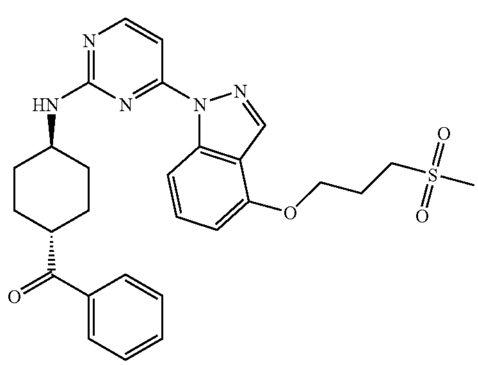 [SMILES: CS(=O)(=O)CCCOc1cccc2c1cnn2-c1ccnc(N[C@H]2CC[C@H](C(=O)c3ccccc3)CC2)n1] | (4-{4-[4-(3-methane-sulfonyl-propoxy)-indazol-1-yl]-pyrimidin-2-ylamino}-cyclohexyl)-phenyl-methanone<br>Mp 174.5-175.5° C.<br>MS (M + H) = 534 | 255 |

TABLE 1-continued

Representative compounds of Formula I.

| Structure | Name | Compound No. |
|---|---|---|
|  | (4-{4-[4-(3-methane-sulfonyl-propoxy)-indazol-1-yl]-pyrimidin-2-ylamino}-cyclohexyl)-pyrid-2-yl-methanone<br>Mp 200.0-201.0° C.<br>MS (M + H) = 535 | 256 |
|  | 1-[2-(4-cyclopropane-sulfonylamino-cyclo-hexylamino)-pyrimidin-4-yl]-1H-indole-4-carboxylic acid methyl ester<br>Mp 250.0-251.0° C.<br>MS (M + H) = 470 | 257 |
|  | Pyrrolidine-1-sulfonic acid (4-{4-[4-(2-hydroxyprop-2-yl)-indol-1-yl]-pyrimidin-2-ylamino}-cyclohexyl)-amide<br>Mp 178.0-179.0° C.<br>MS (M + H) = 499 | 258 |
|  | Morpholine-4-sulfonic acid (4-{4-[4-(2-hydroxyprop-2-yl)-indol-1-yl]-pyrimidin-2-ylamino}-cyclohexyl)-amide<br>Mp >300° C.<br>MS (M + H) = 515 | 259 |

TABLE 1-continued

Representative compounds of Formula I.

| Structure | Name | Compound No. |
|---|---|---|
| 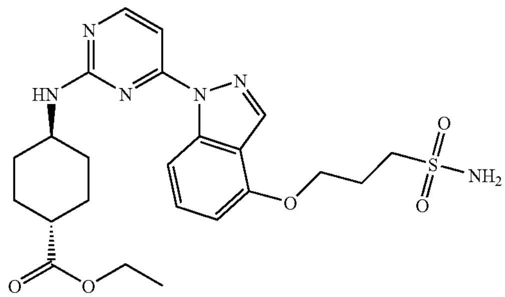 [SMILES: CCOC(=O)[C@H]1CC[C@H](Nc2nccc(-n3ncc4c(OCCCS(N)(=O)=O)cccc43)n2)CC1] | 4-{4-[4-(3-sulfamoyl-propoxy)-indazol-1-yl]-pyrimidin-2-ylamino}-cyclohexanecarboxylic acid ethyl ester<br>Mp 166.0-167.0° C.<br>MS (M + H) = 503 | 260 |
| 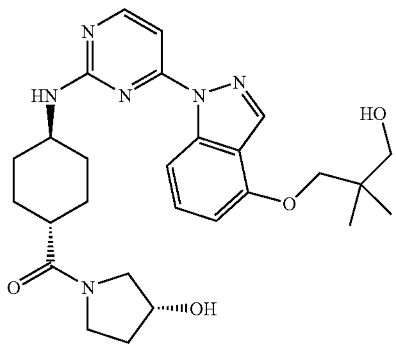 [SMILES: CC(C)(CO)COc1cccc2c1cnn2-c1ccnc(N[C@H]2CC[C@H](C(=O)N3CC[C@@H](O)C3)CC2)n1] | (4-{4-[4-(3-hydroxy-2,2-dimethyl-propoxy)-indazol-1-yl]-pyrimidin-2-ylamino}-cyclohexyl)-(3-hydroxy-pyrrolidin-1-yl)-methanone<br>Mp 214.0-215.0° C.<br>MS (M + H) = 509 | 261 |
| 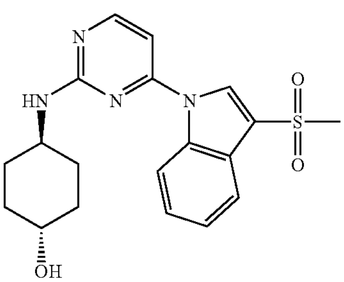 [SMILES: CS(=O)(=O)c1cn(-c2ccnc(N[C@H]3CC[C@H](O)CC3)n2)c2ccccc12] | 4-[4-(3-methane-sulfonyl-indol-1-yl)-pyrimidin-2-ylamino]-cyclohexanol<br>MS (M + H) = 387 | 262 |
| 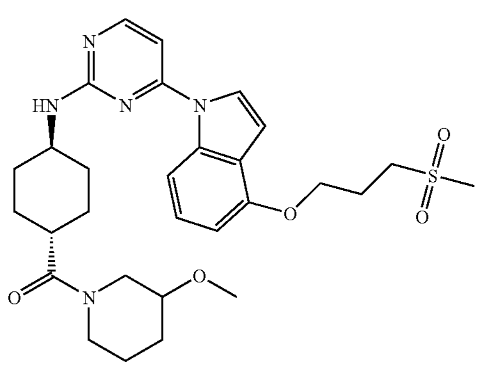 [SMILES: COC1CCCN(C(=O)[C@H]2CC[C@H](Nc3nccc(-n4ccc5c(OCCCS(C)(=O)=O)cccc54)n3)CC2)C1] | (4-{4-[4-(3-methane-sulfonyl-propoxy)-indol-1-yl]-pyrimidin-2-ylamino}-cyclohexyl)-(3-methoxy-piperidin-1-yl)-methanone<br>Mp 121.0-122.0° C.<br>MS (M + H) = 570 | 263 |

TABLE 1-continued

Representative compounds of Formula I.

| Structure | Name | Compound No. |
|---|---|---|
| 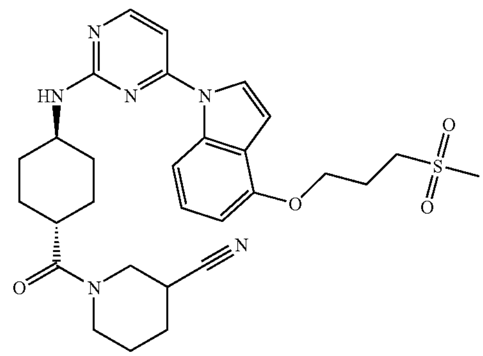 [SMILES: CS(=O)(=O)CCCOc1cccc2c1ccn2-c1ccnc(N[C@H]2CC[C@H](C(=O)N3CCCC(C#N)C3)CC2)n1] | 1-(4-{4-[4-(3-methane-sulfonyl-propoxy)-indol-1-yl]-pyrimidin-2-ylamino}-cyclohexane-carbonyl)-piperidine-3-carbonitrile<br>Mp 132.0-133.0° C.<br>MS (M + H) = 565 | 264 |
| 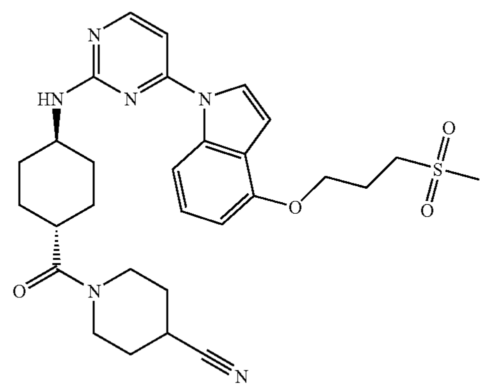 [SMILES: CS(=O)(=O)CCCOc1cccc2c1ccn2-c1ccnc(N[C@H]2CC[C@H](C(=O)N3CCC(C#N)CC3)CC2)n1] | 1-(4-{4-[4-(3-methane-sulfonyl-propoxy)-indol-1-yl]-pyrimidin-2-ylamino}-cyclohexane-carbonyl)-piperidine-4-carbonitrile<br>Mp 150.5-156.5° C.<br>MS (M + H) = 565 | 265 |
| 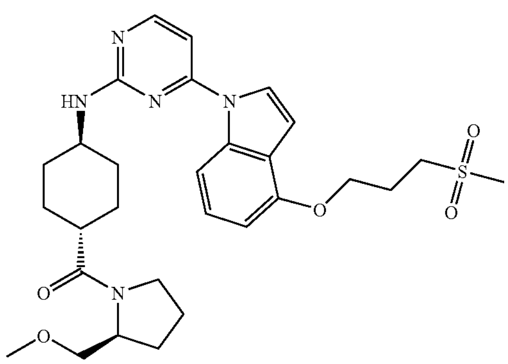 | (4-{4-[4-(3-methane-sulfonyl-propoxy)-indol-1-yl]-pyrimidin-2-ylamino}-cyclohexyl)-(2-methoxymethyl-pyrrolidin-1-yl)-methanone<br>Mp 92.0-93.0° C.<br>MS (M + H) = 570 | 266 |
| 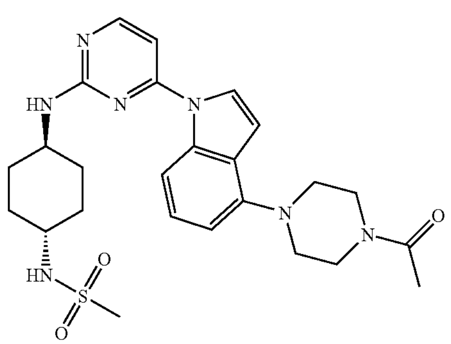 [SMILES: CC(=O)N1CCN(c2cccc3c2ccn3-c2ccnc(N[C@H]3CC[C@H](NS(C)(=O)=O)CC3)n2)CC1] | N-(4-{4-[4-(4-acetyl-piperazin-1-yl)-indol-1-yl]-pyrimidin-2-yl-amino}-cyclohexyl)-methanesulfonamide<br>Mp 268.0-269.0° C.<br>MS (M + H) = 512 | 267 |

TABLE 1-continued

Representative compounds of Formula I.

| Structure | Name | Compound No. |
|---|---|---|
|  | (4-aminomethyl-cyclo-hexyl)-{4-[4-(4,4,4-tri fluorobutoxy)-indol-1-yl]-pyrimidin-2-yl}-amine hydrochloride<br>Mp 274.0-275.0° C.<br>MS (M + H) = 448 | 268 |
|  | N-{4-[4-(4,4,4-trifluoro-butoxy)-indol-1-yl]-pyrimidin-2-yl-amino}-cyclohexylmethyl-acetamide<br>Mp 196.2-196.7° C.<br>MS (M + H) = 490 | 269 |
|  | 3-(1-{2-[4-(3-hydroxy-poyrrolidine-1-carbonyl)-cyclohexylamino]-pyrimidin-4-yl}-1H-indazol-4-yloxy)-propane-1-sulfonic acid methyl amide<br>MS (M + H) = 558 | 270 |
|  | 3-(1-{2-[4-(2,5-di-methyl-pyrrolidine-1-carbonyl)-cyclohexyl-amino]-pyrimidin-4-yl}-1H-indazol4-yloxy)-propane-1-sulfonic acid amide<br>Mp 230.0-231.0° C.<br>MS (M + H) = 556 | 271 |

TABLE 1-continued

Representative compounds of Formula I.

| Structure | Name | Compound No. |
|---|---|---|
| 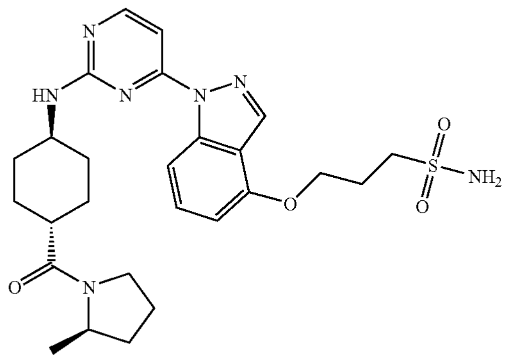 [SMILES: C[C@@H]1CCCN1C(=O)[C@H]1CC[C@H](Nc2nccc(-n3ncc4c(OCCCS(N)(=O)=O)cccc43)n2)CC1] | 3-(1-{2-[4-(2-methyl-pyrrolidine-1-carbonyl)-cyclohexylamino]-pyrimidin-4-yl}-1H-indazol4-yloxy)-propane-1-sulfonic acid amide<br>Mp 230.0-231.0° C.<br>MS (M + H) = 542 | 272 |
| 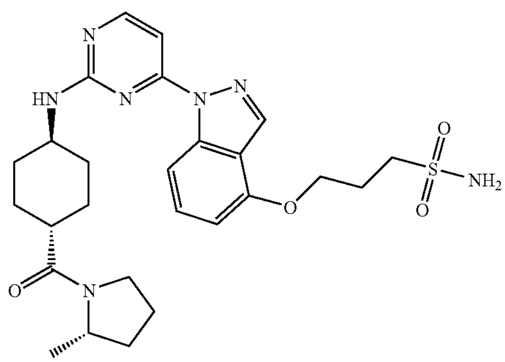 [SMILES: C[C@H]1CCCN1C(=O)[C@H]1CC[C@H](Nc2nccc(-n3ncc4c(OCCCS(N)(=O)=O)cccc43)n2)CC1] | 3-(1-{2-[4-(2-methyl-pyrrolidine-1-carbonyl)-cyclohexylamino]-pyrimidin-4-yl}-1H-indazol-4-yloxy)-propane-1-sulfonic acid amide<br>Mp 230.0-231.0° C.<br>MS (M + H) = 542 | 273 |
| 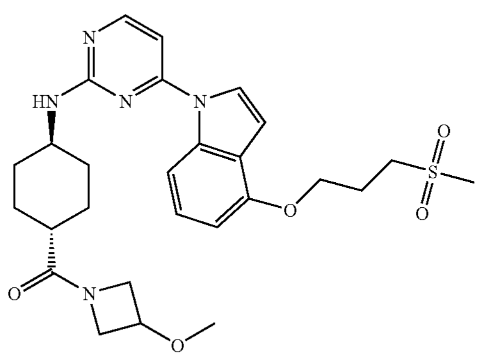 [SMILES: COC1CN(C(=O)[C@H]2CC[C@H](Nc3nccc(-n4ccc5c(OCCCS(C)(=O)=O)cccc54)n3)CC2)C1] | (4-{4-[4-(3-methane-sulfonyl-propoxy)-indol-1-yl]-pyrimidin-2-ylamino}-cyclohexyl)-(3-methoxy-azetidin-1-yl)-methanone<br>Mp 162.0-163.0° C.<br>MS (M + H) = 542 | 274 |
| 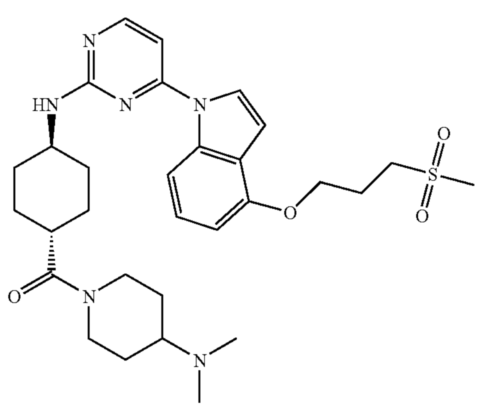 [SMILES: CN(C)C1CCN(C(=O)[C@H]2CC[C@H](Nc3nccc(-n4ccc5c(OCCCS(C)(=O)=O)cccc54)n3)CC2)CC1] | (4-dimethylamino-piperidin-1-yl)-(4-{4-[4-(3-methanesulfonyl-propoxy)indol-1-yl]-pyrimidin-2-ylamino}-cyclohexyl)-methanone<br>Mp 178.9-180.6° C.<br>MS (M + H) = 583 | 275 |

TABLE 1-continued

Representative compounds of Formula I.

| Structure | Name | Compound No. |
|---|---|---|
| 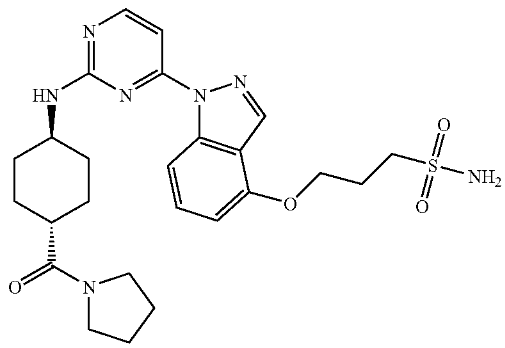 [SMILES: NS(=O)(=O)CCCOc1cccc2c1cnn2-c1ccnc(N[C@H]2CC[C@H](C(=O)N3CCCC3)CC2)n1] | 3-(1-{2-[4-(pyrrolidino-1-carbonyl-cyclohexyl-amino)-pyrimidin-4-yl]-1H-indazol-4-yloxy}-propane-1-sulfonic acid amide<br>Mp 249.0-250.0° C.<br>MS (M + H) = 528 | 276 |
| 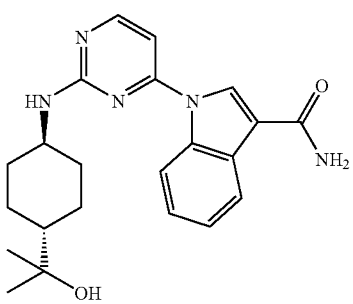 [SMILES: CC(C)(O)[C@H]1CC[C@H](Nc2nccc(-n3cc(C(N)=O)c4ccccc43)n2)CC1] | 1-{2-[4-(2-hydroxy-prop-2-yl)-cyclohexyl-amino]-pyrimidin-4-yl}-1H-indole-3-carboxylic acid amide<br>Mp 222.0-223.0° C.<br>MS (M + H) = 394 | 277 |
| 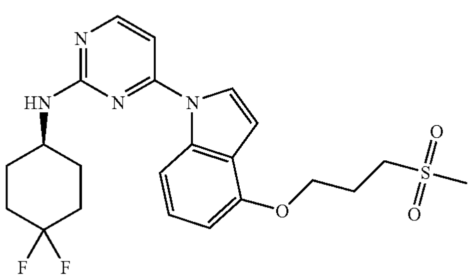 | (4,4-difluorocyclo-hexyl)-{4-[4-(3-methane-sulfonyl-propoxy)-indol-1-yl]-pyrimidin-2-yl}-amine<br>Mp 200.0-201.0° C.<br>MS (M + H) = 465 | 278 |
| 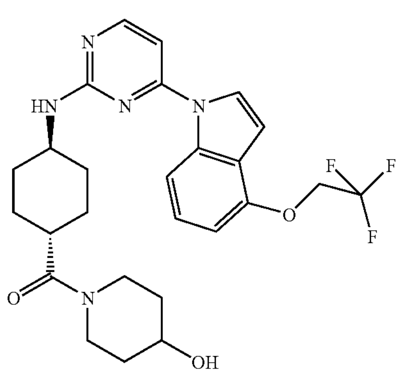 [SMILES: O=C([C@H]1CC[C@H](Nc2nccc(-n3ccc4c(OCC(F)(F)F)cccc43)n2)CC1)N1CCC(O)CC1] | (4-hydroxy-piperidin-1-yl)-(4-{4-[4-(2,2,2-trifluoroethoxy)-indol-1-yl]-pyrimidin-2-yl-amino}-cyclohexyl)-methanone<br>Mp 140.7-143.3° C.<br>MS (M + H) = 518 | 279 |

TABLE 1-continued

Representative compounds of Formula I.

| Structure | Name | Compound No. |
|---|---|---|
| 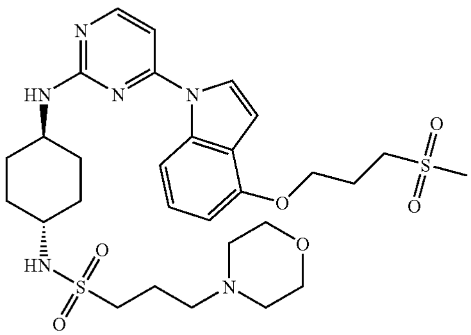 [SMILES: CS(=O)(=O)CCCOc1cccc2c1ccn2-c1ccnc(N[C@H]2CC[C@H](NS(=O)(=O)CCCN3CCOCC3)CC2)n1] | 3-morpholin-4-yl-propane-1-sulfonic acid (4-{4-[4-(3-methane-sulfonyl-propoxy)-indol-1-yl]-pyrimidin-2-yl-amino}-cyclohexyl)-amide<br>Mp 174.0-179.3° C.<br>MS (M + H) = 635 | 280 |
| 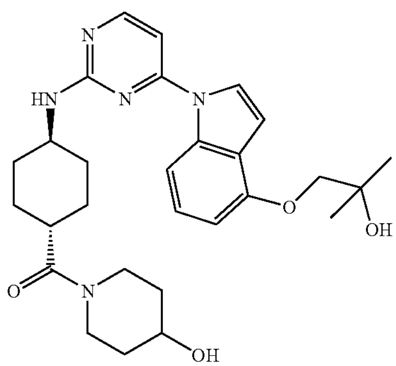 [SMILES: CC(C)(O)COc1cccc2c1ccn2-c1ccnc(N[C@H]2CC[C@H](C(=O)N3CCC(O)CC3)CC2)n1] | (4-{4-[4-(2-hydroxy-2-methyl-propoxy)-indol-1-yl]-pyrimidin-2-yl-amino}-cyclohexyl)-(4-hydroxy-piperidin-1-yl)-methanone<br>Mp 174.0-176.9° C.<br>MS (M + H) = 508 | 281 |
| 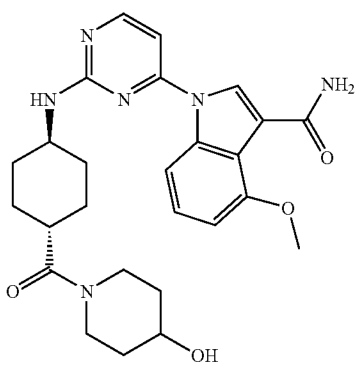 [SMILES: COc1cccc2c1c(C(N)=O)cn2-c1ccnc(N[C@H]2CC[C@H](C(=O)N3CCC(O)CC3)CC2)n1] | 1-{2-[4-(4-hydroxy-piperidine-1-carbonyl)-cyclohexylamino]-pyrimidin-4-yl}-4-methoxy-1H-indole-3-carboxylic acid amide<br>Mp 278.0-280.0° C.<br>MS (M + H) = 493 | 282 |
| 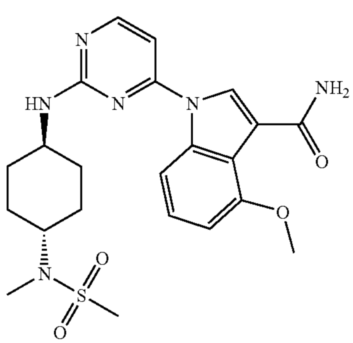 [SMILES: COc1cccc2c1c(C(N)=O)cn2-c1ccnc(N[C@H]2CC[C@H](N(C)S(C)(=O)=O)CC2)n1] | 1-{2-[4-(methane-sulfonyl-methylamino)-cyclohexylamino]-pyrimidin-4-yl}-4-methoxy-1H-indole-3-carboxylic acid amide<br>Mp 285.0-287.0° C.<br>MS (M + H) = 473 | 283 |

TABLE 1-continued

Representative compounds of Formula I.

| Structure | Name | Compound No. |
|---|---|---|
| 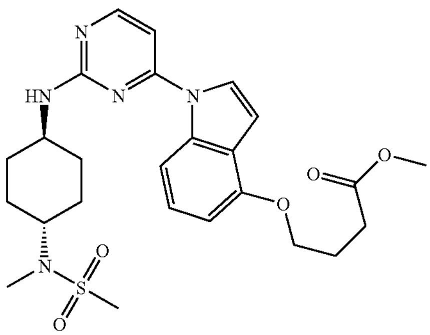 [SMILES: COC(=O)CCCOc1cccc2c1ccn2-c1ccnc(N[C@H]2CC[C@H](N(C)S(C)(=O)=O)CC2)n1] | 4-(1-{2-[4-(methane-sulfonyl-methylamino)-cyclohexylamino]-pyrimidin-4-yl}-1H-indol-4-yloxy)-butyric acid methyl ester<br>Mp 145.0-146.0° C.<br>MS (M + H) = 516 | 284 |
| 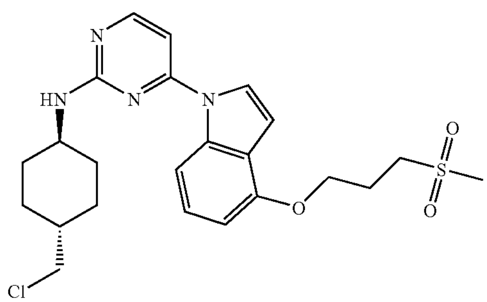 [SMILES: CS(=O)(=O)CCCOc1cccc2c1ccn2-c1ccnc(N[C@H]2CC[C@H](CCl)CC2)n1] | (4-chloromethyl-cyclo-hexyl)-{4-[4-(3-methane-sulfonyl-propoxy)-indol-1-yl]-pyrimidin-2-yl}-amine<br>Mp 152.0-155.0° C.<br>MS (M + H) = 477 | 285 |
| 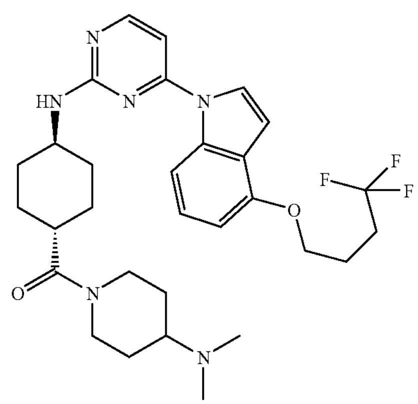 [SMILES: CN(C)C1CCN(C(=O)[C@H]2CC[C@H](Nc3nccc(-n4ccc5c(OCCCC(F)(F)F)cccc54)n3)CC2)CC1] | (4-dimethylamino-piperidin-1-yl)-(4-{4-[4-(4,4,4-trifluorobutoxy)-indol-1-yl]-pyrimidin-2-ylamino}-cyclohexyl)-methanone<br>Mp 179.0-180.0° C.<br>MS (M + H) = 573 | 286 |
| 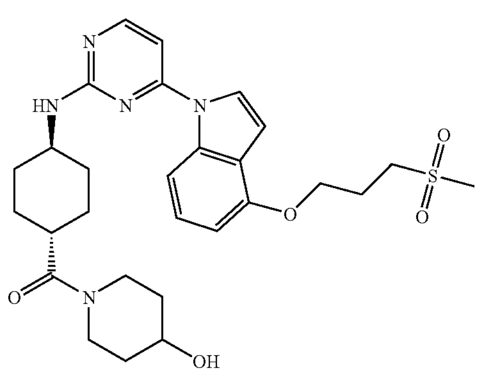 | (4-hydroxy-piperidin-1-yl)-(4-{4-[4-(3-methane-sulfonyl-propoxy)-indol-1-yl]-pyrimidin-2-ylamino}-cyclohexyl)-methanone<br>Mp 144.3-145.8° C.<br>MS (M + H) = 542 | 287 |

TABLE 1-continued

Representative compounds of Formula I.

| Structure | Name | Compound No. |
|---|---|---|
| 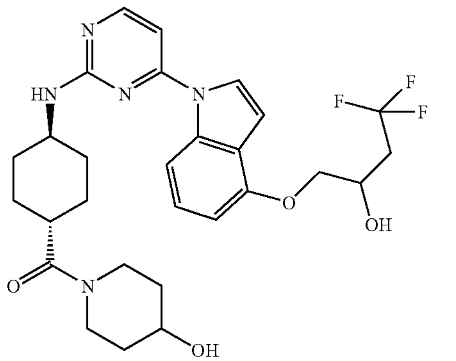 [SMILES: O=C([C@H]1CC[C@H](Nc2nccc(-n3ccc4c(OCC(O)CC(F)(F)F)cccc43)n2)CC1)N1CCC(O)CC1] | (4-hydroxy-piperidin-1-yl)-(4-{4-[4-(4,4,4-trifluoro-2-hydroxy-butoxy-indol-1-yl]-pyrimidin-2-ylamino}-cyclohexyl)-methanone<br>Mp 215.0-215.5° C.<br>MS (M + H) = 562 | 288 |
| 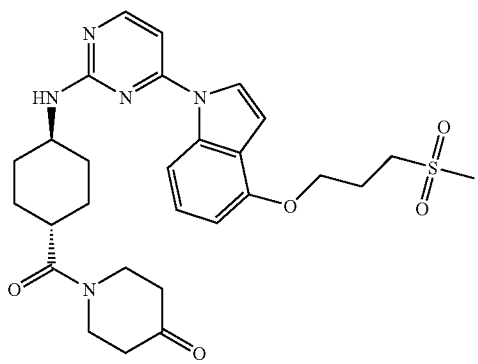 [SMILES: CS(=O)(=O)CCCOc1cccc2c1ccn2-c1ccnc(N[C@H]2CC[C@H](C(=O)N3CCC(=O)CC3)CC2)n1] | 1-(4-{4-[4-(3-methane-sulfonyl-propoxy)-indol-1-yl]-pyrimidin-2-ylamino}-cyclohexane-carbonyl)-piperidin-4-one<br>Mp 155.0-158.2° C.<br>MS (M + H) = 554 | 289 |
| 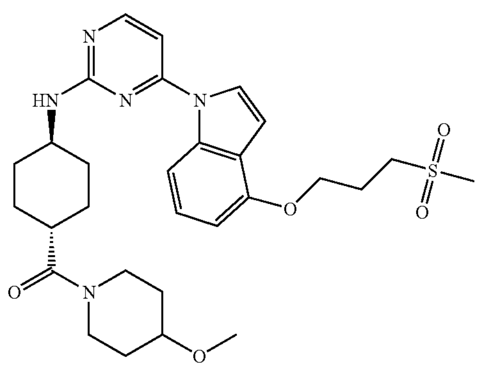 [SMILES: COC1CCN(C(=O)[C@H]2CC[C@H](Nc3nccc(-n4ccc5c(OCCCS(C)(=O)=O)cccc54)n3)CC2)CC1] | (4-{4-[4-(3-methane-sulfonyl-propoxy)-indol-1-yl]-pyrimidin-2-ylamino}-cyclohexyl)-(4-methoxy-piperidin-1-yl)-methanone<br>Mp 165.5-166.9° C.<br>MS (M + H) = 570 | 290 |
| 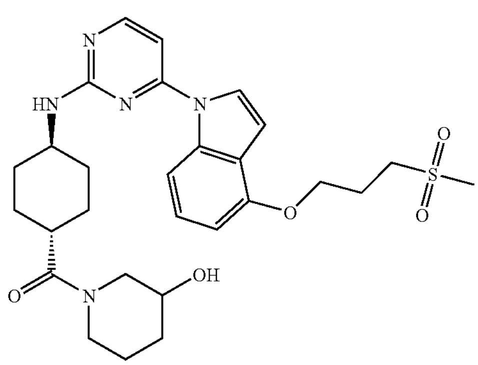 [SMILES: CS(=O)(=O)CCCOc1cccc2c1ccn2-c1ccnc(N[C@H]2CC[C@H](C(=O)N3CCCC(O)C3)CC2)n1] | (3-hydroxy-piperidin-1-yl)-(4-{4-[4-(3-methane-sulfonyl-propoxy)-indol-1-yl]-pyrimidin-2-ylamino}-cyclohexyl)-methanone<br>Mp 167.3-170.5° C.<br>MS (M + H) = 556 | 291 |

TABLE 1-continued

Representative compounds of Formula I.

| Structure | Name | Compound No. |
|---|---|---|
| | (4-hydroxy-4-methyl-piperidin-1-yl)-(4-{4-[4-(3-methanesulfonyl-propoxy)-indol-1-yl]-pyrimidin-2-ylamino}-cyclohexyl)-methanone<br>Mp 132.6-137.7° C.<br>MS (M + H) = 570 | 292 |
| | (4-{4-[4-(3-methane-sulfonyl-propoxy)-indol-1-yl]-pyrimidin-2-ylamino}-cyclohexyl)-(4-methylamino-piperidin-1-yl)-methanone<br>Mp 187.5-189.1° C.<br>MS (M + H) = 569 | 293 |
| | Thiophene-2-sulfonic-acid (4-{4-[4-(3-methane-sulfonyl-propoxy)-indol-1-yl]-pyrimidin-2-ylamino}-cyclohexyl)-amide<br>Mp 226.0-227.0° C.<br>MS (M + H) = 590 | 294 |
| | 1-{2-[4-(4-dimethyl-amino-piperidine-1-carbonyl)-cyclohexyl-amino]-pyrimidin-4-yl}-1H-indole-3-carboxylic acid amide<br>Mp 219.0-221.0° C.<br>MS (M + H) = 490 | 295 |

TABLE 1-continued

Representative compounds of Formula I.

| Structure | Name | Compound No. |
|---|---|---|
| 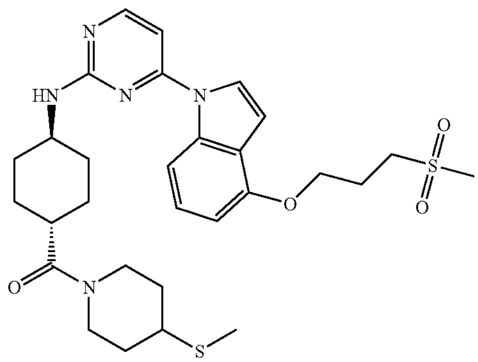 [SMILES: CSC1CCN(C(=O)[C@H]2CC[C@H](Nc3nccc(-n4ccc5c(OCCCS(C)(=O)=O)cccc54)n3)CC2)CC1] | (4-{4-[4-(3-methane-sulfonyl-propoxy)-indol-1-yl]-pyrimidin-2-ylamino}-cyclohexyl)-(4-methylsulfanyl-piperidin-2-yl)-methanone<br>Mp 140-145° C.<br>MS (M + H) = 586 | 296 |
| 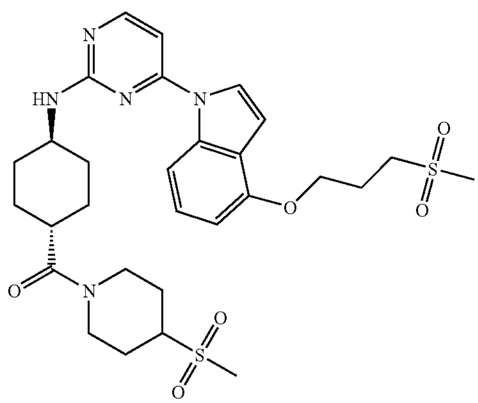 [SMILES: CS(=O)(=O)CCCOc1cccc2c1ccn2-c1ccnc(N[C@H]2CC[C@H](C(=O)N3CCC(S(C)(=O)=O)CC3)CC2)n1] | (4-methanesulfonyl-piperidin-1-yl)-(4-{4-[4-(3-methanesulfonyl-propoxy)-indol-1-yl]-pyrimidin-2-ylamino}-cyclohexyl)-methanone<br>Mp 215-219° C.<br>MS (M + H) = 618 | 297 |
| 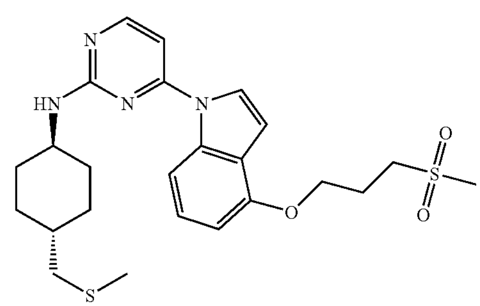 [SMILES: CSC[C@H]1CC[C@H](Nc2nccc(-n3ccc4c(OCCCS(C)(=O)=O)cccc43)n2)CC1] | {4-[4-(3-methane-sulfonyl-propoxy)-indol-1-yl]-pyrimidin-2-yl}-(4-methylsulfanylmethyl-cyclohexyl)-amine<br>Mp 158.7-159.6° C.<br>MS (M + H) = 489 | 298 |
| 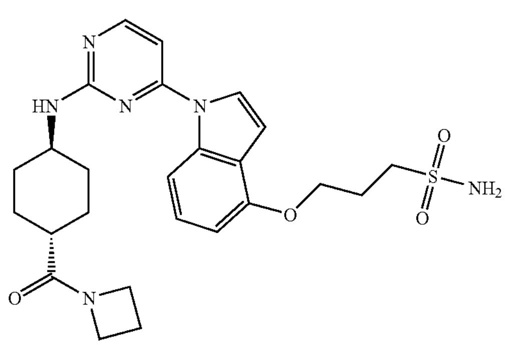 [SMILES: NS(=O)(=O)CCCOc1cccc2c1ccn2-c1ccnc(N[C@H]2CC[C@H](C(=O)N3CCC3)CC2)n1] | 3-(1-{2-[4-(azetidin-1-carbonyl)-cyclohexyl-amino]-pyrimidin-4-yl}-1H-indol-4-yloxy)-propane-1-sulfonic acid amide<br>Mp 218.4-220.9° C.<br>MS (M + H) = 513 | 299 |

TABLE 1-continued

Representative compounds of Formula I.

| Structure | Name | Compound No. |
|---|---|---|
| 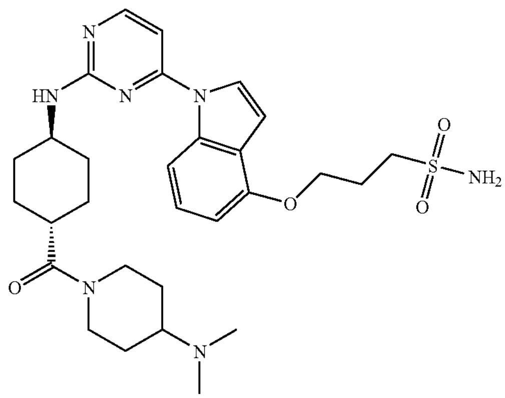 [SMILES: CN(C)C1CCN(C(=O)[C@H]2CC[C@H](Nc3nccc(-n4ccc5c(OCCCS(N)(=O)=O)cccc54)n3)CC2)CC1] | 3-(1-{2-[4-(4-dimethyl-amino-piperidine-1-carbonyl)-cyclohexyl-amino]-pyrimidin-4-yl}-1H-indol-4-yloxy)-propane-1-sulfonic acid amide<br>Mp 135.7-142.7° C.<br>MS (M + H) = 584 | 300 |
| 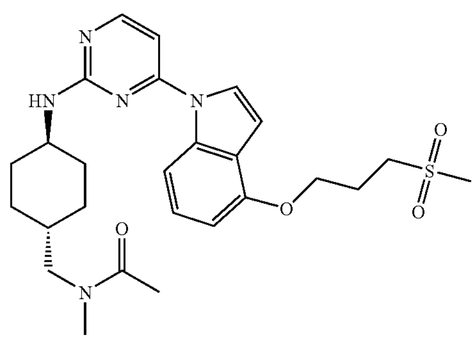 [SMILES: CC(=O)N(C)C[C@H]1CC[C@H](Nc2nccc(-n3ccc4c(OCCCS(C)(=O)=O)cccc43)n2)CC1] | N-(4-{4-[4-(3-methane-sulfonyl-propoxy)-indol-1-yl]-pyrimidin-2-ylamino}-cyclohexyl-methyl)-N-methyl-acetamide<br>MS (M + H) = 514 | 301 |
| 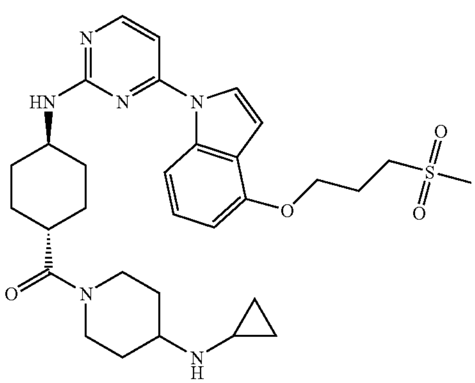 [SMILES: CS(=O)(=O)CCCOc1cccc2c1ccn2-c1ccnc(N[C@H]2CC[C@H](C(=O)N3CCC(NC4CC4)CC3)CC2)n1] | (4-cyclopropylamino-piperidin-1-yl)-(4-{4-[4-(3-methanesulfonyl-propoxy)-indol-1-yl]-pyrimidin-2-ylamino}-cyclohexyl)-methanone<br>Mp 196.3-197.9° C.<br>MS (M + H) = 595 | 302 |
| 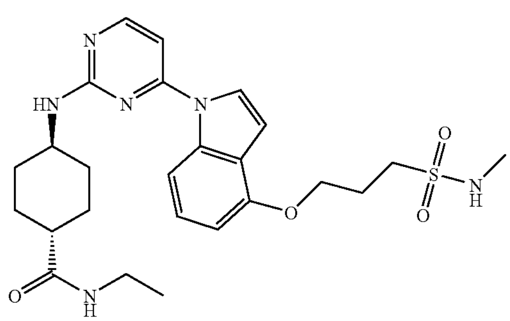 [SMILES: CCNC(=O)[C@H]1CC[C@H](Nc2nccc(-n3ccc4c(OCCCS(=O)(=O)NC)cccc43)n2)CC1] | 4-{4-[4-(3-methane-sulfamoyl-propoxy)-indol-1-yl]-pyrimidin-2-ylamino}-cyclohexane-carboxylic acid ethyl-amide<br>Mp 201.7-203.2° C.<br>MS (M + H) = 515 | 303 |

TABLE 1-continued

Representative compounds of Formula I.

| Structure | Name | Compound No. |
|---|---|---|
| 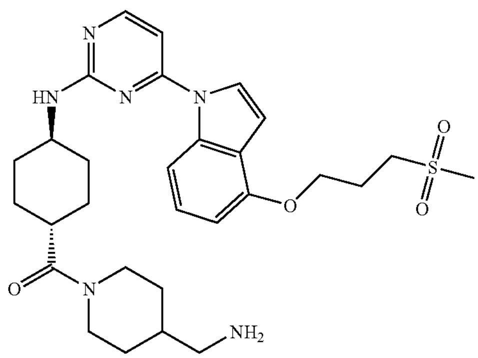 [SMILES: CS(=O)(=O)CCCOc1cccc2c1ccn2-c1ccnc(N[C@H]2CC[C@H](C(=O)N3CCC(CN)CC3)CC2)n1] | (4-aminomethyl-piperidin-1-yl)-(4-{4-[4-(3-methanesulfonyl-propoxy)-indol-1-yl]-pyrimidin-2-ylamino}-cyclohexyl)-methanone<br>Mp 124.1-126.1° C.<br>MS (M + H) = 569 | 304 |
| 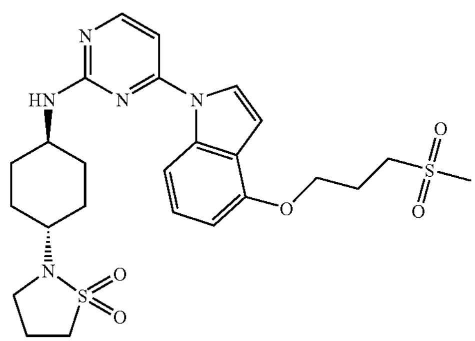 [SMILES: CS(=O)(=O)CCCOc1cccc2c1ccn2-c1ccnc(N[C@H]2CC[C@H](N3CCCS3(=O)=O)CC2)n1] | [4-(1,1-dioxo-isothiazolidin-2-yl)-cyclohexyl]-{4-[4-(3-methane-sulfonyl-propoxy)-indol-1-yl]-pyrimidin-2-yl}-amine<br>Mp 164.1-172.5° C.<br>MS (M + H) = 548 | 305 |
| 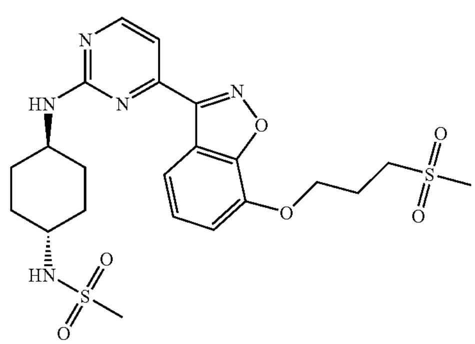 [SMILES: CS(=O)(=O)CCCOc1cccc2c(-c3ccnc(N[C@H]4CC[C@H](NS(C)(=O)=O)CC4)n3)noc12] | N-(4-{4-[7-(3-methane-sulfonyl-propoxy)-benzo[d]isoxazol-3-yl]-pyrimidin-2-ylamino}-cyclohexyl)-methane-sulfonamide<br>Mp 225.0-226.0° C.<br>MS (M + H) = 524 | 306 |
| 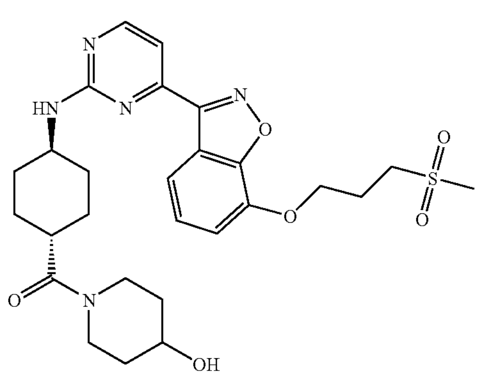 [SMILES: CS(=O)(=O)CCCOc1cccc2c(-c3ccnc(N[C@H]4CC[C@H](C(=O)N5CCC(O)CC5)CC4)n3)noc12] | (4-hydroxy-piperidin-1-yl)-(4-{4-[7-(3-methane-sulfonyl-propoxy)-benzo[d]isoxazol-3-yl]-pyrimidin-2-ylamino}-cyclohexyl)-methanone<br>Mp 186.0-187.0° C.<br>MS (M + H) = 558 | 307 |

TABLE 1-continued

Representative compounds of Formula I.

| Structure | Name | Compound No. |
|---|---|---|
|  | (4-hydroxy-piperidin-1-yl)-(4-{4-[7-(3-methane-sulfonyl-propoxy)-1H-indazol-3-yl]-pyrimidin-2-ylamino}-cyclohexyl)-methanone<br>MS (M + H) = 557 | 308 |
|  | (3-hydroxy-pyrrolidin-1-yl)-(4-{4-[7-(3-methane-sulfonyl-propoxy)-benzo[d]isoxazol-3-yl]-pyrimidin-2-ylamino}-cyclohexyl)-methanone<br>Mp 224.0-225.0° C.<br>MS (M + H) = 544 | 309 |
|  | N-(4-{4-[7-(3-methane-sulfonyl-propoxy)-benzo[d]isoxazol-3-yl]-pyrimidin-2-ylamino}-cyclohexyl)-N-methyl-methanesulfonamide<br>Mp 213.5-214.2° C.<br>MS (M + H) = 538 | 310 |
|  | 2-(1-{2-[4-(4-hydroxy-piperidine-1-carbonyl)-cyclohexylamino]-pyrimidin-4-yl}-1H-indol-4-yl)-2-methyl-propionitrile<br>Mp 214.0-215.0° C.<br>MS (M + H) = 487 | 311 |

TABLE 1-continued

Representative compounds of Formula I.

| Structure | Name | Compound No. |
|---|---|---|
| 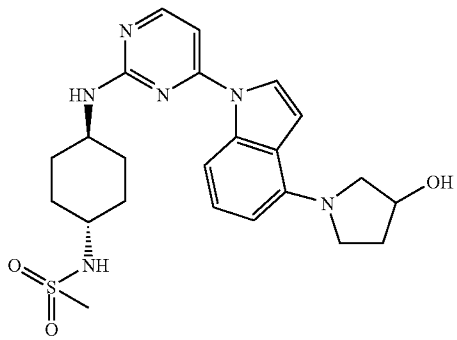 [SMILES: CS(=O)(=O)N[C@H]1CC[C@H](Nc2nccc(-n3ccc4c(N5CCC(O)C5)cccc43)n2)CC1] | N-(4-{4-[4-(3-hydroxy-pyrrolidin-1-yl)-indol-1-yl]-pyrimidin-2-yl-amino}-cyclohexyl)-methanesulfonamide<br>Mp 190.1-200.5° C.<br>MS (M + H) = 471 | 312 |
| 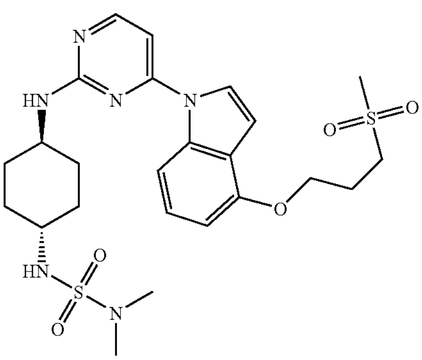 [SMILES: CN(C)S(=O)(=O)N[C@H]1CC[C@H](Nc2nccc(-n3ccc4c(OCCCS(C)(=O)=O)cccc43)n2)CC1] | N-(4-{4-[4-(3-methane-sulfonyl-propoxy)-indol-1-yl]-pyrimidin-2-ylamino}-cyclohexyl)-(dimethamino)-sulfonamide<br>MS (M + H) = 551 | 313 |
| 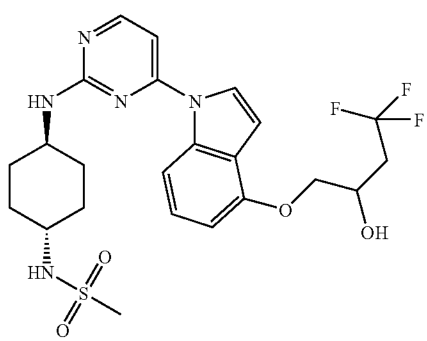 [SMILES: CS(=O)(=O)N[C@H]1CC[C@H](Nc2nccc(-n3ccc4c(OCC(O)CC(F)(F)F)cccc43)n2)CC1] | N-(4-{4-[4-(4,4,4-tri-fluoro-2-hydroxy-butoxy)-indol-1-yl]-pyrimidin-2-ylamino}-cyclohexyl)-methane-sulfonamide<br>Mp 220.7-221.5° C.<br>MS (M + H) = 528 | 314 |
| 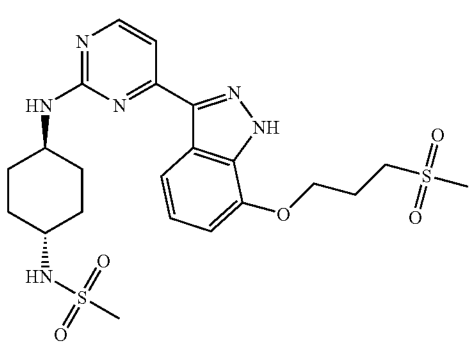 [SMILES: CS(=O)(=O)CCCOc1cccc2c(-c3ccnc(N[C@H]4CC[C@H](NS(C)(=O)=O)CC4)n3)n[nH]c12] | N-(4-{4-[7-(3-methane-sulfonyl-propoxy)-1H-indazol-3-yl]-pyrimidin-2-ylamino}-cyclohexyl)-methanesulfonamide<br>MS (M + H) = 523 | 315 |

TABLE 1-continued

Representative compounds of Formula I.

| Structure | Name | Compound No. |
|---|---|---|
| 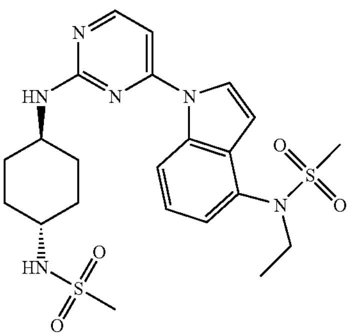 [SMILES: CCN(c1cccc2c1ccn2-c1ccnc(N[C@H]2CC[C@H](NS(C)(=O)=O)CC2)n1)S(C)(=O)=O] | N-ethyl-N-{1-[2-(4-methanesulfonylamino-cyclohexylamino-pyrimidin-4-yl)-1H-indol-4-yl]-methane-sulfonamide<br>MS (M + H) = 507 | 316 |
| 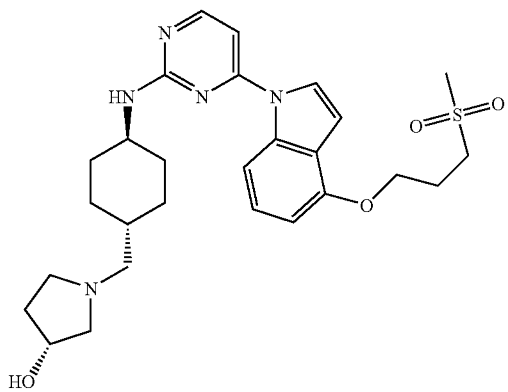 [SMILES: CS(=O)(=O)CCCOc1cccc2c1ccn2-c1ccnc(N[C@H]2CC[C@H](CN3CC[C@@H](O)C3)CC2)n1] | 1-(4-{4-[4-(3-methane-sulfonyl-propoxy)-indol-1-yl]-pyirmidin-2-yl-amino}-cyclohexyl-methyl)-pyrrolidin-3-ol<br>Mp 139.6-150.3° C.<br>MS (M + H) = 528 | 317 |
| 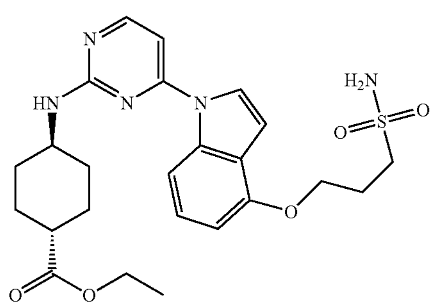 [SMILES: CCOC(=O)[C@H]1CC[C@H](Nc2nccc(-n3ccc4c(OCCCS(N)(=O)=O)cccc43)n2)CC1] | 4-{4-[4-(3-sulfamoyl-propoxy)-indol-1-yl]-pyrimidin-2-ylamino}-cyclohexanecarboxylic acid ethyl ester<br>Mp 145.0-148.0° C.<br>MS (M + H) = 502 | 318 |
| 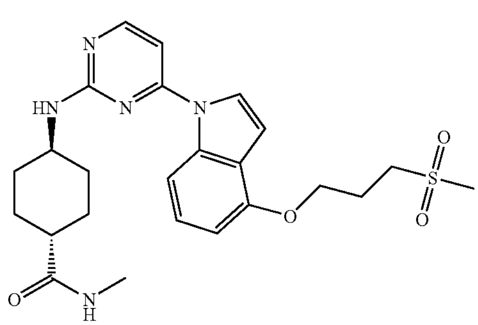 [SMILES: CNC(=O)[C@H]1CC[C@H](Nc2nccc(-n3ccc4c(OCCCS(C)(=O)=O)cccc43)n2)CC1] | 4-{4-[4-(3-sulfamoyl-propoxy)-indol-1-yl]-pyrimidin-2-ylamino}-cyclohexanecarboxylic acid methylamide<br>Mp 215.0-216.0° C.<br>MS (M + H) = 487 | 319 |

TABLE 1-continued

Representative compounds of Formula I.

| Structure | Name | Compound No. |
|---|---|---|
|  | N-(4-{4-[4-(4-acetyl-piperazin-1-yl)-indol-1-yl]-pyrimidin-2-yl-amino}-cyclohexyl)-N-(2-hydroxy-ethyl)-methanesulfonamide<br>Mp 244.5-248.8° C.<br>MS (M + H) = 556 | 320 |
|  | 1-{2-[4-(methane-sulfonyl-methyl-amino)-cyclohexylamino]-pyrimidin-4-yl}-1H-indole-3-sulfonic acid amide<br>Mp 246.6-248.2° C.<br>MS (M + H) = 479 | 321 |
|  | 4-[4-(3-carbamoyl-indol-1-yl)-pyrimidin-2-ylamino]-cyclohexane-carboxylic acid ethyl ester<br>MS (M + H) = 408 | 322 |

Synthesis

Compounds of the present invention can be made by a variety of methods depicted in the illustrative examples shown in the Examples section below. The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplements; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained herein.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reaction described herein preferably are conducted under inert atmosphere, at atmospheric pressure, at a reaction temperature range of from about −78° C. to about 230° C., and most preferably and conveniently at room (or ambient) temperature, e.g., about 20° C.

In the following schemes, if not differently specified, $R^1$, $X^1$, $X^2$, $X^3$, and the like are as defined above; while A is Cl or $SR_b$ $A_1$ is Cl, (S=O)Me, $SO_2Me$ or $SO_2Bu$ $R_a$ is alkyl, cycloalkyl $R_b$ is Me or Bu Z is N or C X is Cl, Br, I $R_e$ and $R_f$ are independently hydrogen, hydroxylakyl, alkoxy, alkyl, cycloalkyl hetheroalkyl, alkylsulfonyl, alkylsulfinyl $R_g$ is lower alkyl
$R_h$ is alkyl or cylcoalkyl
$R_i$ is alkyl, cycloalkyl, heterocyclic undergoes a $S_NAr$ reaction with a variably substituted indole, indazole, azaindole or indoline in presence of a base such as NaH, LiHMDS, NaHMDS or DIPEA, in a polar solvent such

SCHEME I:

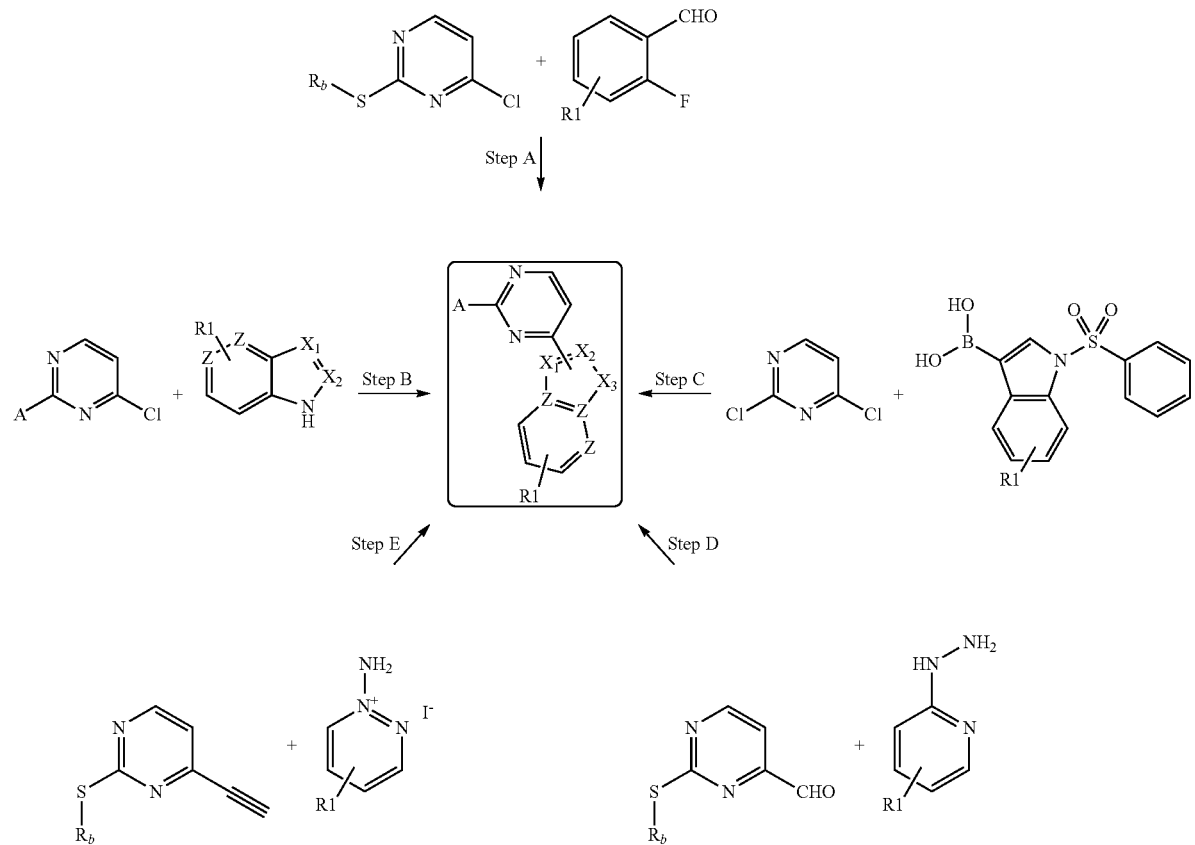

Step A: 1. 1,3-dimethylimidazolium iodide, NaH, 1,4-dioxane, reflux; 2. tert-butyl carbazate, AcOH, MeOH, reflux; or NH₂OH, EtOH, reflux; 3. DBU, THF, MW 150° C.

Step B: NaH, DMF; or LiHMDS or NaHMDS, acetonitrile/THF, low temp; or DIPEA, DMF 100° C.

Step C: tetrakis(triphenylphosphine)palladium(0), Na₂CO₃, acetonitrile, water.

Step D: 1. EtOH, reflux; 2. Iodobenzene diacetate, DCM.

Step E: KOH, water, DCM.

In Step A, 4-chloro-2-methylsulfanyl-pyrimidine or 4-chloro-2-butylsulfanyl-pyrimidine reacts, by heating to reflux, in presence of a strong base, such as sodium hydride, and 1,3-di-methylimidazolium iodide with a variably substituted o-fluorobenzaldehyde in a polar aprotic solvent, such as 1,4-dioxane, to give the corresponding ketone. This product by treatment with tert-butyl carbazate, in the presence of acetic acid, in a polar protic solvent, such as methanol, by heating to reflux gives the corresponding hydrazone which, by heating under microwave conditions, in the presence of a base, such as DBU, and in a polar solvent, such as THF, cyclizes to give the corresponding indazole. When hydroxylamine is used in place of tert-butyl carbazate the corresponding benzoxazole is obtained. In Step B, 4-chloropyrimidine bearing in the 2-position a mercaptoalkyl- or chloro-moiety as DMF, acetonitrile, THF, 1,4-dioxane or a mixture of the above, at temperature ranging from −10° C. to 100° C., to afford the corresponding: N1-arylated indole, N1- or N2-arylated indazole, N1-arylated azaindole and N1-arylated indoline. In Step C, 2,4-dichloropyrimidine undergoes a Buchwald coupling with a variably substituted 3-indole boronic acid, N1 protected, in the presence of a catalyst such as tetrakis(triphenylphosphine)palladium(0), and an inorganic base, such as Na₂CO₃, in a mixture of polar solvents, such as acetonitrile/water, affording the corresponding 2-chloro-4-arylated pyrimidine. In Step D, 2-methylsulfanyl-pyrimidine-4-carbaldehyde reacts with a substituted or unsubstituted pyridin-2-yl-hydrazine in a polar protic solvent, such as ethanol, by heating to reflux, to give the corresponding hydrazone, which cyclizes in the presence of iodobenzene diacetate in an apolar solvent, such as DCM, to give the corresponding variably substituted [1,2,4]triazolo[4,3-a]-pyridine. In Step E, 4-ethynyl-2-methylsulfanyl-pyrimidine reacts with 1-amino-pyridazin-1-ium iodide (*J. Med. Chem.* 2004, 47, 4716-30) in the presence of water and an inorganic base, such as KOH, in an apolar solvent, such as DCM, to afford the corresponding 3-(2-methylsulfanyl-pyrimidin-4-yl)-pyrazolo[1,5-b]pyridazine.

SCHEME II:

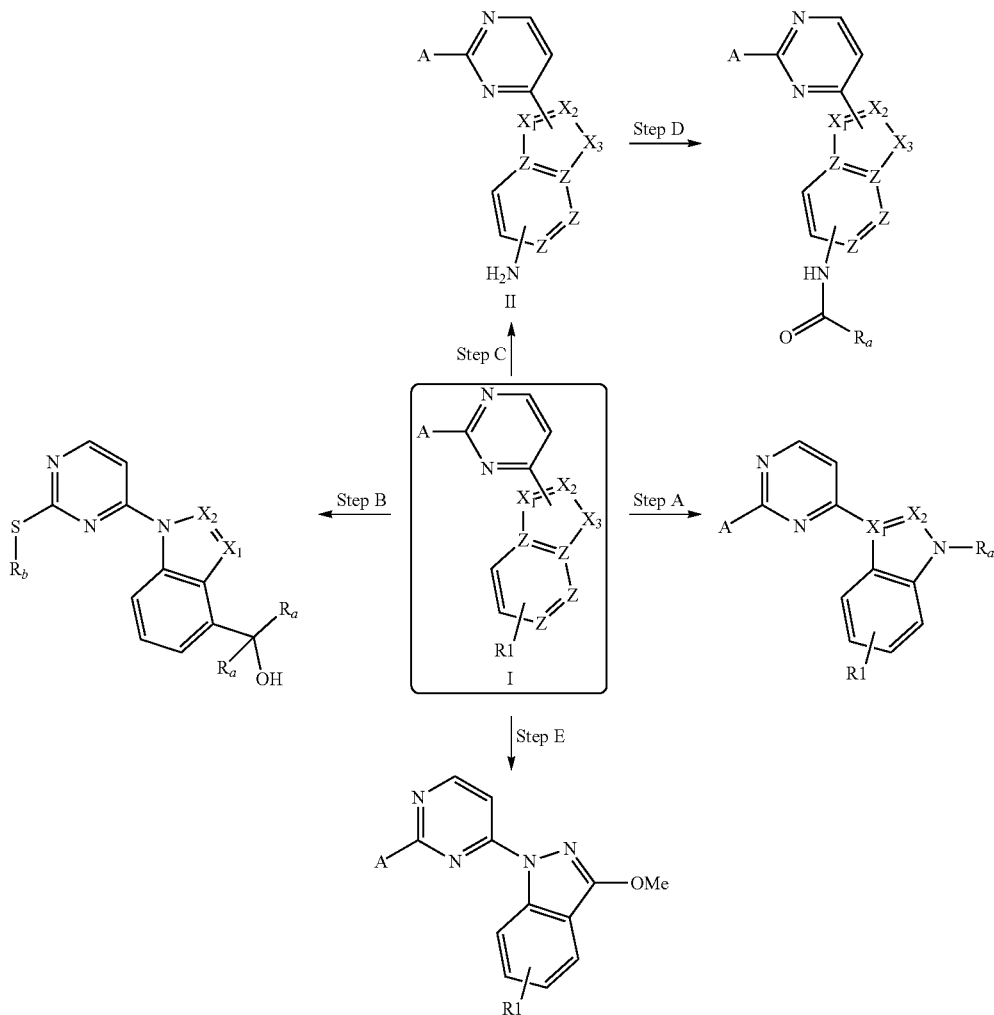

When X³ is NH or NSO₂Ph Step A: NaH, R$_a$X, NMP, or 1. NaOH, MeOH/THF; 2. NaH, R$_a$X, NMP.

When R1 is COOMe Step B: R$_a$MgCl, THF, low temp.

When R1 is NO₂ Step C: Fe(0), NH₄Cl, EtOH, water, heating; Step D: R$_a$COCl, TEA, THF.

When X¹ is C=O Step E: NaH, R$_a$X, DMF, 0° C.

In Step A, a compound of generic structure I when X³ is NH can be alkylated by treatment with a strong base, such as NaH, and the appropriate alkyl or cycloalkyl halide such as MeI in a polar solvent such as NMP. When X³ is a phenylsulfonylamide moiety, a compound of generic structure I can be firstly deprotected by treatment with a strong inorganic base, such as NaOH, in mixture of polar solvents, such as MeOH/THF, and then alkylated as previously described. In Step B, a compound of generic structure I when R1 is a methyl ester moiety can undergo a double addition by a Grignard reactant, such as MeMgCl, at low temperature, in a polar solvent, such as THF, to give the corresponding tertiary alcohol. In Step C, a compound of generic structure I when R¹ is NO₂ can be reduced to the corresponding aniline by heating in presence of a reducing agent, such as Fe(0) Fisher, ammonium chloride and water, in a polar protic solvent such as ethanol. The aniline of generic formula II can subsequently be acylated by treatment with the appropriate acyl chloride in the presence of a base, such as triethylamine, in a polar solvent, such as THF, to give the corresponding secondary amide as described in Step D. In Step E, a compound of generic structure I when X¹ is C=O can be O-alkylated by treatment with an alkylating agent, such as MeI, after deprotonation with a strong base, such as NaH, in a polar solvent, such as DMF, at low temperature.

SCHEME III:

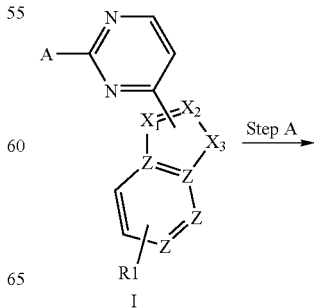

-continued

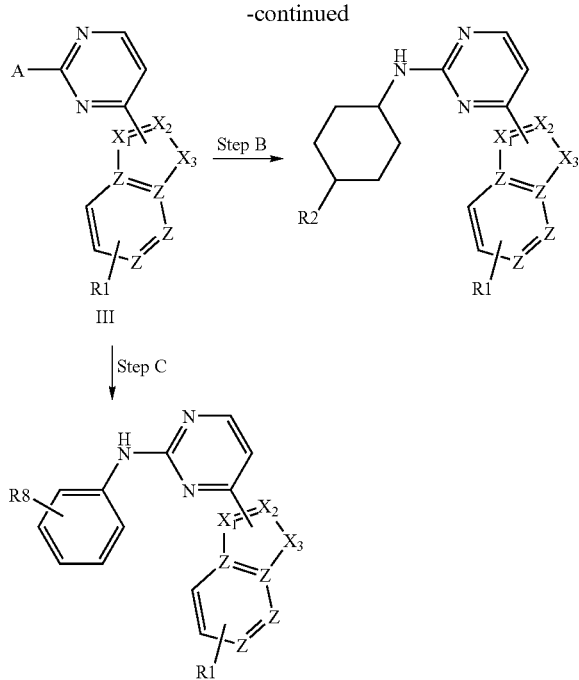

Step A: NCS, NMP or m-CPBA or MeReO$_3$/H$_2$O$_2$, DCM.
Step B: R$^2$C$_6$H$_{10}$NH$_2$, NMP, heating or R$^2$C$_6$H$_{10}$NH$_2$, DIPEA, NMP, heating.
Step C: R$^8$C$_6$H$_4$NH$_2$, p-TSA, i-PrOH, 150° C., MW.

In Step A, a compound of generic formula I, when A is a thiomethyl moiety, can be chlorinated in presence of N-chlorosuccinimide in a polar solvent, such as NMP, at high temperature. Alternatively a compound of generic formula I can be oxidized to the corresponding sulfone or sulfoxide utilizing as oxidizer 3-chloroperoxybenzoic acid or a mixture of methyltrioxorhenium and hydrogen peroxide in an apolar solvent, such as DCM or chloroform, at temperatures ranging between 0° C. and room temperature. The corresponding chloride, sulfone or sulfoxide III can undergo a reaction of S$_N$Ar utilizing a variably substituted or unsubstituted cyclohexylamine, as nucleophile, either with or without a base, such as diisopropylethylamine, in an apolar solvent, such as NMP, at temperature ranging between 90 and 150° C., as described in Step B. Alternatively a sulfoxide of generic structure III can react with a variably substituted or unsubstituted aniline, in the presence of p-toluenesulfonic acid, in a polar protic solvent, such as isopropanol, under microwave conditions at 150° C. as described in Step C.

SCHEME IV:

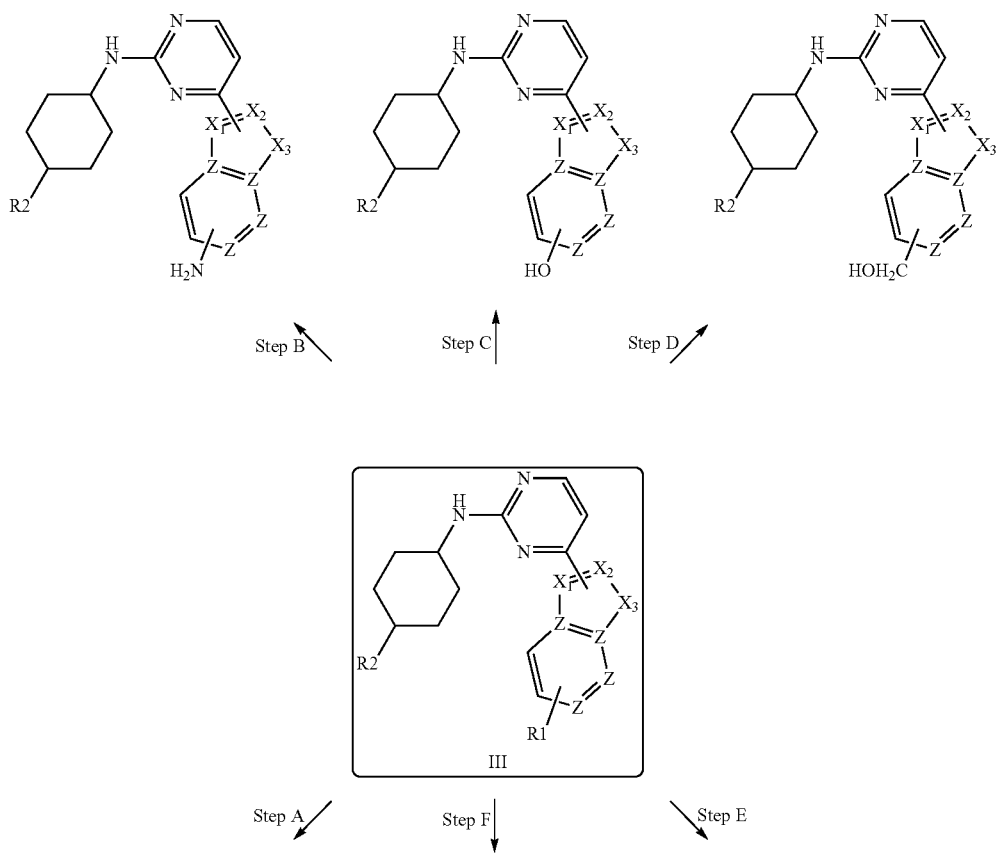

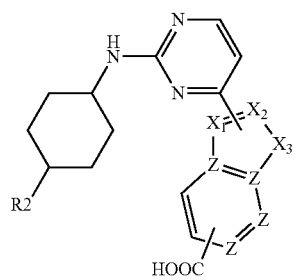

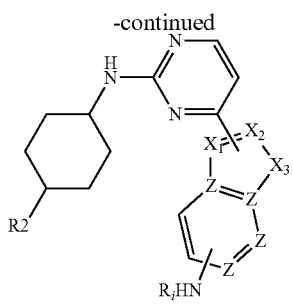

-continued

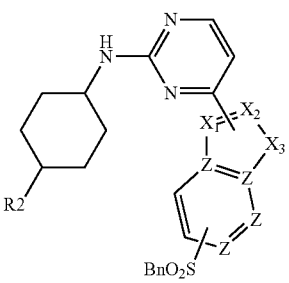

When $R^1$ is COOMe, COOEt: Step A: LiOH or NaOH, THF/MeOH.

When $R^1$ is $NO_2$: Step B: Fe(0), $NH_4Cl$, EtOH, water, heating.

When $R^1$ is OBn: Step C: $H_2$, Pd/C, EtOH.

When $R^1$ is COOMe: Step D: LAH or $LiEt_3BH$, THF $-10°$ C. or RT.

When $R^1$ is SBn: Step E: m-CPBA, chloroform.

When $R^1$ is $NH_2$: Step F: $R_iX$, $Na_2CO_3$, DMF, 80° C.

In Step A, a compound of generic formula IV, when $R^1$ is a methyl- or ethyl-ester moiety, can be hydrolyzed to the corresponding carboxylic acid in the presence of a strong inorganic base, such as sodium or lithium hydroxide, in a mixture of polar solvents such as THF and MeOH. In Step B, a compound of generic formula IV, when $R^1$ is a nitro moiety, can be reduced to the corresponding aniline by heating in the presence of ammonium chloride and water, in a polar protic solvent, such as ethanol, utilizing a reductive agent such as iron Fisher. In Step C, a compound of generic formula IV, when R1 is a benzyloxy moiety, can be reduced to the corresponding phenol, utilizing hydrogen as reductive agent, in the presence of palladium on carbon as catalyst, in polar protic solvent such as ethanol. In Step D, a compound of generic formula IV, when $R^1$ is a methyl- or ethyl-ester moiety, can be reduced to the corresponding benzyl alcohol, utilizing as reductive agent lithium aluminum hydride or lithium trimethylborohydride, in a polar solvent, such as THF, at temperature ranging between $-10°$ C. and room temperature. In Step E, a compound of generic formula IV, when R1 is a mercaptobenzyl moiety, can be oxidized to the corresponding sulfone, utilizing 3-chloroperoxybenzoic acid as oxidized, in an apolar solvent such as chloroform. In Step F, a compound of generic formula IV, when $R^1$ is an amine moiety, can be alkylated to the corresponding secondary or tertiary amine by heating, in the presence of an inorganic base, such as sodium carbonate, in a polar solvent, such as DMF, utilizing an alkyl-, cycloalkyl-, heterocyclic-halide as alkylating agent.

SCHEME V:

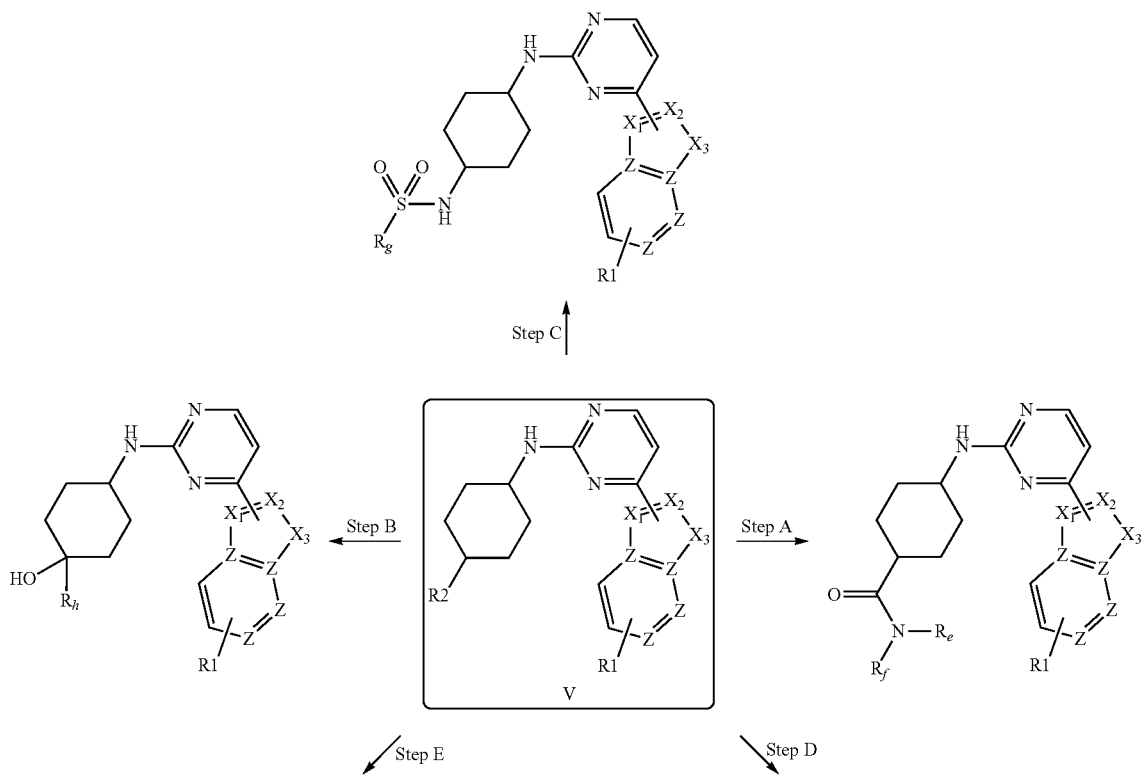

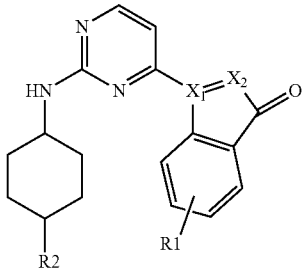
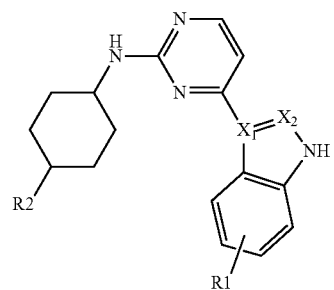

-continued

When $R^2$ is COOEt: Step A: 1. NaOH, THF; 2. $R_eR_fNH$, BOP, DIPEA, THF.

When $R^2$ is $O(CH_2)_2O$: Step B: 1. HCl, THF, heating; 2. $R_hMgCl$, THF, −78° C.

When $R^2$ is $NH_2$: Step C: $(R_gSO_2)O$.

When $X^3$ is $NHSO_2Ph$: Step D: NaOH, MeOH.

When $X^1$ is C-OMe: Step E: TMSI, $CHCl_3$.

In Step A, a compound of generic formula V, when $R^2$ is an ethyl- or methyl-ester moiety, can be hydrolyzed to the corresponding carboxylic acid, in the presence of a strong inorganic base, such as sodium hydroxide, in a polar solvent such as THF. Subsequently the carboxylic acid can be coupled with a hydroxylakyl-, alkoxy-, alkyl-, cycloalkyl-, hetheroalkyl-, alkylsulfonyl-, alkylsulfinyl-amine to give the corresponding amide in the presence of a coupling agent, such as BOP, and a base, such as DIPEA, in a polar solvent such as THF. In Step B, a compound of generic formula V, when $R^2$ is a 1,3-dioxolane moiety, can be hydrolyzed to the corresponding ketone by heating, in the presence of a strong inorganic acid, such as HCl, in a polar solvent such as THF. The ketone obtained in this manner can undergo an addition reaction by a Grignard reactant, at low temperature, in a polar solvent, such as THF, to give the corresponding tertiary alcohol. In Step C, a compound of generic formula V, when R is an amine moiety, can be sulfonylated, in the presence of a sulfonylanhydride, in polar solvent, such as NMP, to give the corresponding sulfonylamide. In Step D, a compound of generic formula V, when $X^3$ is a phenylsulfonylamide moiety, can be hydrolyzed to the corresponding indole, indazole or benzoxazole, in the presence of an inorganic base, such as sodium hydroxide, in a polar solvent such as methanol. In Step E, a compound of generic formula V, when $X^1$ is a methyl ether moiety, can be oxidized to the corresponding ketone by reaction with trimethylsilyliodide in a apolar solvent The products can then be purified, e.g., by extraction, crystallization, preparative HPLC, flash chromatography, thin layer chromatography and the like.

Utility

The compounds of this invention are JNK modulators and as such are expected to be effective in the treatment of a wide range of JNK mediated disorders. Exemplary JNK mediated disorders include, but are not limited to, autoimmune disorder, inflammatory disorder, metabolic disorder, neurological disease, and cancer. Accordingly, compounds of the invention can be used to treat one or more of such disorders. In some embodiments, compounds of the invention can be used to treat a JNK mediated disorder such as rheumatoid arthritis, asthma, type II diabetes, Alzheimer's disease, Parkinson's disease or stroke.

Administration and Pharmaceutical Composition

The invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the invention will be administered in a therapeutically effective amount by any of the accepted modes of administration for agents that serve similar utilities. Suitable dosage ranges are typically 1-500 mg daily, preferably 1-100 mg daily, and most preferably 1-30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

Compounds of the invention may be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) mg of active ingredient or, more broadly, about 0.01 to about one hundred (100) mg, per tablet, are accordingly suitable representative unit dosage forms.

The compounds of the invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxy-methylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention may be formulated for vaginal administration. Pessaries, tampons, creams, gels, pastes, foams or sprays containing in addition to the active ingredient such carriers as are known in the art to be appropriate.

The subject compounds may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chloro-fluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the sub-dermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington. The Science and Practice of Pharmacy 1995, edited by E. W. Martin, Mack Publishing Company, 19th edition, Easton, Pa. Representative pharmaceutical formulations containing a compound of the present invention are described below.

EXAMPLES

Additional objects, advantages, and novel features of this invention will become apparent to those skilled in the art upon examination of the following examples thereof, which are not intended to be limiting.

List of Abbreviations
AcOH Acetic acid
Bn Benzyl
BOP Benzotriazol-1-yloxytris(dimethylamino)phosphonium hexafluorophosphate
(BOC)₂O Di-tert-butyl dicarbonate
CSI Chlorosulfonyl isocyanate
DBU 1,8-Diazabicyclo[5.4.0]-undec-7-ene
DCM Dichloromethane (methylene chloride)
DEA Diethylamine
DIPEA Diisopropylethylamine
DMF N,N-dimethylformamide
EDCI 1-(3-Dimethylaminopropyl)-3-ethylcarbodiimide hydrochloride
Et₂O Diethyl ether
EtOH Ethanol
EtOAc Ethyl acetate
HOBt 1-Hydroxybenzotriazole
i-PrOH Isopropanol
LAH Lithium aluminum hydride
m-CPBA (also MCPBA) 3-Chloroperoxybenzoic acid
MeOH Methanol
MW Microwaves
NCS N-Chlorosuccinimide
NMP 1-Methyl-2-pyrrolidinone
p-TSA p-Toluenesulfonic acid
RT Room temperature
TEA Triethylamine
THF Tetrahydrofuran
TLC Thin layer chromatography Preparation 1

Synthesis of
3-(2-Methylsulfanyl-pyrimidin-4-yl)-1H-indazole

The synthesis of 3-(2-methylsulfanyl-pyrimidin-4-yl)-1H-indazole was carried out according to the process shown in Scheme 1.

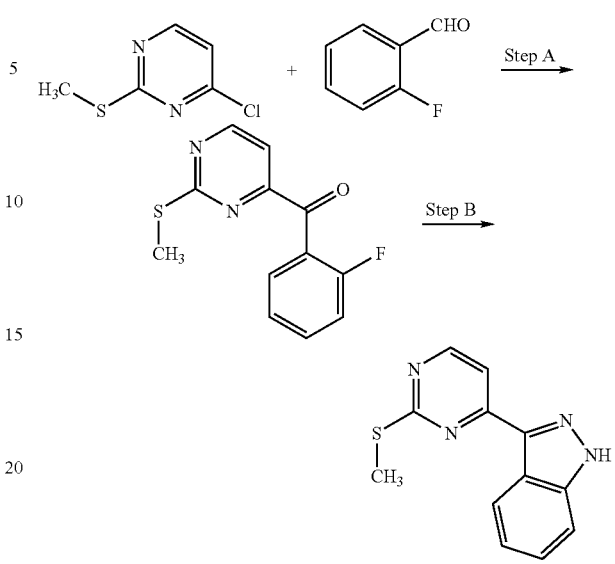

SCHEME 1

Step A: synthesis of (2-fluoro-phenyl)-(2-methylsulfanyl-pyrimidin-4-yl)-methanone Sodium hydride (60% dispersion in mineral oil, 598 mg, 14.94 mmol) was added to a stirring solution of 4-chloro-2-methylthiopyrimidine (1.45 mL, 12.45 mmol), 2-fluorobenzaldehyde (1.57 mL, 14.94 mmol) and 1,3-dimethylimidazolium iodide (517 mg, 4.15 mmol) (prepared as described in Org. Synth. (1986) 64:9) in 1,4-dioxane (20 mL). The resulting mixture was heated at reflux for 1 hour; it was then cooled and partitioned between EtOAc and water. The organic layer was separated and dried over Na₂SO₄, filtered and evaporated under reduced pressure. The crude residue was purified by flash chromatography (hexane/EtOAc, 95/5) to give 840 mg of (2-fluorophenyl)-(2-methylsulfanyl-pyrimidin-4-yl)-methanone.

In the same manner, using the appropriate starting materials, the following compounds were prepared:
(2-Fluoro-3-methoxy-phenyl)-(2-methylsulfanyl-pyrimidin-4-yl)-methanone; and
(2,5-Difluoro-phenyl)-(2-methylsulfanyl-pyrimidin-4-yl)-methanone.

Step B: synthesis of
3-(2-methylsulfanyl-pyrimidin-4-yl)-1H-indazole tert-Butylcarbazate (899 mg, 6.8 mmol) and acetic acid (0.5 mL) were added to a mixture of (2-fluoro-phenyl)-(2-methylsulfanyl-pyrimidin-4-yl)-methanone (840 mg, 3.4 mmol) in MeOH. The resulting mixture was heated at reflux for 16 h; it was then cooled to RT and partitioned between EtOAc and aqueous sodium bicarbonate. The organic layer was separated and dried over Na₂SO₄, filtered and evaporated under reduced pressure. The residue was placed in a sealed tube with DBU (0.79 mL, 5.3 mmol) and THF. The resulting mixture was heated to 150° C. in a microwave reactor for 30 minutes. The reaction mixture was then evaporated under reduced pressure and the crude residue was purified by flash chromatography (hexane/EtOAc, 4/1) to afford 525 mg of 3-(2-methylsulfanyl-pyrimidin-4-yl)-1H-indazole.

In a similar manner, utilizing the appropriate starting material, the following compounds were prepared:
7-Methoxy-3-(2-methylsulfanyl-pyrimidin-4-yl)-1H-indazole, and 3-(2-Methylsulfanyl-pyrimidin-4-yl)-7-trifluoromethyl-1H-indazole.

Preparation 2

Synthesis of 1-Methyl-3-(2-methylsulfanyl-pyrimidin-4-yl)-1H-indazole

The synthesis of 1-methyl-3-(2-methylsulfanyl-pyrimidin-4-yl)-1H-indazole was carried out according to the process shown in Scheme 2.

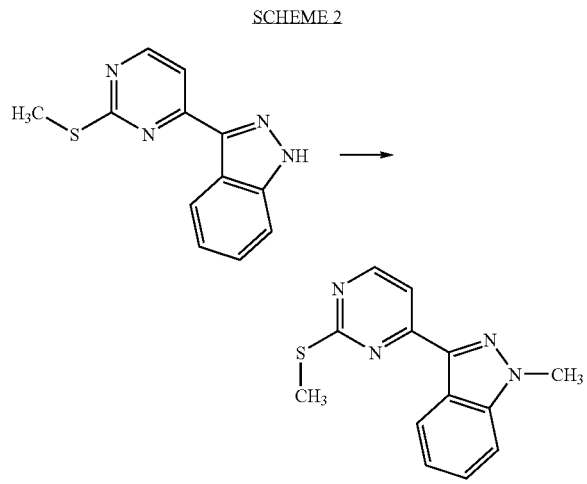

SCHEME 2

Sodium hydride (60% suspension in mineral oil, 99 mg, 2.47 mmol) was added to a stirring solution of 3-(2-methylsulfanyl-pyrimidin-4-yl)-1H-indazole (520 mg, 2.15 mmol) in NMP at 0° C. The mixture was stirred for 15 min and then methyliodide (0.14 mL, 2.25 mmol) was added and the resulting mixture was stirred for 2 h. The reaction mixture was then poured into water and extracted twice with EtOAc. The combined organic extracts were dried over Na$_2$SO$_4$, filtered and evaporated under reduced pressure. The residue was purified by flash chromatography (hexane/EtOAc, 9/1) to give 415 mg of 1-methyl-3-(2-methylsulfanylpyrimidin-4-yl)-1H-indazole.

Preparation 3

Synthesis of 7-Methoxy-3-(2-methylsulfanyl-pyrimidin-4-yl)-benzo[d]isoxazole

The synthesis of 7-methoxy-3-(2-methylsulfanyl-pyrimidin-4-yl)-benzo[d]isoxazole was carried out according to the process shown in Scheme 3.

SCHEME 3

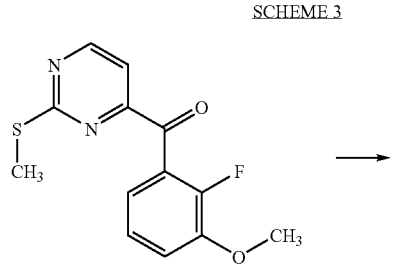

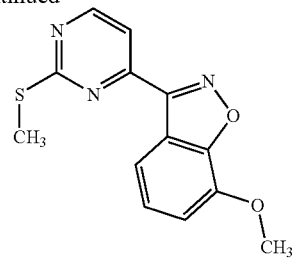

A mixture of (2-fluoro-3-methoxy-phenyl)-(2-methylsulfanyl-pyrimidin-4-yl)-methanone (1 g, 3.59 mmol) and hydroxylamine (50% in water, 1.5 mL) in ethanol was heated to reflux overnight. The resulting mixture was cooled to RT, diluted with EtOAc and then concentrated under reduced pressure. The residue was dissolved in THF and DBU (0.84 mL, 5.6 mmol) was added, the resulting mixture was heated to 150° C. in a microwave reactor for 30 min. The reaction mixture was then concentrated under reduced pressure and the residue was purified by flash chromatography (hexane/EtOAc, 95/5) to give 458 mg of 7-methoxy-3-(2-methylsulfanylpyrimidin-4-yl)-benzo[d]isoxazole.

In the same manner, using the appropriate starting material, the following compounds were prepared:
3-(2-Methylsulfanyl-pyrimidin-4-yl)-benzo[d]isoxazole; and
5-Fluoro-3-(2-methylsulfanyl-pyrimidin-4-yl)-benzo[d]isoxazole.

Preparation 4

Synthesis of 4-Bromo-1-(2-methylsulfanyl-pyrimidin-4-yl)-1H-indazole

The synthesis of 4-bromo-1-(2-methylsulfanyl-pyrimidin-4-yl)-1H-indazole was carried out according to the process shown in Scheme 4.

SCHEME 4

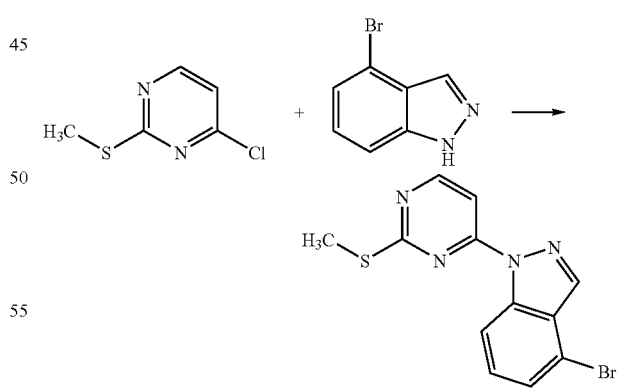

To a solution of 4-bromo-1H-indazole (8.831 g, 44.82 mmol) in DMF (100 mL) was added NaH (60% suspension in mineral oil, 74.7 mmol, 2.988 g) followed by 4-chloro-2-methylsulfanyl-pyrimidine (4.34 mL, 37.35 mmol). The resulting mixture was allowed to stir at RT for 2 h; the solid precipitate was collected by filtration, washed and dried under reduced pressure to give 10.7 g (89% yield) of 4-bromo-1-(2-methylsulfanyl-pyrimidin-4-yl)-1H-indazole.

In a similar manner, utilizing the appropriate starting materials, the following compounds were prepared:
1-(2-Methylsulfanyl-pyrimidin-4-yl)-1H-indazole;
6-Methyl-1-(2-methylsulfanyl-pyrimidin-4-yl)-1H-indazole;
5-Methyl-1-(2-methylsulfanyl-pyrimidin-4-yl)-1H-indazole;
3-Methyl-1-(2-methylsulfanyl-pyrimidin-4-yl)-1H-indole;
6-Fluoro-1-(2-methylsulfanyl-pyrimidin-4-yl)-1H-indole;
4-Benzyloxy-1-(2-methylsulfanyl-pyrimidin-4-yl)-1H-indole;
5-Benzyloxy-1-(2-methylsulfanyl-pyrimidin-4-yl)-1H-indole;
1-(2-Methylsulfanyl-pyrimidin-4-yl)-1H-indole;
1-(2-Methylsulfanyl-pyrimidin-4-yl)-1H-indazole;
1-(2-Methylsulfanyl-pyrimidin-4-yl)-6-nitro-1H-indazole;
1-(2-Methylsulfanyl-pyrimidin-4-yl)-1H-pyrrolo[3,2-b]pyridine (white crystalline solid), MS=243 [M+H]$^+$, MP=120.1-123.0° C.; and
1-(2-Methylsulfanyl-pyrimidin-4-yl)-1H-pyrrolo[3,2-c]pyridine (tan solid), MS=243 [M+H]$^+$, MP=167.7-169.2° C.

Preparation 5

Synthesis of 2-Butylsulfanyl-4-chloro-pyrimidine

The synthesis of 2-butylsulfanyl-4-chloro-pyrimidine was carried out according to the process shown in Scheme 5.

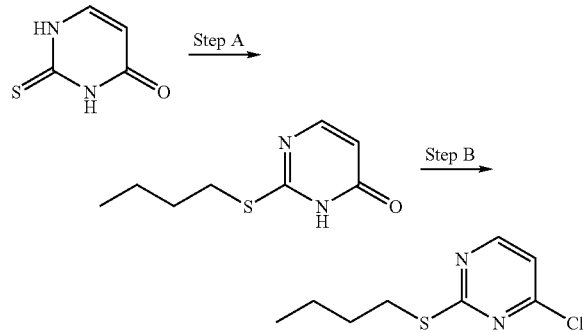

Step A: synthesis of 2-butylsulfanyl-3H-pyrimidin-4-one

2-Thioxo-2,3-dihydro-1H-pyrimidin-4-one (12.8 g) was added to a solution of NaOH (8.0 g) in water (70 mL). After complete dissolution of the solids butyl iodide (12.4 mL) was added to the solution and the resulting mixture was stirred at RT overnight. A second aliquot of butyl iodide (1.2 mL) was then added and the reaction mixture was stirred for 24 h. A third aliquot of butyl iodide (1.2 mL) was added and the resulting mixture was stirred for 6 days. Glacial acetic acid (5.5 mL) was added and the reaction mixture was stirred for 30 min, it was then stored at 4° C. overnight. The precipitate formed was collected by filtration and dried under reduced pressure to give 12.3 g of 2-butylsulfanyl-3H-pyrimidin-4-one.

Step B: synthesis of 2-butylsulfanyl-4-chloro-pyrimidine

A mixture of 2-butylsulfanyl-3H-pyrimidin-4-one (3.0 g) and phosphorus oxychloride (15 mL) was heated at reflux for 3 h; it was then cooled to RT and evaporated under reduced pressure. The residue was poured into an ice-water mixture, and the resulting mixture was extracted with DCM. The combined organic extracts were washed with a diluted aqueous solution of NaHCO$_3$, dried over Na$_2$SO$_4$, filtered and evaporated under reduced pressure to give 1.2 g of 2-butylsulfanyl-4-chloro-pyrimidine.

Preparation 6

Synthesis of 1-(2-Methylsulfanyl-pyrimidin-4-yl)-4-nitro-1H-indole

The synthesis of 1-(2-methylsulfanyl-pyrimidin-4-yl)-4-nitro-1H-indole was carried out according to the process shown in Scheme 6.

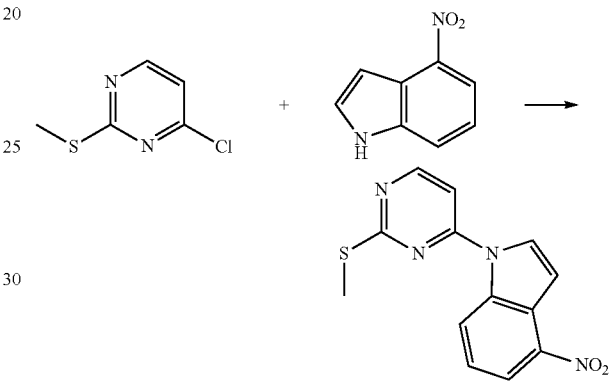

A solution of sodium(bistrimethylsilyl)amide (1 M in THF, 26.42 mL) was slowly added to a cooled (acetone/dry-ice bath) solution of 4-nitroindole (4.2 g, 25.9 mmol) in a mixture of acetonitrile/THF (2/1, 75 mL) and the resulting mixture was stirred for 1 hour. 4-Chloro-4-methylthiopyrimidine (4.202 g, 26.2 mmol) was then added and the reaction mixture was warmed to RT and stirred for 21 h. The resulting mixture was evaporated under reduced pressure and the solid residue was triturated with a mixture of hexane/EtOAc/Et$_2$O (5/1/1). The solid was collected by filtration, washed and dried under reduced pressure to give 2.56 g of 1-(2-methylsulfanyl-pyrimidin-4-yl)-4-nitro-1H-indole which was used without further purification.

In the same manner, utilizing the appropriate starting materials, the following compounds were prepared:
1-(2-Methylsulfanyl-pyrimidin-4-yl)-1H-indole-4-carboxylic acid methyl ester;
4-Methoxy-1-(2-methylsulfanyl-pyrimidin-4-yl)-1H-indole;
6-Methyl-1-(2-methylsulfanyl-pyrimidin-4-yl)-1H-indole
4-Methyl-1-(2-methylsulfanyl-pyrimidin-4-yl)-1H-indole;
4-Fluoro-1-(2-methylsulfanyl-pyrimidin-4-yl)-1H-indole;
5-Fluoro-1-(2-methylsulfanyl-pyrimidin-4-yl)-1H-indole;
1-(2-Methylsulfanyl-pyrimidin-4-yl)-1H-indole-3-carboxylic acid methyl ester;
1-(2-Methylsulfanyl-pyrimidin-4-yl)-1H-indole-5-carboxylic acid methyl ester; and
5-Methoxy-1-(2-methylsulfanyl-pyrimidin-4-yl)-1H-indole.

In the same manner, utilizing the appropriate starting materials and LiHMDS as a base, the following compounds were prepared:
1-(2-Methylsulfanyl-pyrimidin-4-yl)-1H-indole-4-carbonitrile;

1-(2-Methylsulfanyl-pyrimidin-4-yl)-1H-indole-6-carboxylic acid methyl ester; and
5-Methyl-1-(2-methylsulfanyl-pyrimidin-4-yl)-1H-indole.

Preparation 7

Synthesis of 4-Amino-cyclohexanecarboxylic acid dimethylamide hydrochloride salt.

The synthesis of 4-amino-cyclohexanecarboxylic acid dimethylamide hydrochloride salt was carried out according to the process shown in Scheme 7.

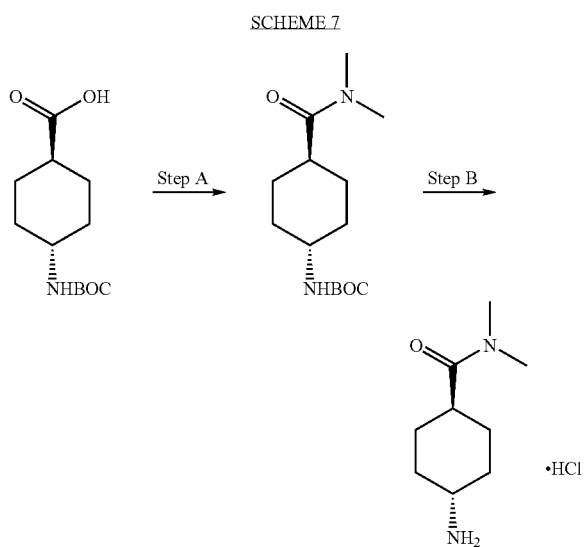

Step A: synthesis of (4-dimethylcarbamoyl-cyclohexyl)-carbamic acid tert-butyl ester A mixture of 4-tert-butoxycarbonylamino-cyclohexanecarboxylic acid (2.43 g, 10 mmol), EDCI (6.52 g, 34 mmol) and HOBt (4.59 g, 34 mmol) in NMP (20 mL) was stirred at RT for 3 h. A solution of dimethylamine (2.0 M in THF, 15 mL, 30 mmol) was added, and the resulting mixture was stirred at RT for 64 h. Water and EtOAc were then added, and the organic layer was separated and washed twice with a saturated aqueous solution of $K_2CO_3$, aqueous HCl (1 M), a saturated aqueous solution of $K_2CO_3$, and brine. The organic layer was dried over $Na_2SO_4$, filtered and evaporated under reduced pressure to give (4-dimethylcarbamoyl-cyclohexyl)-carbamic acid tert-butyl ester (1.6 g, 59% yield) as a white solid.

Step 2: synthesis of 4-amino-cyclohexanecarboxylic acid dimethylamide hydrochloride salt HCl (concentrated, 7 mL) was added to a solution of (4-dimethylcarbamoyl-cyclohexyl)-carbamic acid tert-butyl ester (1.5 g) in 1,4-dioxane (20 mL), and the resulting mixture was stirred at RT for 5 h. Toluene was added and the reaction mixture was evaporated under reduced pressure. The oily residue was triturated with EtOAc to give 4-amino-cyclohexanecarboxylic acid dimethylamide hydrochloride salt (0.9 g).
trans-(4-Amino-cyclohexyl)-morpholin-4-yl-methanone was prepared in a similar manner, utilizing the appropriate starting materials.

Preparation 8

Synthesis of trans-4-Amino-cyclohexanecarboxylic acid ethyl ester

The synthesis of trans-4-amino-cyclohexanecarboxylic acid ethyl ester was carried out according to the process shown in Scheme 8.

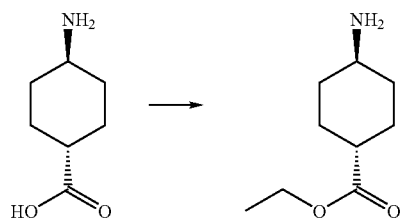

A mixture of trans-4-amino-cyclohexanecarboxylic acid (15 g, 83.8 mmol), sulfuric acid (9 mL) and EtOH (400 mL) was stirred at RT overnight. A saturated aqueous solution of $NaHCO_3$ and $NaHCO_3$ (solid) were added until the pH of the mixture reached 7. The solvent was then removed under reduced pressure. Aqueous $K_2CO_3$ (50%) was added and the resulting mixture was extracted with EtOAc, the organic extracts dried over $Na_2SO_4$, filtered and evaporated under reduced pressure to provide trans-4-amino-cyclohexanecarboxylic acid ethyl ester (12.81 g) as a light yellow oil.

Preparation 9

Synthesis of 2-[1-(2-Methylsulfanyl-pyrimidin-4-yl)-1H-indol-4-yl]-propan-2-ol

The synthesis of 2-[1-(2-methylsulfanyl-pyrimidin-4-yl)-1H-indol-4-yl]-propan-2-ol was carried out according to the process shown in Scheme 9.

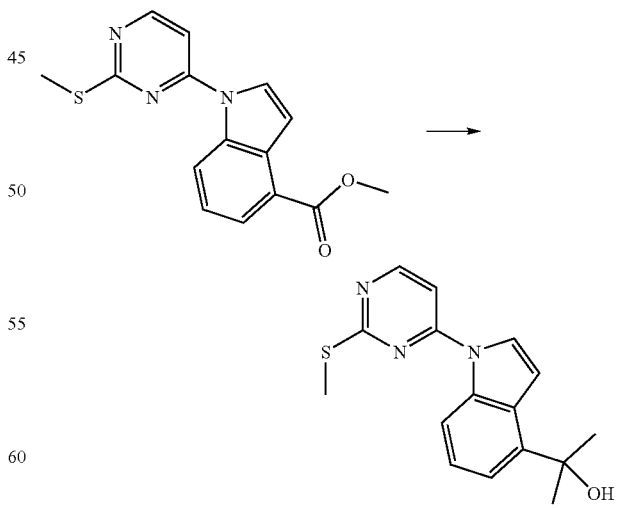

A suspension of 1-(2-methylsulfanyl-pyrimidin-4-yl)-1H-indole-4-carboxylic acid methyl ester (500 mg) in THF (6 mL) was added to a solution of methylmagnesium bromide (3.0 M in $Et_2O$, 3.51 mL) and THF (2 mL), cooled to 0° C., and the resulting mixture stirred under $N_2$ for 5 h. A second aliquot of MeMgBr (3.0 M in $Et_2O$, 1.80 mL) was then added and the reaction mixture was stirred at RT under $N_2$ atmosphere for 30 min. The resulting mixture was then cooled to 0° C., poured into a cold mixture of water/HCl (1 M, 1:1, 75 mL) and extracted with EtOAc. The combined organic extracts were washed with water (1×) and $NaHCO_3$ (2×, sat'd aq), dried over $Na_2SO_4$, filtered and evaporated under reduced pressure to give 2-[1-(2-methylsulfanyl-pyrimidin-4-yl)-1H-indol-4-yl]-propan-2-ol (0.48 g).

Preparation 10

Synthesis of [6-(2,4-Difluoro-phenoxy)-1H-pyrazolo[3,4-d]pyrimidin-3-yl]-isopropyl-amine The synthesis of [6-(2,4-difluoro-phenoxy)-1H-pyrazolo[3,4-d]pyrimidin-3-yl]-isopropyl-amine was carried out according to the process shown in Scheme 10.

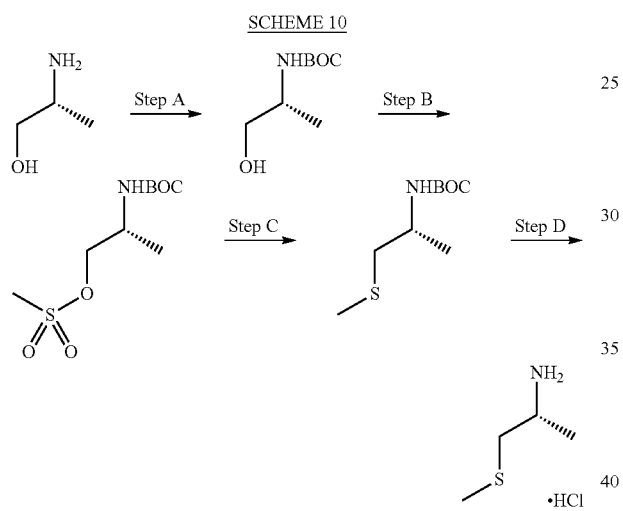

Step A: synthesis of (R)-2-boc-amino-propan-1-ol (R)-2-Amino-propan-1-ol (30.0 g, 0.3994 mol) was dissolved in MeOH (800 mL), and the solution cooled in an ice bath for 30 min. A solution of di-tert-butyl dicarbonate (87.17 g, 0.3994 mol) in MeOH (250 mL) was added in portions to the stirring reaction mixture. The ice bath was removed, and stirring was continued for 3 h. The reaction mixture was evaporated to dryness under reduced pressure to give (R)-2-boc-amino-propan-1-ol, which was used without further purification.

Step B: synthesis of (R)-2-Boc-amino-1-methanesulfonyl-propan-1-ol

DCM (400 mL) and triethylamine (83.9 mL, 0.60 mol) were added to a flask containing (R)-2-boc-amino-propan-1-ol. The reaction mixture was cooled in an ice bath for 30 min, and methanesulfonyl chloride (37.0 mL, 0.478 mol) was added dropwise over a five min period. The resulting mixture was stirred for 1 hour, the ice bath removed, and the mixture stirred for 18 h at RT. The resulting mixture was washed with aqueous NaOH (10%), and the organic layer dried over $MgSO_4$, filtered, and concentrated under reduced pressure to give (R)-2-boc-amino-1-methanesulfonyl-propan-1-ol (91.93 g).

Step C: synthesis of (R)-2-Boc-amino-1-methanesulfanyl-propane

A mixture of (R)-2-boc-amino-1-methanesulfonyl-propan-1-ol (91.93 g, 363 mmol), THF (350 mL) and sodium thiomethoxide (30.0 g, 406 mmol) was stirred at RT for 18 h. The mixture was concentrated under reduced pressure, and the residue partitioned between $Et_2O$ and water. The organic layer was washed with brine, dried over $MgSO_4$, filtered, and concentrated under reduced pressure to give (R)-2-boc-amino-1-methanesulfanyl-propane (70.8 g).

Step D: synthesis of (R)-1-methyl-2-methylsulfanyl-ethylamine

Methanol (400 mL) was cooled in an ice bath for 30 min, and acetyl chloride (100 mL) was added dropwise over a 45 min period. The resulting solution was added to (R)-2-Boc-amino-1-methanesulfanyl-propane (70.47 g, 343 mmol) with stirring at ice bath temperature. The reaction mixture was stirred for 15 min after addition was completed, the ice bath removed, and stirring continued for 2 h. The reaction mixture was concentrated to a solid under reduced pressure, then taken up in THF (700 mL). The resulting mixture was heated to reflux until all solids had dissolved, then cooled to RT, then cooled to 0° C. for 30 min. The resulting precipitate was collected by filtration, washed with cold THF, and dried under reduced pressure to give (R)-1-methyl-2-methylsulfanyl-ethylamine (23.57 g). MS=106 $[M+H]^+$.

(S)-1-Methyl-2-methylsulfanyl-ethylamine was prepared following the above described procedure utilizing the appropriate starting material.

Preparation 11

Synthesis of (R)-2-Methanesulfonyl-1-methyl-ethylamine

The synthesis of (R)-2-methanesulfonyl-1-methyl-ethylamine was carried out according to the process shown in Scheme 11.

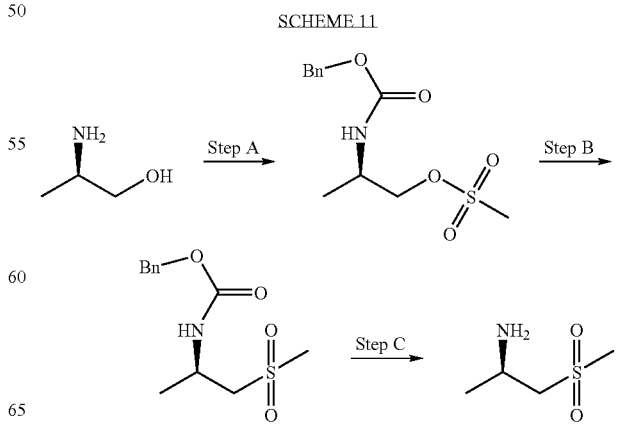

Step A: synthesis of methanesulfonic acid (R)-2-benzyloxycarbonylamino-propyl ester A solution of benzyl chloroformate (10.0 mL) in DCM (25 mL) was added to a stirred, cooled solution of R-(–)-2-amino-1-propanol (5.0 g) and triethylamine (6.8 g) in DCM (75 mL) at a rate to maintain the temperature below –5° C. Cooling and stirring was continued for 1 hour and then a solution of methanesulfonyl chloride (7.7 g) in DCM (25 mL) was added at a rate to maintain the temperature below –5° C. The reaction mixture was allowed to warm to 5° C., then washed twice with water (150 mL). The organic layer was filtered over anhydrous sodium sulfate and the solvent removed by vacuum distillation to yield 19.2 g of a white solid. A portion of this material (15 g) was dissolved in DCM (100 mL), and the resulting solution was distilled. The volume was maintained by addition of methyl-t-butyl ether. When crystallization began, the mixture was distilled to a volume of about 75 mL and heating was stopped. The resulting mixture was diluted to a volume of about 150 mL by dropwise addition of hexane. After cooling, the white crystalline solid was collected, washed with hexane/methyl-t-butyl ether (1:1), and dried to give methanesulfonic acid (R)-2-benzyloxycarbonylamino-propyl ester (11.1 g).

Step B: synthesis of ((R)-2-methanesulfonyl-1-methyl-ethyl)-carbamic acid benzyl ester To a stirring mixture of methanesulfonic acid (R)-2-benzyloxycarbonylamino-propyl ester (11.1 g) in acetonitrile (72 mL) was added aqueous sodium methylmercaptide (15%, 35 mL). The resulting mixture was heated to about 55° C. for 4-5 h; it was then cooled, and the lower aqueous layer separated. The organic layer was shaken with water (10 mL) and the lower layer again separated. Formic acid (15 mL) was added to the organic layer, the resulting mixture stirred, and aqueous $H_2O_2$ (30%, 12 g) was added dropwise. After an initial exotherm, the mixture cooled and was then heated to about 65° C. After 3 h, a second aliquot of $H_2O_2$ (30%, 2 mL) and formic acid (6 mL) was added to the mixture. A similar addition of the two reagents was made after 4 h. The reaction mixture was cooled after 6 h and slowly diluted with water (about 200 mL). A white solid crystallized during the addition. The mixture was cooled in an ice bath and the solid was collected by filtration, washed with water, and dried under reduced pressure to yield ((R)-2-methanesulfonyl-1-methyl-ethyl)-carbamic acid benzyl ester (9.2 g).

Step C: synthesis of (R)-2-methanesulfonyl-1-methyl-ethylamine

A mixture of ((R)-2-methanesulfonyl-1-methyl-ethyl)-carbamic acid benzyl ester (2.7 g), palladium hydroxide on carbon (20%, 0.3 g), and isopropanol (30 mL) was heated to about 65° C. under nitrogen atmosphere. A solution of potassium formate (2.7 g) in water (4 mL) was added to the mixture over a period of about 1 hour. After 6 h the mixture was cooled and filtered. The filtrate was vacuum distilled to a viscous oil, which was dissolved in isopropanol (30 mL). The resulting solution was filtered and evaporated under reduced pressure to yield (R)-2-methane-sulfonyl-1-methyl-ethylamine (1.2 g) as a viscous oil.

Preparation 12

Synthesis of 3-Trimethylsilanyloxy-1-(2-trimethylsilanyloxy-ethyl)-propylamine

The synthesis of 3-trimethylsilanyloxy-1-(2-trimethylsilanyloxy-ethyl)-propylamine was carried out according to the process shown in Scheme 12.

SCHEME 12

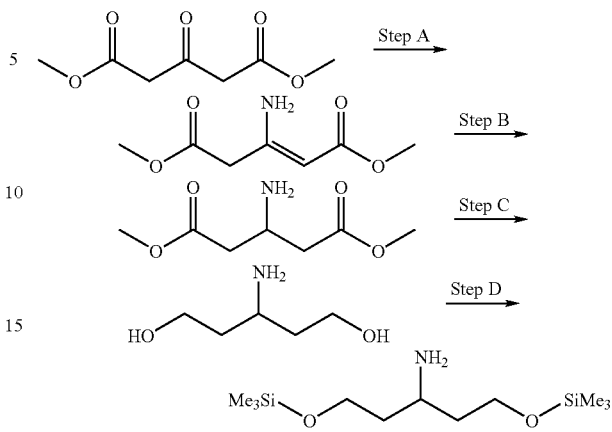

Step A: synthesis of dimethyl-3-aminoglutaconate

A mixture of dimethylacetone-1,3-dicarboxylate (24.55 Kg), ammonium bicarbonate (22.9 Kg) and MeOH (81.8 Kg) was stirred at RT overnight. The solids were removed by filtration, and the filtrate concentrated under reduced pressure. Isopropanol (27.2 Kg) was added and the water of reaction was removed by azeotropic distillation. The remaining solvent was distilled off to provide dimethyl-3-aminoglutaconate (24.705 Kg, 99% yield) as an oil.

Step B: synthesis of 3-amino-pentanedioic acid dimethyl ester

A diluted alcoholic sulfuric acid solution is prepared by adding sulfuric acid (20.69 Kg) to i-PrOH (51.7 Kg) at 0-5° C. The resulting solution was slowly added to a solution of tert-butylamine borane (9.19 Kg) in THF (69.3 Kg), maintaining the temperature below –5° C. Dimethyl-3-aminoglutaconate (18.28 Kg) was slowly added to the resulting mixture, maintaining the temperature below 0° C. The resulting reaction mixture was stirred between 0° C. and 15° C. overnight, then quenched by slow addition to water (166 Kg) while maintaining the temperature below 10° C. and the pH between 5 and 7 by adding concentrated aqueous NaOH. The pH of the mixture was then adjusted to about 9-10 by adding concentrated aqueous NaOH at the end of the quenching process. The phases were separated and the aqueous phase was extracted with DCM. The combined organic extracts were washed with brine (20.6 Kg), filtered through a cotton cartridge and concentrated under reduced pressure to give 3-amino-pentanedioic acid dimethyl ester (17.87 Kg, 97% yield).

Step C: synthesis of 3-amino-pentane-1,5-diol

A solution of 3-amino-pentanedioic acid dimethyl ester (17.67 Kg) in THF (101.5 Kg) was added to a solution of LAH (1.0 M in THF, 90.2 Kg) at a pot temperature between 10-30° C., and the resulting mixture stirred at 25° C. for 14-20 h. The reaction was quenched by slowly adding water and THF (1:1). The solids were filtered and washed with iPrOH/THF/DEA/propyl-amine. The filtrate was evaporated under reduced pressure to give 3-aminopentane-1,5-diol (9.55 Kg, 72% yield) as a thick oil.

Step D: synthesis of 3-trimethylsilanyloxy-1-(2-trim-ethylsilanyloxy-ethyl)-propylamine A slurry of 3-aminopentane-1,5-diol (18.29 Kg) in i-PrOH (16.91 Kg) was added to a reactor, and the solvent evaporated under reduced pressure. Hexamethyldisilazane (31.985 Kg) in THF (55.3 Kg) and trimethylsilylchloride (35.57 Kg) in THF (172.03 Kg) were then added and the resulting mixture refluxed overnight. The reaction mixture was cooled, the solvent evaporated under reduced pressure, and the residue was purified by distillation (97-99° C.) to give 3-trimethylsilanyloxy-1-(2-trimethylsilanyloxyethyl)-propylamine (24.36 Kg).

Preparation 13

Synthesis of 3-(2-Methylsulfanyl-pyrimidin-4-yl)-[1,2,4]triazolo[4,3-a]-pyridine The synthesis of 3-(2-methylsulfanyl-pyrimidin-4-yl)-[1,2,4]triazolo[4,3-a]pyridine was carried out according to the process shown in Scheme 13.

SCHEME 13

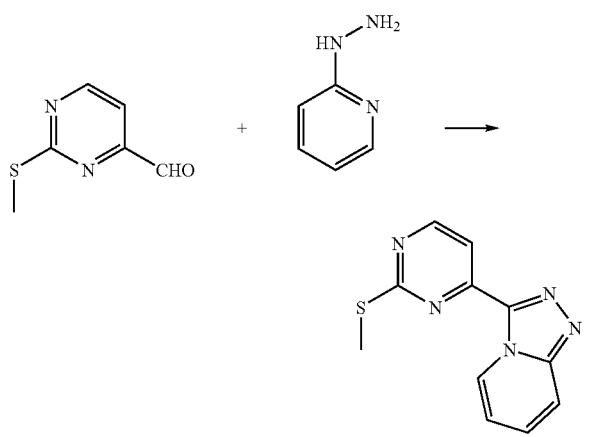

A mixture of 2-methylsulfanyl-pyrimidine-4-carbaldehyde (1.00 g) (U.S. Pat. No. 6,218,537) and 2-hydrazinopyridine (0.71 g) in EtOH (20 mL) was heated to reflux for 24 h, then cooled to RT and the resulting solid collected by filtration to give N-[1-(2-methylsulfanyl-pyrimidin-4-yl)-meth-(E)-ylidene]-N'-pyridin-2-yl-hydrazine (1.26 g). A mixture of this material and DCM (20 mL) was gently heated, and a second aliquot of DCM (10 mL) and chloroform (5 mL) added to facilitate solubilization. Iodobenzene diacetate (1.65 g) was added, and the resulting mixture stirred at RT under $N_2$ for 17 h. The reaction mixture was then evaporated under reduced pressure and the crude residue was triturated with hot $Et_2O$. Once the mixture cooled to RT, the solid was collected by filtration to afford 3-(2-methylsulfanyl-pyrimidin-4-yl)-[1,2,4]triazolo-[4,3-a]pyridine (1.12 g).

Preparation 14

Synthesis of 1-(2-Methylsulfanyl-pyrimidin-4-yl)-2,3-dihydro-1H-indole

The synthesis of 1-(2-methylsulfanyl-pyrimidin-4-yl)-2,3-dihydro-1H-indole was carried out according to the process shown in Scheme 14.

SCHEME 14

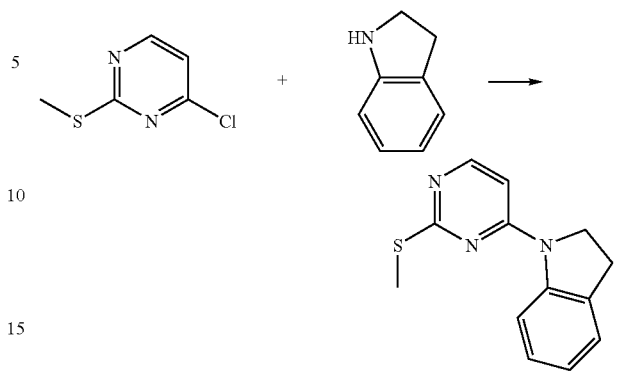

A mixture of 4-chloro-2-methylthiopyrimidine (4.02 g, 25 mmol), 2,3-dihydro-1H-indole (4.0 mL, 36 mmol) and N,N-diisopropyl ethyl amine (4 mL, 22 mmol) in DMF (10 mL) was heated to 100° C. under $N_2$ for 16 h. The solidified reaction mixture was cooled, diluted with EtOAc, and filtered. The collected solids were dissolved in DCM and MeOH and recrystallized from DCM/EtOAc to give 1-(2-methylsulfanyl-pyrimidin-4-yl)-2,3-dihydro-1H-indole (2.32 g, 38% yield) as a light-yellow solid. MS=244[M+H]$^+$.

Example 1

Synthesis of trans-4-[4-(1-Methyl-1H-indazol-3-yl)-pyrimidin-2-ylamino]-cyclohexanol The synthesis of trans-4-[4-(1-methyl-1H-indazol-3-yl)-pyrimidin-2-ylamino]-cyclohexanol was carried out according to the process shown in Scheme 15.

SCHEME 15

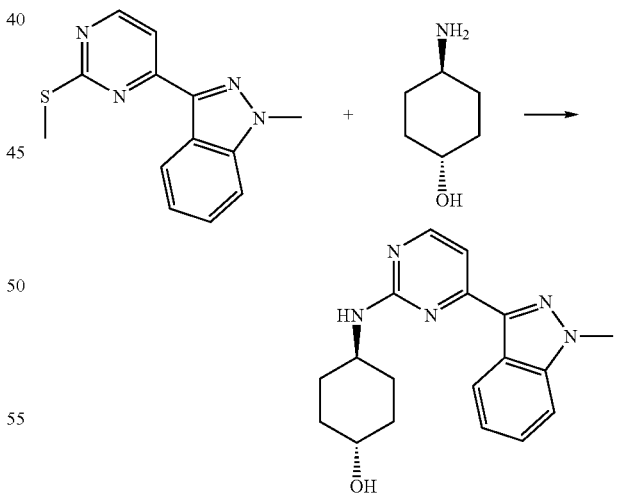

N-Chlorosuccinimide (239 mg, 1.77 mmol) was added to a solution of 1-methyl-3-(2-methylsulfanyl-pyrimidin-4-yl)-1H-indazole (413 mg, 1.6 mmol) in NMP, and the resulting mixture was stirred at 85° C. for 15 min. trans-Aminocyclohexanol was then added, the reaction mixture stirred for 1 h, then poured into water and extracted twice with EtOAc. The combined organic extracts were dried over $Na_2SO_4$, filtered, and evaporated under reduced pressure. The crude residue was purified by preparative TLC to give trans-4-[4-(1-methyl-1H-indazol-3-yl)-pyrimidin-2-ylamino]-cyclohexanol. MS=324 [M+H]+; MP=180-183.3° C. (Compound 77).

trans-4-[4-(4-Bromo-indazol-1-yl)-pyrimidin-2-ylamino]-cyclohexanol (white solid) was prepared in the same manner, utilizing the appropriate starting material. MS=388 [M+H]+; MP=200.5-201.9° C.

Example 2

Synthesis of trans-4-[4-(7-Methoxy-1H-indazol-3-yl)-pyrimidin-2-ylamino]-cyclohexanol The synthesis of trans-4-[4-(7-methoxy-1H-indazol-3-yl)-pyrimidin-2-ylamino]-cyclo-hexanol was carried out according to the process shown in Scheme 16.

SCHEME 16

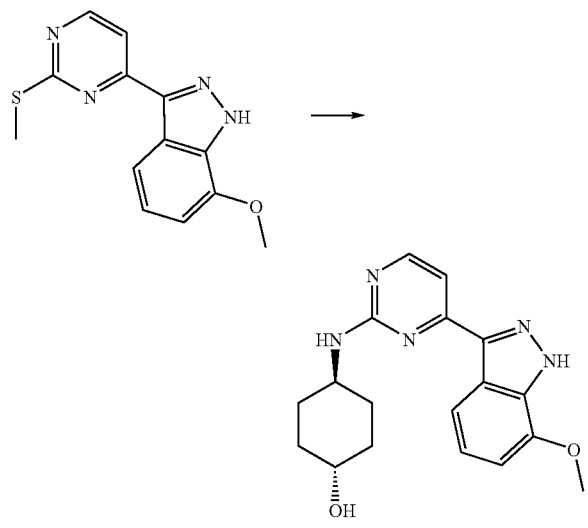

3-Chloroperoxybenzoic acid (77%, 407 mg, 1.82 mmol) was added to a solution of 7-methoxy-3-(2-methylsulfanyl-pyrimidin-4-yl)-1H-indazole (225 mg, 0.8 mmol) in DCM at 0° C., and the resulting mixture stirred for 3 h. The reaction mixture was then diluted with DCM, washed with aqueous NaHCO$_3$ (5%), dried over Na$_2$SO$_4$, filtered and evaporated under reduced pressure to give 3-(2-methanesulfonyl-pyrimidin-4-yl)-7-methoxy-1H-indazole, which was used without further purification. To a solution of this material in NMP was added trans-aminocyclohexanol (190 mg), and the resulting mixture was heated in a sealed tube to 120° C. for 1.5 hour. The reaction mixture was cooled to RT, water added and the resulting suspension stirred for 30 min. The solid precipitate was collected by filtration, washed with water, and dried under reduced pressure overnight to give trans-4-[4-(7-methoxy-1H-indazol-3-yl)-pyrimidin-2-yl-amino]-cyclohexanol. MS=341 [M+H]+; mp=243.3-244.9° C. (Compound 80)

In a similar manner, utilizing the appropriate starting material, the following compounds were prepared:
trans-4-[4-(1H-Indazol-3-yl)-pyrimidin-2-ylamino]-cyclohexanol, MS=310 [M+H]+ (Compound 78);
trans-4-(4-Benzo[d]isoxazol-3-yl-pyrimidin-2-ylamino)-cyclohexanol, MS=311 [M+H]+ (Compound 79);
trans-1-[2-(4-Hydroxy-cyclohexylamino)-pyrimidin-4-yl]-1H-indole-4-carboxylic acid methyl ester (yellow solid), MS=367 [M+H]+; mp=206.7-208.3° C. (Compound 37);
Cyclohexyl-(4-indol-1-yl-pyrimidin-2-yl)-amine (off-white crystalline solid), MS=293 [M+H]+; mp=192.5-193.0° C. (Compound 66);
trans-4-(4-Indol-1-yl-pyrimidin-2-ylamino)-cyclohexanol (off-white solid), MS=309 [M+H]+; mp=202.4-204.4° C.;
trans-N-(4-Indol-1-yl-pyrimidin-2-yl)-cyclohexane-1,4-diamine (off-white solid), MS=308 [M+H]+; mp=270.1-273.3° C. (Compound 52);
trans-4-(4-Indazol-2-yl-pyrimidin-2-ylamino)-cyclohexanol (white needles), MS=310 [M+H]+; mp=214.7-216.0° C.;
trans-4-(4-Indazol-1-yl-pyrimidin-2-ylamino)-cyclohexanol (white solid), MS=310 [M+H]+; mp=232.6-233.7° C. (Compound 10);
trans-4-[4-(6-Nitro-indazol-1-yl)-pyrimidin-2-ylamino]-cyclohexanol (yellow powder), MS=355 [M+H]+; mp=221.8-223.0° C. (Compound 27);
trans-4-(4-[1,2,4]Triazole[4,3-a]pyridin-3-yl-pyrimidin-2-ylamino)-cyclohexanol (off-white solid), MS=311 [M+H]+; mp=253.4-255.7° C. (Compound 85);
trans-4-(4-Pyrazolo[1,5-b]pyridazin-3-yl-pyrimidin-2-ylamino)-cyclohexanol (white needles), (the starting material 3-(2-methylsulfanyl-pyrimidin-4-yl)-pyrazolo[1,5-b]pyridazine was prepared accordingly to the procedure described in J. Med. Chem. 2004, 47, 4716-30), MS=311 [M+H]+; mp=214.9-215.6° C. (Compound 84);
trans-4-(4-Pyrrolo[3,2-b]pyridin-1-yl-pyrimidin-2-ylamino)-cyclohexanol (white solid), MS=310 [M+H]+, mp=198.9-200.3° C.;
trans-4-(4-Pyrrolo[3,2-c]pyridin-1-yl-pyrimidin-2-ylamino)-cyclohexanol (white crystalline solid), MS=310 [M+H]+, mp=229.9-230.2° C.; and
trans-4-[4-(2,3-Dihydro-indol-1-yl)-pyrimidin-2-ylamino]-cyclohexanol (white solid), MS=311 [M+H]+, mp=230.5-231.2° C.

Example 3

Synthesis of trans-4-[4-(7-Trifluoromethyl-1H-indazol-3-yl)-pyrimidin-2-yl-amino]-cyclohexanol The synthesis of trans-4-[4-(7-trifluoromethyl-1H-indazol-3-yl)-pyrimidin-2-ylamino]-cyclohexanol was carried out according to the process shown in Scheme 17.

SCHEME 17

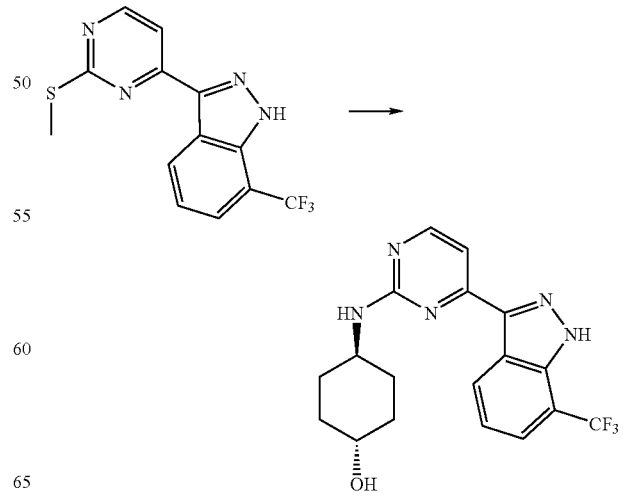

3-Chloroperoxybenzoic acid (77%, 318 mg, 0.64 mmol) was added to a solution of 3-(2-methylsulfanyl-pyrimidin-4-yl)-7-trifluoromethyl-1H-indazole (200 mg, 0.64 mmol) in DCM at 0° C., and the resulting mixture stirred for 2 h. The reaction mixture was then diluted with DCM, washed with aqueous NaHCO$_3$ (5%), dried over Na$_2$SO$_4$, filtered, and evaporated under reduced pressure to give 3-(2-methanesulfonyl-pyrimidin-4-yl)-7-trifluoromethyl-1H-indazole which was used without further purification. To a solution of this material in NMP was added trans-amino-cyclohexanol (148 mg) followed by DIPEA (0.11 mL, 0.64 mmol), the resulting mixture stirred at 120° C. for 1 hour, then cooled to RT and water added. The resulting suspension was stirred for 30 min, the solid precipitate collected by filtration, washed with water, and dried under reduced pressure overnight. The solid material was washed with hot EtOAc, filtered and dried under reduced pressure to give trans-4-[4-(7-trifluoromethyl-1H-indazol-3-yl)-pyrimidin-2-ylamino]-cyclohexanol (75 mg). MS=378 [M+H]$^+$; mp=265.5-270° C.

In the same manner, using the appropriate starting material, the following compounds were prepared:
trans-4-[4-(5-Fluoro-benzo[d]isoxazol-3-yl)-pyrimidin-2-ylamino]-cyclohexanol, MS=329 [M+H]$^+$; mp=172-173.9° C. (Compound 83);
(1,4-Dioxa-spiro[4.5]dec-8-yl)-(4-indazol-1-yl-pyrimidin-2-yl)-amine (white solid), MS=352 [M+H]$^+$; mp=207.5-208.8° C.;
trans-4-[4-(6-Methoxy-indazol-1-yl)-pyrimidin-2-ylamino]-cyclohexanol (pink powder); MS=340 [M+H]$^+$; MP=166.8-167.3° C.;
trans-1-[2-(4-Hydroxy-cyclohexylamino)-pyrimidin-4-yl]-1H-indazole-6-carbonitrile (white powder); MS=335 [M+H]$^+$; mp.=212.0-212.6° C.; and
trans-1-[2-(4-Hydroxy-cyclohexylamino)-pyrimidin-4-yl]-1H-indazole-6-carboxylic acid methyl ester (light yellow powder); MS=368 [M+H]$^+$; MP=214.9-216.3° C.

Example 4

Synthesis of trans-(4-Methyl-cyclohexyl)-[4-(4-nitro-indazol-1-yl)-pyrimidin-2-yl]-amine The synthesis of trans-(4-methyl-cyclohexyl)-[4-(4-nitroindazol-1-yl)-pyrimidin-2-yl]-amine was carried out according to the process shown in Scheme 18.

SCHEME 18

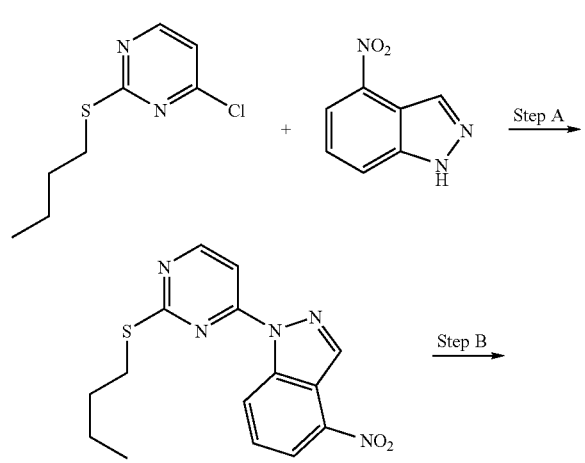

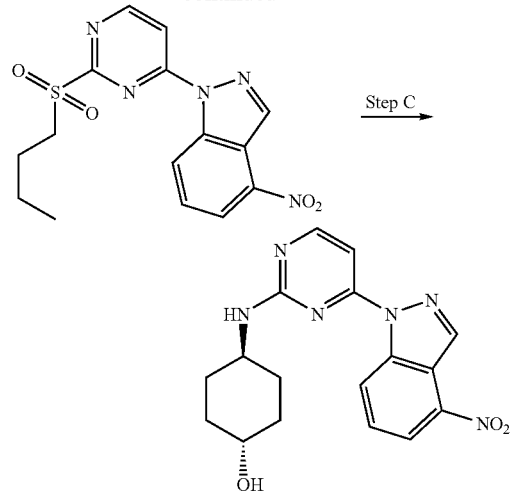

Step A: synthesis of 1-(2-butylsulfanyl-pyrimidin-4-yl)-4-nitro-1H-indazole

To a flask loaded with 2-butylsulfanyl-4-chloro-pyrimidine (202 mg) was added 4-nitro-1H-indazole (228 mg), followed by NaH (60% dispersion in mineral oil, 84 mg) and NMP (4 mL). The resulting mixture was stirred at RT overnight, water added, and the mixture extracted with EtOAc. The combined organic extracts were washed with water, dried over Na$_2$SO$_4$, filtered and evaporated under reduced pressure. The crude residue was purified by flash chromatography (hexane/EtOAc, 80:20) to give 1-(2-butylsulfanyl-pyrimidin-4-yl)-4-nitro-1H-indazole (156 mg).

In a similar manner, utilizing the appropriate starting materials, the following compounds were prepared:
1-(2-Butylsulfanyl-pyrimidin-4-yl)-1H-indazole-6-carbonitrile (the starting material, 1H-indazole-6-carbonitrile, was prepared following the method described in *J. Med. Chem.* 2000, 43(23):4398-415);
1-(2-Butylsulfanyl-pyrimidin-4-yl)-6-methoxy-1H-indazole (the starting material, 6-methoxy-1H-indazole, was prepared following the method described in *Annalen der Chemie* 1980, 908-27); and
1-(2-Butylsulfanyl-pyrimidin-4-yl)-1H-indazole-6-carboxylic acid methyl ester (the starting material, 1H-indazole-6-carboxylic acid methyl ester, was prepared following the method described in *J. Med. Chem.* 2000, 43, 47).

Step B: synthesis of 1-[2-(butane-1-sulfonyl)-pyrimidin-4-yl]-4-nitro-1H-indazole To a solution of 1-(2-butylsulfanyl-pyrimidin-4-yl)-4-nitro-1H-indazole (660 mg) in DCM cooled to 0° C. was added methyltrioxorhenium (30 mg), followed by aqueous H$_2$O$_2$ (30%, 1.3 mL). The reaction mixture was stirred at RT for 2 h, then poured into a mixture of water and DCM. The organic layer was separated, and the aqueous layer was extracted with DCM. The combined organic extracts were washed twice with aqueous Na$_2$SO$_3$, once with brine, dried over Na$_2$SO$_4$, filtered and evaporated under reduced pressure to give 1-[2-(butane-1-sulfonyl)-pyrimidin-4-yl]-4-nitro-1H-indazole (680 mg).

Step C: synthesis of trans-(4-methyl-cyclohexyl)-[4-(4-nitroindazol-1-yl)-pyrimidin-2-yl]-amine A mixture of 1-[2-(butane-1-sulfonyl)-pyrimidin-4-yl]-4-nitro-1H-indazole (480 mg) and trans-aminocyclohexanol (500 mg) was heated neat to 120° C. After the formation of a precipitate, NMP (0.8 mL) was added. The reaction mixture was stirred for 2 h, then cooled to RT and poured into a mixture of water and DCM. The solid precipitate was collected by filtration and dried under reduced pressure to give trans-(4-methyl-cyclohexyl)-[4-(4-nitro-indazol-1-yl)-pyrimidin-2-yl]-amine (160 mg) as a yellow powder. MS=355 [M+H]$^+$; MP=253.9-254.8° C.

Example 5

Synthesis of trans-4-(4-Indazol-1-ylpyrimidin-2-ylamino)-cyclohexane-carboxylic acid (3-hydroxy-butyl)-amide The synthesis of trans-4-(4-indazol-1-yl-pyrimidin-2-ylamino)-cyclohexanecarboxylic acid (3-hydroxy-butyl)-amide was carried out according to the process shown in Scheme 19.

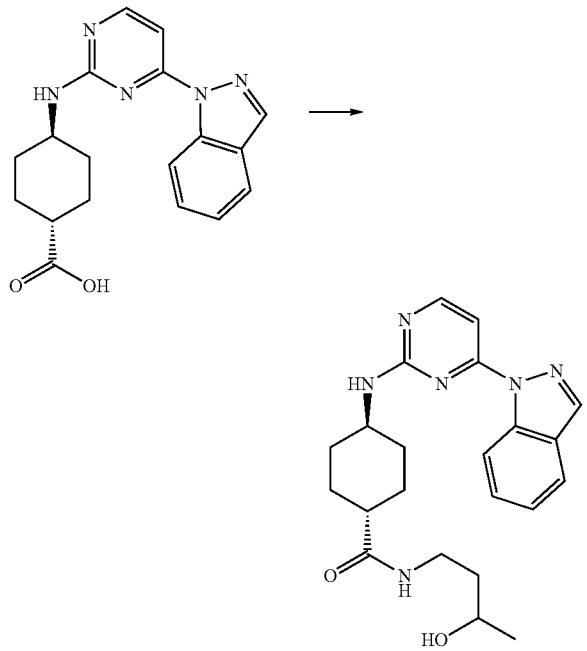

SCHEME 19

A mixture of trans-4-(4-indazol-1-ylpyrimidin-2-ylamino)-cyclohexanecarboxylic acid (100 mg, 0.30 mmol), 2-amino-2-butanol (39.2 mg, 0.44 mmol), BOP (194.6 mg, 0.44 mmol), DIPEA (77.4 mg, 0.60 mmol) in THF (8 mL) was stirred at RT overnight. Water (20 mL) was added to the resulting suspension: the solids first dissolved, then precipitated with the addition of more water (100 mL). The precipitate was collected by filtration, washed with water and Et$_2$O, and dried under reduced pressure to give trans-4-(4-indazol-1-yl-pyrimidin-2-ylamino)-cyclo-hexanecarboxylic acid (3-hydroxy-butyl)amide (78 mg) as white solid. MS=409 [M+H]$^+$.

In the same manner, utilizing the appropriate starting materials, the following compounds were prepared:

trans-4-(4-Indazol-1-ylpyrimidin-2-ylamino)-cyclohexanecarboxylic acid (2-methanesulfonylethyl)-amide (light brown solid), MS=443 [M+H]$^+$; MP=229.6-231.2° C.;

trans-4-(4-Indazol-1-ylpyrimidin-2-ylamino)-cyclohexanecarboxylic acid ((R)-2-methane-sulfonyl-1-methylethyl)-amide (white powder), MS=457 [M+H]$^+$; MP=289.0-291.0° C.;

trans-4-(4-Indazol-1-ylpyrimidin-2-ylamino)-cyclohexanecarboxylic acid [3-hydroxy-1-(2-hydroxyethyl)propyl]-amide (white solid), MS=439 [M+H]$^+$; MP=215.0-217.8° C.;

trans-4-(4-Indazol-1-ylpyrimidin-2-ylamino)-cyclohexanecarboxylic acid (1-hydroxymethylpropyl)amide (white powder), MS=409 [M+H]$^+$; MP=222.0-224.7° C.;

trans-4-(4-Indazol-1-ylpyrimidin-2-ylamino)-cyclohexanecarboxylic acid (2,3-dihydroxypropyl)-amide (white powder), MS=411 [M+H]$^+$; MP=243.3-245.1° C.;

trans-4-(4-Indazol-1-ylpyrimidin-2-ylamino)-cyclohexanecarboxylic acid (3-hydroxy-1-methylpropyl)-amide (white solid), MS=409 [M+H]$^+$; MP=231.9-234.4° C.;

trans-(4-Hydroxypiperidin-1-yl)-[4-(4-indazol-1-ylpyrimidin-2-ylamino)-cyclohexyl]-methanone (light brown solid), MS=421 [M+H]$^+$; MP=125.5-128.8° C.;

trans-1-[4-(4-Indazol-1-ylpyrimidin-2-ylamino)-cyclohexanecarbonyl]-pyrrolidin-3-one (light brown powder) (the amine starting material was prepared by a standard BOC deprotection of the commercially available 3-oxo-pyrrolidine-1-carboxylic acid tert-butyl ester), MS=405 [M+H]$^+$; MP=172.6-174.8° C.;

trans-4-(4-Indazol-1-ylpyrimidin-2-ylamino)-cyclohexanecarboxylic acid isopropylamide (white solid), MS=379 [M+H]$^+$; MP=270.0-271.0° C.;

trans-4-(4-Indazol-1-ylpyrimidin-2-ylamino)-cyclohexanecarboxylic acid ((S)-2-hydroxy-1-methylethyl)amide (white powder), MS=395 [M+H]$^+$; MP=254.6-256.9° C.;

trans-4-(4-Indazol-1-ylpyrimidin-2-ylamino)-cyclohexanecarboxylic acid (2-methoxyethyl)-amide (white powder), MS=395 [M+H]$^+$; MP=216.9-219.1° C.;

trans-4-(4-Indazol-1-ylpyrimidin-2-ylamino)-cyclohexanecarboxylic acid (2-hydroxy-1-hydroxymethylethyl)-amide (white powder), MS=411 [M+H]$^+$; MP=239.1-240.9° C.;

trans-((R)-3-Hydroxypyrrolidin-1-yl)-[4-(4-indazol-1-ylpyrimidin-2-ylamino)-cyclohexyl]-methanone (white powder), MS=407 [M+H]$^+$; MP=203.3-204.0° C.;

trans-((S)-3-Hydroxypyrrolidin-1-yl)-[4-(4-indazol-1-ylpyrimidin-2-ylamino)-cyclohexyl]-methanone (white solid), MS=407 [M+H]$^+$; MP=201.7-202.7° C.;

trans-4-(4-Indazol-1-ylpyrimidin-2-ylamino)-cyclohexanecarboxylic acid (2-hydroxy-1,1-dimethylethyl)-amide (white powder), MS=409 [M+H]$^+$; MP=256.5-259.5° C.;

trans-4-(4-Indazol-1-ylpyrimidin-2-ylamino)-cyclohexanecarboxylic acid (2-hydroxy-2-methylpropyl)amide (white solid) (the amine starting material was prepared following J. Med. Chem. 1998, 41, 3347), MS=409 [M+H]$^+$; MP=224.2-225.9° C.;

trans-4-(4-Indazol-1-ylpyrimidin-2-ylamino)-cyclohexanecarboxylic acid (2-hydroxyethyl)-methyl-amide (white solid), MS=395 [M+H]$^+$; MP=168.1-169.6° C.;

trans-4-(4-Indazol-1-ylpyrimidin-2-ylamino)-cyclohexanecarboxylic acid ((R)-1-methyl-2-methylsulfanylethyl)-amide (white solid), MS=425 [M+H]$^+$; MP=215.1-218.8° C.;

trans-4-(4-Indazol-1-ylpyrimidin-2-ylamino)-cyclohexanecarboxylic acid ((S)-2-hydroxy-1,2-dimethylpropyl)amide (light brown powder) (the amine starting material was synthesized as described in WO 2002064594), MS=423 [M+H]$^+$; MP=214.2-215.2° C.;

trans-4-(4-Indazol-1-ylpyrimidin-2-ylamino)-cyclohexanecarboxylic acid (2-hydroxypropyl)amide (off-white powder), MS=395 [M+H]⁺; MP=234.0-236.6° C.;

trans-4-(4-Indazol-1-ylpyrimidin-2-ylamino)-cyclohexanecarboxylic acid ((S)-1-methyl-2-methylsulfanyl-ethyl)-amide (white solid), MS=425 [M+H]⁺; MP=221.5-222.5° C.;

trans-4-(4-Indazol-1-ylpyrimidin-2-ylamino)-cyclohexanecarboxylic acid ethyl-(2-hydroxyethyl)amide (white solid), MS=409 [M+H]⁺; MP=111.5-113.0° C.;

trans-4-(4-Indazol-1-ylpyrimidin-2-ylamino)-cyclohexanecarboxylic acid cyclopropylmethylamide (white solid), MS=391 [M+H]⁺; MP=248.5-252.5° C.; and trans-4-(4-Indazol-1-ylpyrimidin-2-ylamino)-cyclohexanecarboxylic acid cyclopentylamide (white powder), MS=405 [M+H]⁺; MP=272.2-274.4° C.

Example 6

Synthesis of trans-[4-(4-Indazol-1-yl-pyrimidin-2-ylamino)-cyclohexyl]-morpholin-4-yl-methanone The synthesis of trans-[4-(4-indazol-1-ylpyrimidin-2-ylamino)cyclohexyl]-morpholin-4-yl-methanone was carried out according to the process shown in Scheme 20.

SCHEME 20

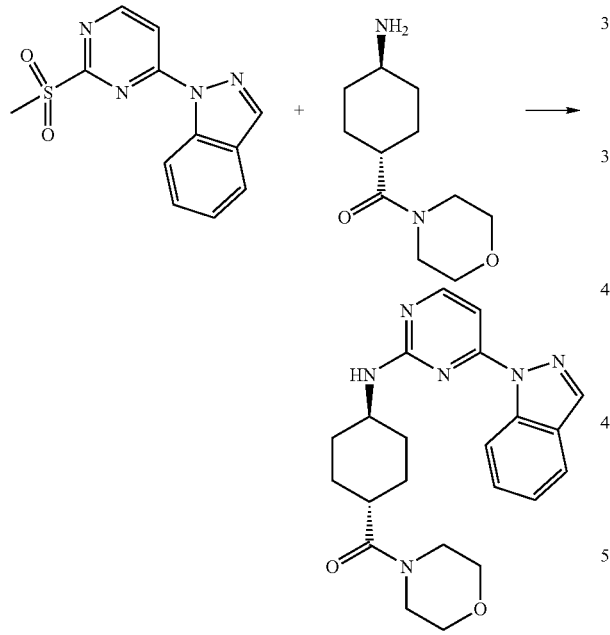

A sealable (5 mL) tube was loaded with trans-(4-aminocyclohexyl)-morpholin-4-yl-methanone (89.3 mg, 0.36 mmol), DIPEA (0.19 mL, 1.10 mmol) and NMP (1 mL). A second sealable (10 mL) tube was loaded with 1-(2-methanesulfonyl-pyrimidin-4-yl)-1H-indazole (100 mg, 0.36 mmol) and NMP (1 mL). Both mixtures were heated to 120° C., until complete dissolution of the solids. The solution of 1-(2-methanesulfonyl-pyrimidin-4-yl)-1H-indazole was then transferred via cannula into the vial containing the amine mixture, and the resulting mixture was heated to 120° C. for 3 h. The reaction mixture was then cooled to RT and stirred for 2 days, then partitioned between aqueous NH₄Cl (saturated) and DCM. The organic layer was separated and the aqueous layer was extracted with DCM. The combined organic extracts were dried over Na₂SO₄, filtered and evaporated under reduced pressure to give an amber colored oil. This crude material was recrystallized from Et₂O, the supernatant decanted away, and the resulting crystals were washed with Et₂O. The crystalline material was recrystallized from DCM to give 57 mg of a pale beige crystalline material which was purified by flash chromatography (EtOAc/hexane, gradient from 50:50 to 70:30) to give trans-[4-(4-indazol-1-ylpyrimidin-2-ylamino)-cyclohexyl]-morpholin-4-yl-methanone (34 mg) as an off-white powder. MS=407 [M+H]⁺; MP=191.0-192.0° C.

In a similar manner, utilizing the appropriate starting materials, the following compounds were prepared:

trans-4-[4-(6-Methylindazol-1-yl)-pyrimidin-2-ylamino]-cyclohexanol (yellow powder), MS=324 [M+H]⁺; MP=211.0-212.5° C.;

trans-4-(4-Indazol-1-ylpyrimidin-2-ylamino)-cyclohexanecarboxylic acid dimethylamide (white powder), MS=365 [M+H]⁺; MP=223.0-225.0° C.; and trans-4-[4-(5-Methylindazol-1-yl)-pyrimidin-2-ylamino]-cyclohexanol (off-white powder), MS=324 [M+H]⁺; MP=221.5-223.5° C.

Example 7

Synthesis of trans-1-[2-(4-Hydroxy-cyclohexylamino)-pyrimidin-4-yl]-1H-indole-4-carboxylic acid The synthesis of trans-1-[2-(4-hydroxycyclohexylamino)-pyrimidin-4-yl]-1H-indole-4-carboxylic acid was carried out according to the process shown in Scheme 21.

SCHEME 21

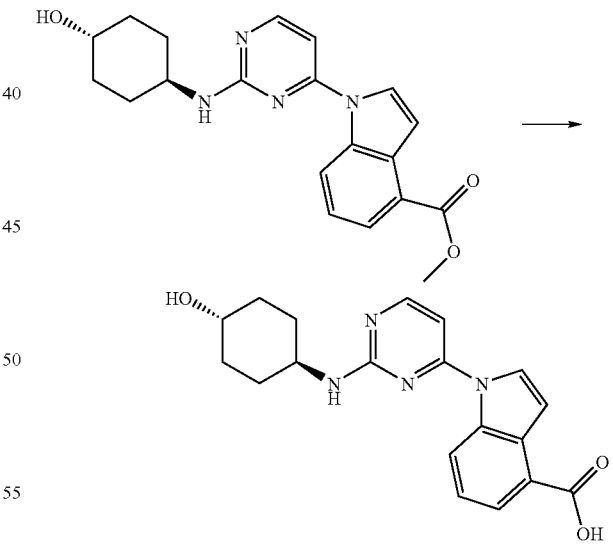

LAH (327 mg, 13.6 mmol) was added to a suspension of 1-[2-(4-hydroxycyclohexylamino)-pyrimidin-4-yl]-1H-indole-4-carboxylic acid methyl ester (1.0 g, 2.7 mmol) in a mixture of THF (4 mL), water (4 mL) and MeOH (1 mL). The reaction mixture was stirred at RT for 16 h, then evaporated under reduced pressure to give a beige solid. Aqueous HCl (1 M, 14 mL) was added to the residue, and the resulting mixture was stirred and evaporated under reduced pressure. The residue was triturated with MeOH to give trans-1-[2-(4-hydroxycyclohexylamino)-pyrimidin-4-yl]-1H-indole-4-carboxylic acid (700 mg) as an off-white solid. MS=353 [M+H]⁺; MP=259.0-261.0° C.

Example 8

Synthesis of trans-4-[4-(4-Aminoindol-1-yl)-pyrimidin-2-ylamino]-cyclohexanol

The synthesis of trans-4-[4-(4-aminoindol-1-yl)-pyrimidin-2-ylamino]-cyclohexanol was carried out according to the process shown in Scheme 22.

SCHEME 22

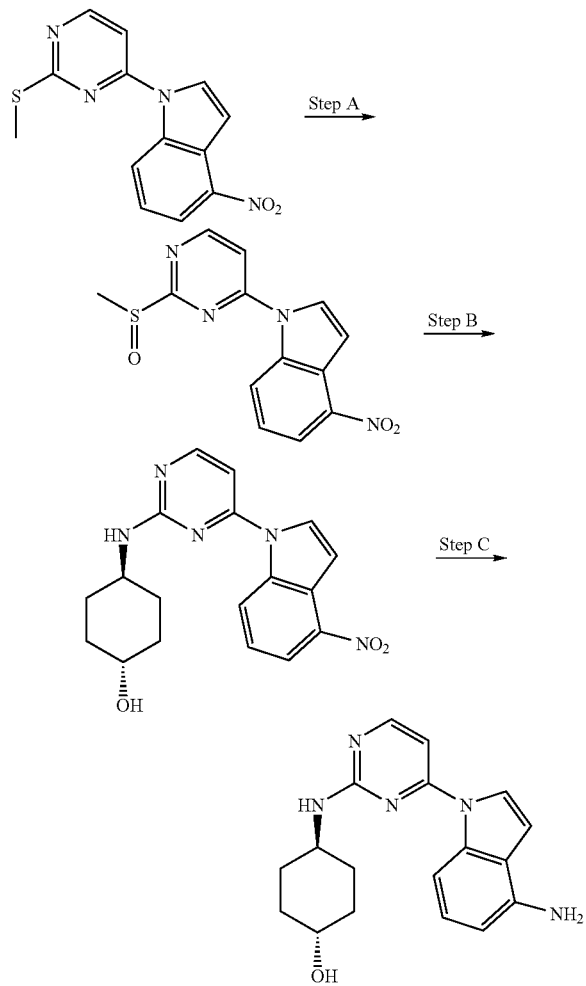

Step A: synthesis of 1-(2-methanesulfinylpyrimidin-4-yl)-4-nitro-1H-indole

A suspension of 3-chloroperoxybenzoic acid (77%, 3.11 g) in $CHCl_3$ (40 mL) was slowly added at 0° C. under $N_2$ to a mixture of 1-(2-methylsulfanylpyrimidin-4-yl)-4-nitro-1H-indole (3.93 g, 14.0 mmol) in $CHCl_3$ (50 mL). The resulting mixture was allowed to warm up to RT, and stirred overnight. The reaction mixture was then diluted with DCM (200 mL) and washed with aqueous $NaHCO_3$ (saturated). The resulting yellow precipitate was collected by filtration and dried under reduced pressure to give 1-(2-methanesulfinyl-pyrimidin-4-yl)-4-nitro-1H-indole (2.36 g). The mother liquors were dried over $Na_2SO_4$, filtered and evaporated under reduced pressure to give a second aliquot (690 mg).

Step B: synthesis of trans-4-[4-(4-nitroindol-1-yl)-pyrimidin-2-ylamino]-cyclohexanol A round bottom flask loaded with 1-(2-methanesulfinylpyrimidin-4-yl)-4-nitro-1H-indole (3.02 g) and trans-aminocyclohexanol (2.87 g) was placed in an oil bath at 75° C., and NMP (5 mL) was added. The resulting mixture was heated to 105° C. for 20 min, then stirred at RT overnight. The resulting solid was triturated 3 times with hexane/$Et_2O$ (1:1, 50 mL), the supernatant discarded, and the residual solvent evaporated under reduced pressure. The solid residue was suspended in water (70 mL) with stirring, then collected by filtration and dried under reduced pressure to give trans-4-[4-(4-nitroindol-1-yl)-pyrimidin-2-ylamino]-cyclohexanol (2.47 g), which was used without further purification.

In the same manner, utilizing the appropriate starting material, the following compounds were prepared:

trans-4-[4-(4-Methoxyindol-1-yl)-pyrimidin-2-ylamino]-cyclohexanol (off-white solid), MS=339 [M+H]⁺; MP=208.0-209.8° C.;

trans-4-[4-(3-Methylindol-1-yl)-pyrimidin-2-ylamino]-cyclohexanol (white solid), MS=323 [M+H]⁺; MP=213.9-215.7° C.;

trans-4-[4-(6-Fluoroindol-1-yl)-pyrimidin-2-ylamino]-cyclohexanol (white solid), MS=327 [M+H]⁺; MP=188.0-190.0° C.;

trans-4-[4-(4-Benzyloxyindol-1-yl)-pyrimidin-2-ylamino]-cyclohexanol (light yellow solid), MS=415 [M+H]⁺; MP=171.1-173.2° C.;

trans-4-[4-(5-Benzyloxyindol-1-yl)-pyrimidin-2-ylamino]-cyclohexanol (off-white solid), MS=415 [M+H]⁺; MP=185.1-186.7° C.;

trans-4-[4-(6-Methylindol-1-yl)-pyrimidin-2-ylamino]-cyclohexanol (white solid), MS=323 [M+H]⁺; MP=207.0-208.0° C.;

trans-4-[4-(4-Methylindol-1-yl)-pyrimidin-2-ylamino]-cyclohexanol (off-white solid), MS=323 [M+H]⁺; MP=205.5-205.9° C.;

trans-4-[4-(4-Fluoroindol-1-yl)-pyrimidin-2-ylamino]-cyclohexanol (white solid), MS=327 [M+H]⁺; MP=210.5-212.0° C.;

trans-4-[4-(5-Fluoroindol-1-yl)-pyrimidin-2-ylamino]-cyclohexanol (white solid), MS=327 [M+H]⁺; MP=217.2-217.8° C.;

trans-1-[2-(4-Hydroxycyclohexylamino)-pyrimidin-4-yl]-1H-indole-3-carboxylic acid methyl ester (off-white solid), MS=367 [M+H]⁺; MP=177.5-178.8° C.;

trans-1-[2-(4-Hydroxycyclohexylamino)-pyrimidin-4-yl]-1H-indole-5-carboxylic acid methyl ester (white solid), MS=367 [M+H]⁺; MP=238.5-239.2° C.;

trans-4-[4-(5-Methoxyindol-1-yl)-pyrimidin-2-ylamino]-cyclohexanol (off-white powder), MS=339 [M+H]⁺; MP=203.6-204.0° C.;

trans-1-[2-(4-Hydroxycyclohexylamino)-pyrimidin-4-yl]-1H-indole-4-carbonitrile (off-white solid), MS=334 [M+H]⁺; MP=234.9-235.3° C.;

trans-1-[2-(4-Hydroxycyclohexylamino)-pyrimidin-4-yl]-1H-indole-6-carboxylic acid methyl ester (light yellow solid), MS=367 [M+H]⁺; MP=232.2-234.5° C.;

trans-4-[4-(5-Methylindol-1-yl)-pyrimidin-2-ylamino]-cyclohexanol (off-white solid), MS=323 [M+H]⁺; MP=202.5-203.5° C.; and trans-4-{4-[4-(1-Hydroxy-1-methylethyl)-indol-1-yl]-pyrimidin-2-ylamino}-cyclohexanol (off-white solid), MS=367 [M+H]⁺; MP=168.0-169.0° C.

Step C: synthesis of trans-4-[4-(4-aminoindol-1-yl)-pyrimidin-2-ylamino]-cyclohexanol A mixture of trans-4-[4-(4-nitroindol-1-yl)-pyrimidin-2-ylamino]-cyclohexanol (2.44 g), EtOH (35 mL) and water (11 mL) was heated to 80° C. To the hot suspension was added ammonium chloride (1.46 g) followed by iron(0) (Fisher, 1.55 g) and the resulting mixture heated to 80° C. for 2 h, then to 50° C. for an additional 24 h. The reaction mixture was filtered through a CELITE™ pad, the filter cake washed with EtOAc/MeOH (3:2), and the filtrate evaporated under reduced pressure. The crude residue was purified by flash chromatography (MeOH/DCM, gradient from 2.5:97.5 to 10:90) to give trans-4-[4-(4-aminoindol-1-yl)-pyrimidin-2-ylamino]-cyclohexanol as a light yellow solid. MS=324 [M+H]⁺; MP=218.9-220.1° C.

trans-4-[4-(6-Amino-indazol-1-yl)-pyrimidin-2-ylamino]-cyclohexanol was prepared in the same manner, utilizing the appropriate starting material. MS=325 [M+H]⁺; MP=236.5-237.5° C.

Example 9

Synthesis of trans-1-[2-(4-Hydroxycyclohexylamino)-pyrimidin-4-yl]-1H-indol-5-ol The synthetic procedure described in this Example was carried out according to the process shown in Scheme 23.

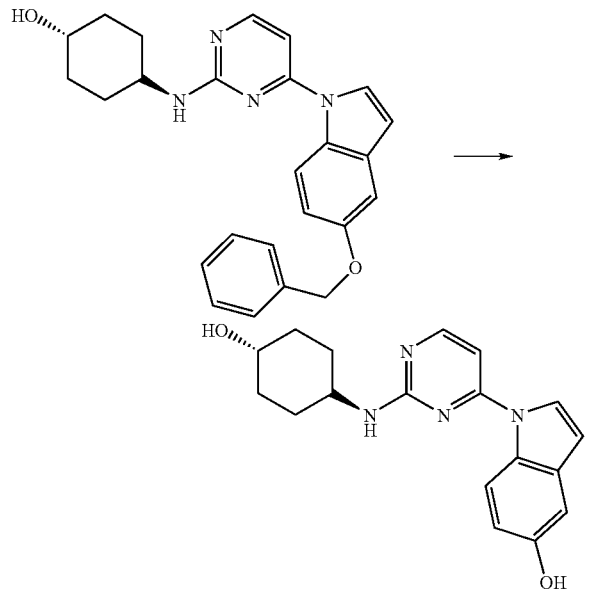

SCHEME 23

A mixture of 4-[4-(5-benzyloxyindol-1-yl)-pyrimidin-2-ylamino]-cyclohexanol (70 mg) and Pd/C (15%, 38 mg) in EtOH was stirred under H₂ (balloon pressure) at RT for 4 days. The reaction mixture was then filtered through a CELITE™ pad, the filter cake washed with EtOH, and the filtrate evaporated under reduced pressure. The residue was purified by flash chromatography (DCM/MeOH, 95:5) to give trans-1-[2-(4-hydroxy-cyclohexylamino)-pyrimidin-4-yl]-1H-indol-5-ol (51 mg) as an off-white solid. MS=325 [M+H]⁺; MP=246.5-248.0° C.

Example 10

Synthesis of trans-4-[4-(4-Hydroxymethylindol-1-yl)-pyrimidin-2-ylamino]-cyclohexanol The synthesis of trans-4-[4-(4-hydroxymethylindol-1-yl)-pyrimidin-2-ylamino]-cyclohexanol was carried out according to the process shown in Scheme 24.

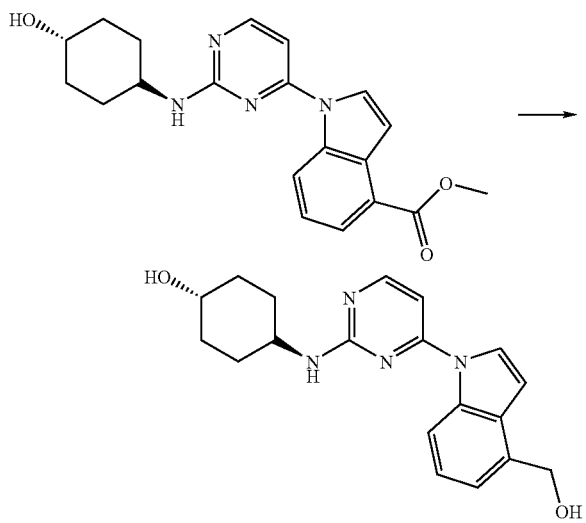

SCHEME 24

A solution of LAH (1 M in THF, 0.57 mL) was slowly added at −10° C. under argon atmosphere to a solution of 1-[2-(4-hydroxycyclohexylamino)-pyrimidin-4-yl]-1H-indole-4-carboxylic acid methyl ester (100 mg) in THF (0.3 mL). The resulting mixture was stirred at −10° C. for 30 min, and at RT overnight. The reaction mixture was then cooled to 0° C. and water (20 µL) was added, followed by aqueous NaOH (15%, 20 µL) and a second aliquot of water (70 µL). The resulting mixture was stirred for 30 min, then filtered through a CELITE™ pad. The inorganic salts were triturated, the supernatant added to the filtrate, and the solution evaporated under reduced pressure to give trans-4-[4-(4-hydroxymethylindol-1-yl)-pyrimidin-2-ylamino]-cyclohexanol (32.5 g, 35% yield) as a white solid. MS=339 [M+H]⁺; MP=212.0-213.3° C.

trans-4-[4-(5-Hydroxymethylindol-1-yl)-pyrimidin-2-ylamino]-cyclohexanol (white solid) was prepared in a similar manner, utilizing the appropriate starting materials. MS=339 [M+H]⁺; MP=232.0-233.9° C.

Example 11

Synthesis of trans-4-(4-indazol-1-ylpyrimidin-2-ylamino)-cyclohexane-carboxylic acid The synthesis of trans-4-(4-indazol-1-ylpyrimidin-2-ylamino)-cyclohexanecarboxylic acid was carried out according to the process shown in Scheme 25.

SCHEME 25

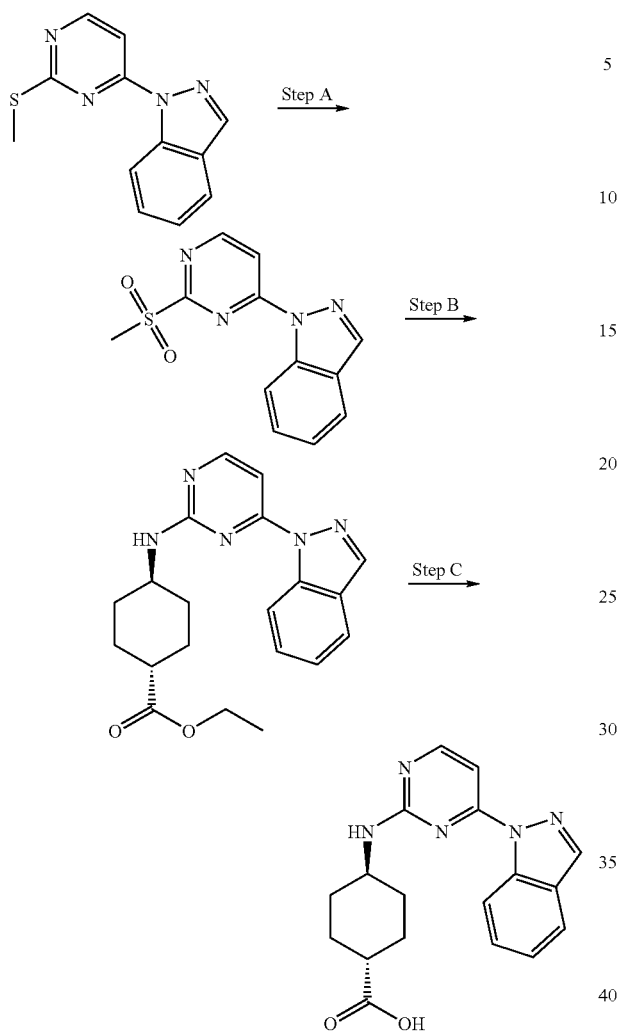

Step A: synthesis of 1-(2-methanesulfonyl-pyrimidin-4-yl)-1H-indazole

3-Chloroperoxybenzoic acid (77%, 14.97 g, 86.7 mmol) was added to a solution of 1-(2-methansulfanyl-pyrimidin-4-yl)-1H-indazole (10 g, 41.3 mmol) in $CHCl_3$ (50 mL) cooled in an ice/acetone bath, and the resulting mixture stirred overnight. The reaction mixture was washed with aqueous sodium bisulfite (10%). The resulting solid was filtered off, and the filtrate phases separated. The aqueous layer was extracted with DCM, the combined organic extracts washed with aqueous NaOH, aqueous $NaHCO_3$ (saturated), dried over $MgSO_4$, filtered and evaporated under reduced pressure to give 1-(2-methanesulfonyl-pyrimidin-4-yl)-1H-indazole (6.4 g) as an orange solid, used without further purification. MS=275 $[M+H]^+$; MP=177.0-181.1° C.

In the same manner, utilizing the appropriate starting materials, the following compounds where prepared:

1-(2-Methanesulfonylpyrimidin-4-yl)-6-methyl-1H-indazole; and 1-(2-Methanesulfonylpyrimidin-4-yl)-5-methyl-1H-indazole.

Step B: synthesis of trans-4-(4-indazol-1-ylpyrimidin-2-ylamino)-cyclohexanecarboxylic acid ethyl ester 1-(2-Methanesulfonylpyrimidin-4-yl)-1H-indazole (6.4 g) was suspended in THF and the mixture heated to 60° C. until complete dissolution of the solids. trans-4-Amino-cyclohexane-carboxylic acid ethyl ester (7.99 g, 46.6 mmol) was added, followed by TEA (9.7 mL, 69.9 mmol), and the resulting mixture stirred overnight. The reaction mixture was concentrated under reduced pressure until solids started to precipitate, and was then heated to 60° C. for 24 h. THF (4 mL) was added, and the reaction mixture stirred for 64 h at 60° C. The resulting mixture was extracted with EtOAc, the combined organic extracts washed with water, dried over $MgSO_4$, filtered, and evaporated under reduced pressure. The crude residue was purified by flash chromatography (DCM/MeOH, 98:2) and the brown solid obtained was triturated with $Et_2O$ to give trans-4-(4-indazol-1-ylpyrimidin-2-ylamino)-cyclohexanecarboxylic acid ethyl ester (2.883 g) as a white solid.

Step C: synthesis of trans-4-(4-indazol-1-ylpyrimidin-2-ylamino)cyclohexanecarboxylic acid A mixture of trans-4-(4-indazol-1-ylpyrimidin-2-ylamino)-cyclohexanecarboxylic acid ethyl ester (2.88 g, 7.9 mmol), aqueous NaOH (2 M, 65 mL) and THF (65 mL) was stirred overnight. MeOH (40 mL) was added, and the reaction mixture stirred for an additional 105 min. Aqueous HCl (1M) was added to reach pH 3, and the resulting solid collected by filtration to give trans-4-(4-indazol-1-yl-pyrimidin-2-ylamino)-cyclohexanecarboxylic acid (2.739 g) without further purification.

Example 12

Synthesis of trans-N-[4-(4-Indazol-1-ylpyrimidin-2-ylamino)-cyclohexyl]-methanesulfonamide The synthesis of trans-N-[4-(4-indazol-1-ylpyrimidin-2-ylamino)-cyclohexyl]-methane-sulfonamide was carried out according to the process shown in Scheme 26.

SCHEME 26

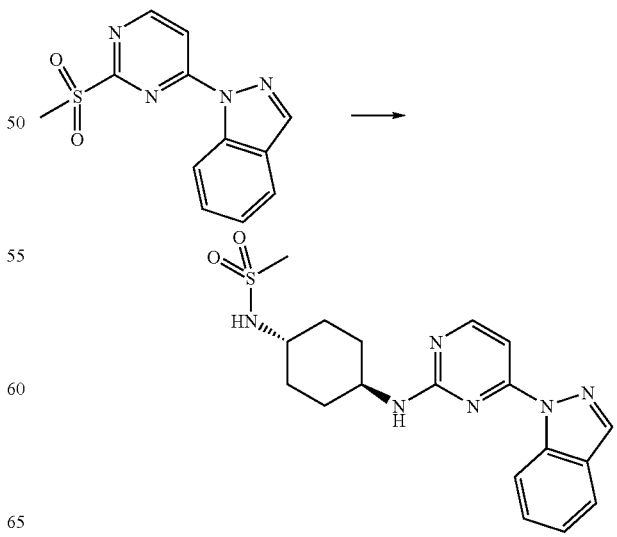

A mixture of trans-cyclohexane-1,4-diamine (0.62 g, 5.5 mmol) and NMP (10 mL) was heated to 120° C. for 5 min, then 1-(2-methanesulfonyl-pyrimidin-4-yl)-1H-indazole (300 mg) in NMP (10 mL) was added dropwise and the resulting mixture was stirred for 15 min. Methane-sulfonic anhydride (1.88 g, 10.8 mmol) was slowly added, and the reaction mixture stirred for 30 min. The solvent was evaporated by distillation under vacuum, EtOAc added to the residue, and the resulting solution washed with water. The organic layer was dried over $Na_2SO_4$, filtered and evaporated under reduced pressure. The crude residue was purified by trituration with hot DCM/MeOH (90:10) to give trans-N-[4-(4-indazol-1-yl-pyrimidin-2-ylamino)-cyclohexyl]-methanesulfonamide (38.0 mg) as a white solid. $MS=387 [M+H]^+$; MP=269.6-270.4° C.

Example 13

Synthesis of 4-(4-Indazol-1-ylpyrimidin-2-ylamino)-1-methylcyclohexanol

The synthesis of 4-(4-indazol-1-ylpyrimidin-2-ylamino)-1-methylcyclohexanol was carried out according to the process shown in Scheme 27.

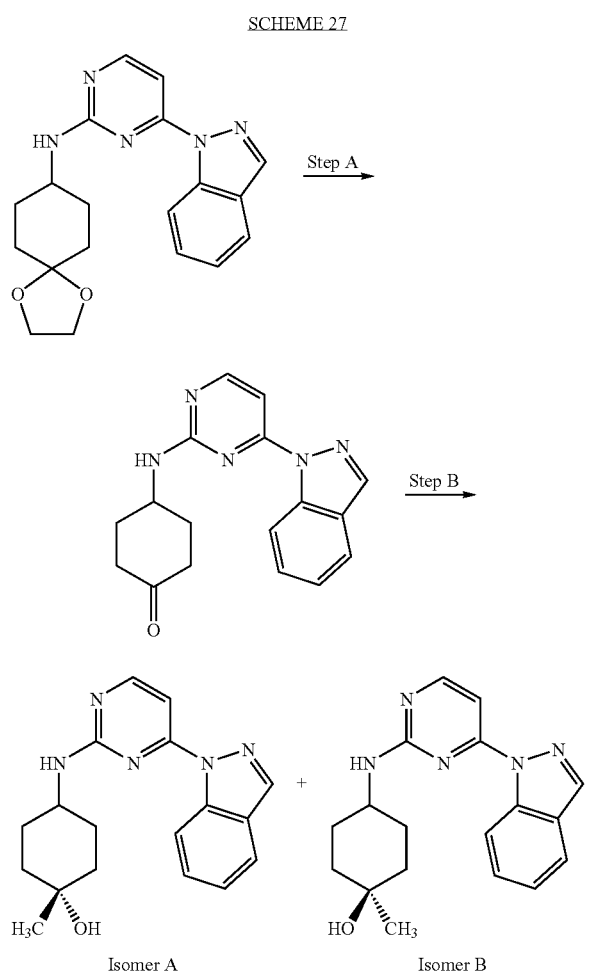

SCHEME 27

Step A: synthesis of 4-(4-indazol-1-ylpyrimidin-2-ylamino)-cyclohexanone

Aqueous HCl (3 M, 40 mL) was added to (1,4-dioxaspiro[4.5]dec-8-yl)-(4-indazol-1-yl-pyrimidin-2-yl)-amine (1.89 g, 5 mmol) in THF (40 mL), and the resulting mixture heated to 80° C. for 1 h. The reaction mixture was cooled and poured onto a mixture of ice and aqueous NaOH (1 M, 120 mL), and the resulting suspension filtered. The collected solids were washed with water, taken up in DCM/MeOH, and a portion of the solvent evaporated under reduced pressure. The resulting suspension was filtered, the collected solids washed with hexanes, and dried under reduced pressure to give 4-(4-indazol-1-ylpyrimidin-2-ylamino)-cyclohexanone (1.57 g, 95% yield) as a white powder. $MS=308 [M+H]^+$; MP=211.8-213.2° C.

Step B: synthesis of 4-(4-indazol-1-yl-pyrimidin-2-ylamino)-1-methyl-cyclohexanol A solution of methylmagnesium chloride (3 M in THF, 2.4 mL, 7.2 mmol) was slowly added to a suspension of 4-(4-indazol-1-ylpyrimidin-2-ylamino)-cyclohexanone (600 mg, 2 mmol) in THF (100 mL) at −78° C. under $N_2$. The reaction mixture was stirred for 15 min, a second aliquot of methylmagnesium chloride (3 M in THF, 1.0 mL, 3 mmol) added, and the resulting mixture stirred at −78° C. for 30 min. The reaction mixture was then warmed to RT and stirred for 4 h, then poured onto a mixture of ice and aqueous $NH_4Cl$ (saturated). The resulting mixture was extracted with EtOAc, the combined organic extracts washed with brine, dried over $MgSO_4$, filtered, and evaporated under reduced pressure to give a white solid (609 mg, 96% yield). This crude material was purified by flash chromatography twice (MeOH/DCM, gradient from 3:97 to 5:95,) to give 4-(4-indazol-1-yl-pyrimidin-2-ylamino)-1-methyl-cyclohexanol (123 mg, 19% yield of the less-polar isomer as a white solid; and 360 mg, 57% yield of the more polar isomer as a white solid). Both isomers were recrystallized from DCM/hexanes (about 1:1) to give a white solid for the less polar isomer A (100 mg) and a crystalline free-flowing solid for the more polar isomer B (290 mg).

Isomer A: $MS=324 [M+H]^+$; MP=211.9-213.3° C.
Isomer B: $MS=324 [M+H]^+$; MP=168.1-170.1° C.

Example 14

Synthesis of trans-4-[4-(4-Phenylmethanesulfonylindol-1-yl)-pyrimidin-2-yl-amino]-cyclohexanol The synthesis of trans-4-[4-(4-phenylmethanesulfonylindol-1-yl)-pyrimidin-2-ylamino]-cyclohexanol was carried out according to the process shown in Scheme 28

SCHEME 28

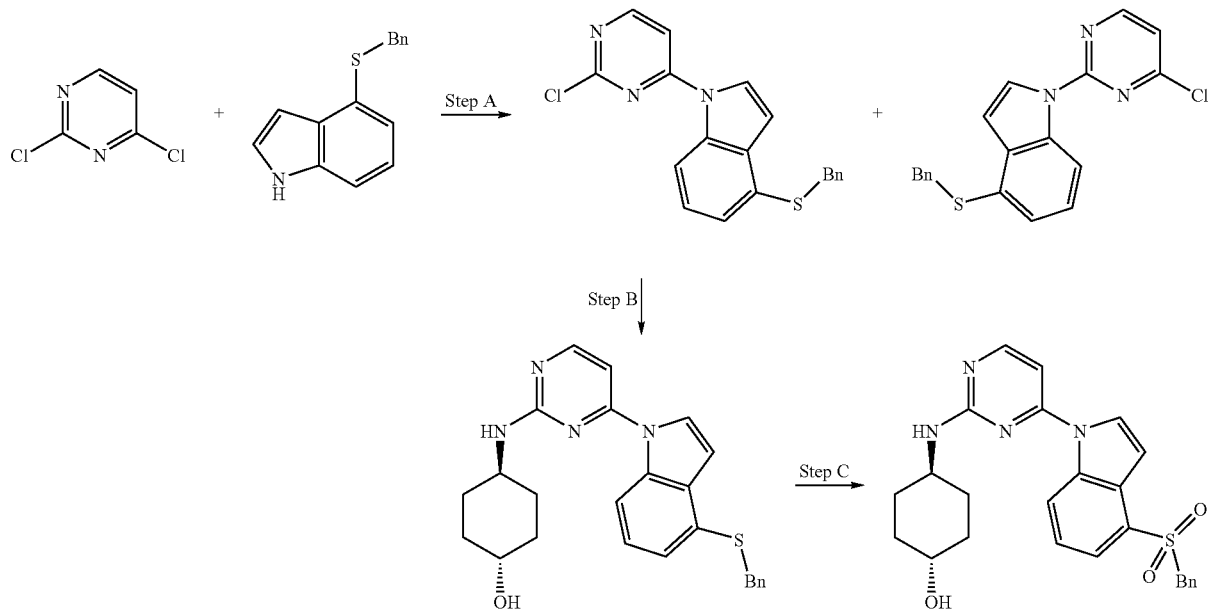

Step A: Synthesis of 4-benzylsulfanyl-1-(2-chloro-pyrimidin-4-yl)-1H-indole and 4-benzyl-sulfanyl-1-(4-chloro-pyrimidin-2-yl)-1H-indole 4-Benzylsulfanyl-1H-indole (5.00 g, 21 mmol) (*Can. J. Chem.* 1962, 40, 511) was slowly added to a suspension of NaH (60% dispersion in mineral oil, 1.37 g, 34 mmol) in DMF (40 mL) at 0° C. The reaction mixture was stirred for 15 min until the gas evolution ceased, then 2,4-di-chloropyrimidine (3.03 g, 20 mmol) was added portionwise, followed by an additional aliquot of DMF (10 mL). The resulting mixture was slowly warmed to RT, then poured onto a slurry of ice and water and extracted with EtOAc. The organic layer was washed twice with a mixture of water and brine, dried over $Na_2SO_4$, filtered and evaporated under reduced pressure. The crude residue was purified by flash chromatography (EtOAc/hexanes, gradient from 10:90 to 50:50) to give 4-benzylsulfanyl-1-(4-chloropyrimidin-2-yl)-1H-indole (979 mg, 14% yield) as a pale-yellow waxy solid and a mixture of 4-benzyl-sulfanyl-1-(2-chloropyrimidin-4-yl)-1H-indole and the bisubstituted product (691 mg) after precipitation from DCM/EtOAc. This mixture was repurified by flash chromatography (EtOAc/hexanes, 20:80) to give 4-benzylsulfanyl-1-(2-chloropyrimidin-4-yl)-1H-indole (270 mg, 4% yield) as an off-white solid. MS=352 [M+H]$^+$; MP=159.0-161.2° C.

Step B: synthesis of trans-4-[4-(4-benzylsulfanylindol-1-yl)-pyrimidin-2-ylamino]-cyclo-hexanol trans-4-Aminocyclohexanol (1.37 g, 12 mmol) was added to a solution of 4-benzyl-sulfanyl-1-(2-chloro-pyrimidin-4-yl)-1H-indole and the disubstituted product (673 mg, 2 mmol) in NMP (10 mL), and the resulting mixture heated to 110° C. for 4 h. The reaction mixture was cooled and partitioned between water and EtOAc, the organic layer washed twice with water, dried over $Na_2SO_4$, filtered, and evaporated under reduced pressure. The crude residue was purified by flash chromatography (EtOAc/hexanes, from 10:90 to 20:80) to give after recrystallization from DCM/hexanes/EtOAc trans-4-[4-(4-benzylsulfanyl-indol-1-yl)-pyrimidin-2-yl-amino]-cyclohexanol (309 mg, 38% yield) as a white solid. An additional aliquot of the product was recovered from the mother liquor. MS=431 [M+H]$^+$; MP=150.2-150.9° C.

Step C: synthesis of trans-4-[4-(4-phenylmethane-sulfonylindol-1-yl)-pyrimidin-2-ylamino]-cyclohexanol 3-Chloroperoxybenzoic acid (0.55 g, 2.5 mmol) was added to trans-4-[4-(4-benzylsulfanylindol-1-yl)-pyrimidin-2-ylamino]-cyclohexanol (397 mg, 0.9 mmol) in chloroform (25 mL), and the resulting mixture stirred at RT for 1 hour. A second aliquot of 3-chloroperoxybenzoic acid (150 mg) was added, the reaction mixture heated briefly; then cooled and concentrated under reduced pressure. The residue was partitioned between aqueous $NaHCO_3$ and EtOAc. The organic layer was separated, washed twice with aqueous $NaHCO_3$ and water, dried over $Na_2SO_4$, filtered, and evaporated under reduced pressure onto silica gel. The residue was purified by flash chromatography (MeOH/DCM, 5:95) to give trans-4-[4-(4-phenylmethane-sulfonylindol-1-yl)-pyrimidin-2-ylamino]-cyclohexanol (30 mg, 7% yield) as a light-yellow solid.

MS=463 [M+H]$^+$; MP=132.1-134.5° C.

Example 15

Synthesis of trans-4-[4-(1H-Indol-3-yl)-pyrimidin-2-ylamino]-cyclohexanol

The synthesis of trans-4-[4-(1H-indol-3-yl)-pyrimidin-2-ylamino]-cyclohexanol was carried out according to the process shown in Scheme 29.

SCHEME 29

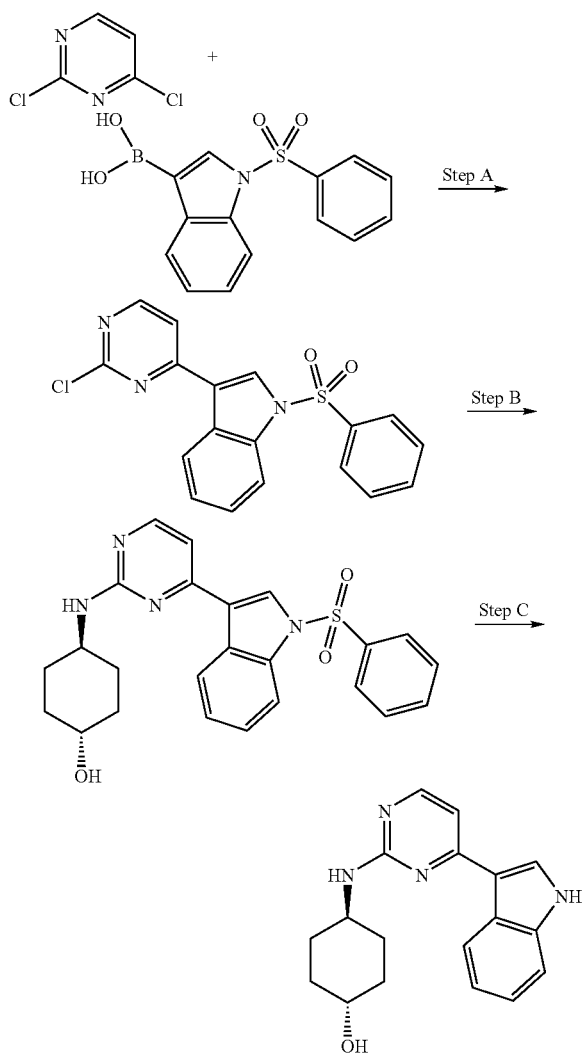

Step A: synthesis of 1-benzenesulfonyl-3-(2-chloro-pyrimidin-4-yl)-1H-indole

A solution of 2,4-dichloropyrimidine (2.42 g, 16 mmol), 1-(phenylsulfonyl)-1H-indol-3-ylboronic acid (3.89 g, 13 mmol) and sodium carbonate (5.03 g, 47 mmol) in acetonitrile/water (2:1, 60 mL) was degassed with argon, then tetrakis(triphenylphosphine)palladium (300 mg, 1.6 mol) was added. The resulting mixture was heated to reflux for 2 h while a white suspension formed. The precipitate was cooled and filtered through a CELITE™/Silica gel plug. The filter cake was washed with EtOAc, the organic layer separated, washed with brine, dried over $Na_2SO_4$, filtered, and evaporated under reduced pressure. The residue was recrystallized from EtOAc/hexanes to give 1-benzenesulfonyl-3-(2-chloro-pyrimidin-4-yl)-1H-indole as a light-pink solid. The solid filtrate from the reaction mixture was dissolved in DCM, dried over $Na_2SO_4$, filtered, and combined with the previous batch of product. The collected solids were dissolved in DCM, the solvent was evaporated under reduced pressure and EtOAc was added to form a suspension, the product was filtered and washed with hexanes, to give 1-benzenesulfonyl-3-(2-chloro-pyrimidin-4-yl)-1H-indole (2.0 g, 33% yield) as a light-pink solid. An additional 0.45 g of product was obtained from the mother liquors.

Step B: synthesis of trans-4-[4-(1-benzenesulfonyl-1H-indol-3-yl)-pyrimidin-2-ylamino]-cyclohexanol A solution of 1-benzenesulfonyl-3-(2-chloropyrimidin-4-yl)-1H-indole (0.45 g, 1 mmol) and trans-4-aminocyclohexanol (0.50 g, 4 mmol) in NMP (8 mL) was heated to 120° C. for 3 h under $N_2$. The mixture was then cooled and partitioned between water and EtOAc, the organic layer separated, washed twice with brine, dried over $Na_2SO_4$, filtered and evaporated under reduced pressure. The crude residue was purified by flash chromatography (MeOH/DCM, 5:95) to give 405 mg of a yellow foam. This material was dissolved into EtOAc, washed twice with water, dried over $Na_2SO_4$, filtered and evaporated under reduced pressure. The solid residue was triturated with hexanes and dried under high vacuum to give trans-4-[4-(1-benzenesulfonyl-1H-indol-3-yl)-pyrimidin-2-ylamino]-cyclohexanol (365 mg, 19% yield) as a light-yellow amorphous solid. MS=449 [M+H]$^+$; MP=132.1-133.3° C.

Step C: synthesis of trans-4-[4-(1H-indol-3-yl)-pyrimidin-2-ylamino]-cyclohexanol NaOH (200 mg, 5 mmol) was added to a solution of trans-4-[4-(1-benzenesulfonyl-1H-indol-3-yl)-pyrimidin-2-ylamino]-cyclohexanol (296 mg, 0.66 mmol) in MeOH (15 mL), and the resulting mixture stirred at RT for 6 h. The reaction mixture was concentrated under reduced pressure, the residue neutralized by addition of aqueous HCl (1 M), and then partitioned between water and EtOAc. The organic layer was separated, washed with water, dried over $Na_2SO_4$, filtered and evaporated under reduced pressure to give a crude yellow solid. This crude material was purified by flash chromatography (MeOH/DCM, 5:95) to give trans-4-[4-(1H-indol-3-yl)-pyrimidin-2-ylamino]-cyclohexanol (115 mg, 57% yield) as a white powder. MS=309 [M+H]$^+$; MP=258.1-259.9° C.

Example 16

Synthesis of trans-1-[2-(4-hydroxycyclohexylamino)-pyrimidin-4-yl]-1,2-dihydroindazol-3-one The synthesis of trans-1-[2-(4-hydroxycyclohexylamino)-pyrimidin-4-yl]-1,2-dihydro-indazol-3-one was carried out according to the process shown in Scheme 30.

SCHEME 30

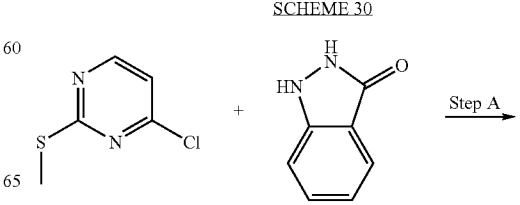

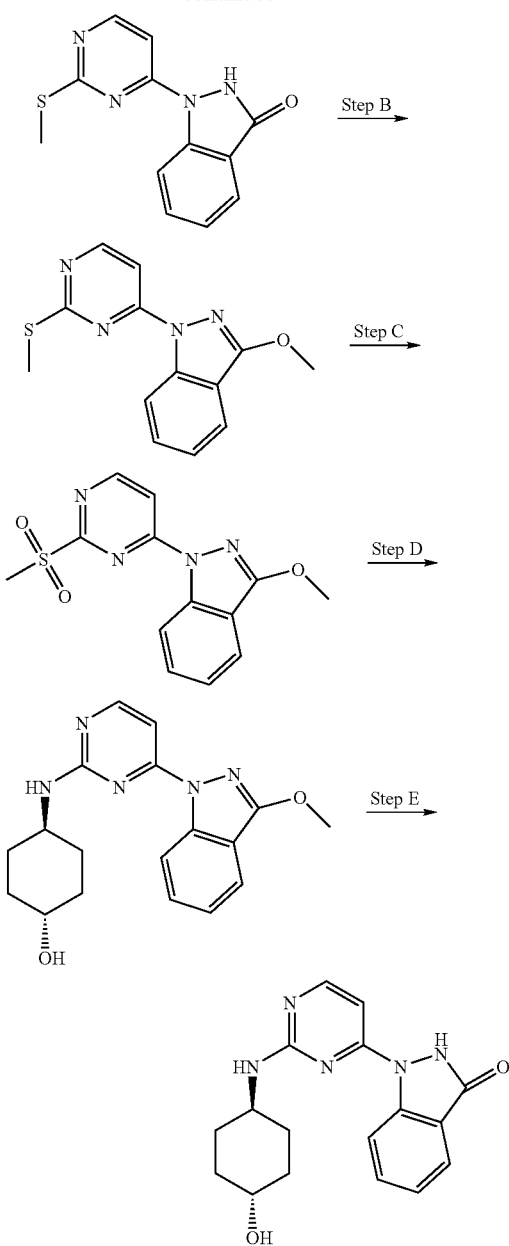

Step A: synthesis of 1-(2-methylsulfanylpyrimidin-4-yl)-1,2-dihydroindazol-3-one 3-Indazolinone (5.07 g, 38 mmol) was added portionwise at 0° C. to a suspension of NaH (~60% dispersion in mineral oil, 2.18 g, 55 mmol) in DMF (50 mL), and the resulting mixture stirred for 20 min, until gas evolution ceased. 4-Chloro-2-methylthiopyrimidine (6.10 g, 38 mmol) was added, and the reaction mixture warmed to RT, then heated to 10° C. for 3 h. The resulting mixture was cooled, poured into water (150 mL), neutralized with aqueous HCl (1 M), and EtOAc added. The resulting insoluble suspension was filtered and dried to give 1-(2-methyl-sulfanylpyrimidin-4-yl)-1,2-dihydroindazol-3-one (7.05 g, 72% yield) as an off-white solid. MS=259 [M+H]$^+$; MP=277.0-280.9° C.

Step B: synthesis of 3-methoxy-1-(2-methylsulfanylpyrimidin-4-yl)-1H-indazole

NaH (~60% dispersion in mineral oil, 0.75 g, 19 mmol) was added to 1-(2-methyl-sulfanylpyrimidin-4-yl)-1,2-dihydroindazol-3-one (2.70 g, 10 mmol) in DMF (30 mL) at 0° C., and the resulting mixture stirred until the gas evolution ceased. Iodomethane (0.90 mL, 14 mmol) was added, the mixture stirred for 30 min, then poured into water (100 mL) and extracted with EtOAc (100 mL). The combined organics were washed twice with water (100 mL), dried over Na$_2$SO$_4$, filtered, and evaporated under reduced pressure. The crude residue was purified by flash chromatography (EtOAc/hexanes, from 20:80 to 50:50) and recrystallized from hexanes to give 3-methoxy-1-(2-methylsulfanyl-pyrimidin-4-yl)-1H-indazole (286 mg, 10% yield) as a white solid. MS=272.9 [M+H]$^+$.

Step C: synthesis of 1-(2-methanesulfonylpyrimidin-4-yl)-3-methoxy-1H-indazole

3-Chloroperoxybenzoic acid (about 77%, 2.86 g, 18 mmol) was added to a solution of 3-methoxy-1-(2-methylsulfanylpyrimidin-4-yl)-1H-indazole (1.34 g, 5 mmol) in chloroform (30 mL) and the reaction mixture stirred at RT for 20 min. The resulting mixture was poured into aqueous NaHCO$_3$, stirred for 1 hour, then extracted with DCM. The combined organic extracts were washed twice with aqueous NaHCO$_3$ and with water, dried over Na$_2$SO$_4$, filtered and evaporated under reduced pressure. The crude residue was purified by flash chromatography (EtOAc/hexanes, gradient from 50:50 to 100:0) and recrystallized from DCM/hexanes/EtOAc to give 2 crops of 1-(2-methanesulfonylpyrimidin-4-yl)-3-methoxy-1H-indazole as an off-white solid (927 mg, 62% yield). An additional amount of product was recovered from the mother liquor as a yellow solid (0.44 g, 29% yield). MS=305 [M+H]$^+$; MP=206.3-207.8° C.

Step D: synthesis of trans-4-[4-(3-methoxyindazol-1-yl)-pyrimidin-2-ylamino]-cyclohexanol trans-4-Aminocyclohexanol (870 mg, 8 mmol) was added to 1-(2-methanesulfonyl-pyrimidin-4-yl)-3-methoxy-1H-indazole (440 mg, 1 mmol) in NMP (15 mL), and the resulting mixture heated to 120° C. for 3 h. The reaction mixture was cooled and partitioned between EtOAc and water. The organic layer was separated, washed with water, dried over Na$_2$SO$_4$, filtered, and concentrated under reduced pressure to give a crude yellow solid. This crude material was purified by flash chromatography (MeOH/DCM, 5:95) and recrystallized from DCM/hexanes to give trans-4-[4-(3-methoxy-indazol-1-yl)-pyrimidin-2-ylamino]-cyclohexanol (181 mg (37% yield) as a white solid. MS=340 [M+H]$^+$; MP=202.3-205.1° C.

Step E: synthesis of trans-1-[2-(4-hydroxycyclohexylamino)-pyrimidin-4-yl]-1,2-dihydro-indazol-3-one Trimethylsilyliodide (0.80 mL, 5.6 mmol) was added under N$_2$ to a suspension of trans-4-[4-(3-methoxyindazol-1-yl)-pyrimidin-2-ylamino]-cyclohexanol (251 mg, 0.7 mmol) in chloroform (10 mL). The reaction mixture immediately became homogeneous, but within 1 hour a suspension formed, and the resulting mixture was stirred for 3 days. An additional aliquot of trimethylsilyliodide (2 mL, 14 mmol) was added, and the resulting mixture was heated to reflux overnight and stirred at RT for one day. The reaction mixture was then poured onto ice water and extracted with DCM. The insoluble solids were filtered and dissolved in a mixture of MeOH and DCM, the combined organic layers dried over Na$_2$SO$_4$, filtered and concentrated under reduced pressure onto silica gel. The residue was purified by flash chromatography (MeOH/DCM, gradient from 3:97 to 5:95) to give trans-1-[2-(4-hydroxycyclohexylamino)-pyrimidin-4-yl]-1,2-dihydroindazol-3-one (71 mg, 30% yield) as an off-white solid. MS=326 [M+H]$^+$; MP=263.5-264.4° C.

Example 17

Synthesis of trans-4-[4-(1-Methyl-1H-indol-3-yl)-pyrimidin-2-ylamino]-cyclohexanol The synthetic procedure described in this Example was carried out according to the process shown in Scheme 31.

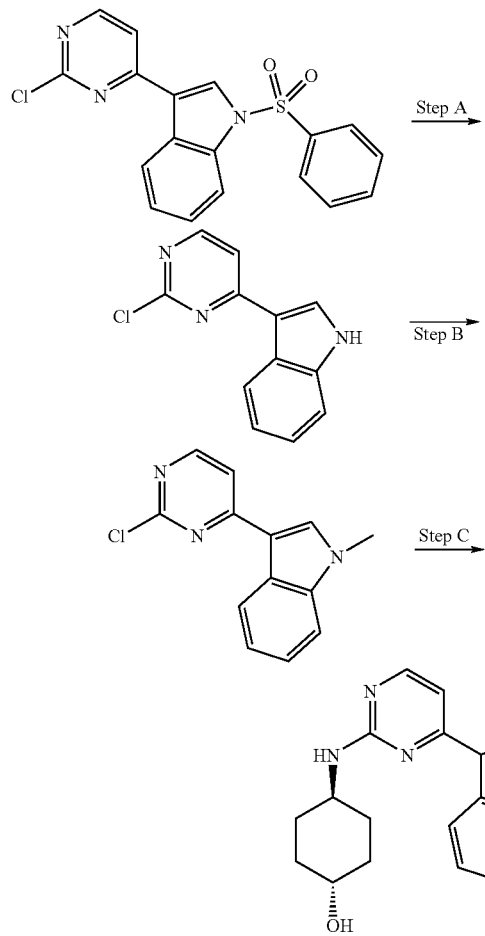

Step A: synthesis of 3-(2-chloro-pyrimidin-4-yl)-1H-indole

A suspension of freshly crushed NaOH (740 mg) in MeOH (20 mL) was added at 0° C. to a suspension of 1-benzenesulfonyl-3-(2-chloropyrimidin-4-yl)-1H-indole (0.91 g, 2 mmol) in MeOH/THF (1:1, 40 mL). The reaction mixture was warmed to RT and stirred for 2 h until homogeneous. The resulting mixture was neutralized with aqueous HCl (1 M), and concentrated under reduced pressure. The residue was partitioned between water and EtOAc, the organic layer separated, washed with water, dried over Na$_2$SO$_4$, filtered, and concentrated under reduced pressure to give a bright yellow solid (0.63 g). This crude material was purified by flash chromatography (1:1 EtOAc/hexanes) to give 3-(2-chloro-pyrimidin-4-yl)-1H-indole (502 mg, 89% yield) as a yellow solid.

Step B: synthesis of 3-(2-chloro-pyrimidin-4-yl)-1-methyl-1H-indole

NaH (60% dispersion in mineral oil, 0.16 g, 7 mmol) was added at 0° C. to 3-(2-chloro-pyrimidin-4-yl)-1H-indole (0.24 g, 1 mmol) in DMF (8 mL). The resulting mixture was stirred for 10 min, then iodomethane (0.20 mL, 3.2 mmol) was added, and the reaction mixture was warmed to RT and poured onto ice water. The resulting mixture was extracted with EtOAc, the combined organics washed twice with water, dried over Na$_2$SO$_4$, filtered and concentrated under reduced pressure to give 3-(2-chloro-pyrimidin-4-yl)-1-methyl-1H-indole (270 mg) as a yellow solid.

Step C: synthesis of trans-4-[4-(1-methyl-1H-indol-3-yl)-pyrimidin-2-ylamino]-cyclohexanol trans-4-Aminocyclohexanol (0.45 g, 4 mmol) was added to 3-(2-chloropyrimidin-4-yl)-1-methyl-1H-indole (0.23 g, 1 mmol) in NMP (8 mL), and the resulting mixture heated to 120° C. for 3 h. A second aliquot of trans-4-aminocyclohexanol (0.16 g, 1 mmol) was added, and the resulting mixture was heated to 130° C. The reaction mixture was cooled and partitioned between water and EtOAc, the organic layer separated, washed twice with water, dried over Na$_2$SO$_4$, filtered, and concentrated under reduced pressure. The crude residue was recrystallized from DCM/EtOAc/hexanes to give trans-4-[4-(1-methyl-1H-indol-3-yl)-pyrimidin-2-ylamino]-cyclohexanol (148 mg, 46% yield) as a light-yellow solid. MS=323 [M+H]$^+$; MP=194.5-195.3° C.

Example 18

Synthesis of trans-4-{4-[6-(2-Hydroxyethylamino)-indazol-1-yl]-pyrimidin-2-ylamino}-cyclohexanol The synthesis of trans-4-{4-[6-(2-hydroxy-ethylamino)-indazol-1-yl]-pyrimidin-2-ylamino}-cyclohexanol was carried out according to the process shown in Scheme 32.

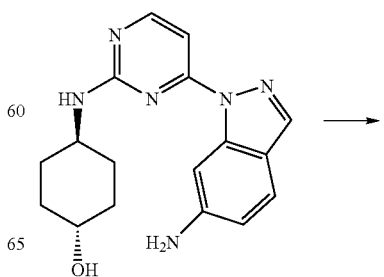

-continued

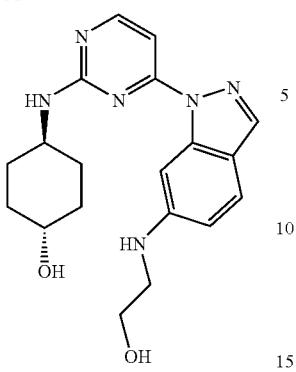

2-Bromoethanol (42 µL, 0.6 mmol) was added to a mixture of trans-4-[4-(6-amino-indazol-1-yl)-pyrimidin-2-ylamino]-cyclohexanol (100 mg, 0.30 mmol) and sodium bicarbonate (25 mg, 0.30 mmol) in acetonitrile (1 mL), and the resulting mixture heated to 80° C. for 2 h. DMF (0.5 mL) was added, and the resulting mixture heated to 80° C. overnight. A second aliquot of 2-bromoethanol (20 µL) was added, and heating continued for 3 days. The resulting mixture was diluted with MeOH, and Et$_2$O was added. The gummy residue which crashed out of solution was purified by preparative TLC to give trans-4-{4-[6-(2-hydroxyethylamino)-indazol-1-yl]-pyrimidin-2-ylamino}-cyclohexanol (29 mg) as a yellow solid. MS=369 [M+H]$^+$.

Example 19

Synthesis of trans-N-{1-[2-(4-Hydroxycyclohexylamino)-pyrimidin-4-yl]-1H-indazol-6-yl}-acetamide The synthesis of trans-N-{1-[2-(4-hydroxycyclohexylamino)-pyrimidin-4-yl]-1H-indazol-6-yl}-acetamide was carried out according to the process shown in Scheme 33.

SCHEME 33

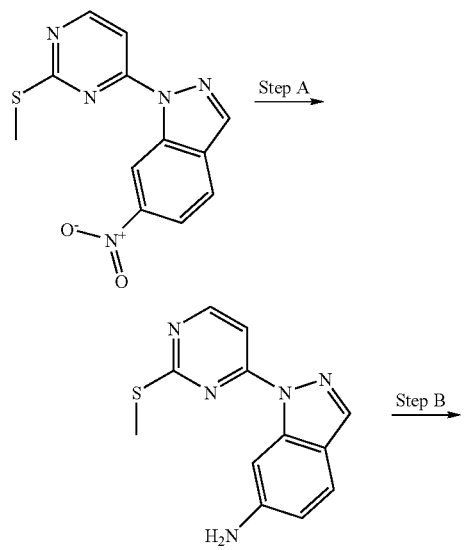

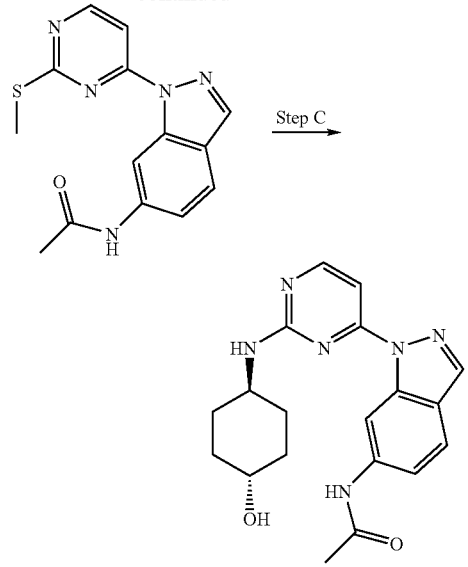

Step A: Synthesis of 1-(2-methylsulfanylpyrimidin-4-yl)-1H-indazol-6-ylamine 1-(2-Methylsulfanylpyrimidin-4-yl)-6-nitro-1H-indazole was reduced following the procedure described in Example 8.

Step B: Synthesis of N-[1-(2-methylsulfanylpyrimidin-4-yl)-1H-indazol-6-yl]-acetamide Acetyl chloride (10 drops) was added dropwise at RT to 1-(2-methylsulfanylpyrimidin-4-yl)-1H-indazol-6-ylamine (0.13 g, 0.5 mmol) and triethylamine (15 drops) in THF (5 mL), and the resulting mixture stirred for 30 min. The reaction mixture was diluted with DCM and MeOH, washed twice with aqueous NaHCO$_3$ and once with brine, dried over Na$_2$SO$_4$, filtered and concentrated under reduced pressure. The crude residue was treated with Et$_2$O and hexane, and the precipitate was collected by filtration to give N-[1-(2-methylsulfanylpyrimidin-4-yl)-1H-indazol-6-yl]-acetamide (146 mg) as an off-white solid.

Step C: synthesis of trans-N-{1-[2-(4-hydroxycyclohexylamino)-pyrimidin-4-yl]-1H-indazol-6-yl}-acetamide 3-Chloroperoxybenzoic acid (77%, 200 mg, 0.87 mmol) was added to a slurry of N-[1-(2-methylsulfanylpyrimidin-4-yl)-1H-indazol-6-yl]-acetamide (0.43 mmol, 0.13 g) in chloroform (5 mL), and the resulting mixture stirred at RT overnight. The reaction mixture was diluted with DCM/MeOH (4:1, 25 mL), washed with aqueous NaOH (0.1 M) and with brine, dried over MgSO$_4$, filtered, and concentrated under reduced pressure. The residue was triturated with Et$_2$O to give N-[1-(2-methanesulfonyl-pyrimidin-4-yl)-1H-indazol-6-yl]-acetamide (120 mg) as an off-white solid. A portion of this material (100 mg) was mixed with trans-4-aminocyclohexanol (0.12 g) and the mixture was heated to 130° C. for 85 min. The residue was treated with DCM/MeOH and the solvent evaporated under reduced pressure. The residue was treated with MeOH (5 mL) and Et$_2$O, the liquid supernatant decanted away, and the gummy solid which formed was treated with a second aliquot of MeOH (5 mL) and EtOAc (15 mL). The resulting fine precipitate was collected by filtration to give trans-N-{1-[2-(4-hydroxycyclohexylamino)-pyrimidin-4-yl]-1H-indazol-6-yl}-acetamide (72 mg, 65% yield) as an off-white solid. MS=367 [M+H]$^+$; MP=288.0-289.5° C.

Example 20

Synthesis of trans-4-[4-(6-Hydroxymethylindazol-1-yl)-pyrimidin-2-ylamino]-cyclohexanol The synthesis of trans-4-[4-(6-hydroxymethylindazol-1-yl)-pyrimidin-2-ylamino]-cyclohexanol was carried out according to the process shown in Scheme 34.

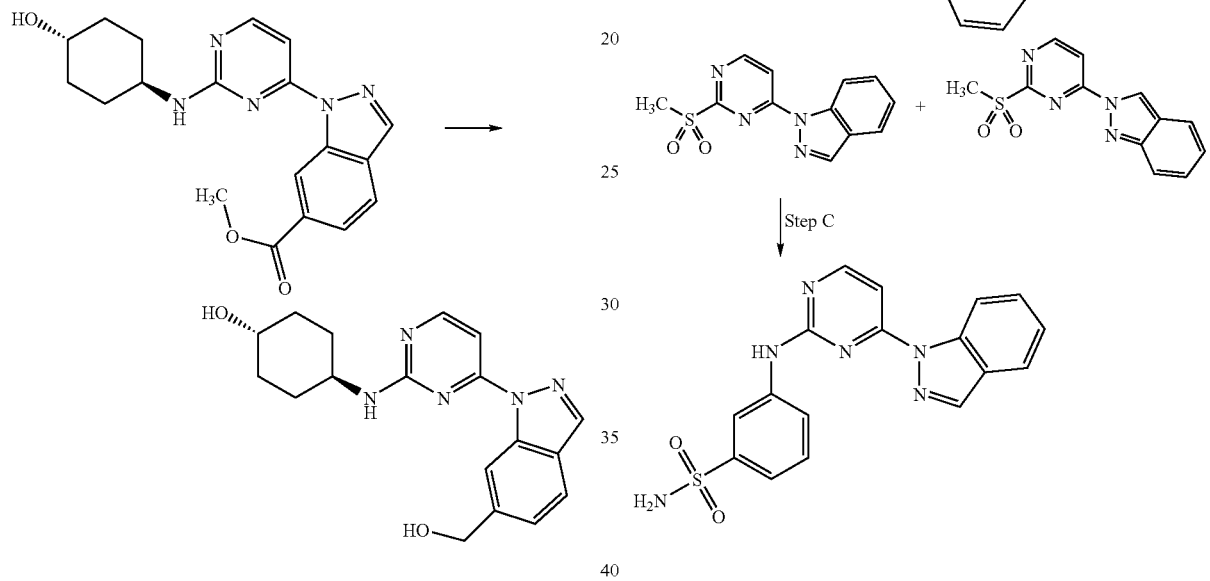

A solution of lithium triethylborohydride (1 M in THF, 0.8 mL) was slowly added at RT to trans-1-[2-(4-hydroxycyclohexylamino)-pyrimidin-4-yl]-1H-indazole-6-carboxylic acid methyl ester (100 mg) in THF (3 mL). The resulting mixture was stirred for 30 min, and AcOH/EtOH (1:1, 2 mL) was added. The reaction mixture was stirred for 30 min, then poured onto aqueous HCl (0.1 M). The resulting mixture was basified to pH 8 with aqueous NaOH and aqueous NaHCO$_3$, then extracted with DCM. The combined organic extracts were dried over Na$_2$SO$_4$, filtered and concentrated under reduced pressure. The crude residue was purified by preparative TLC (DCM/MeOH, 95:5) to give of trans-4-[4-(6-hydroxymethyl-indazol-1-yl)-pyrimidin-2-ylamino]-cyclohexanol (22 mg) as a white solid. MS=340 [M+H]$^+$; MP=216.0-217.7° C.

Example 21

Synthesis of 3-(4-Indazol-1-ylpyrimidin-2-ylamino)-benzenesulfonamide

The synthesis of 3-(4-indazol-1-ylpyrimidin-2-ylamino)-benzenesulfonamide was carried out according to the process shown in Scheme 35.

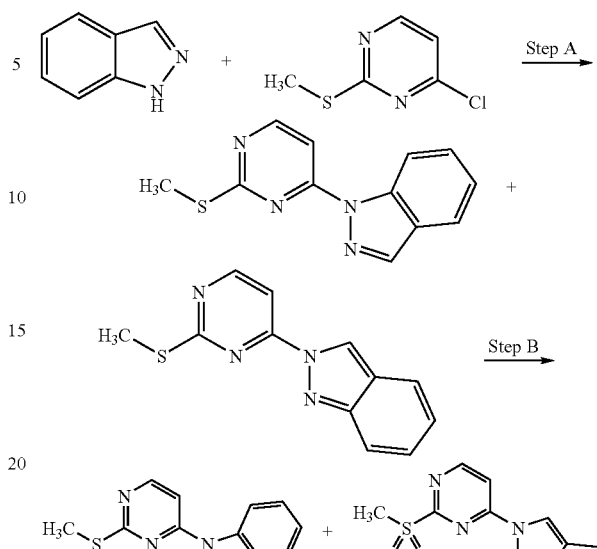

Step A: Synthesis of 1-(2-methylsulfanyl-pyrimidin-4-yl)-1H-indazole and 2-(2-methyl-sulfanylpyrimidin-4-yl)-2H-indazole A solution of 1H-indazole (2.36 g, 20.0 mmol) in anhydrous DMF (100 mL) was treated with NaH (60% dispersion in mineral oil, 1.60 g, 40.0 mmol) at RT for 10 min. 4-Chloro-2-methylthiopyrimidine (2.55 ml, 22.0 mmol) was then added in one portion at RT, and the resulting mixture stirred at 70° C. for 2.5 h. The reaction mixture was cooled to RT, quenched with aqueous HCl (1 M), and extracted with EtOAc. The layers were separated, the organic layer washed with brine, dried over anhydrous sodium sulfate, filtered, and concentrated under reduced pressure. The crude product was absorbed onto silica gel and purified by flash chromatography (ethyl acetate/hexane, gradient from 5:95 to 25:75) to afford a mixture of 1-(2-methyl-sulfanyl-pyrimidin-4-yl)-H-indazole and 2-(2-methylsulfanyl-pyrimidin-4-yl)-2H-indazole (3.77 g, 78% yield) as a beige solid.

Step B: Synthesis of 1-(2-methanesulfonylpyrimidin-4-yl)-1H-indazole and 2-(2-methane-sulfonyl-pyrimidin-4-yl)-2H-indazole A mixture of 1-(2-methylsulfanyl-pyrimidin-4-yl)-1H-indazole and 2-(2-methylsulfanyl-pyrimidin-4-yl)-2H-indazole (3.77 g, 15.55 mmol) in chloroform (80 mL) was treated with 3-chloroperoxybenzoic acid (80%, 7.37 g, 34.21 mmol). The reaction mixture was stirred at 50° C. for 1.5 hour, then quenched with aqueous NaOH (1 M). The resulting mixture was extracted with DCM, the layers separated, and the organic layer washed with brine, dried over anhydrous sodium sulfate, filtered and concentrated under reduced pressure. The crude product was absorbed onto silica gel and purified by flash chromatography (DCM/ethyl acetate, gradient from 0:100 to 5:95) to afford 1-(2-methylsulfanyl-pyrimidin-4-yl)-1H-indazole (less polar isomer) (1.92 g, 45% yield) and 2-(2-methylsulfanyl-pyrimidin-4-yl)-2H-indazole (more polar isomer) (1.04 g, 24% yield).

Step C: synthesis of 3-(4-indazol-1-ylpyrimidin-2-ylamino)-benzenesulfonamide

A solution of 1-(2-methylsulfonyl-pyrimidin-4-yl)-1H-indazole (100 mg, 0.36 mmol) and p-toluenesulfonic acid (139 mg, 0.73 mmol) in i-PrOH (4 ml) was treated with 3-aminobenzene-sulfonamide (251 mg, 1.46 mmol) in a microwave synthesizer at 150° C. for 20 min. The mixture was partitioned between water and ethyl acetate, the organic layer separated, washed with brine, dried over anhydrous sodium sulfate, filtered and concentrated under reduced pressure. The crude residue was absorbed on silica gel and purified by flash chromatography (EtOAc/hexane, gradient from 30:70 to 50:50) to afford the title compound. This residue was triturated with aqueous NaOH (1 M), the solid collected by filtration, washed with water and dried under vacuum to afford 3-(4-indazol-1-ylpyrimidin-2-ylamino)-benzenesulfonamide (50 mg, 37% yield). MS=367 [M+H]$^+$.

4-(4-Indazol-1-yl-pyrimidin-2-ylamino)-cyclohexyl]-carbamic acid tert-butyl ester (white solid) was prepared in the same manner, utilizing the appropriate starting materials. MS=409.2 [M+H]$^+$.

Example 22

Formulations

Pharmaceutical preparations for delivery by various routes are formulated as shown in the following Tables. "Active ingredient" or "Active compound" as used in the Tables means one or more of the Compounds of Formula I.

| Composition for Oral Administration | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration | |
|---|---|
| Ingredient | % wt./wt. |
| Active ingredient | 20.0% |
| Magnesium stearate | 0.5% |
| Crosscarmellose sodium | 2.0% |

-continued

| Composition for Oral Administration | |
|---|---|
| Ingredient | % wt./wt. |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration | |
|---|---|
| Ingredient | Amount |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation | |
|---|---|
| Ingredient | % wt./wt. |
| Active ingredient | 0.25 g |
| Sodium Chloride | qs to make isotonic |
| Water for injection | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation | |
|---|---|
| Ingredients | grams |
| Active compound | 0.2-2 |
| Span 60 | 2 |

-continued

Topical Formulation

| Ingredients | grams |
|---|---|
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Nasal Spray Formulations

Several aqueous suspensions containing from about 0.025-0.5 percent active compound are prepared as nasal spray formulations. The formulations optionally contain inactive ingredients such as, for example, microcrystalline cellulose, sodium carboxymethylcellulose, dextrose, and the like. Hydrochloric acid may be added to adjust pH. The nasal spray formulations may be delivered via a nasal spray metered pump typically delivering about 50-100 µL of formulation per actuation. A typical dosing schedule is 2-4 sprays every 4-12 h.

Example 23

JNK Assay In Vitro

JNK activity was measured by phosphorylation of GST-ATF2 (19-96) with [γ-$^{33}$P] ATP. The enzyme reaction was conducted at Km concentrations of ATP and the substrate at final volume of 40 µl in buffer containing 25 mM HEPES, pH 7.5, 2 mM dithiothreitol, 150 mM NaCl, 20 mM MgCl$_2$, 0.001% Tween® 20, 0.1% BSA and 10% DMSO. Human JNK2α2 assay contains 1 nM enzyme, 1 µM ATF2, 8 µM ATP with 1 µCi [γ-$^{33}$P] ATP. Human JNK1α1 assay contains 2 nM enzyme, 1 µM ATF2, 6 µM ATP with 1 µCi [γ-$^{33}$P] ATP. Human JNK3 (Upstate Biotech #14-501M) assay contains 2 nM enzyme, 1 µM ATF2, 4 µM ATP with 1 µCi [γ-33P] ATP. The enzyme assay was carried out in the presence or absence of several compound concentrations. JNK and compound were pre-incubated for 10 min., followed by initiation of the enzymatic reaction by adding ATP and the substrate. The reaction mixture was incubated at 30° C. for 30 min. At the end of incubation, the reaction was terminated by transferring 25 µl of the reaction mixture to 150 µl of 10% glutathione Sepharose® slurry (Amersham # 27-4574-01) containing 135 mM EDTA. The reaction product was captured on the affinity resin, and washed on a filtration plate (Millipore, MABVNOB50) with phosphate buffered saline for six times to remove free radionucleotide. The incorporation of $^{33}$P into ATF2 was quantified on a microplate scintillation counter (Packard Topcount). Compound inhibition potency on JNK was measured by IC$_{50}$ value generated from ten concentration inhibition curves fitted into the 3-parameter model: % inhibition=Maximum/(1+(IC$_{50}$/[Inhibitor])$^{slope}$). Data were analyzed on Microsoft Excel for parameter estimation. The results are shown in Table 2 below:

TABLE 2

| | p(IC$_{50}$) | | |
|---|---|---|---|
| Compound | JNK1 (µM) | JNK2 (µM) | c-jun (µM) |
| 3 | 0.0412 | 0.4578 | ND |
| 15 | 0.0678 | 0.4583 | 1.286 |
| 16 | 0.0708 | 0.5924 | 4.133 |
| 18 | 0.0735 | 0.3375 | 1.9533 |
| 26 | 0.085 | 0.6949 | 1.894 |
| 86 | 0.0228 | 0.1777 | ND |
| 87 | 0.0297 | 0.1908 | 1.706 |
| 88 | 0.0709 | 0.4803 | ND |

Example 24

Rat in vivo TNFα-induced IL-6 Production Assay

Female Wistar-Han rats procured from Charles River Laboratories were allowed to acclimate for one week prior to use and achieve an approximate body weight of 95-130 g. Rats were administered test compound via oral gavage 30 min prior to an intraperitoneal challenge of 0.5 µg recombinant rat TNF-α (Biosource). Blood was collected via cardiocentesis 90 min after TNF-α challenge. Plasma was prepared using lithium heparin separation tubes (BD microtainer) and frozen at −80° C. until analyzed. IL-6 levels were determined using a rat specific IL-6 ELISA kit (Biosource). The percent inhibition and ED$_{50}$ values (calculated as the dose of compound at which TNF-α production is 50% of the control value) were determined. The results are shown in Table 3 below:

TABLE 3

| Inhibition of IL-6 Production | | |
|---|---|---|
| Compound | Dose (mg/Kg) | IL-6 Inhibition (%) |
| 16 | 30 | 47.4 |
| 26 | 30 | 59.6 |
| 87 | 10 | 64 |
| 148 | 20 | 74.3 |
| 157 | 10 | 52.5 |
| 159 | 10 | 57.6 |
| 166 | 10 | 48.5 |
| 166 | 20 | 75.2 |
| 224 | 20 | 68.6 |
| 225 | 20 | 50.9 |
| 233 | 20 | 57.8 |
| 311 | 20 | 50.9 |

Example 25

Rodent Collagen-Induced Arthritis

Female Lewis rats procured from Harlan Laboratories at 7-8 weeks of age are allowed to acclimate for one week prior to use and achieve an approximate body weight of 120-140 g. On day 0 of study, rats are primed intradermally (i.d.) on several sites on the back with an emulsion of 100 µg Bovine Type II Collagen (Chondrex) in Incomplete Freund's adjuvant (IFA; total of 0.1 ml in 2-3 sites). Arthritis induction is generally observed 12-14 days from priming; however a booster injection of 100 µg collagen/IFA is given around days 7-10 (i.d. up to 0.1 ml total) at the base of the tail or an alternate site on back to synchronize disease induction. Compound dosing can be prophylactic (starting at time of boost or 1-2 days prior) or therapeutic (beginning after boost and coinciding with initial disease scores of 1-2-see clinical scoring below). Animals are evaluated for the development and progression of disease over the next 21 days.

Rats are evaluated using a scoring system (described below), paw volume measurements using a plethysmometer for each paw, or measuring paw or joint thickness with a caliper. Base-line measurements are performed on day 0, and starting again at the first signs of swelling for up to three times per week until the end of the experiment. Scoring is evaluated as follows for each paw:

1=swelling and/or redness of paw or one digit.
 2=swelling in two or more joints.
 3=gross swelling of the paw with more than two joints involved.
 4=severe arthritis of the entire paw and digits.

The arthritic index for each rat is evaluated by adding the four scores of the individual paws, giving a maximum score of 16. In order to serially measure disease onset and progression, the paw volume of the hind paws is also determined through the use of a plethysmometer.

At the end of the study, the hind paws (and other tissues) are harvested for weight determination, histology, cellular and/or molecular analysis. Additionally, blood is collected via cardiocentesis, plasma is prepared using lithium heparin separation tubes (BD microtainer) and frozen at −70° C. until analyzed. Inflammatory cytokine levels (e.g., TNF-α, IL-1 and IL-6) from the plasma or from homogenized joint tissue are determined using rat-specific ELISA kits (R&D). The level of disease protection or inhibition is determined as a composite of changes in clinical scores, paw volumes and histopathology compared to control animals.

Example 26

IL-8 Production Assay in TNFα-Induced Human Chondrosarcoma SW1353 Cells

SW1353 cells are purchased from the American Tissue Culture Collection and maintained in growth media consisting of DMEM medium (Invitrogen) with 10% fetal bovine serum (Invitrogen), ascorbic acids (Sigma) and penicillin (Invitrogen) under the culture condition of 37° C. in 5% $CO_2$. Cells are plated at a density of $1.0 \times 10^4$ cells per well in 100 µl of media 48 hours before the compound treatment. Immediately before the compound treatment, media is replaced with 160 µl of fresh media. Compound stock (10 mM) is diluted in growth media and added to each well as a 10× concentrated solution in a volume of 20 µl, mixed and allowed to pre-incubate with cells for 30 min. The compound vehicle (DMSO) is maintained at a final concentration of 1% in all samples. After 30 min, the cells are activated with 10 ng/ml of TNF-α (Roche Biochem). TNF-α is added as a 10× concentrated solution made up in growth media and added in a volume of 20 µl per well. Cell plates are cultured for 5 h. Cell media are harvested and stored at −20° C. Media aliquots are analyzed by sandwich ELISA for the presence of IL-8 as per the manufacturer's instructions (BD Bioscience). The $IC_{50}$ values are calculated as the concentration of the compound at which the IL-8 production was reduced to 50% of the control value using Xlfit3 in Microsoft Excel program. Certain compounds have an $IC_{50}$ value ranging from 0.1-20 µM in this assay.

Example 27

Synthesis of (4-dimethylamino-piperidin-1-yl)-(4-{4-[4-(3-methanesulfonyl-propoxy)-indol-1-yl]-pyrimidin-2-ylamino}-cyclohexyl)-methanone (A) (2-Fluoro-4-methoxy-phenyl)-(2-methylsulfanyl-pyrimidin-4-yl)-methanone (4.12 g, 114.83 mmol) was dissolved in DCM and cooled on an ice bath, and 6 mL $BBr_3$ was added quickly and the reaction mixture was allowed to stir for 1 h. The mixture was slowly added to ice cold water, and the resulting precipitate was filtered, washed several times with water until the pH was neutral and solvent removed in vacuo to yield (2-fluoro-4-hydroxyphenyl)-(2-methyl-sulfanyl-pyrimidin-4-yl)-methanone (3.365 g).

(B) (2-Fluoro-4-hydroxyphenyl)-(2-methylsulfanyl-pyrimidin-4-yl)-methanone (2.26 g, 12.7 mmol), $K_2CO_3$ (3.5 g, 25.4 mmol) and 1-methylthio-4-tosylbutane (8.5 g, 44.5 mmol) were stirred in NMP for 1 h at 100° C., cooled to RT, filtered, diluted with water, and extracted into EtOAc. The combined organic layers were dried over sodium sulfate, filtered, concentrated in vacuo and purified by flash chromatography on a silica column eluting with hexane:ethyl acetate 9:1 to 3:2 to yield [2-fluoro-4-(4-methylsulfanyl-butoxy)-phenyl]-(2-methylsulfanyl-pyrimidin-4-yl)-methanone (3.42 g).

(C) [2-Fluoro-4-(4-methylsulfanyl-butoxy)-phenyl]-(2-methylsulfanyl-pyrimidin-4-yl)-methanone (1.7 g, 4.8 mmol) was treated with $NH_2NHBoc$ (1.28 g, 9.6 mmol) and acetic acid (0.7 mL) in MeOH and heated at reflux overnight. The reaction mixture was partitioned with $EtOAc/NaHCO_3$, and the organic layer was dried over sodium sulfate, filtered, concentrated, the residue dissolved in THF (8 mL), and DBU (1.2 mL, 7.5 mmol) was added. The reaction mixture was then heated to 150° C. in a microwave oven for 70 minutes, concentrated under vacuum, and purified by flash chromatography on a silica column eluting with hexane:EtOAc 9:1 to yield 3-(2-methanesulfinyl-pyrimidin-4-yl)-7-(4-methylsulfanyl-butoxy)-1H-indazole (430 mg).

(D) [2-Fluoro-4-(4-methylsulfanyl-butoxy)-phenyl]-(2-methylsulfanyl-pyrimidin-4-yl)-methanone (1.7 g, 4.8 mmol) was treated with $NH_2OH$ (4.2 mL) in EtOH, and heated to reflux overnight. After cooling to RT, the reaction mixture was concentrated in vacuo, dissolved in EtOAc, dried over sodium sulfate, filtered, concentrated, the residue dissolved in THF (7 mL) and treated with DBU (1.2 mL, 7.5 mmol). The reaction mixture was then heated to 150° C. in a microwave oven for 30 minutes, concentrated under vacuum, and purified by flash chromatography on a silica column eluting with hexane:EtOAc 95:5 to yield 3-(2-methanesulfinyl-pyrimidin-4-yl)-7-(4-methylsulfanyl-butoxy)-benzo[d]isoxazole (855 mg).

(E) MCPBA (68.71 g, 306.52 mM, 77%) was added with stirring over approximately 3 h to a solution of 4-(3-methylsulfanyl-propoxy)-1-(2-methylsulfanyl-pyrimidin-4-yl)-H-indole (35.3 g, 102.18 mM) in $CH_2Cl_2$ (1000 mL) cooled in an ice bath. After 2 h of mixing, the reaction mixture was quenched with 10% sodium thiosulfate solution, diluted in $CH_2Cl_2$, and washed with 10% $Na_2CO_3$, $H_2O$ and brine. The organic layer was dried and solvent removed in vacuo to give crude product, which was heated in EtOH to yield 4-butoxy-1-(2-methanesulfinyl-pyrimidin-4-yl)-1H-indole as a solid upon cooling to RT (30.7 g, 76.5%) (M+Na 416).

(F) 4-(3-methylsulfanyl-propoxy)-1-(2-methylsulfanyl-pyrimidin-4-yl)-1H-indazole (428 mg, 1.24 mmol) was dissolved in DCM, cooled in an ice bath, and MCPBA (830 mg, 3.71 mmol) was added and the mixture stirred for 1 h. The reaction mixture was then diluted with DCM, washed with 5% $NaHCO_3$, the resulting precipitate was collected, the filtrate dried over sodium sulfate, filtered, concentrated and precipitate collected to provide 4-butoxy-1-(2-meth-anesulfinyl-pyrimidin-4-yl)-1H-indazole.

(G) A mixture of 1-(2-methanesulfinyl-pyrimidin-4-yl)-4-(3-methanesulfonyl-propoxy)-1H-indole (25 g, 64 mM) and 4-amino-cyclohexanecarboxylic acid ethyl ester (16.3 g, 95.3 mM) in dioxane (400 mL) and heated at 110° C. for approximately 5 h. The solution was concentrated in vacuo to give a white residue. The residue was suspended in H₂O, filtered and washed in H₂O, and dried at 60° C. in vacuo to yield 4-{4-[4-(3-methanesulfonyl-propoxy)-indol-1-yl]-pyrimidin-2-ylamino}-cyclohexanecarboxylic acid ethyl ester (31.7 g, 99.7%).

(H) A mixture of (4-amino-cyclohexyl)-(4-hydroxy-piperidin-1-yl)-methanone (400 mg, 1.5 mmol), DIPEA (0.31 mL, 1.78 mmol) and NMP (1 mL) was stirred at RT for 1 h. Then, 7-(3-methanesulfonyl-propoxy)-3-(2-methanesulfinyl-pyrimidin-4-yl)-1H-indazole (200 mg, 0.5 mmol) was added to the mixture and stirred at 130° C. for 2.5 hours. The reaction mixture was then poured into water, and the precipitate was purified on a silica column using flash chromatography, eluting with hexane:EtOAc:MeOH 5:4.5:0.5 to yield (4-hydroxy-piperidin-1-yl)-(4-{4-[7-(3-methanesulfonyl-propoxy)-1H-indazol-3-yl]-pyrimidin-2-ylamino}-cyclohexyl)-methanone (Compound 308).

(I) To a suspension of 4-{4-[4-(3-methanesulfonyl-propoxy)-indol-1-yl]-pyrimidin-2-yl-amino}-cyclohexanecarboxylic acid ethyl ester (35.4 g, 70 mmol) in THF (180 mL) and MeOH (200 mL) was added a solution of LiOH-H₂O (14.69 g) in H₂O (150 mL). The resulting mixture was briefly heated in a steam bath and stirred at RT with a mechanical stirrer for 1 h to provide a light yellow solution. The reaction mixture was concentrated in vacuo and diluted with cold H₂O and the pH was adjusted to 6 with 10% HCl. The resulting solid was filtered, washed several times with cold H₂O and finally with EtOH at 0° C. The resulting solid product was then dried in vacuo to provide 4-{4-[4-(3-methanesulfonyl-propoxy)-indol-1-yl]-pyrimidin-2-ylamino}-cyclo-hexanecarboxylic acid (32.2 g, 97.4%).

(J) CDI (7.13 g, 44.0 mmol) was added to a mixture of 4-{4-[4-(3-methanesulfonyl-propoxy)-indol-1-yl]-pyrimidin-2-ylamino}-cyclohexanecarboxylic acid (16.00 g, 33.86 mmol) in dry DMF (100 mL) and heated to 40° C. under N₂. After stirring for 10 min, more DMF (100 mL) was added, heated to 40° C., and stirred for an additional 40 min. Piperidin-4-ol (3.94 g, 38.9 mmol) was added and allowed to stir overnight at RT. The reaction mixture was concentrated in vacuo, and the residue diluted with EtOAc and washed with cold H₂O (4×), 5% NaOH aq (4×), H₂O and brine. The organic layer was dried, and the remaining solvent removed in vacuo. The product, (4-hydroxy-piperidin-1-yl)-(4-{4-[4-(3-methanesulfonyl-propoxy)-indol-1-yl]-pyrimidin-2-ylamino}-cyclohexyl)-methanone was crystallized from EtOH/H₂O as a white solid (Compound 180, 15.8 g, 84%). MS M+1 (556) mp. 147.5-152.5° C.

(K) (4-hydroxy-piperidin-1-yl)-(4-{4-[4-(3-methane-sulfonyl-propoxy)-indol-1-yl]-pyrimidin-2-ylamino}-cyclohexyl)-methanone (0.855 g, 2.116 mM) and piperidin-4-ylmethyl-carbamic acid t-butyl ester (0.907 g, 4.232 mM) were mixed in THF (40 mL) for approximately 2 h with diisopropylethylamine (1.47 mL, 8.464 mM) and BOP (1.87 g, 4.23 mM) to yield a fine solid that was purified on an alumina column with 1-3% MeOH/CH₂Cl₂, dried and extracted into EtOAc to yield [1-(4-{4-[4-(3-methanesulfonyl-propoxy)-indol-1-yl]-pyrimidin-2-ylamino}-cyclohexanecarbonyl)-piperidin-4-ylmethyl]-carbamic acid t-butyl ester as a white powder upon drying in vacuo (0.856 g).

(L) A solution of [1-(4-{4-[4-(3-methanesulfonyl-propoxy)-indol-1-yl]-pyrimidin-2-yl-amino}-cyclohexanecarbonyl)-piperidin-4-ylmethyl]-carbamic acid t-butyl ester (0.827 g, 1.236 mM) in 10 mL of 10% HCl soln./EtOH was briefly heated on a steam bath, stirred for 7 hours at RT, concentrated to half volume and cooled in an ice bath. The light yellow solid was collected by filtration, washed with cold EtOH, and dried at 60° C. in vacuo. The product was extracted into DCM, crystallized from EtOH, and dried in vacuo at 60° C. to yield (4-aminomethyl-piperidin-1-yl)-(4-{4-[4-(3-methanesulfonyl-propoxy)-indol-1-yl]-pyrimidin-2-ylamino}-cyclohexyl)-methanone (Compound 304) as a white solid (0.41 g, mp 124-126° C.).

(M) CDI (7.13 g, 44.0 mmol) was added to a mixture of 4-{4-[4-(3-methanesulfonyl-propoxy)-indol-1-yl]-pyrimidin-2-ylamino}-cyclohexanecarboxylic acid (16.00 g, 33.86 mmol) in dry DMF (100 mL) heated to 40° C. under N₂. After stirring for 10 min, 100 mL of DMF was added, heated to 40° C., and stirred for an additional 40 min. N,N-dimethyl-piperidin-4-ylamine (5.00 g, 38.9 mmol) was added and allowed to stir overnight at RT. The reaction mixture was concentrated in vacuo, the residue diluted with EtOAc and washed with cold H₂O (4×), 5% NaOH aqueous solution (4×), H₂O and brine. The organic layer was dried and the remaining solvent removed in vacuo. The product, (4-dimethylamino-piperidin-1-yl)-(4-{4-[4-(3-methane-sulfonyl-propoxy)-indol-1-yl]-pyrimidin-2-ylamino}-cyclohexyl)-methanone (Compound 275), was crystallized from EtOH/H₂O as a white solid (11.9 g, 60.3%). MS M+1 (583), mp 182.4-183° C.

Example 28

Synthesis of N-[4-(4-{4-[3-(hydroxy)-pyrrolidin-1-yl]-indol-1-yl}-pyrimidin-2-ylamino)-cyclohexyl]-methanesulfonamide (A) Imidazole (38 g, 557.5 mmol) was added to pyrrolidin-3-ol (9.7 g, 111.5 mmol) in THF (350 mL), the mixture cooled to 0° C. with stirring, and t-butyl-dimethyl-silyl chloride (TB-DMS-Cl, 418 g, 278.8 mmol) was added portionwise and stirred overnight. The resulting filtrate was concentrated in vacuo, washed with hexane, and dried in vacuo. The residue was then extracted into EtOAc and washed with H₂O several times, dried, and solvent removed in vacuo to yield the protected alcohol (3 g).

(B) NaO(t-Bu) (612 mg, 6.57 mmol) was added to 3-(t-butyl-dimethylsilyloxy)-pyrrolidine (1.10 g, 5.46 mmol) in dry THF (15 mL) and allowed to stir overnight. Next, 4-bromo-1-(2-methylsulfanyl-pyrimidin-4-yl)-1H-indol (582.6 mg, 1.82 mmol), Pd(OAc)₂ (41 mg, 0.182 mmol), and P(t-Bu)₃ (37 mg, 0.182 mmol) were added, and the reaction mixture was heated in a sealed tube at 120° C. for approximately 1.5 h. The filtrate was isolated, washed, dried, and concentrated in vacuo to yield 4-[3-(t-butyl-dimethylsilyloxy)pyrrolidin-lyl]-1-(2-methyl-sulfanyl-pyrimidin-4-yl)-1H-indole (422 mg).

(C) m-CPBA (537 mg, 2.40 mmol) in anhydrous DCM (10 mL) was added dropwise over 15 min to 4-[3-(t-butyl-dimethylsilyloxy)pyrrolidin-lyl]-1-(2-methylsulfanyl-pyrimidin-4-yl)-1H-indole (422 mg, 0.959 mmol) in DCM (10 mL) at 0° C. After addition of 2 more eq of m-CPBA over approximately 1.5 h at 0° C., PS-Ph₃P (2.6 g, 3.84 mmol) was added and allowed to stand overnight. The mixture was filtered, concentrated in vacuo, and the residue washed with DCM to yield 4-[3-(t-butyl-dimethylsilyloxy)pyrrolidin-1-yl]-1-(2-methylsulfonyl-pyrimidin-4-yl)-1H-indole (320 mg).

(D) 4-[3-(t-Butyl-dimethylsilyloxy)pyrrolidin-1-yl]-1-(2-methylsulfonyl-pyrimidin-4-yl)-1H-indole (about 160 mg, 0.35 mmol), N-(4-amino-cyclohexyl)-methanesulfonamide hydro-chloride (743 mg, 3.255 mmol) and DIEA (0.169 mL, 4.32 mmol) were mixed in NMP (7 mL) under Ar at 130° C. for 2.5 h. The reaction mixture was washed with NH₄Cl/H₂O and extracted into EtOAc (6×15 mL), and further washed with H$_2$O (6×30 mL). The solvent was removed in vacuo to yield N-[4-(4-{4-[3-(t-butyl-dimethylsilanyloxy)-pyrrolidin-1-yl]-indol-1-yl}-pyrimidin-2-ylamino)-cyclohexyl]-methanesulfonamide (150 mg).

(E) N-[4-(4-{4-[3-(t-butyl-dimethylsilanyloxy)-pyrrolidin-1-yl]-indol-1-yl}-pyrimidin-2-ylamino)-cyclohexyl]-methanesulfonamide (0.35 mmol) was mixed with TBAF (10 eq, 3.5 mL) in anhydrous THF (15 mL) and allowed to stir for 1.5 h at RT, and then heated to 68° C. The reaction mixture was washed with NH$_4$Cl/H$_2$O, extracted into EtOAc (6×15 mL), and further washed with H$_2$O (6×30 mL). The product was isolated via chromatography (prep. TLC in NH$_4$OH/MeOH/DCM) as N-[4-(4-{4-[3-(hydroxy)-pyrrolidin-1-yl]-indol-1-yl}-pyrimidin-2-yl-amino)-cyclohexyl]-methanesulfonamide (Compound 311, 35 mg).

Example 29

Synthesis of N-ethyl-N-{1-[2-(4-methanesulfonylamino-cyclohexylamino-pyrimidin-4-yl)-1H-indol-4-yl]-methanesulfonamide (A) Tri-isopropylsilyl chloride (TIPS-Cl, 15.86 mL) and imidazole (5.62 g) were added to 1H-indol-4-ol (10 g) in DMC (200 mL), and stirred at RT overnight. The resulting solid was filtered and washed with DCM. The filtrate was concentrated and purified on a column with 100% hexane to 25% EtOAc/hexane, and the fractions collected, concentrated, triturated with cold hexane, and the resulting solid was filtered and dried at 50° C. to yield 4-(triisopropylsilyl-oxy)-1H-indole (17 g, ~80%).

(B) NaH (1.826 g) was added to DMF (400 mL) and cooled to 0° C. 4-(Triisopropyl-silyloxy)-1H-indole (12 g) was added portionwise at 0° C., and allowed to stir at 0° C. for 1 h. 4-Chloro-2-methylsulfanyl-pyrimidine (5.28 mL) was added dropwise, and the reaction mixture stirred at 0° C. for 4 h and then quenched with water. The aqueous layer was acidified with 1N HCl. The organic layer was extracted into DCM, and dried over sodium sulfate, filtered and the filtrate was concentrated and purified on a column with 100% hexane to 25% EtOAc/hexane to yield 1-(2-methylsulfanyl-pyrimidin-4-yl)-4-triisopropylsilanyloxy-1H-indole (11 g).

(C) 1-(2-methylsulfanyl-pyrimidin-4-yl)-4-triisopropylsilanyloxy-1H-indole (7.75 g) in THF (50 mL) was mixed with TBAF/THF (8 mL) and allowed to stir at RT for 2 h, then quenched with water. The aqueous layer was acidified with 1N HCl. The resulting solid was filtered, washed with water and dried at 50° C. in vacuo overnight to yield 1-(2-methylsulfanyl-pyrimidin-4-yl)-1H-indol-4-ol (4.5 g).

(D) 1-(2-methylsulfanyl-pyrimidin-4-yl)-4-triisopropylsilanyloxy-1H-indole (1.25 g) was mixed with 1,1,1-trifluoro-2-methoxy-ethane (2.5 g) and H$_2$CO$_3$ (2.68 g) in NMP (5 mL) at 110° C. for 30 min, cooled to RT, quenched with water, extracted into DCM, and the filtrate purified on a column with hexane to EtOAc/hexane. The fractions collected yielded an oil which was triturated with water to precipitate a solid, which was filtered and dried to yield 4,4,4-tri-fluoro-1-[1-(2-methylsulfanyl-pyrimidin-4-yl)-1H-indol-4-yloxy]-butan-2-ol (1.5 g).

(E) 4,4,4-Trifluoro-1-[1-(2-methylsulfanyl-pyrimidin-4-yl)-1H-indol-4-yloxy]-butan-2-ol (1.5 g) in CHCl$_3$ (200 mL) at 0° C. was stirred for 3 h with MCPBA (0.962 g) at 0° C., then quenched with 10% aqueous sodium thiosulfate. The organic layer was separated, washed with saturated NaHCO$_3$ and brine, dried over sodium sulfate, filtered, concentrated in vacuo and purified on a column with 100% DCM to 15% MeOH/DCM (product eluting at 5% MeOH) to yield 4,4,4-trifluoro-1-[1-(2-methylsulfinyl-pyrimidin-4-yl)-1H-indol-4-yloxy]-butan-2-ol (~1.4 g).

(F) 1-(2-Methylsulfanyl-pyrimidin-4-yl)-1H-indole-4-carbaldehyde (14.38 g, 53.39 mmol) was suspended in a mixture of MeOH (200 mL) and DCM (100 mL), cooled in an ice bath, treated with NaBH$_4$, and stirred for 1 h. Water was then added, and the solvents concentrated in vacuo. The residue was them partitioned between water and EtOAc, filtered, and the precipitate was triturated with ether, filtered and solvent removed in vacuo overnight to yield [1-(2-methylsulfanyl-pyrimidin-4-yl)-1H-indol-4-yl]-methanol (10 g).

(G) [1-(2-Methylsulfanyl-pyrimidin-4-yl)-1H-indol-4-yl]-methanol (10 g) and HBr (60 mL) were stirred at 50° C. for 4 h, then cooled to RT and filtered. The precipitate was stirred in a mixture of 5% NaHCO$_3$ and EtOAc for 30 min, filtered, the filtrate separated, and the organic layer dried over sodium sulfate, filtered, and the solvent evaporated in vacuo to yield 4-bromo-methyl-1-(2-methylsulfanyl-pyrimidin-4-yl)-1H-indole (8.8 g).

(H) MCPBA (1.1 g, 4.93 mmol) was added to 4-bromomethyl-1-(2-methylsulfanyl-pyrimidin-4-yl)-1H-indole (1.5 g, 4.48 mmol) in DCM at 0° C., the mixture stirred for 40 min, diluted with DCM, washed with 5% NaHCO$_3$, dried over sodium sulfate, filtered, and concentrated in vacuo to yield the corresponding sulfoxide (1.38 g). The sulfoxide was then dissolved in acetonitrile (5 mL) with K$_2$CO$_3$ (980 mg) and N-(2-methoxyethyl)methylamine (0.5 mL, 4.7 mmol) and stirred at RT overnight. The precipitate was filtered off, and the filtrate concentrated in vacuo and purified by flash chromatography on a silica column to yield [1-(2-methanesulfinyl-pyrimidin-4-yl)-1H-indol-4-ylmethyl]-(2-methoxyethyl)-methyl-amine (380 mg).

(I) 2-methylsulfanyl-ethanol (0.29 mL, 3.36 mmol) was dissolved in THF (5 mL), cooled in an ice bath, and NaH (148 mg, 3.7 mmol) was the added portionwise. After 30 min, a suspension of 4-bromomethyl-1-(2-methylsulfanyl-pyrimidin-4-yl)-1H-indole (750 mg, 2.24 mmol) in THF (5 mL) was added, and the mixture was stirred at RT overnight. The mixture was then concentrated in vacuo, and the residue purified using flash chromatography on a silica column, eluting with hexane:ethyl acetate 4:1 to 3:7 to yield 1-(2-methanesulfinyl-pyrimidin-4-yl)-4-(2-methylsulfanyl-ethoxymethyl)-1H-indole (390 mg).

(J) 4,4,4-Trifluoro-1-[1-(2-methylsulfinyl-pyrimidin-4-yl)-1H-indol-4-yloxy]-butan-2-ol (0.3 g), N-(4-aminocyclohexyl)-methanesulfonamide (0.514 g) and TEA (0.523 mL) were stirred in NMP (3 mL) at 110° C. for 3 h. After cooling, the resulting solid was filtered washed with H$_2$O and dried. The product was purified on a column using 70% EtOH/hexane to 100% EtOAc, the fractions collected, concentrated in vacuo at 50° C. overnight to yield N-(4-{4-[4-(4,4,4-trifluoro-2-hydroxy-butoxy)-indol-1-yl]-pyrimidin-2-ylamino}-cyclohexyl)-methanesulfonamide (Compound 314, 0.227 g).

(K) 1-(2-Methanesulfinyl-pyrimidin-4-yl)-4-(2-methylsulfanyl-ethoxymethyl)-1H-indole (0.3 g), N',N'-dimethylamino-(4-aminocyclohexyl)sulfonic acid amide hydrochloride (0.59 g), and TEA (0.53 mL) were stirred in NMP (3 mL) at 110° C. for 7 h. The reaction mixture was cooled, quenched with water, the solid separated, washed with water and dried. The product was purified on a column with 5% DCM/MeOH to 20% MeOH/DCM, the fractions collected, and concentrated in vacuo. The residue was triturated with EtOAc to precipitate a solid which was filtered and dried at 50° C. to yield N-(4-{4-[4-(3-methansulfonyl-propoxy)-indol-1-yl]- pyrimidin-2-ylamino}-cyclohexyl)-(dimethamino)-sulfonamide (Compound 313, 127.6 mg).

(L) DIEA (0.31 mL) and N-(4-aminocyclohexyl)-methanesulfonamide (348 mg) were stirred in NMP (1 mL) at RT for 1 hour. 3-(2-Methanesulfinyl-pyrimidin-4-yl)-7-(3-methane-sulfonyl-propoxy)-1H-indazole (200 mg, 0.5 mmol) was added to the mixture and stirred at 130° C. for 2.5 h. The reaction mixture was then poured into water and the precipitate purified on a silica column using flash chromatography, eluting with hexane:EtOAc:MeOH 5:4.5:0.5 to yield N-(-4-{4-[7-(3-methanesulfonyl-propoxy)-1H-indazol-3-yl]-pyrimidin-2-ylamino}-cyclo-hexyl)-methanesulfonamide (Compound 315).

(M) N-(4-amino-cyclohexyl)-N-methyl-methanesulfonamide (567 mg, 2.12 mmol) and DIEA (0.44 mL) were stirred in NMP (0.7 mL) at RT for 1 h. [1-(2-Methanesulfinyl-pyrimidin-4-yl)-1H-indol-4-ylmethyl]-(2-methoxyethyl)-methyl-amine (305 mg, 0.85 mmol) in NMP (0.8 mL) was added, and the tube sealed and heated to 130° C. for 1 h. The mixture was then cooled to RT, decanted into water, stirred at RT overnight, and the filtrate filtered off and dried in vacuo, dissolved in DCM/ether, the precipitate filtered off, and the residue concentrated and crystallized from DCM/ether to yield N-{4-[4-(4-{[(2-methoxy-ethyl)-methyl-amino]-methyl}-indol-1-yl)-pyrimidin-2-ylamino]-cyclohexyl}-N-methyl-methanesulfonamide (Compound 203).

(N) 4-(2-Methylsulfanyl-ethoxymethyl)-1-(2-methylsulfanyl-pyrimidin-4-yl)-1H indole (196 mg, 0.36 mmol) was dissolved in DCM, cooled on an ice bath, and MCPBA (635 mg, 2.83 mmol) was added and the mixture was stirred at RT overnight. The mixture was then diluted with DCM, washed with 5% NaHCO₃, dried over sodium sulfate, filtered, concentrated in vacuo, and the residue dissolved in NMP and added to a suspension of N-(4-amino-cyclohexyl)-N-methyl-methanesulfonamide (409 mg, 1.98 mmol), 0.39 mL DIEA (2.27 mmol) and molecular sieves (previously stirred at RT for 1 h). The mixture was stirred at 120° C. for 1 h, cooled to RT, the mixture decanted into water, stirred for 30 min, filtered, and the precipitate purified by flash chromatography, eluting with DCM:MeOH 97:3. The product was then stirred in ether, filtered, and the solvent removed in vacuo overnight to yield N-methyl-N-(4-{4-[4-(2-methylsulfanyl-ethoxymethyl)-indol-1-yl]-pyrimidin-2-ylamino}-cyclohexyl)-methanesulfonamide (47 mg).

(O) N-[1-(2-Methylsulfanyl-pyrimidin-4-yl)-1H-indol-4-yl]-methanesulfonamide (0.4 g) in DMF (2 mL) was treated with K₂CO₃ (0.83 g) followed by EtI (0.2055 g), stirred at RT overnight, diluted with water, the solid filtered, washed with water and dried at 50° C. in vacuo overnight to yield N-ethyl-N-[1-(2-methylsulfanyl-pyrimidin-4-yl)-1H-indol-4-yl]-methane-sulfonamide (0.4 g).

(P) N-ethyl-N-[1-(2-methylsulfanyl-pyrimidin-4-yl)-1H-indol-4-yl]-methanesulfonamide (0.4 g) in CHCl₃ (60 mL) was cooled to 0° C. and MCPBA (0.247 g) added and stirred at 0° C. for 5 h before quenching with 10% sodium thiosulfate solution. The organic layer was separated, dried over sodium sulfate, filtered, concentrated and purified on a column using 100% DCM to 15% MeOH/DCM to yield N-ethyl-N-[1-(2-methylsulfinyl-pyrimidin-4-yl)-1H-indol-4-yl]-methane-sulfonamide (0.386 g).

(Q) N-Ethyl-N-[1-(2-methylsulfinyl-pyrimidin-4-yl)-1H-indol-4-yl]-methanesulfonamide (0.386 g), N-(4-amino-cyclohexyl)-methanesulfonamide (0.7 g), and TEA (0.53 mL) were stirred in NMP (3 mL) at 110° C. for 8 h. The reaction mixture was cooled, quenched with water, the solid filtered, washed with water and dried. The product was purified on a column with 100% DCM to 15% MeOH/DCM, the pure fractions collected, and concentrated in vacuo. The residue was triturated with EtOAc to precipitate a solid which was filtered and dried at 50° C. to yield N-ethyl-N-{1-[2-(4-methanesulfonylamino-cyclohexylamino-pyrimidin-4-yl)-1H-indol-4-yl]-methanesulfonamide (Compound 316, 299.8 mg).

Example 30

Synthesis of N-[4-(5-fluoro-4-indol-1-yl-pyrimidin-2-ylamino)-cyclohexyl]-methanesulfonamide (A) Indole (1.0 g, 8.54 mmol) was added in portions to a suspension of NaH (0.358 g, 8.96 mmol) in DMF (10 mL) at 0° C. under N₂ and stirred for 15 minutes at RT. 2,4-Dichloro-5-fluoro-pyrimidine (1.49 g, 8.96 mmol) was then added in portions and allowed to stir at RT overnight. The reaction mixture was poured into cold water, extracted into DCM, washed in brine, dried with Na₂SO₄, filtered, and dried in vacuo to obtain an oil. The residue was purified using flash chromatography on a silica column eluting with hexane:EtOAc (1000:25) to (1000:50), to yield 1-(2-chloro-5-fluoro-pyrimidin-4-yl)-1H-indole after drying the collected fraction (0.11 g, 5%).

(B) 1-(2-Chloro-5-fluoro-pyrimidin-4-yl)-1H-indole (0.095 g, 0.38 mmol), N-(4-amino-cyclohexyl)-methanesulfonamide (0.17 g, 0.76 mmol), and DIEA (0.13 mL, 0.76 mmol) were stirred in NMP (2 mL) at 170° C. for 4.5 hours. The solvent was removed at 100° C. in vacuo to yield an oil which was then dissolved in DCM, washed with cold water and brine, and fried with sodium sulfate. The solvent was removed in vacuo to yield an oil. The product was purified using flash chromatography (SiO₂) eluting with 1% MeOH/DCM to obtain N-[4-(5-fluoro-4-indol-1-yl-pyrimidin-2-ylamino)-cyclohexyl]-methanesulfonamide as a white solid (Compound 115, 0.025 g, 16%, mp 270.0-270.5° C.).

Example 31

Synthesis of 2-(4-{4-[4-(3-methanesulfonyl-propoxy)-indol-1-yl]-pyrimidin-2-ylamino}-cyclohexyl)-propan-2-ol (A) 1-(t-Butoxycarbonyl)-amino-4-aminocyclohexane (21.4 g, 0.1 mol) and Cs₂CO₃ (71.7 g, 0.22 mol) were stirred in acetonitrile (500 mL) on an ice bath under Ar. Benzyl bromide (26 mL, 0.22 mol) in acetonitrile (20 mL) was then added dropwise, the reaction mixture was then allowed to warm to RT and was stirred overnight. The reaction mixture was then diluted with EtOAc, washed with water (×2) and brine, dried over sodium sulfate, filtered, and dried in vacuo to provide the dibenzyl derivative. The product was then dissolved in dry THF added via cannula under Ar, stirred initially at RT and then cooled to 0° C. using an ice bath prior to the portionwise addition of NaH (8 g, 60%), and was allowed to stir at 0° C. for 25 min. CH₃I (18 mL) in THF (7 mL) was then added dropwise over 15 min. The reaction mixture was allowed to stir at RT overnight. The reaction mixture was then cooled on an ice bath and NaH (2 g) was added portionwise and allowed to stir for 45 min. CH₃I (4.5 mL) was then added and the mixture allowed to stir and reach RT The reaction was then slowly quenched with water. The reaction mixture was then diluted with EtOAc, washed with water (×2) and brine, dried over sodium sulfate, filtered, and dried in vacuo and purified on silica column with 0% to 60% EtOAc/hexane to yield 1-[N-(t-butoxycarbonyl)-N-methyl-amino]-4-(N',N'-dibenzyl-amino)-cyclohexane (35 g, 0.086 mol). This was then stirred in MeOH (675 mL) at RT under Ar. HCl (675 mL, 2 N) was then added and allowed to stir for approximately 5 hours. After concentrating in vacuo, the mixture was poured into saturated NaHCO₃ and the organic phase extracted into DCM. NaOH (2 N aq) was added to the aqueous layer until basic, and the organic layer was then extracted into DCM (×³), washed with brine and dried over sodium sulfate, filtered and solvent removed in vacuo to yield N,N-dibenzyl-N'-methyl-cyclohexane-1,4-diamine (23.02 g). TEA (39 mL) was added to the N,N-dibenzyl-N'-methyl-cyclohexane-1,4-diamine (23 g) in DCM (500 mL) under Ar. The reaction was then cooled on an ice bath and MsCl (7.25 mL) was added dropwise and allowed to stir and reach RT. The reaction was then diluted with DCM, washed with NaHCO₃, water, and brine, and filtered and dried over sodium sulfate to yield N-(4-dibenzylamino-cyclohexyl)-N-methyl-methanesulfonamide (25.14 g). This was mixed with Pd(OH)₂ (17 g, 20%) in EtOH (650 mL abs). Acetic acid (9.3 mL) was then added and H₂ was added over 3.5 hours and the reaction allowed to stir overnight. The product was concentrated in vacuo and then stirred overnight in EtOAc, filtered, washed with ether, and the solvent removed in vacuo at 45° C. for 2 days to yield N-(4-amino-cyclohexyl)-N-methyl-methanesulfonamide (12.03 g).

(B) 4-Amino-cyclohexanecarboxylic acid (16 g, 0.11 mol) was treated with K₂CO₃ (46.8 g) in MeCN (225 mL) at 80° C. under Ar. Benzyl bromide (46.6 mL) in MeCN (140 mL) was then added dropwise and stirred at 80° C. for approximately 20 hours and allowed to cool to RT, to yield 4-dibenzylamino-cyclohexanecarboxylic acid benzyl ester (55.04 g) after workup.

(C) 4-Dibenzylamino-cyclohexanecarboxylic acid benzyl ester (55.04 g, 0.11 mol) in THF (3.7 L) was treated with MeMgBr (370 mL, 3N) dropwise under N₂ on an ice bath, and allowed to stir and reach RT. The mixture was cooled on an ice bath, and NH₄Cl (4 L, 15%) was added, dropwise at first, then more steadily, and allowed to stir for several hours, and the aqueous and organic phased separated. The organic layer was washed with saturated NaHCO₃, then with brine. The aqueous layers were back extracted with EtOAc. Both organic layers were then dried over sodium sulfate, filtered, and the solvent removed in vacuo. The product was purified on a column (SiO₂) with 100% hexane to 30% EtOH/hexane to yield 2-(4-dibenzyl-amino-cyclohexyl)-propan-2-ol (30.43 g) after removing excess solvent in vacuo.

(D) 2-(4-Dibenzylamino-cyclohexyl)-propan-2-ol (15 g) in EtOH (300 mL, abs) was treated with Pd(OH)₂ (12.5 g). Acetic acid (6.3 mL) was added, and H₂ was added slowly over 4.5 h. The reaction mixture was allowed to stand, then was filtered through a glass frit, washed with EtOH, filtered through a second glass frit, and the solvent removed in vacuo. The product was dissolved in hexane, and the hexane removed in vacuo (×3). The product was then triturated with ether, and the resultant solid filtered. The filtrate was evaporated, the residue dissolved in EtOH and solvent removed in vacuo. The product was then triturated in ether and the product filtered. The solvent was removed from both solid portions to yield 2-(4-aminocyclohexyl)-propan-2-ol acetate (6.52 g).

(E) Acetoxy acetic acid (1.13 g) was dissolved in DCM (20 mL), and EDCI (2.112 g) and TEA (1.023 mL) were then added and allowed to stir. N,N-Dibenzyl-cyclohexane-1,4-diamine (2.162 g, 7.34 mmol) was then added dropwise and the solution allowed to stir for 14 h at RT The reaction mixture was then concentrated and water (100 mL, pH 5) added. The mixture was extracted with EtOAc, the organic layers combined, washed with water (×2) and saturated NaHCO₃. The organic layer was then dried over sodium sulfate, filtered, and the solvent removed in vacuo to yield acetic acid (4-dibenzylamino-cyclohexylcarbamoyl)-methyl ester (2.35 g, 5.96 mmol). This intermediate was then dissolved in THF (20 mL) under Ar and cooled to −78° C., LAH (12.5 mL) slowly added, and the reaction mixture slowly allowed to reach RT. The reaction mixture was then heated to 60° C. for 16 h, and then to 85° C. for 4 h. After allowing the mixture to cool to RT, water (0.46 mL), NaOH (0.46 mL, 15%), and water (1.35 mL) were added. The precipitate was filtered and washed with THF/EtOAc, which was then filtered, dried over sodium sulfate, filtered, and solvent removed in vacuo to give 2-(4-dibenzylamino-cyclo-hexylamino)-ethanol (1.886 g, 94.7%). This intermediate (1.70 g, 5.02 mmol), TBDMSiCl (0.757 g), and imidazole (0.513 g) were combined in DMF (10 mL) and allowed to stir at RT for 1 day. Further portions of TBDMSiCl (0.757 g) and imidazole (0.170 g) were then added, and the reaction mixture allowed to stir for 3.5 h at RT The reaction was then poured into water, extracted with EtOAc, the organics washed with water, dried over sodium sulfate, filtered, solvent removed in vacuo, and purified on a silica column with 0% to 5% MeOH/DCM w/0.1% NH₄OH to yield 1-(t-butyl-dimethylsilanyloxy)-2-(4-dibenzylamino-cyclohexylamino)-ethane (1.926 g, 84.7%). This intermediate (3.969 g, 8.77 mmol) and CH₃(SO₂)O(SO₂)CH₃ (1.680 g) were combined in DCM (30 mL) under N2 and cooled in an ice bath. TEA (1.3 mL) was then slowly added, and the reaction allowed to stir for 5 min on an ice bath, then stirred at RT for 16 h. Water was then added to the mixture, extracted with DCM, the organics dried over sodium sulfate, filtered, solvent removed in vacuo to yield a thick oil which was triturated with petroleum ether, filtered, and the solvent removed in vacuo to yield N-[2-(t-butyl-dimethyl-silanyloxy)-ethyl]-N-(4-dibenzylamino-cyclohexyl)-methanesulfonamide (3.632 g).

(F) N-[2-(t-Butyl-dimethyl-silanyloxy)-ethyl]-N-(4-dibenzylamino-cyclohexyl)-methanesulfonamide (3.282 g, 6.18 mmol) and Pd(OH)₂ (0.40 g) were combined in EtOH/MeOH under Ar, and treated with H₂ (45 psi) at RT for 1 day. The reaction mixture was then filtered, the solid washed with EtOH, the filtrates combined, and solvent removed in vacuo to yield N-[2-(t-butyl-dimethyl-silanyloxy)-ethyl]-N-(4-amino-cyclohexyl)-methanesulfonamide (2.123 g).

(G) 1-(2-Methanesulfinyl-pyrimidin-4-yl)-4-(3-methanesulfonyl-propoxy)-1H-indole (5.0 g, 13 mmol) and (4-aminocyclohexyl)-methanol hydrochloride (2.46 g, 19 mmol) were heated at reflux in EtOH (100 mL) under N₂ for 16 h. The reaction mixture was then cooled, the suspension filtered, the filtrate volume reduced by half, diluted with EtOAc and washed with water, dried over sodium sulfate, filtered and concentrated until precipitate formed. This suspension was filtered, and the filtrate concentrated again until precipitation, and the suspension filtered, and both precipitates were combined and solvent removed in vacuo to yield (4-{4-[4-(3-methanesulfonyl-propoxy)-indol-1-yl]-pyrimidin-2-ylamino}-cyclohexyl)-methanol (Compound 214, 2.93 g), as a light yellow powder.

(H) p-Toluenesulfonic anhydride (1.44 g, 4 mmol) was added to (4-{4-[4-(3-methane-sulfonyl-propoxy)-indol-1-yl]-pyrimidin-2-ylamino}-cyclohexyl)-methanol (1.79 g, 4 mmol) in pyridine (12 mL), and the reaction mixture was allowed to stir at RT overnight. The suspension was then diluted with water, filtered, the collected solids were washed with water, EtOAc and hexanes, and dried to yield the product as a powder. The filtrate was diluted with DCM, washed with 1 N HCl (×3), dried over sodium sulfate, filtered, the solvent concentrated in vacuo and diluted with EtOAc, the suspension filtered and both precipitates were combined and the solvent removed in vacuo to yield benzenesulfonic acid 4-{4-[4-(3-methanesulfonyl-propoxy)-indol-1-yl]-pyirmidin-2-ylamino}-cyclohexylmethyl ester (0.52 g, 22%), as a light powder.

(I) Benzenesulfonic acid 4-{4-[4-(3-methanesulfonyl-propoxy)-indol-1-yl]-pyrimidin-2-ylamino}-cyclohexylmethyl ester (343 mg, 0.6 mmol) and pyrrolidino-3-ol (185 mg, 2.1 mmol) were combined in dioxane (5 mL) and heated to 120° C. in a sealed tube for 3 h, cooled, dissolved in MeOH/DCM and the resulting product purified on a silica gel column by flash chromatography (10:90 MeOH/DCM+NH$_4$OH) and recrystallized from EtOAc/hexanes to yield 1-(4-{4-[4-(3-methanesulfonyl-propoxy)-indol-1-yl]-pyirmidin-2-ylamino}-cyclohexylmethyl)-pyrrolidin-3-ol (Compound 317, 233 mg, 79%) as off white needles.

(J) 1-(2-Methanesulfinyl-pyrimidin-4-yl)-4-(3-methanesulfonyl-propoxy)-1H-indole (538 mg, 1.4 mmol), 4-(2-hydroxyprop-2-yl)-cyclohexylammonium acetate (400 mg, 2 mmol), and DIEA (0.8 mL, 5 mmol) were combined in NMP (10 mL) and heated to 126° C. in a sealed tube for 4 h, cooled, and partitioned between water and EtOAc. The organic layer was separated and washed twice with water, dried over sodium sulfate, filtered and purified by flash chromatography (SiO$_2$) with 3:97 MeOH/DCM, and recrystallized from MeOH/DCM, triturated with EtOAc and solvent evaporated to yield 2-(4-{4-[4-(3-methanesulfonyl-propoxy)-indol-1-yl]-pyrimidin-2-ylamino}-cyclohexyl)-propan-2-ol (Compound 166, 391 mg, 59%) as a white powder.

(L) Dioxane (90 mL), NaOH (230 mL, 1 N aq) and H$_2$O (45 mL) were stirred on an ice bath under Ar. 4-Aminocyclohexane carboxylic acid (20 g) was added, followed by Boc anhydride (33.5 g), and the reaction mixture stirred overnight, warming to RT. Concentrated HCl was then added to bring the reaction mixture to pH 5.6, the mixture extracted into ethyl acetate, the organics combined, washed with brine and dried over sodium sulfate, filtered, and solvent removed in vacuo to yield 4-(BOC)aminocyclohexane carboxylic acid (26.97 g). This intermediate (1 g, 0.025 mol), EDCI (16.3 g, 0.085 mol) and HOBT (11.5 g) in NMP (40 mL) were allowed to stir at RT under Ar prior to addition of (S)-(−)-3-hydroxypyrrolidine (6 mL) and continued stirring at RT overnight. The reaction mixture was then cooled in an ice bath and H$_2$O (100 mL) was added dropwise, the reaction mixture was extracted with ethyl acetate, the precipitate filtered off, repeated extraction with ethyl acetate, the organics combined, dried over sodium sulfate, filtered, and the solvent removed in vacuo at 70° C. overnight. The crude product was then purified on a silica column (0% to 60% Magic Base/DCM) to yield 4-(BOC-amino)-cyclohexyl-(3-hydroxy-pyrrolidino-1-yl)-methanone (3.13 g). This intermediate (3.31 g) was stirred in MeOH (40 mL) at RT under Ar and treated with HCl (80 mL, 2 N) in MeOH and stirred overnight. The solvent was then removed in vacuo, and replaced with MeOH, and the solvent again removed in vacuo. The residue was then stirred in ether/MeOH, and the solvent again removed in vacuo. The residue was then triturated in ether to form a precipitate, which was then filtered, washed with ether, and the solvent removed in vacuo overnight at 55° C. to yield 4-aminocyclohexyl-(3-hydroxy-pyrrolidino-1-yl)-methanone (2.73 g).

Example 32

Synthesis of 4-{4-[4-(3-sulfamoyl-propoxy)-indol-1-yl]-pyrimidin-2-ylamino}-cyclohexanecarboxylic acid methylamide (A) 4-Methoxy-1H-indole (16.97 g, 0.108 mol) was dissolved in NMP (16 mL), cooled to 0° C. and treated with NaH (4.74 g, 0.118 mol) added portionwise and stirred for 1 h. 2-Butyl-sulfanyl-4-chloropyrimidine (20 g, 0.099 mol) was then added and stirred at RT overnight. Water was then added and the mixture allowed to stir for 1 h, the precipitate filtered, washed with water and then a small amount of hexane and the solvent removed in vacuo at 50° C. over-night to yield 1-(2-butylsulfanyl-pyrimidin-4-yl)-4-methoxy-1H-indole (96.6%). This intermediate (30 g) was dissolved in DCM (150 mL), and BBr$_3$ added at −78° C., allowed to warm to RT and stirred overnight. Water was added, the mixture sonicated, and filtered. The filtered solid was thoroughly washed with water and then dried in vacuo with heat to yield 1-(2-butyl-sulfanyl-pyrimidin-4-yl)-4-hydroxy-1H-indole. This intermediate (13.138 g, 43.88 mmol), [1,2]oxathiolane-2,2-dioxide (5.869 g), and K$_2$CO$_3$ (24.259 g) were mixed in acetone (150 mL) and heated at reflux overnight. HCl in ether was added, as well as DCM and MeOH to dissolve product. The solution was filtered, and the filtrate concentrated in vacuo to yield 3-[1-(2-butyl-sulfanyl-pyrimidin-4-yl)-1H-indol-4-yloxy]-propane-1-sulfonic acid. This intermediate (43.88 mmol) was treated with POCl$_3$ (500 mL) and heated at reflux overnight. The POCl$_3$ was then removed in vacuo, and the product dried to yield 3-[1-(2-butylsulfanyl-pyrimidin-4-yl)-1H-indol-4-yloxy]-propane-1-sulfonyl chloride. This intermediate (21.94 mmol) in THF was added dropwise to NH$_4$OH (70 mL, aq) at 0° C., stirred for 30 min, and allowed to warm to RT. The reaction mixture was poured into ice water, extracted with EtOAc, washed with water and brine, dried with sodium sulfate, filtered, and the solvent removed in vacuo to yield 3-[1-(2-butyl-sulfanyl-pyrimidin-4-yl)-1H-indol-4-yloxy]-propane-1-sulfonic acid amide.

(B) 3-[1-(2-Butylsulfanyl-pyrimidin-4-yl)-1H-indol-4-yloxy]-propane-1-sulfonyl chloride (10.97 mmol) was dissolved in THF (25 mL) and added dropwise to H$_2$NMe (30 mL) in EtOH at 0° C. and stirred for 30 min, and then allowed to warm to RT The reaction mixture was then poured into ice water, extracted with EtOAc, washed with water and brine, dried with sodium sulfate, filtered, and the solvent removed in vacuo to yield 3-[1-(2-butylsulfanyl-pyrimidin-4-yl)-1H-indol-4-yloxy]-propane-1-sulfonic acid methylamide.

(C) 3-[1-(2-Butylsulfanyl-pyrimidin-4-yl)-1H-indol-4-yloxy]-propane-1-sulfonyl chloride (10.97 mmol) was dissolved in THF (25 mL) and added dropwise to HNMe$_2$ (30 mL, 40% wt in H$_2$O) at 0° C. and stirred for 30 min, and then allowed to warm to RT The reaction mixture was then poured into ice water, extracted with EtOAc, washed with water and brine, dried with sodium sulfate, filtered, and the solvent removed in vacuo to yield 3-[1-(2-butyl-sulfanyl-pyrimidin-4-yl)-1H-indol-4-yloxy]-propane-1-sulfonic acid dimethylamide.

(D) MCPBA (77%) was added dropwise to 3-[1-(2-butylsulfanyl-pyrimidin-4-yl)-1H-indol-4-yloxy]-propane-1-sulfonic acid amide (1.317 g, 3.13 mmol) in DCM (20 mL) at 0° C. The reaction mixture was allowed to warm to RT, and stirred for 1 h. Sodium bisulfite (10%) was them added, the mixture extracted with DCM, washed with NaHCO$_3$ solution, water, and brine, dried over sodium sulfate, filtered and the solvent removed in vacuo to yield 3-[1-(2-butyl-sulfinyl-pyrimidin-4-yl)-1H-indol-4-yloxy]-propane-1-sulfonic acid amide (77.5%).

(E) 4-Aminocyclohexane carboxylic acid ethyl ester (588.4 mg, 3.44 mmol) was dissolved in NMP (5 mL) and treated with DIEA (0.993 mL, 5.7 mmol) and the reaction mixture allowed to stir at RT for 5 min. 3-[1-(2-Butylsulfinyl-pyrimidin-4-yl)-1H-indol-4-yloxy]-propane-1-sulfonic acid amide (500 mg, 1.14 mmol) was then added, and the reaction mixture heated to 120° C. for 1 h. The reaction was then allowed to cool to RT, water was added, the mixture was sonicated, filtered, and the solid dried in vacuo to yield 4-{4-[4-(3-sulfamoyl-propoxy)-indol-1-yl]-pyrimidin-2-ylamino}-cyclohexanecarboxylic acid ethyl ester (Compound 318).

(F) 4-{4-[4-(3-Sulfamoyl-propoxy)-indol-1-yl]-pyrimidin-2-ylamino}-cyclohexane-carboxylic acid ethyl ester (590 mg, 1.176 mmol) and LiOH.H$_2$O (493.5 mg, 11.76 mmol) were combined in THF (2.5 mL), H$_2$O (2.5 mL), and EtOH (2.0 mL) and allowed to stir overnight at RT. 10% HV1 solution was then added and the product precipitated. The organic solvents were removed in vacuo and the remaining suspension was filtered, washed with water and the yellow solid dried to yield 4-{4-[4-(3-sulfamoyl-propoxy)-indol-1-yl]-pyrimidin-2-ylamino}-cyclo-hexanecarboxylic acid (Compound 220, 550 mg, 99%).

(G) 4-{4-[4-(3-Sulfamoyl-propoxy)-indol-1-yl]-pyrimidin-2-ylamino}-cyclohexane-carboxylic acid (75 mg, 0.158 mmol), BOP (105.08 mg, 0.238 mmol), DIEA (55 μL, 0.317 mmol), and H$_2$NMe (0.120 μL, 20% soln. in THF, 0.238 mmol) were combined in THF and allowed to stir at RT overnight. Water was then added to the reaction mixture and the mixture sonicated, and the solid filtered, washed with water, dried and recrystallized to yield 4-{4-[4-(3-sulfamoyl-propoxy)-indol-1-yl]-pyrimidin-2-ylamino}-cyclohexanecarboxylic acid methylamide (Compound 319, 53.3 mg, 69.3%).

Example 33

Synthesis of N-(4-{4-[4-(4-acetyl-piperazin-1-yl)-indol-1-yl]-pyrimidin-2-yl-amino}-cyclohexyl)-N-(2-hydroxy-ethyl)-methanesulfonamide (A) 4-(1H-Indol-4-yl)-piperazine-1-carboxylic acid t-butyl ester (10.00 g, 33.2 mmol) was dissolved in NMP (40 mL) and treated with NaH (1.53 g, 60%) added slowly. The reaction was cooled on an ice bath as it became exothermic, and stirred for 1 h. 4-Chloro-2-methyl-sulfanyl-pyrimidine (4.2 mL) was then added to the cooled reaction mixture and allowed to reach RT, then stirred for 20 h under N$_2$. Ice water was added to the reaction mixture to double the volume, EtOAc (15 mL) and water (100 mL) were added, and the mixture agitated for 30 min. The crude product was filtered off, washed with water, and solvent removed in vacuo, and recrystallized in petroleum ether/EtOAc to yield 4-[1-(2-methylsulfanyl-pyrimidin-4-yl)-1H-indol-4-yl]-piperazine-1-carboxylic acid-t-butyl ester (8.399 g). This intermediate (0.200 g, 0.47 mmol) was dissolved in DCM (10 mL), the solution cooled to 0° C., and MCPBA (0.212 g) in DCM (4 mL) was added dropwise. The reaction mixture allowed to stir cooled under N$_2$ for 2 h, and PPh$_3$ (0.37 g) was added and stirred at RT under N$_2$ for 20 h. DCM was then added to dilute to 100 mL, the solution washed with sat. NaHCO$_3$, dried over sodium sulfate, filtered, the solvent removed in vacuo, and the product purified on a silica column eluting with 0% to 2.5% MeOH/CH$_2$Cl$_2$ to yield 4-[1-(2-methylsulfinyl-pyrimidin-4-yl)-1H-indol-4-yl]-piperazine-1-carboxylic acid t-butyl ester (0.165 g, 79%).

(B) 4-{1-[2-(4-{[2-(t-Butyl-dimethyl-silanyloxy)-ethyl]-methanesulfonylamino}-cyclo-hexylamino)-pyrimidin-4-yl]-1H-indol-4-yl}-piperazin-1-carboxylic acid t-butyl ester (0.251 g, 0.345 mmol) and hexafluoroisopropanol (10 mL) were combined and heated to 150° C. for 2 h in a microwave oven. The solvent was removed in vacuo to yield crude 1-{1-[2-(4-{[2-(t-Butyl-dimethyl-silanyloxy)-ethyl]-methanesulfonylamino}-cyclohexylamino)-pyrimidin-4-yl]-1H-indol-4-yl}-piperazine (0.267 g). This intermediate (0.193 g) and acetic anhydride (0.03 mL) in NMP (0.3 mL) was allowed to stir at RT for 6 h. EtOAc and water were then added, the organic layer separated and the organic layers combined, washed with water, sat. NaHCO$_3$, dried over sodium sulfate, filtered, the solvent removed in vacuo, and the product purified on a silica column eluting with 0% to 10% MeOH/EtOAc to yield 1-{1-[2-(4-{[2-(t-butyl-dimethyl-silanyloxy)-ethyl]-methanesulfonylamino}-cyclohexylamino)-pyrimidin-4-yl]-1H-indol-4-yl}-4-acetyl-piperazine (0.119 g, 58%).

(C) 1-{1-[2-(4-{[2-(t-Butyl-dimethyl-silanyloxy)-ethyl]-methanesulfonylamino}-cyclo-hexylamino)-pyrimidin-4-yl]-1H-indol-4-yl}-4-acetyl-piperazine (0.119 g, 0.178 mmol) in THF (2.5 mL) was cooled in an ice bath under N$_2$, and TBAF (0.18 mL, 1.01 eq) slowly added. The reaction mixture was allowed to warm to RT slowly, and stirred at RT for 15 h. The product was taken up in water and EtOAc, extracted with EtOAc, and the organic fractions washed with water, dried over Na$_2$SO$_4$, concentrated, and chromatographed (0% to 5% MeOH/DCM) to provide N-(4-{4-[4-(4-acetyl-piperazin-1-yl)-indol-1-yl]-pyrimidin-2-ylamino}-cyclohexyl)-N-(2-hydroxy-ethyl)-methanesulfonamide (Compound 320, 61.4 mg, 62%).

Example 34

Synthesis of 1-{2-[4-(Methanesulfonyl-methyl-amino)-cyclohexylamino]-pyrimdin-4-yl}-1H-indole-3-sulfonic acid amide (A) t-Butanol (3 mL) was dissolved in dry benzene (10 mL) and cooled to 0° C. Chloro-sulfonyl isocyanate (CSI, 2 mL, 23.3 mmol) was added dropwise under N$_2$, warmed up to RT, and stirred for 1 h. Hexane (40 mL) was added, cooled to 0° C. while stirring under N$_2$, and the resulting white solid filtered off to provide N-Boc sulfamoyl chloride (4.55 g, 91.8% yield).

(B) TEA (4.2 mL, 30 mmol) was added to a solution of indole (1.17 g, 10 mmol) in dry THF (12.0 mL) at 0° C. and stirred for 10 min. N-Boc sulfamoyl chloride (4.31 g, 20 mmol) was added, the mixture allowed to warm to RT, and stirred overnight. The reaction mixture was poured into water, and the crude product extracted into EtOAc. The organic layer was evaporated to dryness, and dried under vacuum overnight to provide N-Boc 1H-indole-3-sulfonamide (1.57 g, 53% yield).

(C) N-Boc 1H-indole-3-sulfonamide (1.47 g, 4.96 mmol) was dissolved in CH$_3$CN (75 mL), and NaI (3.72 g, 24.80 mmol) added. The mixture was cooled to 0° C. under N$_2$, and tri-methylsilyl chloride (TMS-Cl, 2.69 g, 24.80 mmol) added dropwise, the mixture stirred for 15 min at 0° C., then stirred at RT overnight. The mixture was poured into water, the resulting off-white precipitate filtered, washed with water and hexane, and air dried to provide 1H-indole-3-sulfonic acid amide (947 mg, 97% yield), which was used without further purification.

(D) NaH (147 mg, 3.67 mmol, 60% dispersion) was added to a solution of 1H-indole-3-sulfonic acid amide (600 mg, 3.06 mmol) in DMF (5 mL) at 0° C., and stirred for 15 min. 2-Butylsulfanyl-4-chloro-pyrimidine (682 mg, 3.36 mmol) was added, and washed down with additional DMF (2 mL). The reaction mixture was allowed to warm to RT, and stirred overnight under N$_2$. The reaction mixture was then poured into water, extracted with hot EtOAc, washed with water, brine, and filtered. The mixture was concentrated to half volume, heated on a steam bath, and allowed to crystallize.

The resulting white solid was filtered off, washed with DCM, and air-dried to provide 1-(2-butylsulfanyl-pyrimidin-4-yl)-1H-indole-3-sulfonic acid amide (868 mg, 71.4% yield).

(E) MCPBA (1.127 g, 5.03 mmol) was added to a suspension of 1-(2-butylsulfanyl-pyrimidin-4-yl)-1H-indole-3-sulfonic acid amide (868 mg, 2.395 mmol) in DCM (120 mL) at RT. MeOH (10 mL) was added to improve solubility, and the mixture stirred at RT overnight. The reaction mixture was then evaporated to dryness, and the product recrystallized from ethanol-free CHCl$_3$. The resulting white solid was filtered, washed with Et$_2$O (3×50 mL), and air-dried to provide 1-(2-butylsulfonyl-pyrimidin-4-yl)-1H-indole-3-sulfonic acid amide (854 mg, 90% yield).

(F) 1-(2-Butylsulfonyl-pyrimidin-4-yl)-1H-indole-3-sulfonic acid amide (250 mg, 0.634 mmol), trans-(N-methyl-N-methylsulfonyl)cyclohexyldiamine acetate (422 mg, 1.584 mmol) and N-ethyl-diisopropylamine (205 mg, 1.584 mmol) were combined in a microwave vial, NMP added under N$_2$, and the vial capped and stirred for 5 min at RT. The vial was then heated to 170° C. in a microwave reactor for 2.5 h, and left to stand at RT overnight. The mixture was then poured into ice water, and the resulting light yellow solid filtered, washed with water (30 mL) and Et$_2$O (40 mL) and air-dried. The crude product was recrystallized from EtOAc-CHCl$_3$ to provide 1-{2-[4-(methanesulfonyl-methyl-amino)-cyclohexylamino]-pyrimdin-4-yl}-1H-indole-3-sulfonic acid amide (183 mg, 60% yield) as a light yellow solid (Compound 321).

Example 35

Synthesis of 1-{2-[4-(4-Dimethylamino-piperidine-1-carbonyl)-cyclohexyl-amino]-pyrimidin-4-yl}-1H-indole-3-carboxylic acid amide (A) CSI (0.578 mL, 6.63 mmol) was added dropwise to a solution of indole (777 mg, 6.63 mmol) in dry CH$_3$CN (125 mL) at 0° C., and the mixture stirred at 0° C. for 1 h. Water (10 mL) was added, with HCl (1 drop, conc. aq), and the mixture heated to 100° C. for 2 h with stirring, then stirred at RT for 2.5 h, then refrigerated over the weekend. The reaction mixture was then evaporated to dryness, recrystallized from aqueous acetonitrile, filtered, and dried under vacuum overnight to provide 1H-indole-3-carboxylic acid amide (700 mg, 66% yield).

(B) NaH (480 mg, 12 mmol, 60% suspension) was added to a solution of 1H-indole-3-carboxylic acid amide (1.6 g, 10 mmol) in DMF (5 mL) at 0° C. and stirred for 20 min. A solution of 2-butylsulfanyl-4-chloro-pyrimidine (2.23 g) in DMF (5 mL) was added at 0° C., and the mixture allowed to warm to RT overnight. Water was added to the mixture, and the resulting white solid filtered off, washed with water (20 mL) and DCM (20 mL) and air-dried overnight to provide 1-(2-butylsulfanyl-pyrimidin-4-yl)-1H-indole-3-carboxylic acid amide (3.224 g, 98.77% yield) as a crude product.

(C) MCPBA (3.902 g, 16.96 mmol) was added to a solution of 1-(2-butylsulfanyl-pyrimidin-4-yl)-1H-indole-3-carboxylic acid amide (2.637 g, 8.08 mmol) in DCM (250 mL) at 0° C., and the mixture allowed to warm up to RT overnight with stirring. The resulting white solid was filtered off, washed with DCM (20 mL) and Et$_2$O (70 mL), and dried under vacuum at RT to provide 1-(2-butylsulfonyl-pyrimidin-4-yl)-1H-indole-3-carboxylic acid amide (2.77 g, 96% yield), which was used without further purification.

(D) 1-(2-Butylsulfonyl-pyrimidin-4-yl)-1H-indole-3-carboxylic acid amide (1.5568 g, 4.349 mmol) was dissolved in dry dioxane (150 mL), and 4-amino-cyclohexanecarboxylic acid ethyl ester (1.86 g, 10.87 mmol) was added. The mixture was heated at reflux overnight, then evaporated to dryness, poured into water, extracted into EtOAc, and dried under vacuum. The product was recrystallized from EtOH-free CHCl$_3$ to provide 4-[4-(3-carbamoyl-indol-1-yl)-pyrimidin-2-ylamino]-cyclohexanecarboxylic acid ethyl ester (1.477 g, 83% yield) as a white solid (Compound 322).

(E) 4-[4-(3-Carbamoyl-indol-1-yl)-pyrimidin-2-ylamino]-cyclohexanecarboxylic acid ethyl ester (1.397 g, 3.44 mmol) was dissolved in THF, and LiOH (3.4 mL, 1M aq) was added, and the mixture stirred at RT for 6 h, and additional aliquot of LiOH (6.8 mL) added, and the mixture stirred overnight. A light yellow solid formed in the flask. The mixture was concentrated in vacuo to remove THF, more was added, and the solid filtered off, washed with DCM and Et$_2$O, and air-dried overnight to provide 4-[4-(3-carbamoyl-indol-1-yl)-pyrimidin-2-ylamino]-cyclo-hexanecarboxylic acid (1.15 g, 89% yield).

(F) To a suspension of 4-[4-(3-carbamoyl-indol-1-yl)-pyrimidin-2-ylamino]-cyclo-hexanecarboxylic acid (150 mg, 0.395 mmol) in THF was added BOP, followed by Hünig's base (103 µL, 0.593 mmol), the mixture stirred for 10 min, and 4-(N,N-dimethylamino)-piperidine (76 mg, 0.593 mmol) was added and stirred for 6 days at RT. The resulting white solid was filtered off, washed with dry THF (20 mL) and DCM (30 mL), and air-dried overnight. The product was purified by prep-TLC using 5% MeOH/DCM+NH$_4$OH, and dried under vacuum to provide 1-{2-[4-(4-dimethylamino-piperidine-1-carbonyl)-cyclohexylamino]-pyrimidin-4-yl}-1H-indole-3-carboxylic acid amide (78 mg, 40.3% yield) as a yellow solid (Compound 295).

Example 36

Synthesis of 1-{2-[4-(4-Hydroxy-piperidine-1-carbonyl)-cyclohexyl-amino]-pyrimidin-4-yl}-4-methoxy-1H-indole-3-carboxylic acid amide (A) A solution of 4-methoxy-indole (1.47 g, 10 mmol) in dry CH$_3$CN (125 mL) was cooled to −10° C., CSI (0.91 mL, 10.5 mmol) was added dropwise, and stirred at 0° C. for 1.5 h. The resulting yellow solid was filtered, and heated in water (75 mL) with conc. HCl (1 drop) over a steam bath for 1 h. The resulting off-white solid was filtered, washed with water and DCM, and air-dried overnight to provide 4-methoxy-1H-indole-3-carboxylic acid amide (1.5748 g, 82.8% yield).

(B) NaH (397 mg, 9.94 mmol, 60% dispersion) was added to a solution of 4-methoxy-1H-indole-3-carboxylic acid amide (1.575 g, 8.28 mmol) in dry DMF (5 mL) at 0° C., stirred for 20 min, and a solution of 2-butylsulfanyl-4-chloropyrimidine (1.846 g, 9.108 mmol) in DMF (4 mL) added at 0° C. The mixture was allowed to warm up to RT without stirring, whereupon a solid precipitated. Dry THF (20 mL) was added, and the mixture stirred overnight. Water was added to the mixture, and the resulting white solid was filtered off, washed with water (20 mL) and DCM (20 mL), and air-dried for 3 h to provide 1-(2-butylsulfanyl-pyrimidin-4-yl)-4-methoxy-1H-indole-3-carboxylic acid amide (2.916 g, 98.8% yield) as a crude solid.

(C) MCPBA (3.27 g, 14.24 mmol) was added to a solution of 1-(2-butylsulfanyl-pyrimidin-4-yl)-4-methoxy-1H-indole-3-carboxylic acid amide (2.416 g, 6.779 mmol) in DCM (250 mL) at 0° C. The reaction mixture was allowed to warm up to RT overnight with stirring. An additional aliquot of MCPBA (200 mg) was added, and the mixture stirred for 4 h. The reaction mixture was concentrated to half volume, taken up in EtOAc (300 mL), and extracted with NaOH (1 M aq), water, and brine, and evaporated to dryness under reduced pressure. The product was treated with NaOH (1 M), extracted into EtOAc, dried over MgSO$_4$, filtered, concentrated to dryness, and dried under vacuum for 2 h to provide 1-(2-butylsulfonyl-pyrimidin-4-yl)-4-methoxy-1H-indole-3-carboxylic acid amide (1.726 g, 65.5% yield), which was used without further purification.

(D) 1-(2-Butylsulfonyl-pyrimidin-4-yl)-4-methoxy-1H-indole-3-carboxylic acid amide (250 mg, 0.644 mmol), (4-amino-cyclohexyl)-(4-hydroxy-piperidin-1-yl)-methanone (423 mg, 1.61 mmol), Hünig's base (281 µL, 1.61 mmol), and ethyl-diisopropylamine (1.61 mmol) were combined in a microwave vial, dry NMP added under N$_2$, and the vial capped and stirred for 5 min at RT. The vial was then heated to 170° C. in a microwave reactor for 2.5 h, and left to stand at RT overnight. The product was extracted into EtOAc, washed with water and brine, dried over MgSO$_4$, filtered, and dried under vacuum. The product was purified by column chromatography using a gradient of 0-5% MeOH in DCM, eluted with 1:2 MB:DCM (MB=10 MeOH:60 DCM:1 NH$_4$OH), evaporated to dryness, and recrystallized from CH$_3$CN to provide 1-{2-[4-(4-hydroxy-piperidine-1-carbonyl)-cyclohexylamino]-pyrimidin-4-yl}-4-methoxy-1H-indole-3-carboxylic acid amide (Compound 282, 77 mg, 24.3% yield).

Example 37

Synthesis of {4-[4-(4-Methanesulfonyl-indol-1-yl)-pyrimidin-2-ylamino]-cyclo-hexyl}-pyrrolidin-1-yl-methanone (A) To a solution of 1,5,6,7-tetrahydro-indol-4-one (4.51 g, 33.36 mmol) in dry THF (300 mL) was added Lawesson's reagent (3.495 g, 33.36 mmol) at 0° C. as a solid, in portions. The reaction mixture was warmed to RT and stirred for 35 min. The reaction mixture was then poured into saturated NaHCO$_3$, the product extracted into Et$_2$O, dried over MgSO$_4$, filtered, evaporated, and dried under vacuum overnight. The product was purified by filtration through SiO$_2$ using 30% EtOAc/hexane, evaporated to dryness, and dried under vacuum for 1 h to provide 1,5,6,7-tetrahydro-indole-4-thione (4.354 g, 86.3% yield).

(B) NaH (637 mg, 15.87 mmol, 60% dispersion) was added in portions to a solution of 1,5,6,7-tetrahydro-indole-4-thione (2 g, 13.23 mmol) in THF (100 mL) at −20° C. under N$_2$ and stirred for 20 min. MeI (1.3 mL, 19.84 mmol) was added in dry THF (10 mL), and the reaction mixture stirred at −20° C. for 1 h. The reaction mixture was then poured into NaHCO$_3$ (sat'd aq), and the crude product extracted into benzene (~250 mL). The organic layer was washed with brine, and dried over Na$_2$SO$_4$. To this was added DDQ (3 g, 13.23 mmol), and the mixture stirred at RT for 1 h. The solvent was removed under vacuum, the residue taken up in CHCl$_3$, and the insoluble solid filtered off. The solvent was removed by evaporation to dryness and the solid immobilized on silica gel. The product was purified by column chromatography (0 to 25% EtOAc/hexane) to provide 4-methylsulfanyl-1H-indole (1.2568 g, 58.2% yield).

(C) NaH (379 mg, 9.47 mmol, 60% dispersion) was added to a solution of 4-methyl-sulfanyl-1H-indole (1.257 g, 7.70 mmol) in THF (50 mL) at 0° C., and stirred for 20 min. The ice bath was then removed, a solution of 2-butylsulfanyl-4-chloro-pyrimidine (1.717 g, 8.47 mmol) in dry DMF (10 mL) added to the mixture, and the reaction mixture heated in an oil bath at 70° C. for 2 h. The reaction mixture was then cooled and poured into ice water (150 mL) and extracted with EtOAc. The organic layer was washed with brine, dried over MgSO$_4$, filtered, and evaporated. The product was purified by column chromatography (0 to 35% EtOAc/hexane), the clear product collected, concentrated to dryness, and dried overnight to provide 4-methylsulfanyl-1-(2-butylsulfanyl-pyrimidin-4-yl)-1H-indole (2.169 g, 85.5% yield).

(D) MCPBA (3.37 g, 13.66 mmol) was added to a collusion of 4-methylsulfanyl-1-(2-butylsulfanyl-pyrimidin-4-yl)-1H-indole (1 g, 3.035 mmol) in DCM (125 mL) at 0° C. and stirred for 20 min, then allowed to stir at RT overnight. Na$_2$CO$_3$ (sat'd) was added, and the crude product extracted into DCM, washed with water and brine, filtered, concentrated to dryness, taken up in hexane, and concentrated again to dryness. The product was dried in vacuo for 30 min to provide 4-methylsulfonyl-1-(2-butylsulfonyl-pyrimidin-4-yl)-1H-indole (1.3 g) as a yellow foam.

(E) 4-Methylsulfonyl-1-(2-butylsulfonyl-pyrimidin-4-yl)-1H-indole (250 mg, 0.636 mmol), (4-amino-cyclohexyl)-pyrrolidin-1-yl-methanone hydrochloride (444 mg, 1.91 mmol), ethyl-diisopropylamine (333 µL, 1.91 mmol), and dry EtOH (5 mL) were placed in a vial, sealed, and heated in a microwave reactor at 170° C. for 1 h. The product was concentrated to dryness and purified by column chromatography (5% MeOH in DCM), clear fractions collected and evaporated to dryness, and dried overnight under vacuum. The product was recrystallized from CH$_3$CN and dried under vacuum to provide {4-[4-(4-methanesulfonyl-indol-1-yl)-pyrimidin-2-ylamino]-cyclohexyl}-pyrrolidin-1-yl-methanone (Compound 200, 89 mg).

Example 38

Synthesis of N-{4-[4-(3-Methanesulfonyl-indol-1-yl)-pyrimidin-2-ylamino]-cyclohexyl}-methane-sulfonamide (A) Me$_2$S (955 µL, 13 mmol) was added to a solution of N-chlorosuccinimide (NCS, 1.47 g, 11 mmol) in DCM (80 mL) at 0° C., and stirred under N$_2$ for 35 min. A solution of indole (1.17 g, 10 mmol) in DCM was added slowly, stirring at 0° C. for 2 h. While still cold, Et$_2$O was added, and the white gum that formed was filtered off, dried under vacuum for 1.5 h, and stored at RT overnight. The intermediate was dissolved in DMSO, and the mixture heated to 100° C. under vacuum for 25 min. The product was poured into water, extracted with Et$_2$O, and concentrated to dryness to yield 3-methylsulfanyl-1H-indole (1.609 g, 98.6% yield).

(B) NaH (206 mg, 5.15 mmol, 60% dispersion) was added to a solution of 3-methyl-sulfanyl-1H-indole (700 mg, 5.15 mmol) in THF (50 mL) at 0° C., and stirred for 20 min. The ice bath was then removed, a solution of 2-butylsulfanyl-4-chloro-pyrimidine (957 mg, 4.72 mmol) in dry DMF (5 mL) added to the mixture, and the reaction mixture heated in an oil bath at 70° C. for 2 h. The reaction mixture was then cooled and poured into ice water (150 mL) and extracted with EtOAc. The organic layer was washed with brine, dried over MgSO$_4$, filtered, and evaporated. The product was purified by column chromatography (0 to 30% EtOAc/hexane), the clear product collected, concentrated to dryness, and dried under vacuum for 2 h to provide 3-methylsulfanyl-1-(2-butylsulfanyl-pyrimidin-4-yl)-1H-indole (1.055 g, 75% yield).

(C) MCPBA (1.556 g, 6.31 mmol) was added to a solution of 3-methylsulfanyl-1-(2-butylsulfanyl-pyrimidin-4-yl)-1H-indole (1.04 g, 3.156 mmol) in DCM (120 mL) at 0° C., the mixture warmed to RT, and stirred overnight. The white solid that formed was filtered off, and the filtrate washed with Na$_2$CO$_3$, water, and brine to provide 3-methylsulfonyl-1-(2- butyl-sulfonyl-pyrimidin-4-yl)-1H-indole as a light yellow solid (1.22 g, 98% yield, plus 321 mg from filtrate).

(D) 3-Methylsulfonyl-1-(2-butylsulfonyl-pyrimidin-4-yl)-1H-indole (350 mg, 0.89 mmol), N-(4-amino-cyclohexyl)-methanesulfonamide (610 mg, 2.67 mmol), Hünig's base (465 mg, 2.67 mmol) and dry NMP (3.5 mL) were sealed in a vial, stirred for 30 min at RT, heated to 170° C. for 1.5 h in a microwave reactor, and stored at RT overnight. Water was added to the reaction mixture, and the resulting solids filtered off and recrystallized from hot $CH_3CN$ to provide N-{4-[4-(3-methanesulfonyl-indol-1-yl)-pyrimidin-2-ylamino]-cyclohexyl}-methane-sulfonamide (Compound 245, 103 mg, 25% yield).

Example 39

Ovalbumin-sensitized Asthma Model (A) Male Brown-Norway rats are sensitized i.p. with 100 μg of OA (ovalbumin) in 0.2 ml alum once every week for three weeks (day 0, 7, and 14). The week following the last sensitization, the rats are ready for testing. One to 2 days prior to challenge, animals are weighed. On day 21, the rats are dosed q.d. with either vehicle or compound formulation subcutaneously 30 minutes before OA aerosol challenge (1% OA for 45 minutes) and terminated 4 or 24 hours after challenge. At time of sacrifice, rats are anesthetized (urethane, approx. 2 g/kg, i.p.). Plasma is collected from rats for PK at termination. Blood is drawn from the abdominal aorta at termination. A tracheal cannula is inserted and the lungs are lavaged with 3×3 ml PBS. The BAL fluid is analyzed for total leukocyte number and differential leukocyte counts. Total leukocyte number in an aliquot of the cells (20-100 μl) is determined using a Coulter Counter. For differential leukocyte counts, 50-200 μl of the sample is centrifuged in a Cytospin and the slide stained with Diff-Quik. The proportions of monocytes, eosinophils, neutrophils and lymphocytes are counted under light microscopy using standard morphological criteria and expressed as a percentage. The remaining BAL fluid is centrifuged (1500 rpm, 10 min) and the supernatant is stored at −80° C. Lungs are also harvested for protein and/or RNA analyses.

(B) Compound 157 was administered p.o. at 10 mg/kg and 30 mg/kg, and compared with vehicle/PBS, vehicle/OA, and dexamethasone (10 mg/kg) following the procedure set forth in part (A) above. Compound 157 (at both doses) and dexamethasone demonstrated statistically significant changes in macrophage and neutrophil influx into BAL.

TABLE 2

Inhibition of Inflammatory Cell Infiltration into BAL

| Compound | Neutrophils (count*, % inhibition) | Eosinophils (count*, % inhibition) | Total cells (count*, % inhibition) |
|---|---|---|---|
| Vehicle + OA | 1.60 ± 0.19 | 0.31 ± 0.09 | 2.76 ± 0.24 |
| Compound 157 (10 mg/kg) | 0.94 ± 0.10 41.3% | 0.29 ± 0.09 6.5% | 2.67 ± 0.13 3.3% |
| Compound 157 (30 mg/kg) | 0.47 ± 0.12 70.6% | 0.24 ± 0.05 22.6% | 2.46 ± 0.18 10.9% |
| Dexamethasone (10 mg/kg) | 0.04 ± 0.01 97.5% | 0.18 ± 0.11 41.9% | 2.12 ± 0.14 23.2% |

*Cell count × $10^5$ per mL

Example 40

CFA Induced Thermal Hyperalgesia Assay

Male Wistar rats (~200 g) were purchased from Charles River Laboratories. Food and water was allowed ad-libitum prior to study. On Day 0 animals were injected with 50 μl (1.0 mg/ml) of 100% Complete Freund's Adjuvant (CFA; Sigma Chemical Co, St. Louis, Mo., USA) into the plantar side of the right hind paw under isoflurane anesthesia. Following recovery from anesthesia, rats were moved to the study room and placed in the clear rectangle plastic boxes where the thermal hyperalgesia test was to be performed for 30 min. After habituation, rats were returned to their normal housing.

On Day 1, rats are fasted overnight, and on Day 2 (48 h post CFA injection) rats are moved back to the study room and habituated to the room for at least 1 h. Rats are then placed individually in clear plastic boxes atop a clear plastic floor for 10 min before the study begins. The Hargreaves test is used to measure thermal paw withdrawal thresholds. Fiber optic radiant heat (intensity setting 60) using a plantar tester (Ugo Basile, Italy) is applied through the plastic floor to each rear hind paw. The time for the rat to remove its paw from the heat source is recorded. The target threshold for the contra-lateral paw was ~10 s. Each paw is tested 3× with at least 5 min interval, alternating between the ipsi-lateral and contra-lateral paws. After the baseline is determined, rats are dosed with either vehicle or drug and the test repeated as above 30-120 min post dose. The tester is blinded to the treatment groups. Rats are euthanized by $CO_2$ inhalation at the end of the study, and observed for 5 to 10 min to ensure death occurs. Compounds of the invention effectively reduce pain in this assay.

What is claimed:
1. A compound of formula I:

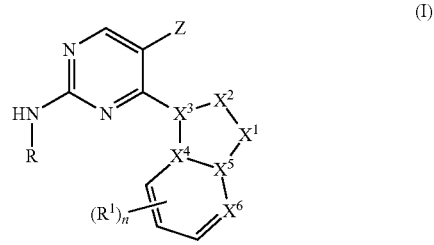

(I)

wherein
$X^1$ is N, N—$R^3$, C—$R^3$, or O;
$X^2$ is N, N—$R^a$, or C—$R^a$;
$X^3$ is N,
where only one or two of $X^1$, $X^2$, and $X^3$ are N;
$X^4$, $X^5$ are each independently C or N;
$X^6$ is N or C—$R^1$;
where not more than two of $X^4$, $X^5$, and $X^6$ are N;
and where the bonds between $X^1$ and $X^2$, $X^2$ and $X^3$, $X^3$ and $X^4$, $X^4$ and $X^5$, $X^5$ and $X^1$, and $X^5$ and $X^6$ may each independently be either single, double, or form an aromatic ring, with the proviso that a chemically stable structure results;

R is

where $R^9$ is H, halo, or lower alkyl, or $R^2$ and $R^9$ together form =O or a ketal thereof;
n is 0, 1, or 2;

Each $R^1$ is independently halo, nitro, —CN, —CH$_2$CN, —OH, —NH$_2$, —COOH, —OCH$_2$C≡N, H, cyano-lower alkyl, —Y$^1$R$^4$, -(lower alkyl), —Y$^1$R$^4$, -(lower alkyl-oxy)-Y$^1$R$^4$, -(lower alkyl-amino)-Y$^1$R$^4$, -(lower alkyl(lower alkyl)amino)-Y$^1$R$^4$, -(lower alkyl-sulfanyl)-Y$^1$R$^4$, -(lower alkyl-oxy-lower alkyl)-Y$^1$R$^4$, -(lower alkyl-amino-alkyl)-Y$^1$R$^4$, where lower alkyl may be substituted with one or two hydroxy, or R$^1$ is

—A$^2$⟨⟩A$^1$, where A$^1$ is CHR$^c$, O, S, S(O), S(O)$_2$, or NR$^c$, where R$^c$ is H, OH, lower alkyl, lower acyl, SO$_2$CH$_3$, or benzyloxy-carbonyl, and A$^2$ is N or C—R$^d$, where R$^d$ is H, —CH$_3$, or —OH;

Y$^1$ is —O—, —NH—, —N(lower alkyl)-, —S—, —SO—, —SO$_2$—, —NHSO$_2$—, —N(lower alkyl)SO$_2$—, —NHC(O)—, —C(O)NH—, —C(O)O—, —OC(O)NH—, or a bond;

R$^4$ is —CN, —CF$_3$, —NH$_2$, —NH(lower alkyl), —N(lower alkyl)$_2$, lower alkyl, cycloalkyl, cycloalkyl-lower alkyl, acyl, benzyl, heterocyclyl (having one or two N, O, or S), heterocyclyl-lower alkyl, each of which is substituted with 0-1 methylsulfanyl, 0-3 hydroxy and 0-3 halo;

R$^3$ is lower alkyl, lower alkoxy, —SO$_2$NH$_2$, —SO$_2$-lower alkyl, —C(O)-lower alkyl, —C(O)-lower alkoxy, —C(O)NH$_2$, —C(O)NH-lower alkyl, cyano, or hydroxy-lower alkyl;

R$^2$ is halo, —OH, —SO$_2$NH$_2$, —CN, or —Y$^2$—R$^5$, where Y$^2$ is —C(O)—, —C(O)NR$^a$—, —SO$_2$—, —O—, —N(hydroxy-lower alkyl), —NHC(O)—, or —NHSO$_2$—;

R$^5$ is lower alkyl, cycloalkyl, phenyl, heterocyclyl, or heteroaryl, wherein R$^5$ is optionally substituted with —OH, halo, lower alkyl, hydroxy-lower alkyl, alkoxy-lower alkyl, oxo, cyano, or —NR$^a$R$^b$ wherein each R$^a$ and R$^b$ is independently H or lower alkyl;

R$^8$ is H, lower alkyl, —OR$^e$, —SO$_2$NH$_2$, —NHSO$_2$R$^e$, —COOR$^e$, —SO$_2$R$^e$, —NH$_2$, —CONR$^a$R$^e$, —NHC(O)R$^e$, —CF$_3$, —NO$_2$, halo, or —CN, where R$^e$ is H, lower alkyl, benzyl, or phenyl;

Z is hydrogen, halo, alkyl, or NH$_2$;

or a pharmaceutically acceptable salt thereof.

2. The compound of claim 1, wherein:
X$^1$ is N or N—R$^3$, X$^2$ is CR$^a$, X$^4$, and X$^5$ are each C, and X$^6$ is CR$^1$;
X$^1$ is N or N—R$^3$, X$^2$ is N or N—R$^a$, and X$^4$ and X$^5$ are each C, and X$^6$ is CR$^1$;
X$^1$ is O, X$^2$ is N or N—R$^a$, and X$^4$ and X$^5$ are each C, and X$^6$ is CR$^1$;
X$^1$ is C or C—R$^3$, X$^2$ is N or N—R$^a$, X$^3$ is N, and X$^4$, and X$^5$ are each C, and X$^6$ is CR$^1$;
X$^1$ is C or C—R$^3$, X$^2$ is C—R$^a$, X$^3$ is N, and X$^4$ and X$^5$ are each C, and X$^6$ is CR$^1$;
X$^1$ is N or N—R$^3$, X$^2$ is CR$^a$, X$^4$ is C, and X$^5$ and X$^6$ are each N; or
X$^1$ is N or N—R$^3$, X$^2$ is N or N—R$^a$, X$^5$ is C, X$^4$ is N, and X$^6$ is CR$^1$.

3. The compound of claim 2, wherein X$^4$ and X$^5$ are each C, and X$^6$ is CR$^1$.

4. The compound of claim 3, wherein R is

—⟨⟩—R$^2$ with R$^9$

5. The compound of claim 4, wherein R$^2$ is OH.

6. The compound of claim 4, wherein R$^2$ is —Y$^2$—R$^5$, where Y$^2$ is —C(O)—, R$^5$ is heterocyclyl or heterocyclyl substituted with one or two hydroxy, halo, amino, or lower alkyl.

7. The compound of claim 4, wherein R$^2$ is —Y$^2$—R$^5$, where Y$^2$ is —NHSO$_2$—, and R$^5$ is lower alkyl or heterocyclyl, substituted with one or two hydroxy, halo, amino, or lower alkyl.

8. The compound of claim 4, wherein R$^1$ is

—A$^2$⟨⟩A$^1$, where A$^1$ is O, and A$^2$ is C—R$^d$, where R$^d$ is H.

9. The compound of claim 4, wherein R$^1$ is

—A$^2$⟨⟩A$^1$, where A$^1$ is SO$_2$, and A$^2$ is C—R$^d$, where R$^d$ is H.

10. The compound of claim 4, wherein R$^1$ is

—A$^2$⟨⟩A$^1$, where A$^1$ is NR$^c$, where R$^c$ is H, OH, lower alkyl, lower acyl, SO$_2$CH$_3$, or benzyloxy-carbonyl, and A$^2$ is N.

11. The compound of claim 4, wherein R$^1$ is -(lower alkoxy)-Y$^1$R$^4$.

12. The compound of claim 11, wherein Y$^1$ is —SO$_2$— and R$^4$ is —NH$_2$, —NH(lower alkyl), —N(lower alkyl)$_2$, or lower alkyl.

13. The compound of claim 4, wherein R$^1$ is —Y$^1$R$^4$.

14. The compound of claim 13, wherein Y$^1$ is —O— and R$^4$ is lower alkyl substituted with 0-3 halo and 0-3 hydroxy.

15. The compound of claim 14, wherein R$^4$ is 4,4,4-trifluoro-2-hydroxybutyl.

16. The compound of claim 12 wherein R$^1$ is 3-(methylsulfanyl)propoxy.

17. A pharmaceutical composition, comprising:
a compound of formula I:

(I)

wherein
X¹ is N, N—R³, C—R³, or O;
X² is N, N—Rᵃ, or C—Rᵃ;
X³ is N,
  where only one or two of X¹, X², and X³ are N;
X⁴, X⁵ are each independently C or N;
X⁶ is N or C—R¹;
  where not more than two of X⁴, X⁵, and X⁶ are N;
  and where the bonds between X¹ and X², X² and X³ and X³ and X⁴, X⁴ and X⁵, X⁵ and X¹, and X⁵ and X⁶ may each independently be either single, double, or form an aromatic ring, with the proviso that a chemically stable structure results;
R is

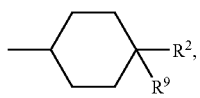

where R⁹ is H, halo, or lower alkyl, or R² and R⁹ together form =O or a ketal thereof;
n is 0, 1, or 2;
Each R¹ is independently halo, nitro, —CN, —CH₂CN, —OH, —NH₂, —COOH, —OCH₂C≡N, H, cyano-lower alkyl, —Y¹R⁴, -(lower alkyl)-Y¹R⁴, -(lower alkyl-oxy)-Y¹R⁴, -(lower alkyl -amino)-Y¹R⁴, -(lower alkyl(lower alkyl)amino)-Y¹R⁴, -(lower alkyl-sulfanyl)-Y¹R⁴, -(lower alkyl-oxy-lower alkyl)-Y¹R⁴, -(lower alkyl-amino-alkyl)-Y¹R⁴, where lower alkyl may be substituted with one or two hydroxy, or R¹ is

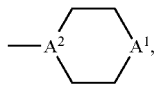

where A¹ is CHRᶜ, O, S, S(O), S(O)₂, or NRᶜ, where Rᶜ is H, OH, lower alkyl, lower acyl, SO₂CH₃, or benzyloxy-carbonyl, and A² is N or C—Rᵈ, where Rᵈ is H, —CH₃, or —OH;
Y¹ is —O—, —NH—, —N(lower alkyl)-, —S—, —SO—, —SO₂—, —NHSO₂—, —N(lower alkyl)SO₂—, —NHC(O)—, —C(O)NH—, —C(O)O—, —OC(O)NH—, or a bond;
R⁴ is —CN, —CF₃, —NH₂, —NH(lower alkyl), —N(lower alkyl)₂, lower alkyl, cycloalkyl, cycloalkyl-lower alkyl, acyl, benzyl, heterocyclyl (having one or two N, O, or S), heterocyclyl-lower alkyl, each of which is substituted with 0-1 methylsulfanyl, 0-3 hydroxy and 0-3 halo;
R³ is H, lower alkyl, lower alkoxy, —SO₂NH₂, —SO₂-lower alkyl, —C(O)-lower alkyl, —C(O)NH₂, —C(O)NH-lower alkyl, cyano, or hydroxy-lower alkyl;
R² is halo, —OH, —SO₂NH₂, —CN, or —Y²—R⁵, where Y² is —C(O)—, —C(O)NRᵃ—, —SO₂—, —O—, —N(hydroxy-lower alkyl)-, —NHC(O)—, —NHSO₂—;
R⁵ is lower alkyl, cycloalkyl, phenyl, heterocyclyl, or heteroaryl, wherein R⁵ is optionally substituted with —OH, halo, lower alkyl, hydroxy-lower alkyl, alkoxy-lower alkyl, oxo, cyano, or —NRᵃRᵇ wherein each Rᵃ and Rᵇ is independently H or lower alkyl;
R⁸ is H, lower alkyl, —ORᵉ, —SO₂NH₂, —NHSO₂Rᵉ, —COORᵉ, —SO₂Rᵉ, —NH₂, —CONRᵃRᵉ, —NHC(O) Rᵉ, —CF₃, —NO₂, halo, or —CN, where Rᵉ is H, lower alkyl, benzyl, or phenyl;

Z is hydrogen, halo, alkyl, or NH₂;
or a pharmaceutically acceptable salt thereof.

18. A compound selected from the group consisting of:
4-[4-(4-benzyloxy-indol-1-yl)-pyrimidin-2-ylamino]-cyclohexanol;
4-[4-(4-bromoindol-1-yl)-pyrimidin-2-ylamino]-cyclohexanol;
4-(4-indol-1-yl)-pyrimidin-2-ylamino]-cyclohexane carboxylic acid (2-methane-sulfonylethyl)amide;
4-[4-(4-fluoroindol-1-yl)-pyrimidin-2-ylamino]-cyclohexanol;
4-[4-(4-methoxy-indol-1-yl)-pyrimidin-2-ylamino]-cyclohexanol;
4-[4-(4-methyl-indol-1-yl)-pyrimidin-2-ylamino]-cyclohexanol;
4-[4-(4-cyano-indol-1-yl)-pyrimidin-2-ylamino]-cyclohexanol;
4-[4-(4-indazol-1-yl)-pyrimidin-2-ylamino]-cyclohexane carboxylic acid (3-hydroxybutyl)-amide;
4-[4-(4-nitro-indazol-1-yl)-pyrimidin-2-ylamino]-cyclohexanol;
4-(4-indazol-1-yl)-pyrimidin-2-ylamino-cyclohexanol;
N-[4-(4-indazol-1-yl)-pyrimidin-2-ylamino-cyclohexyl] methanesulfonamide;
4-(4-indol-1-yl)-pyrimidin-2-ylamino-cyclohexanol;
4-(4-indazol-1-yl)-pyrimidin-2-ylamino]-cyclohexane carboxylic acid (1-methylsulfonyl-prop-2-yl)-amide;
4-(4-indazol-1-yl)-pyrimidin-2-ylamino]-cyclohexane carboxylic acid (1,5-dihydroxy-pent-3-yl)-amide;
4-(4-indazol-1-yl)-pyrimidin-2-ylamino]-cyclohexane carboxylic acid (1-hydroxy-but-2-yl)-amide;
4-(4-indazol-1-yl)-pyrimidin-2-ylamino]-cyclohexane carboxylic acid (2,3-dihydroxy-prop-1-yl)-amide;
4-(4-indazol-1-yl)-pyrimidin-2-ylamino]-cyclohexane carboxylic acid (1-hydroxybut-3-yl)-amide;
4-[4-(4-(2-hydroxyprop-2-yl)-indol-1-yl)-pyrimidin-2-ylamino]-cyclohexanol;
(4-hydroxypiperidin-1-yl)-[4-(4-indazol-1-yl-pyrimidin-2-ylamino)-cyclohexyl]-methanone;
(3-pyrrolidon-1-yl)-[4-(4-indazol-1-yl-pyrimidin-2-ylamino)-cyclohexyl]-methanone;
4-[4-(4-hydroxymethylindol-1-yl)-pyrimidin-2-ylamino]-cyclohexanol;
4-[4-(5-methoxy-indol-1-yl)-pyrimidin-2-ylamino]-cyclohexanol;
4-(4-indazol-1-ylpyrimidin-2-ylamino)cyclohexane carboxylic acid isopropylamide;
4-(4-indazol-1-ylpyrimidin-2-ylamino)cyclohexane carboxylic acid 1-hydroxyprop-2-ylamide;
4-(4-indazol-1-ylpyrimidin-2-ylamino)cyclohexane carboxylic acid 2-methoxyethyl-amide;
4-(4-indazol-1-ylpyrimidin-2-ylamino)cyclohexane carboxylic acid 1,3-dihydroxyprop-2-ylamide;
4-[4-(6-nitroindazol-1-ylpyrimidin-2-ylamino)cyclohexanol;
(3-hydroxypyrrolidin-1-yl)-[4-(4-indazol-1-ylpyrimidin-2-ylamino)-cyclohexyl]-methanone;
(3-hydroxypyrrolidin-1-yl)-[4-(4-indazol-1-ylpyrimidin-2-ylamino)-cyclohexyl]-methanone;
4-(4-indazol-1-ylpyrimidin-2-ylamino)cyclohexane carboxylic acid 3-hydroxy-2-methyl-prop-2-yl-amide;
1-[2-(4-hydroxycyclohexylamino)-pyrimidin-4-yl]-1H-indol-5-ol;
[4-(4-indazol-1-yl-pyrimidin-2-ylamino)-cyclohexyl]-morpholin-4-yl-methanone;
4-[4-(4-aminoindol-1-yl)-pyrimidin-2-ylamino]-cyclohexanol;

1-[2-(4-hydroxycyclohexylamino)-pyrimidin-4-yl]-1H-indazole-6-carboxylic acid methyl ester;
4-[4-(5-methylindol-1-yl)-pyrimidin-2-ylamino]-cyclohexanol;
4-[4-(6-fluoroindol-1-yl)-pyrimidin-2-ylamino]-cyclohexanol;
1-[2-(4-hydroxycyclohexylamino)-pyrimidin-4-yl]-1H-indole-4-carboxylic acid methyl ester;
4-[4-(6-methylindol-1-yl)-pyrimidin-2-ylamino]-cyclohexanol;
4-(4-indazol-1-yl-pyrimidin-2-ylamino)-cyclohexane carboxylic acid (2-hydroxy-2-methylpropyl)amide;
4-[4-(3-methylindol-1-yl)-pyrimidin-2-ylamino]-cyclohexanol;
4-[4-(3-methoxyindazol-1-yl)pyrimidin-2-ylamino]-cyclohexanol;
4-(4-indazol-1-ylpyrimidin-2-ylamino)-cyclohexane carboxylic acid (2-hydroxyethyl)-methyl-amide;
1-[2-(4-hydroxycyclohexylamino)-pyrimidin-2-yl]-1H-indole-6-carboxylic acid methyl ester;
4-[4-(5-fluoroindol-1-yl)-pyrimidin-2-ylamino]-cyclohexanol;
4-(4-indazol-1-ylpyrimidin-2-ylamino)-cyclohexane carboxylic acid (1-methyl-2-methyl-sulfanyl)ethylamide;
4-[4-(6-methylindazol-1-yl)-pyrimidin-2-ylamino]-cyclohexanol;
4-[4-(6-hydroxymethylindazol-1-yl)-pyrimidin-2-ylamino]-cyclohexanol;
4-(4-indazol-1-yl-pyrimidin-2-ylamino)-cyclohexane carboxylic acid (2-hydroxy-2-methylbut-3-yl)amide;
4-(4-indazol-1-ylpyrimidin-2-ylamino)-cyclohexane carboxylic acid (2-hydroxypropyl)-amide;
4-(4-indazol-1-ylpyrimidin-2-ylamino)-cyclohexane carboxylic acid (1-methylsulfanyl-prop-2-yl)amide;
4-(4-indazol-1-ylpyrimidin-2-ylamino)-cyclohexane carboxylic acid N-(2-hydroxyethyl)-N-ethyl-amide;
N-(4-indol-1-ylpyrimidin-2-yl)-cyclohexane-1,4-diamine;
N-(1-[2-(4-hydroxycyclohexylamino)-pyrimidin-4-yl]-1H-indazol-6-yl)-acetamide;
4-(4-indazol-1-ylpyrimidin-2-ylamino)-cyclohexane carboxylic acid cyclopropylmethyl amide;
4-(4-indazol-1-ylpyrimidin-2-ylamino)-cyclohexane carboxylic acid dimethylamide;
4-[4-(5-methylindazol-1-yl)-pyrimidin-2-ylamino]-cyclohexanol;
4-(4-indazol-1-ylpyrimidin-2-ylamino)-1-methylcyclohexanol;
3-(4-indazol-1-ylpyrimidin-2-ylamino)-benzenesulfonamide;
4-[4-(5-hydroxymethylindol-1-yl)pyrimidin-2-ylamino]-cyclohexanol;
4-[4-(6-aminoindazol-1-yl)-pyrimidin-2-ylamino]-cyclohexanol;
1-[2-(4-hydroxycyclohexylamino)-pyrimidin-4-yl]-1H-indole-3-carboxylic acid methyl ester;
4-(4-[6-(2-hydroxyethylamino)-indazol-1-yl]-pyrimidin-2-ylamino)-cyclohexanol;
4-(4-indazol-1-ylpyrimidin-2-ylamino)-1-methyl-cyclohexanol;
4-[4-(5-benzyloxyindol-1-yl)-pyrimidin-2-ylamino]-cyclohexanol;
4-[4-(4-benzylsulfanyl-indol-1-yl)-pyrimidin-2-ylamino]-cyclohexanol;
Cyclohexyl-(4-indol-1-ylpyrimidin-2-yl)amine;
1-[2-(4-hydroxycyclohexylamino)-pyrimidin-4-yl]-1H-indole-5-carboxylic acid methyl ester;
4-(4-indazol-1-yl-pyrimidin-2-ylamino)-cyclohexanone;
(1,4-dioxaspiro[4.5]dec-8-yl)-(4-indazol-1-ylpyrimidin-2-yl)amine;
1-[2-(4-hydroxycyclohexylamino)-pyrimidin-4-yl]-1H-indole-4-carboxylic acid;
4-[4-(4-benzylsulfonyl-indol-1-yl)pyrimidin-2-ylamino]cyclohexanol;
4-(4-indazol-1-yl-pyrimidin-2-ylamino)-cyclohexanecarboxylic acid cyclopentylamide;
[4-(4-indazol-1-ylpyrimidin-2-ylamino)-cyclohexyl]-carbamic acid t-butyl ester;
4-[4-(1-phenylsulfonyl-1H-indol-3-yl)-pyrimidin-2-ylamino]-cyclohexanol;
4-[4-(1H-indol-3-yl)pyrimidin-2-ylamino]-cyclohexanol;
4-[4-(1-methyl-1H-indol-3-yl)pyrimidin-2-ylamino]-cyclohexanol;
4-[4-(1-methyl-1H-indazol-3-yl)pyrimidin-2-ylamino]-cyclohexanol;
4-[4-(1H-indazol-3-yl)pyrimidin-2-ylamino]-cyclohexanol;
4-(4-benzo[d]isoxazol-3-ylpyrimidin-2-ylamino)-cyclohexanol;
4-[4-(7-methoxy-1H-indazol-3-yl)-pyrimidin-2-ylamino]-cyclohexanol;
4-[4-(7-methoxybenzo[d]isoxazol-3-yl)-pyrimidin-2-ylamino]-cyclohexanol;
4-[4-(7-methyl-1H-indazol-3-yl)-pyrimidin-2-ylamino]-cyclohexanol;
4-[4-(5-fluorobenzo[d]isoxazol-3-yl)-pyrimidin-2-ylamino]-cyclohexanol;
4-(4-pyrazolo[1,5-b]pyridazin-3-ylpyrimidin-2-ylamino)-cyclohexanol;
4-(4-[1,2,4]triazolo[4,3-a]pyridine-3-ylpyrimidin-2-ylamino)-cyclohexanol;
4-[4-(4-methoxyindazol-1-yl)-pyrimidin-2-ylamino]-cyclohexanol;
(1-[2-(4-hydroxycyclohexylamino)-pyrimidin-4-yl]-1H-indazol-4-yloxy)acetonitrile; and
N-(1-[2-(4-hydroxycyclohexylamino)-pyrimidin-4-yl]-1H-indazol-4-yl)-isobutyramide.

19. A method for treating an arthritis comprising administering to a patient in need thereof a therapeutically effective amount of the compound of claim 1.

* * * * *